(12) United States Patent
Kawakami et al.

(10) Patent No.: US 7,919,773 B2
(45) Date of Patent: Apr. 5, 2011

(54) AROMATIC AMINE COMPOUND, AND LIGHT-EMITTING ELEMENT, LIGHT-EMITTING DEVICE, AND ELECTRONIC APPLIANCE USING THE AROMATIC AMINE COMPOUND

(75) Inventors: Sachiko Kawakami, Isehara (JP); Nobuharu Ohsawa, Zama (JP); Harue Nakashima, Atsugi (JP); Satoko Shitagaki, Isehara (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 12/548,612

(22) Filed: Aug. 27, 2009

(65) Prior Publication Data
US 2010/0001638 A1    Jan. 7, 2010

Related U.S. Application Data

(62) Division of application No. 11/717,680, filed on Mar. 14, 2007, now abandoned.

(30) Foreign Application Priority Data

Mar. 20, 2006 (JP) .................. 2006-077631

(51) Int. Cl.
    *H01L 35/24* (2006.01)
(52) U.S. Cl. ..... 257/40; 257/94; 257/103; 257/E51.051; 257/E51.018; 313/504; 428/690; 428/917
(58) Field of Classification Search .............. 313/504; 428/690, 917; 257/40, E51.051, 94, 103, 257/E51.018
    See application file for complete search history.

(56) References Cited

U.S. PATENT DOCUMENTS 6,660,410 B2   12/2003   Hosokawa
(Continued)

FOREIGN PATENT DOCUMENTS

CN   1610470   4/2005
(Continued)

OTHER PUBLICATIONS

Notice of Submission of Documents from Third Party (Application No. 2007-072528) dated Aug. 8, 2008 with full English translation.
(Continued)

*Primary Examiner* — Tu-Tu V Ho
(74) *Attorney, Agent, or Firm* — Eric J. Robinson; Robinson Intellectual Property Law Office, P.C.

(57) ABSTRACT

An object of the present invention is to provide a novel aromatic amine compound, and a light-emitting element, a light-emitting device, and an electronic appliance with high luminous efficiency. An aromatic amine compound expressed by General Formula (1) and a light-emitting element, a light-emitting device, and an electronic appliance formed using the aromatic amine compound expressed by General Formula (1) are provided. By the use of the aromatic amine compound expressed by General Formula (1), the light-emitting element, the light-emitting device, and the electronic appliance can have high luminous efficiency.

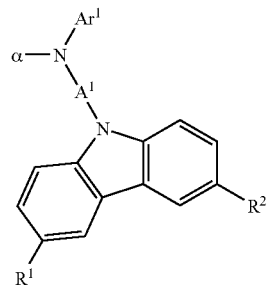

(1)

42 Claims, 72 Drawing Sheets

U.S. PATENT DOCUMENTS

| | | |
|---|---|---|
| 6,773,830 B2 | 8/2004 | Aziz et al. |
| 6,979,414 B2 | 12/2005 | Hosokawa |
| 7,226,546 B2 | 6/2007 | Hosokawa |
| 2005/0037232 A1* | 2/2005 | Tyan et al. .............. 428/690 |
| 2005/0084712 A1 | 4/2005 | Kido et al. |
| 2005/0106419 A1* | 5/2005 | Endoh et al. ............ 428/690 |
| 2005/0140291 A1* | 6/2005 | Hirakata et al. ......... 313/512 |
| 2006/0046098 A1* | 3/2006 | Hosokawa ............... 428/690 |

FOREIGN PATENT DOCUMENTS

| | | |
|---|---|---|
| EP | 1524706 A | 4/2005 |
| JP | 09-249876 | 9/1997 |
| JP | 11-144873 | 5/1999 |
| JP | 11-149987 | 6/1999 |
| JP | 11-288783 | 10/1999 |
| JP | 2001-226331 | 8/2001 |
| JP | 2004-103467 | 4/2004 |
| JP | 2004-339064 | 12/2004 |
| JP | 2004-345960 | 12/2004 |
| JP | 2005-089382 | 4/2005 |
| JP | 2007-110093 | 4/2007 |

OTHER PUBLICATIONS

Information from Third Party (U.S. Appl. No. 11/717,680) dated Nov. 6, 2008, and correction dated Nov. 7, 2008.

Information from Third Party (U.S. Appl. No. 11/717,680) dated Nov. 21, 2008.

Information from Third Party (U.S. Appl. No. 11/717,680) dated Jan. 8, 2009.

Meng-Huan Ho et al., "P-131: Novel Deep Blue Dopants for Organic Light Emitting Devices," SID Digest '05: SID International Symposium Digest of Technical Papers, 2005, vol. 36, pp. 802-805.

A. Balionyte et al., "Carbazolyl-Substituted Triphenyldiamine Derivatives as Novel Photoconductive Amorphous Molecular Materials," Journal of Photochemistry and Photobiology A: Chemistry, vol. 162, 2004, pp. 249-252.

Chinese Office Action (Application No. 200910006729.9) dated May 28, 2010.

* cited by examiner

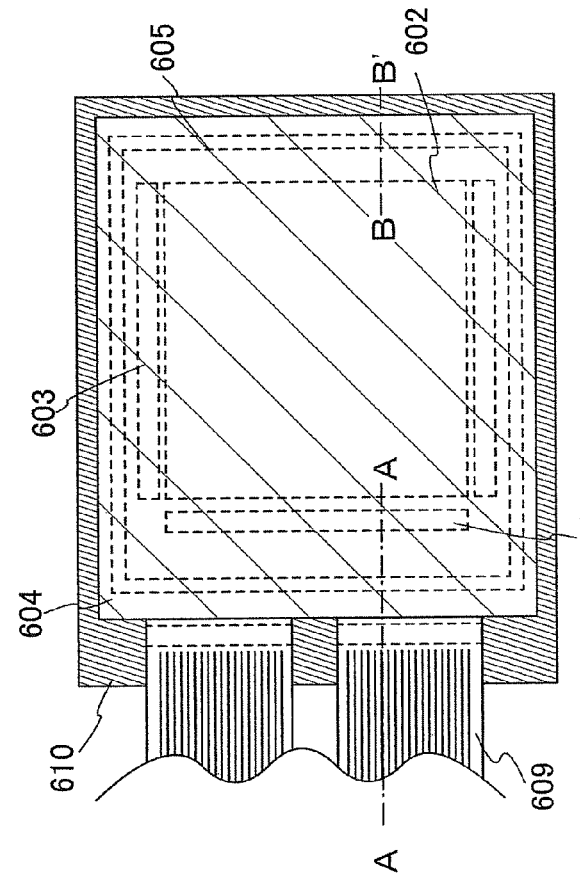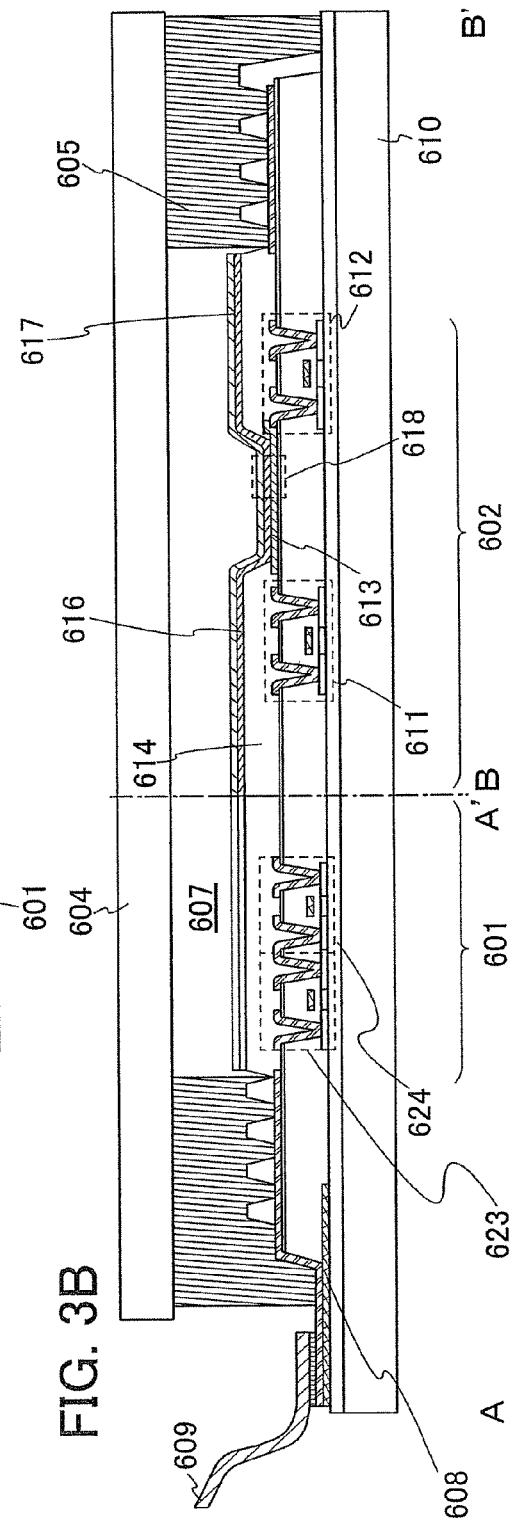
FIG. 3A
FIG. 3B

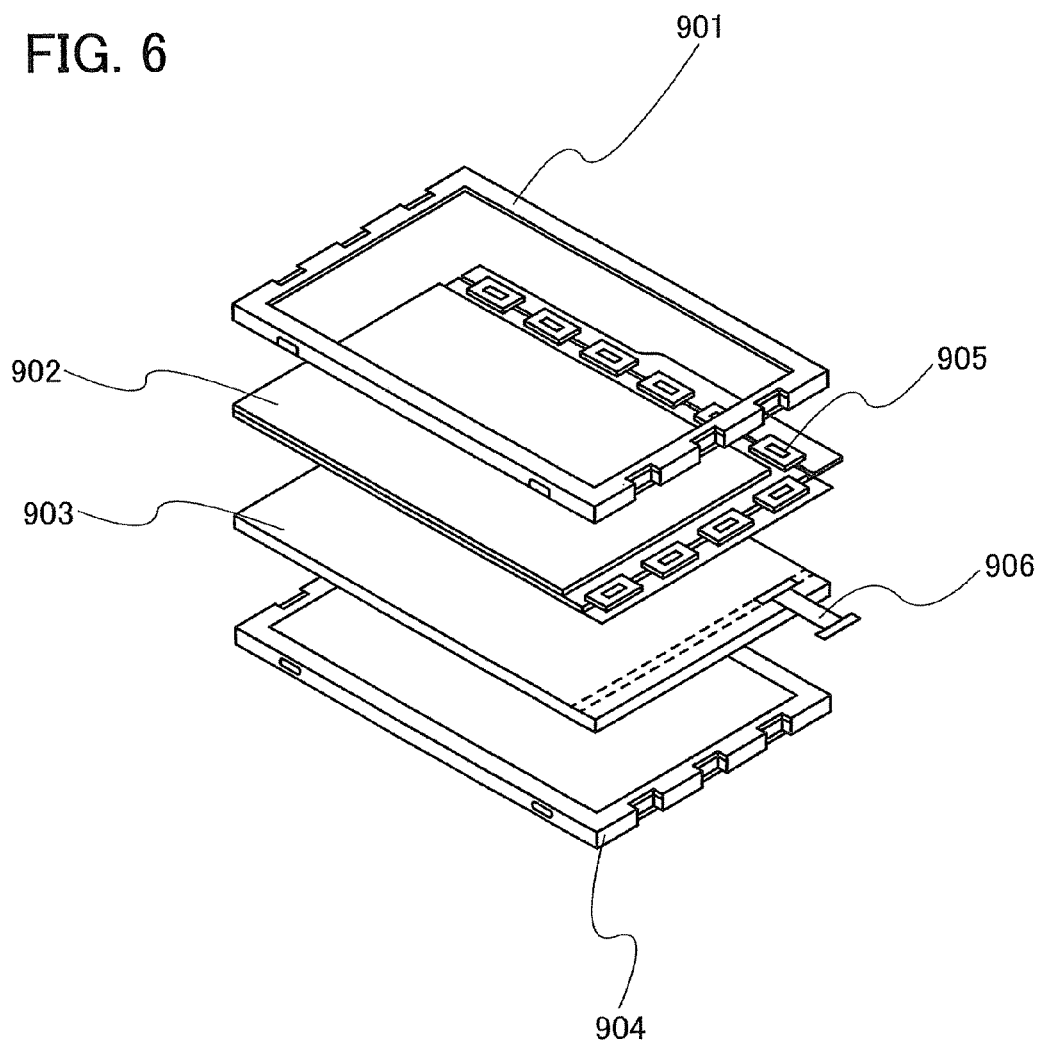

AROMATIC AMINE COMPOUND, AND LIGHT-EMITTING ELEMENT, LIGHT-EMITTING DEVICE, AND ELECTRONIC APPLIANCE USING THE AROMATIC AMINE COMPOUND

BACKGROUND OF THE INVENTION

1. Field of Invention

The present invention relates to an aromatic amine compound, and a light-emitting element, a light-emitting device, and an electronic appliance each using the aromatic amine compound.

2. Description of the Related Art

In recent years, research and development have been extensively conducted on a light-emitting element using a compound with a light-emitting property. In a basic structure of such a light-emitting element, a layer containing an organic compound with a light-emitting property is sandwiched between a pair of electrodes. By application of voltage to this element, electrons and holes are injected from the pair of electrodes to the layer containing an organic compound with a light-emitting property to cause current flow. Then, by recombination of these carriers (electrons and holes), the organic compound with a light-emitting property forms an excited state, and light is emitted when the excited state returns to a ground state. Because of such a mechanism, this kind of light-emitting element is called a light-emitting element of current excitation type.

A great advantage of such a light-emitting element lies in its thinness and lightness in weight because the light-emitting element is formed by, for example, an organic thin film with a thickness of about 0.1 μm. Moreover, another advantage thereof is high response speed because the time it takes for light emission after carrier injection is about 1 μs or shorter. In view of these advantages, it is considered that the light-emitting element is suitable for a flat panel display element.

Since the light-emitting element is formed into a film shape, surface light emission can be easily obtained by forming a large-area element. This is a feature which is difficult to be obtained in point light sources typified by an incandescent lamp and an LED or line light sources typified by a fluorescent lamp. Accordingly, the utility value of the light-emitting element is also high as a surface light source applicable to illumination and the like.

In order to overcome many problems derived from materials of such a light-emitting element and to improve its element characteristics, improvement of an element structure, material development, and so on are carried out.

For example, Nonpatent Document 1 describes a light-emitting element using a blue light-emitting material.

[Nonpatent Document 1] Meng-Huan Ho, Yao-Shan Wu and Chin H. Chen, 2005 SID International Symposium Digest of Technical Papers, p 802-805

SUMMARY OF THE INVENTION

In a light-emitting element described in Nonpatent Document 1, 4,4'-bis[N-(1-naphthyl)-N-phenylamino]biphenyl (NPB) is used for a layer which is in contact with a light-emitting layer. However, NPB has low singlet-excitation energy and the energy may transfer from a light-emitting material in an excited state. In particular, in a case of a light-emitting material for emitting blue light, which has a short wavelength, the energy is more likely to transfer to NPB because of a high energy level in an excited state. The energy transfer to NPB causes a problem of decrease in luminous efficiency of a light-emitting element.

Therefore, it is an object of the present invention to provide a novel aromatic amine compound.

It is another object of the present invention to provide a light-emitting element, a light-emitting device, and an electronic appliance each having high luminous efficiency.

An aspect of the present invention is an aromatic amine compound expressed by General Formula (1).

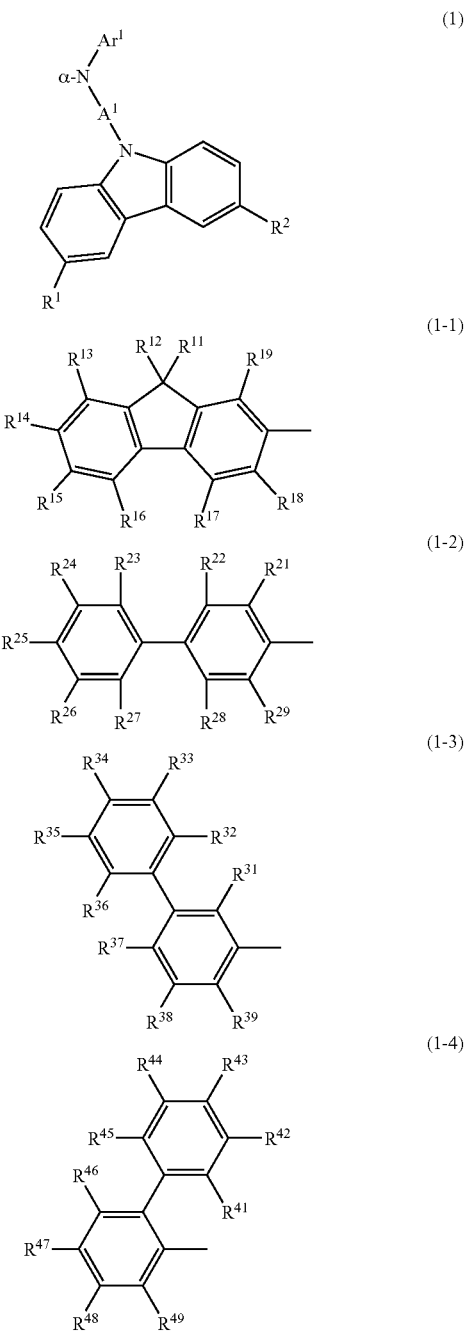

(In the formula, $R^1$ and $R^2$ each represent any of a hydrogen atom, an alkyl group having 1 to 4 carbon atoms, and an aryl group having 6 to 25 carbon atoms; $A^1$ represents an arylene group having 6 to 25 carbon atoms; and $Ar^1$ represents an aryl group having 6 to 25 carbon atoms. Moreover, α represents a substituent expressed by any of General Formulae (1-1) to (1-4). In General Formulae (1-1) to (1-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represent a hydrogen atom or an alkyl group having 1 to 4 carbon atoms.)

Among the aromatic amine compounds that can be expressed by General Formula (1), an aromatic amine compound expressed by General Formula (3) is preferable.

(3)

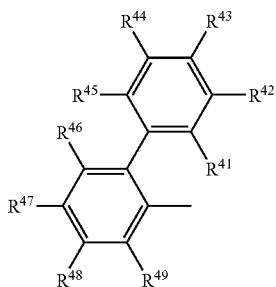

(3-1)

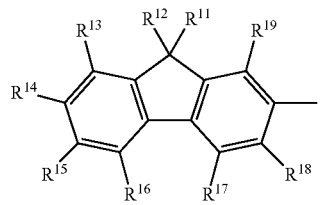

(3-2)

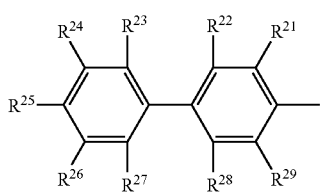

(3-3)

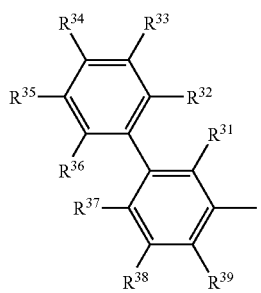

(3-4)

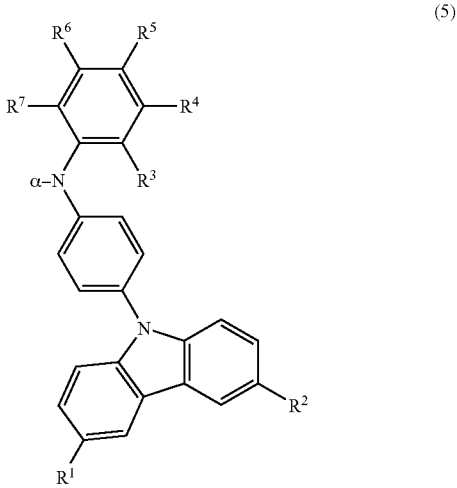

(In the formula, $R^1$ and $R^2$ each represent any of a hydrogen atom, an alkyl group having 1 to 4 carbon atoms, and an aryl group having 6 to 25 carbon atoms; and $Ar^1$ represents an aryl group having 6 to 25 carbon atoms. Moreover, α represents a substituent expressed by any of General Formulae (3-1) to (3-4). In General Formulae (3-1) to (3-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represent a hydrogen atom or an alkyl group having 1 to 4 carbon atoms.)

An aromatic amine compound expressed by General Formula (5) is more preferable.

(5)

(5-1)

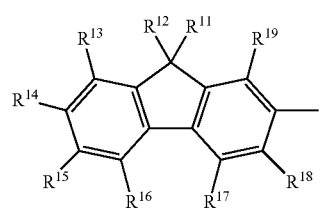

(5-2)

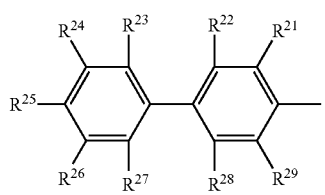

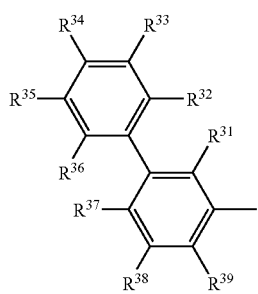

(5-3)

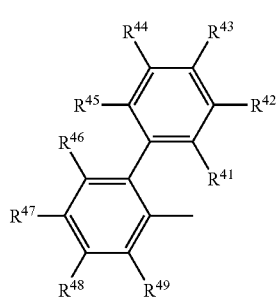

(5-4)

(In the formula, $R^1$ and $R^2$ each represent any of a hydrogen atom, an alkyl group having 1 to 4 carbon atoms, and an aryl group having 6 to 25 carbon atoms; and $R^3$ to $R^7$ each represent any of a hydrogen atom, an alkyl group having 1 to 4 carbon atoms, and a phenyl group. Moreover, α represents a substituent expressed by any of General Formulae (5-1) to (5-4). In General Formulae (5-1) to (5-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represent a hydrogen atom or an alkyl group having 1 to 4 carbon atoms.)

An aromatic amine compound expressed by General Formula (7) is more preferable.

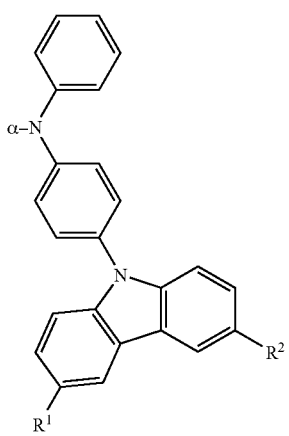

(7)

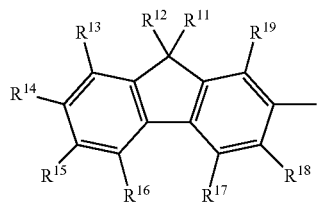

(7-1)

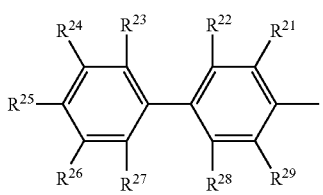

(7-2)

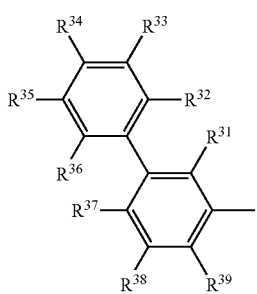

(7-3)

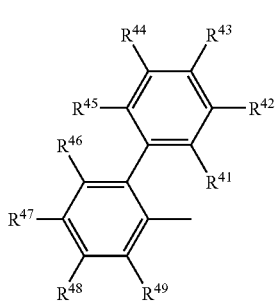

(7-4)

(In the formula, $R^1$ and $R^2$ each represent any of a hydrogen atom, an alkyl group having 1 to 4 carbon atoms, and an aryl group having 6 to 25 carbon atoms. Moreover, α represents a substituent expressed by any of General Formulae (7-1) to (7-4). In General Formulae (7-1) to (7-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represents a hydrogen atom or an alkyl group having 1 to 4 carbon atoms.)

An aromatic amine compound expressed by General Formula (9) or (10) is preferable.

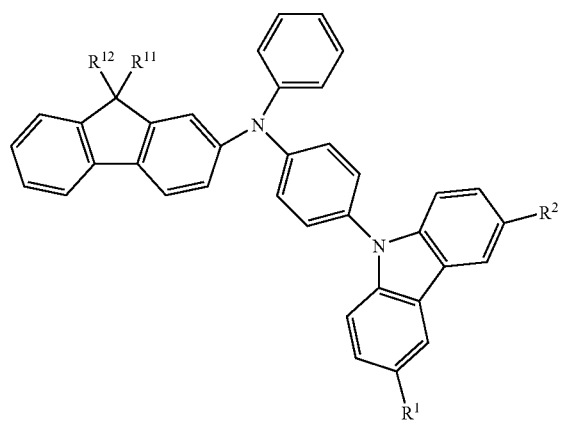

(In the formula, $R^1$ and $R^2$ each represent any of a hydrogen atom, an alkyl group having 1 to 4 carbon atoms, and an aryl group having 6 to 25 carbon atoms. Moreover, $R^{11}$ and $R^{12}$ each represent any of a hydrogen atom, an alkyl group having 1 to 4 carbon atoms, and an aryl group having 6 to 12 carbon atoms.)

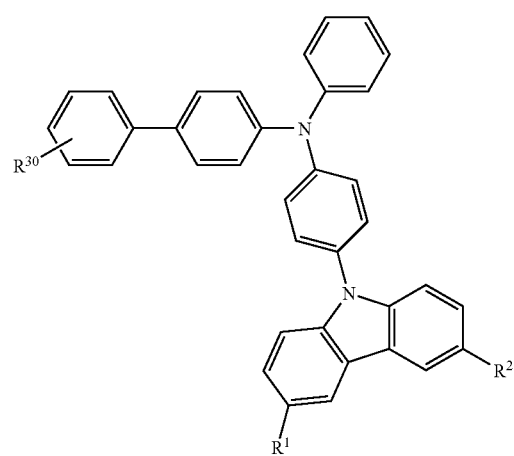

(In the formula, $R^1$ and $R^2$ each represent any of a hydrogen atom, an alkyl group having 1 to 4 carbon atoms, and an aryl group having 6 to 25 carbon atoms. Moreover, $R^{30}$ represents a hydrogen atom or an alkyl group having 1 to 4 carbon atoms.)

An aspect of the present invention is an aromatic amine compound expressed by General Formula (2).

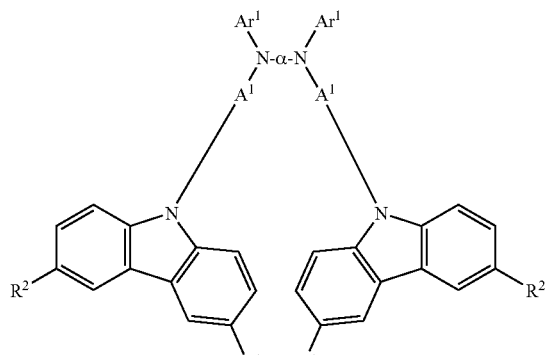

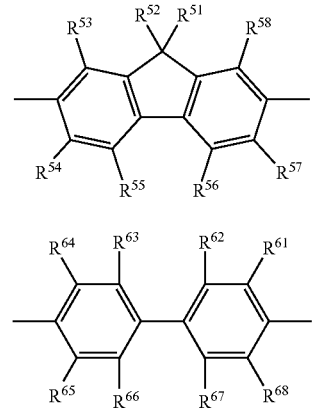

(In the formula, $R^1$ and $R^2$ each represent any of a hydrogen atom, an alkyl group having 1 to 4 carbon atoms, and an aryl group having 6 to 25 carbon atoms; $A^1$ represents an arylene group having 6 to 25 carbon atoms; and $Ar^1$ represents an aryl group having 6 to 25 carbon atoms. Moreover, α represents a substituent expressed by either of General Formulae (2-1) and (2-2). In General Formulae (2-1) and (2-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

Among the aromatic amine compounds that can be expressed by General Formula (2), an aromatic amine compound expressed by General Formula (4) is preferable.

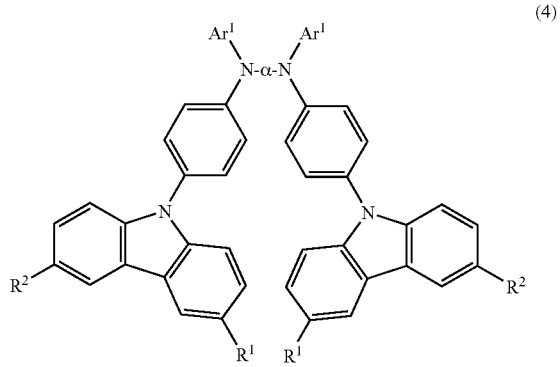

(4-1)

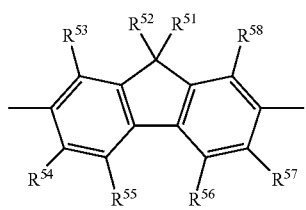

(4-2)

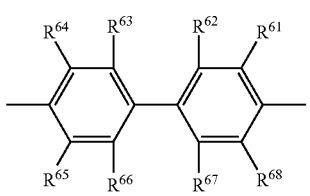

(In the formula, $R^1$ and $R^2$ each represent any of a hydrogen atom, an alkyl group having 1 to 4 carbon atoms, and an aryl group having 6 to 25 carbon atoms; and $Ar^1$ represents an aryl group having 6 to 25 carbon atoms. Moreover, α represents a substituent expressed by either of General Formulae (4-1) and (4-2). In General Formulae (4-1) and (4-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

An aromatic amine compound expressed by General Formula (6) is more preferable.

(6)

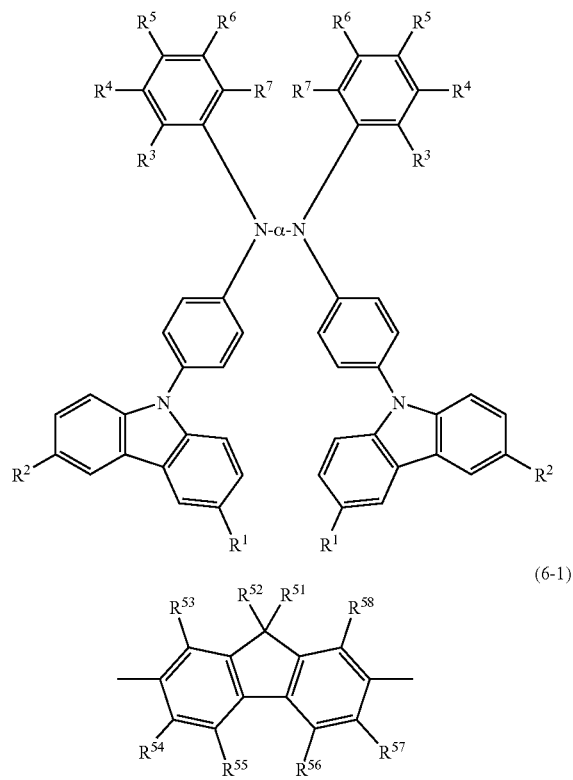

(6-1)

(6-2)

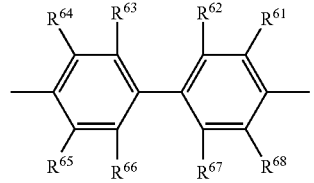

(In the formula, $R^1$ and $R^2$ each represent any of a hydrogen atom, an alkyl group having 1 to 4 carbon atoms, and an aryl group having 6 to 25 carbon atoms; and $R^3$ to $R^7$ each represent any of a hydrogen atom, an alkyl group having 1 to 4 carbon atoms, and a phenyl group. Moreover, α represents a substituent expressed by either of General Formulae (6-1) and (6-2). In General Formulae (6-1) and (6-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

An aromatic amine compound expressed by General Formula (8) is more preferable.

(8)

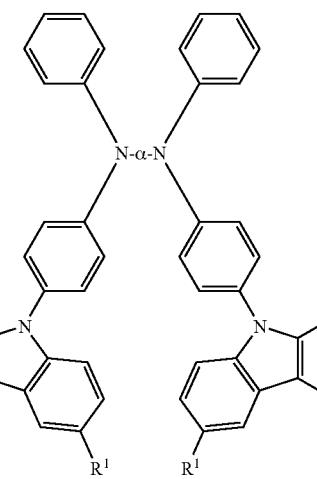

(8-1)

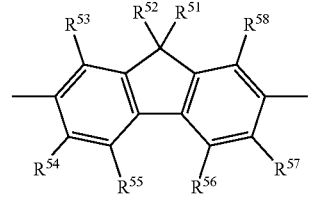

(8-2)

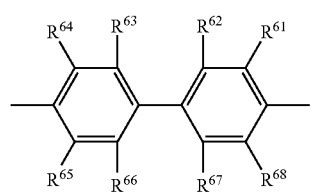

(In the formula, $R^1$ and $R^2$ each represent any of a hydrogen atom, an alkyl group having 1 to 4 carbon atoms, and an aryl group having 6 to 25 carbon atoms. Moreover, α represents a substituent expressed by either of General Formulae (8-1) and (8-2). In General Formulae (8-1) and (8-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

An aromatic amine compound expressed by General Formula (11) or (12) is more preferable.

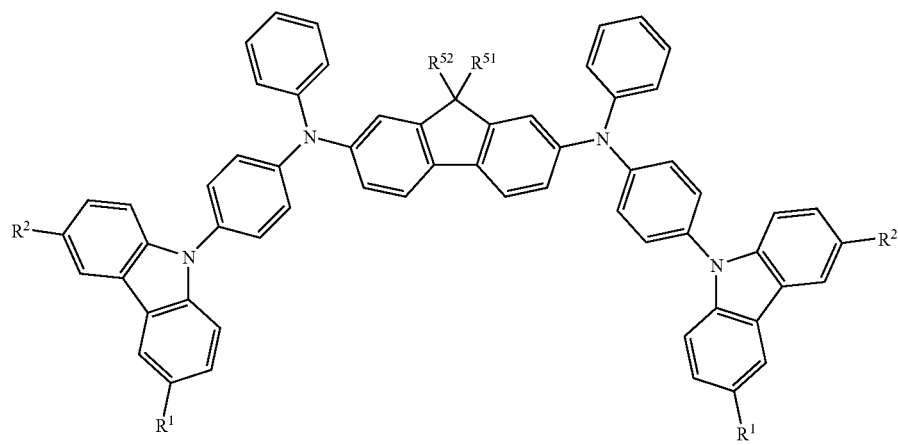

(11)

(In the formula, $R^1$ and $R^2$ each represent any of a hydrogen atom, an alkyl group having 1 to 4 carbon atoms, and an aryl group having 6 to 25 carbon atoms. Moreover, $R^{51}$ and $R^{52}$ each represent any of a hydrogen atom, an alkyl group having 1 to 4 carbon atoms, and an aryl group having 6 to 12 carbon atoms.)

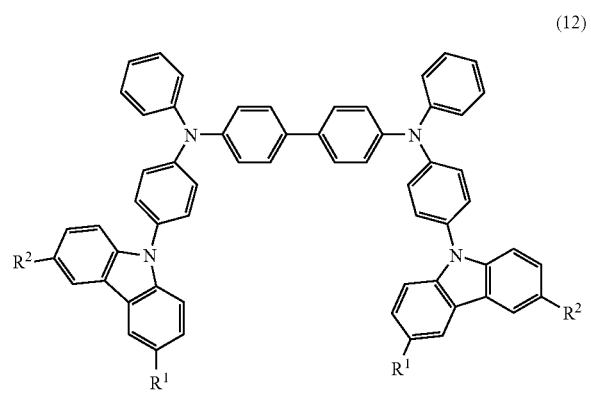

(12)

(In the formula, $R^1$ and $R^2$ each represent any of a hydrogen atom, an alkyl group having 1 to 4 carbon atoms, and an aryl group having 6 to 25 carbon atoms.)

An aspect of the present invention is a light-emitting element having the aforementioned aromatic amine compound between a pair of electrodes.

An aspect of the present invention is a light-emitting element including a light-emitting layer and a layer containing the aforementioned aromatic amine compound between a pair of electrodes. In the light-emitting element, the layer containing the aromatic amine compound is in contact with the light-emitting layer.

An aspect of the present invention is a light-emitting element including a light-emitting layer and the aforementioned aromatic amine compound between a pair of electrodes, in which the aromatic amine compound is included in the light-emitting layer.

In the above structure, the light-emitting layer includes a phosphorescent material which emits phosphorescent light. In particular, an advantageous effect of the present invention can be obtained more in a case of including a phosphorescent material which emits green light.

In the above structure, the light-emitting layer includes a fluorescent material which emits fluorescent light. In particular, an advantageous effect of the present invention can be obtained more in a case of including a fluorescent material which emits blue light.

Moreover, a light-emitting device of the present invention has a light-emitting element including the aforementioned aromatic amine compound and a controller for controlling light emission of the light-emitting element. It is to be noted that the light-emitting device in this specification includes an image display device, a light-emitting device, and a light source (including an illumination apparatus). Further, the light-emitting device includes a module in which a connector such as an FPC (Flexible Printed Circuit), a TAB (Tape Automated Bonding) tape, or a TCP (Tape Carrier Package) is attached to a panel, a module in which a print wiring board is provided at an end of a TAB tape or an TCP, and a module in which an IC (Integrated Circuit) is directly mounted on a light-emitting device by a COG (Chip On Glass) method.

An electronic appliance using the light-emitting element of the present invention in its display portion is also included in the category of the present invention. Therefore, an electronic appliance of the present invention has a display portion provided with the aforementioned light-emitting element and a controller for controlling light emission of the light-emitting element.

The aromatic amine compound of the present invention has a wide band gap and can be used for a layer which is in contact with a light-emitting material, and moreover can be used as a material for dispersing a light-emitting material. When the aromatic amine compound of the present invention is provided in contact with a light-emitting material, the transfer of excitation energy of the light-emitting material can be prevented and the luminous efficiency can be improved. Further, even if the aromatic amine compound of the present invention is excited, the energy can transfer from the aromatic amine compound of the present invention to the light-emitting material; therefore, the luminous efficiency can be improved.

With the aromatic amine compound of the present invention used for a light-emitting element, a light-emitting device, and an electronic appliance, the light-emitting element, the light-emitting device, and the electronic appliance can have high luminous efficiency.

BRIEF DESCRIPTION OF THE DRAWINGS

In the accompanying drawings:

FIGS. 3A and 3B explain a light-emitting device of the present invention;

FIG. 6 explains an electronic appliance of the present invention;

DETAILED DESCRIPTION OF THE INVENTION

Figure 1A:
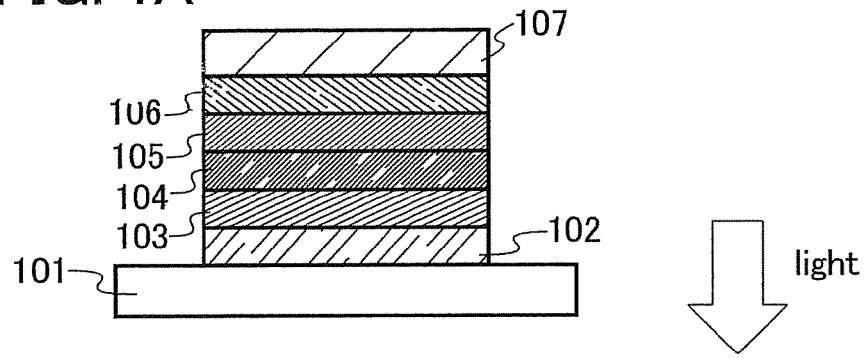
FIGS. 1A to 1C explain light-emitting elements of the present invention.

Embodiment modes and embodiments of the present invention will be hereinafter described with reference to the drawings. However, the present invention is not limited to the following description and it is easily understood by those skilled in the art that the mode and detail can be variously changed without departing from the scope and spirit of the present invention. Therefore, the present invention is not construed as being limited to the description of the embodiment modes and embodiments hereinafter shown.

Embodiment Mode 1

Embodiment Mode 1 will explain an aromatic amine compound of the present invention.

An aromatic amine compound of the present invention is an aromatic amine compound expressed by General Formula (1).

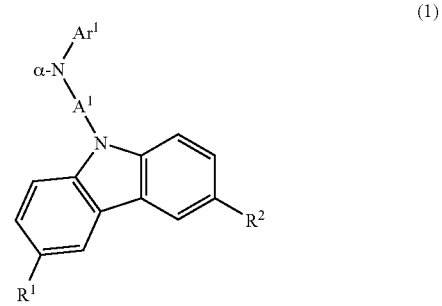

(1)

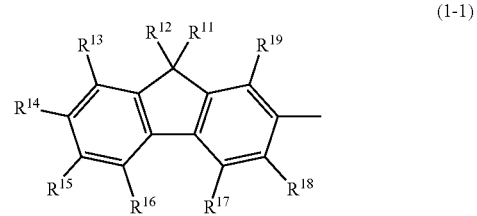

(1-1)

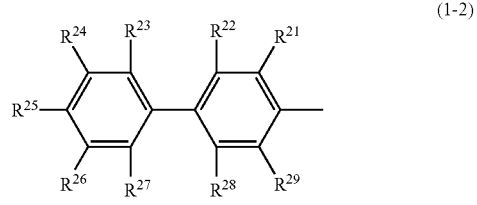

(1-2)

-continued

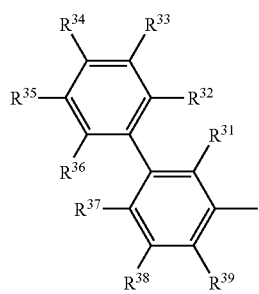
(1-3)

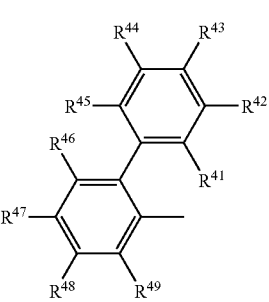
(1-4)

(In the formula, $R^1$ and $R^2$ each represent any of a hydrogen atom, an alkyl group having 1 to 4 carbon atoms, and an aryl group having 6 to 25 carbon atoms; $A^1$ represents an arylene group having 6 to 25 carbon atoms; and $Ar^1$ represents an aryl group having 6 to 25 carbon atoms. Moreover, α represents a substituent expressed by any of General Formulae (1-1) to (1-4). In General Formulae (1-1) to (1-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represent a hydrogen atom or an alkyl group having 1 to 4 carbon atoms.)

In General Formula (1), $R^1$ and $R^2$ each represent a hydrogen atom, an alkyl group having 1 to 4 carbon atoms, and an aryl group having 6 to 25 carbon atoms. Specifically, a substituent shown by any of Structure Formulae (13-1) to (13-12) is given.

 (13-1)

 (13-2)

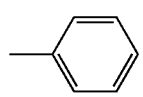 (13-3)

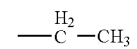 (13-4)

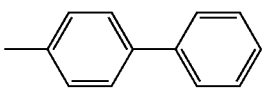 (13-5)

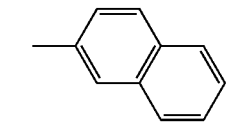 (13-6)

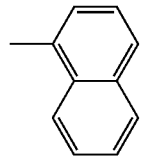 (13-7)

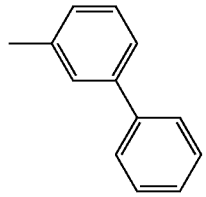 (13-8)

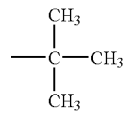 (13-9)

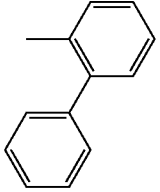 (13-10)

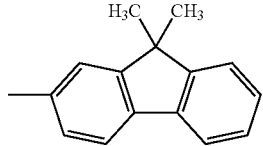 (13-11)

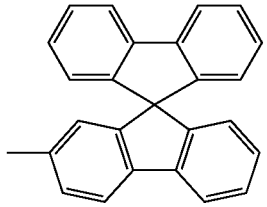 (13-12)

In General Formula (1), $A^1$ represents an arylene group having 6 to 25 carbon atoms. Specifically, a substituent shown by any of Structure Formulae (14-1) to (14-6) is given.

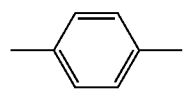 (14-1)

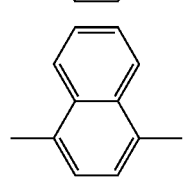 (14-2)

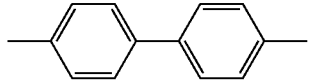 (14-3)

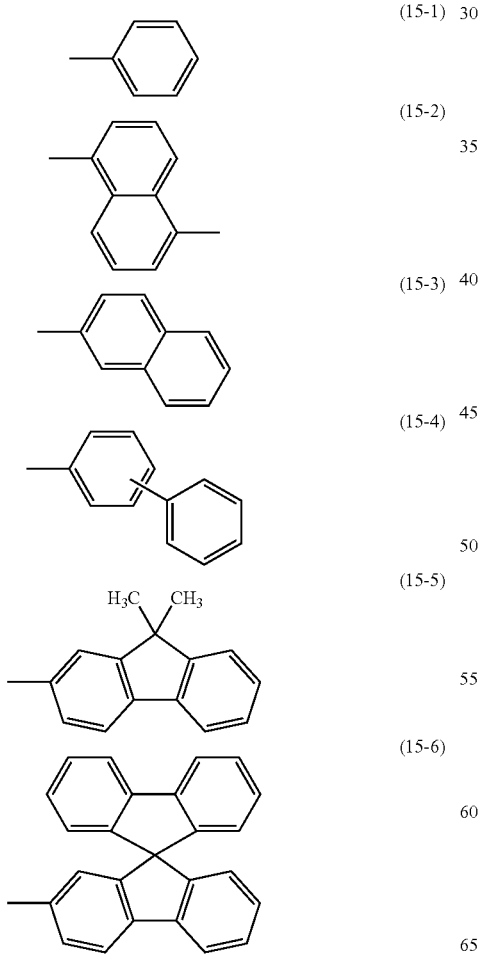

In General Formula (1), $Ar^1$ represents an aryl group having 6 to 25 carbon atoms. Specifically, a substituent shown by any of Structure Formulae (15-1) to (15-6) is given.

Among the aromatic amine compounds that can be expressed by General Formula (1), an aromatic amine compound expressed by General Formula (3) is preferable.

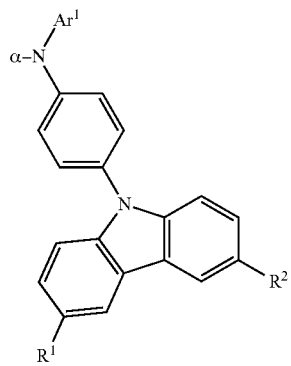

(3)

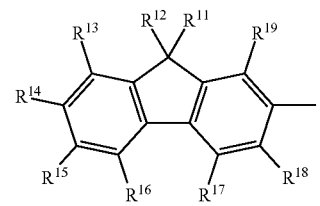

(3-1)

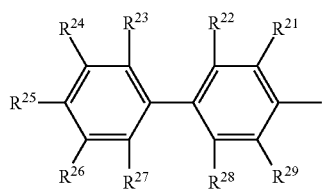

(3-2)

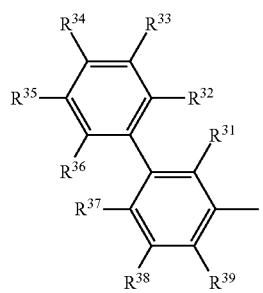

(3-3)

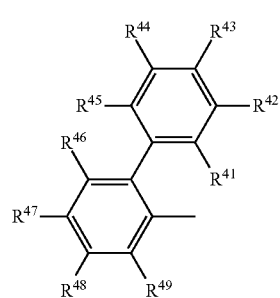

(3-4)

(In the formula, $R^1$ and $R^2$ each represent any of a hydrogen atom, an alkyl group having 1 to 4 carbon atoms, and an aryl group having 6 to 25 carbon atoms; and $Ar^1$ represents an aryl group having 6 to 25 carbon atoms. Moreover, α represents a substituent expressed by any of General Formulae (3-1) to (3-4). In General Formulae (3-1) to (3-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represent a hydrogen atom or an alkyl group having 1 to 4 carbon atoms.)

An aromatic amine compound expressed by General Formula (5) is more preferable.

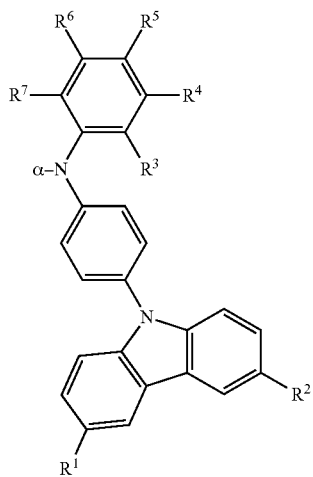
(5)

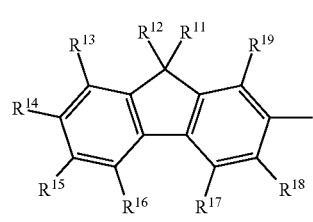
(5-1)

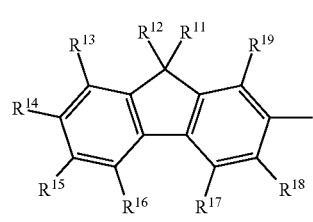
(5-2)

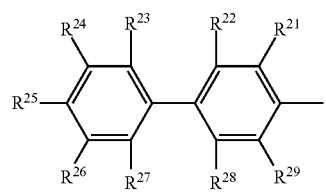
(5-3)

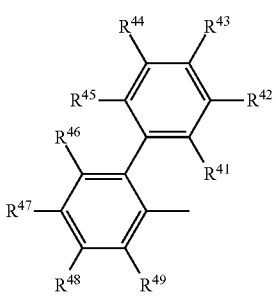
(5-4)

(In the formula, $R^1$ and $R^2$ each represent any of a hydrogen atom, an alkyl group having 1 to 4 carbon atoms, and an aryl group having 6 to 25 carbon atoms; and $R^3$ to $R^7$ each represent any of a hydrogen atom, an alkyl group having 1 to 4 carbon atoms, and a phenyl group. Moreover, α represents a substituent expressed by any of General Formulae (5-1) to (5-4). In General Formulae (5-1) to (5-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represent a hydrogen atom or an alkyl group having 1 to 4 carbon atoms.)

An aromatic amine compound expressed by General Formula (7) is more preferable.

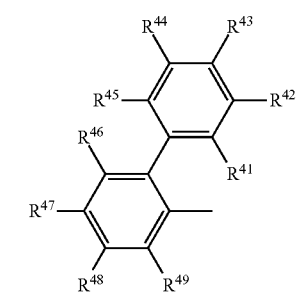
(7)

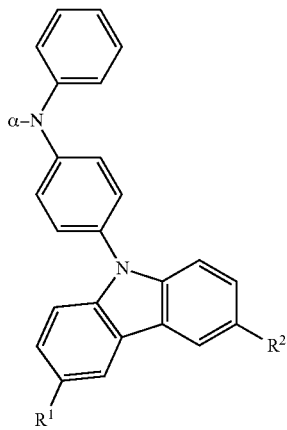
(7-1)

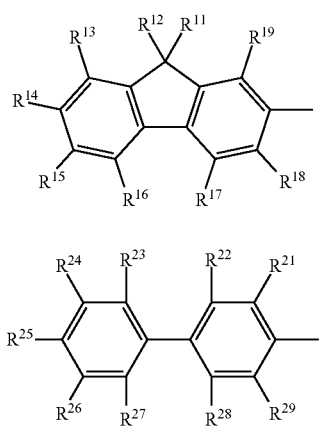
(7-2)

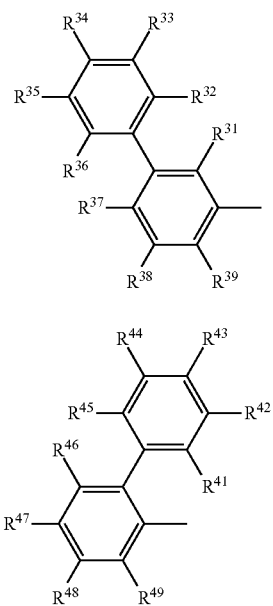

(7-3)

(7-4)

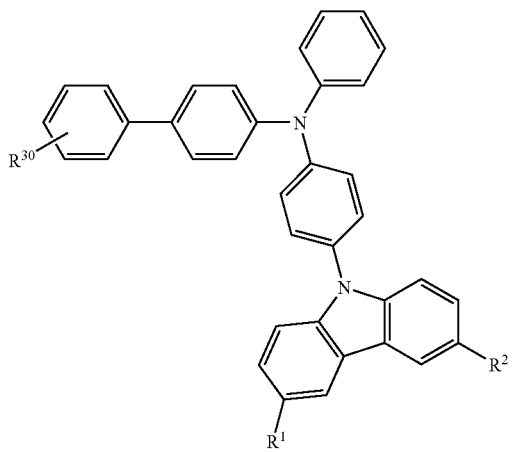

(10)

(In the formula, $R^1$ and $R^2$ each represent any of a hydrogen atom, an alkyl group having 1 to 4 carbon atoms, and an aryl group having 6 to 25 carbon atoms; and $R^{30}$ represents a hydrogen atom or an alkyl group having 1 to 4 carbon atoms.)

An aromatic amine compound of the present invention is an aromatic amine compound expressed by General Formula (2).

(In the formula, $R^1$ and $R^2$ each represent any of a hydrogen atom, an alkyl group having 1 to 4 carbon atoms, and an aryl group having 6 to 25 carbon atoms. Moreover, α represents a substituent expressed by any of General Formulae (7-1) to (7-4). In General Formulae (7-1) to (7-4), $R^{11}$ and $R^{12}$ each represent any of a hydrogen atom, an alkyl group having 1 to 4 carbon atoms, and an aryl group having 6 to 12 carbon atoms; and $R^{13}$ to $R^{19}$, $R^{21}$ to $R^{29}$, $R^{31}$ to $R^{39}$, and $R^{41}$ to $R^{49}$ each represents a hydrogen atom or an alkyl group having 1 to 4 carbon atoms.)

An aromatic amine compound expressed by General Formula (9) or (10) is preferable.

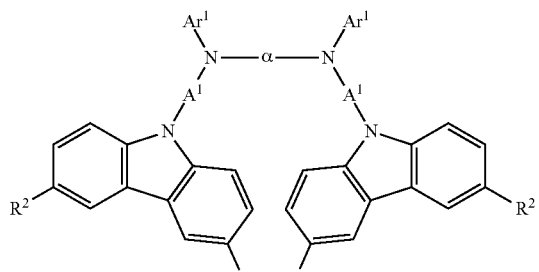

(2)

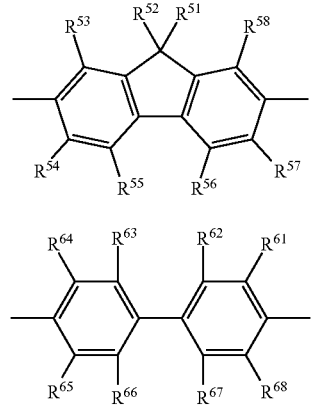

(2-1)

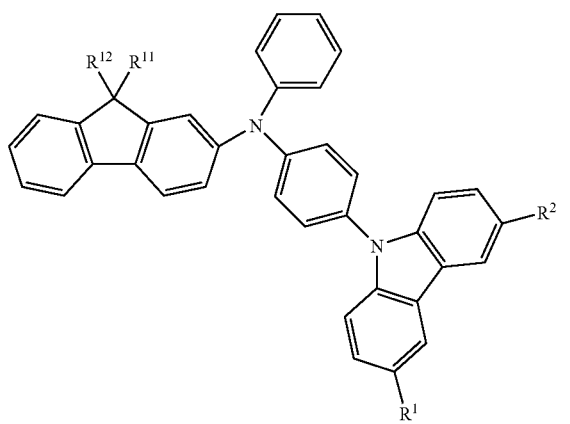

(9)

(2-2)

(In the formula, $R^1$ and $R^2$ each represent any of a hydrogen atom, an alkyl group having 1 to 4 carbon atoms, and an aryl group having 6 to 25 carbon atoms; and $R^{11}$ and $R^{12}$ each represent any of a hydrogen atom, an alkyl group having 1 to 4 carbon atoms, and an aryl group having 6 to 12 carbon atoms.)

(In the formula, $R^1$ and $R^2$ each represent any of a hydrogen atom, an alkyl group having 1 to 4 carbon atoms, and an aryl group having 6 to 25 carbon atoms; $A^1$ represents an arylene group having 6 to 25 carbon atoms; and $Ar^1$ represents an aryl group having 6 to 25 carbon atoms. Moreover, α represents a substituent expressed by either of General Formulae (2-1) and (2-2). In General Formulae (2-1) and (2-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

In General Formula (2), $R^1$ and $R^2$ each represent any of a hydrogen atom, an alkyl group having 1 to 4 carbon atoms, and an aryl group having 6 to 25 carbon atoms. Specifically, a substituent shown by any of Structure Formulae (13-1) to (13-12) is given.

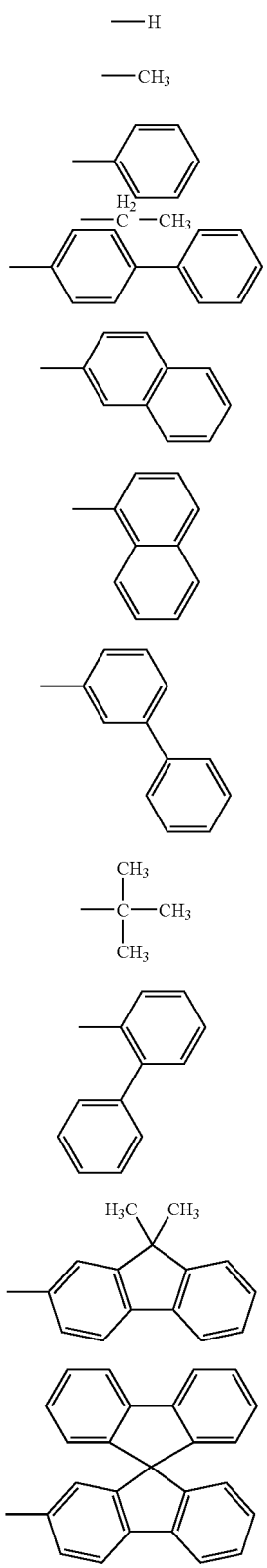

In General Formula (2), $A^1$ represents any of an arylene group having 6 to 25 carbon atoms. Specifically, a substituent shown by any of Structure Formulae (14-1) to (14-6) is given.

In General Formula (2), $Ar^1$ represents any of an aryl group having 6 to 25 carbon atoms. Specifically, a substituent shown by any of Structure Formulae (15-1) to (15-6) is given.

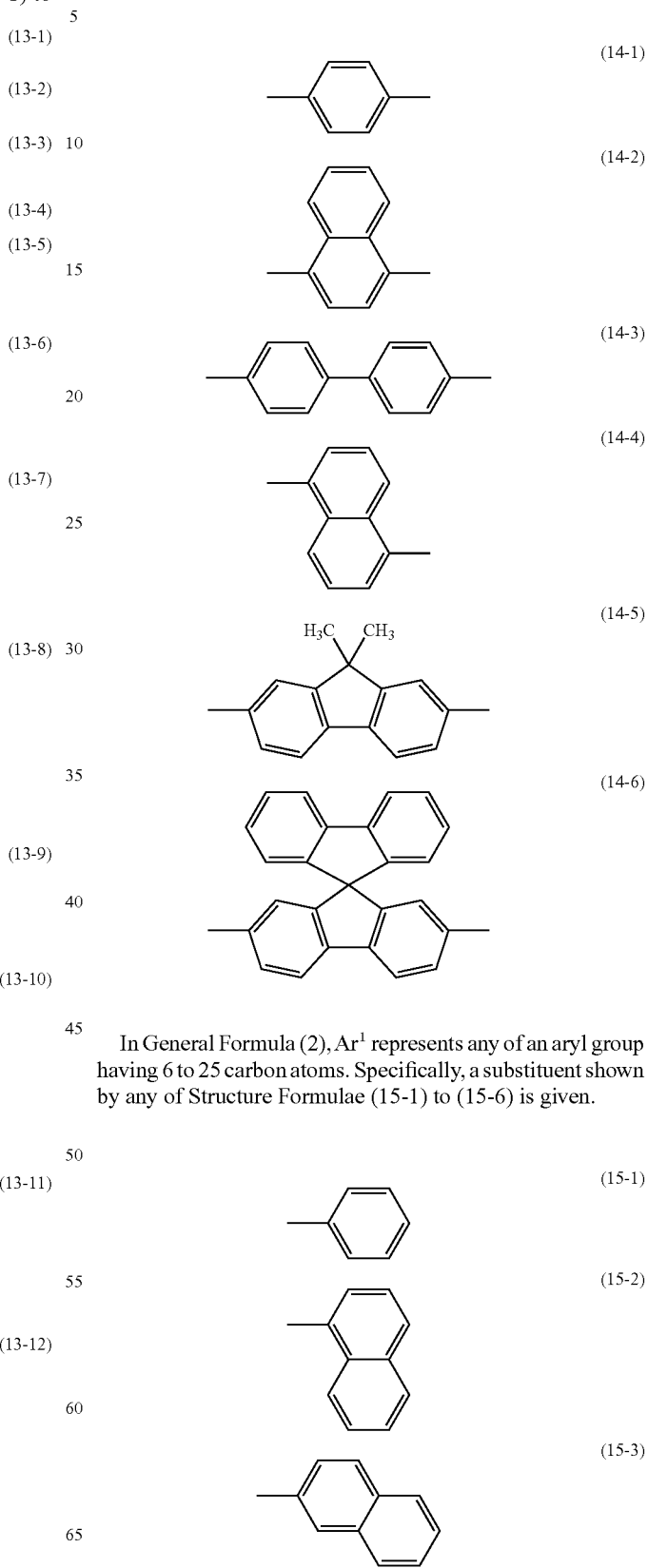

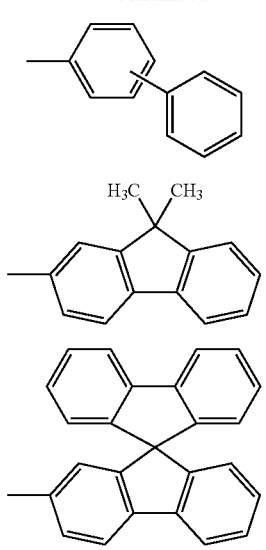

(15-4)

(15-5)

(15-6)

Among the aromatic amine compounds expressed by General Formula (2), an aromatic amine compound expressed by General Formula (4) is preferable.

(4)

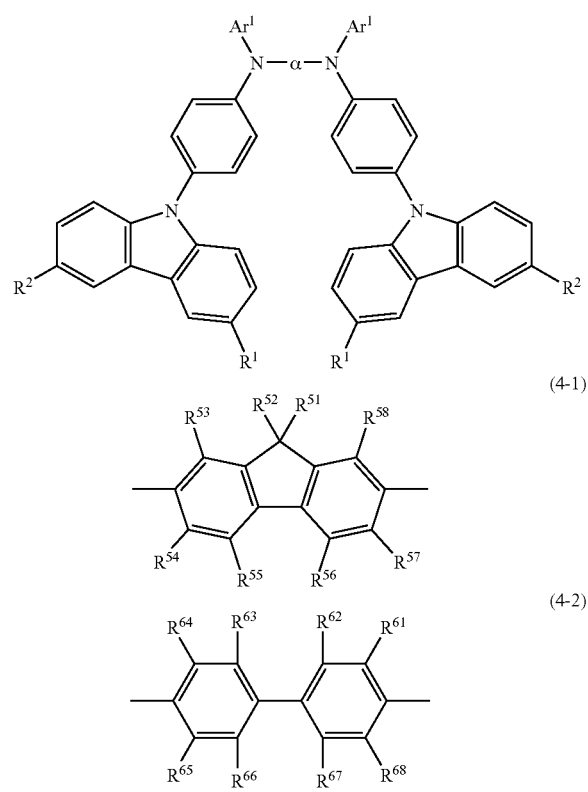

(4-1)

(4-2)

(In the formula, $R^1$ and $R^2$ each represent any of a hydrogen atom, an alkyl group having 1 to 4 carbon atoms, and an aryl group having 6 to 25 carbon atoms; and $Ar^1$ represents an aryl group having 6 to 25 carbon atoms. Moreover, α represents a substituent expressed by either of General Formulae (4-1) and (4-2). In General Formulae (4-1) and (4-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

An aromatic amine compound expressed by General Formula (6) is more preferable.

(6)

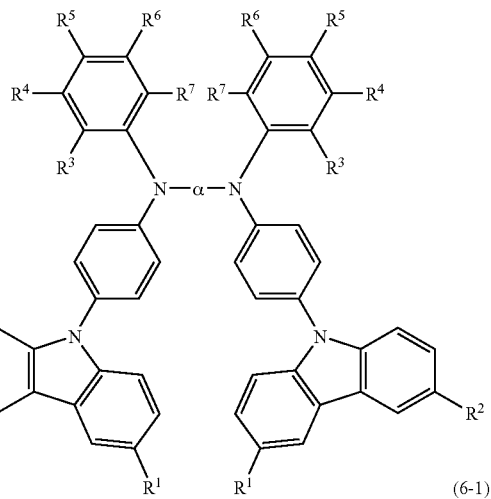

(6-1)

(6-2)

(In the formula, $R^1$ and $R^2$ each represent any of a hydrogen atom, an alkyl group having 1 to 4 carbon atoms, and an aryl group having 6 to 25 carbon atoms; and $R^3$ to $R^7$ each represent any of a hydrogen atom, an alkyl group having 1 to 4 carbon atoms, and a phenyl group. Moreover, α represents a substituent expressed by either of General Formulae (6-1) and (6-2). In General Formulae (6-1) and (6-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

An aromatic amine compound expressed by General Formula (8) is more preferable.

(8)

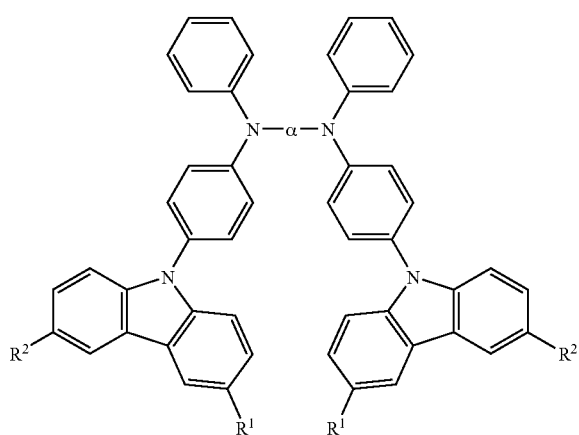

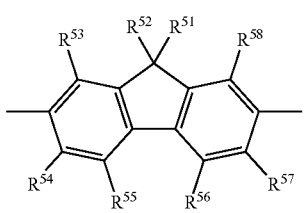
(8-1)

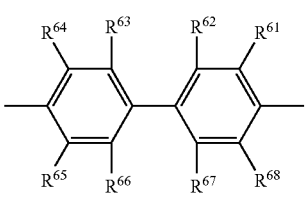
(8-2)

(In the formula, $R^1$ and $R^2$ each represent any of a hydrogen atom, an alkyl group having 1 to 4 carbon atoms, and an aryl group having 6 to 25 carbon atoms. Moreover, α represents a substituent expressed by either of General Formulae (8-1) and (8-2). In General Formulae (8-1) and (8-2), $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.)

An aromatic amine compound expressed by General Formula (11) or (12) is preferable.

(In the formula, $R^1$ and $R^2$ each represent any of a hydrogen atom, an alkyl group having 1 to 4 carbon atoms, and an aryl group having 6 to 25 carbon atoms. Moreover, $R^{51}$ and $R^{52}$ each represent any of a hydrogen atom, an alkyl group having 1 to 4 carbon atoms, and an aryl group having 6 to 12 carbon atoms.)

(12)

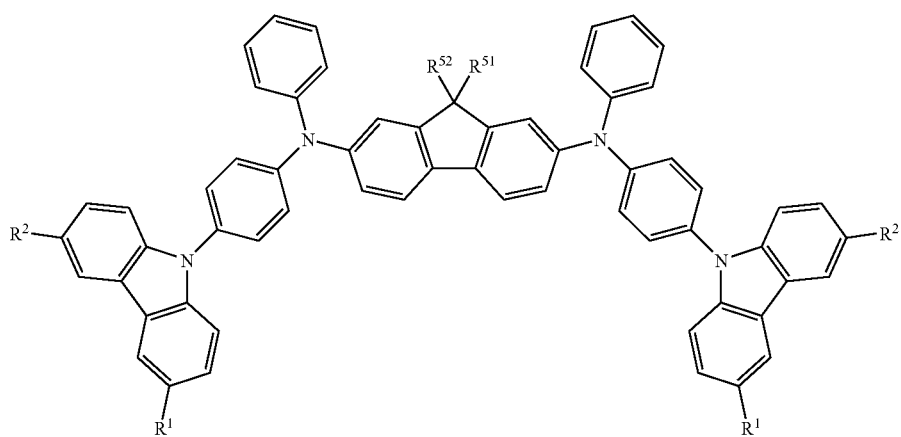

(In the formula, $R^1$ and $R^2$ each represent any of a hydrogen atom, an alkyl group having 1 to 4 carbon atoms, and an aryl group having 6 to 25 carbon atoms.)

As a specific example of the aromatic amine compound of the present invention, an aromatic amine compound expressed by any of Structure Formulae (21) to (119) is given. However, the present invention is not limited to these.

(11)

(21)
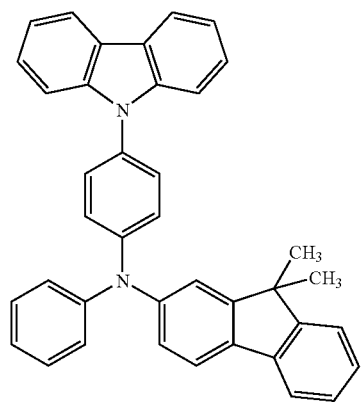
(22)
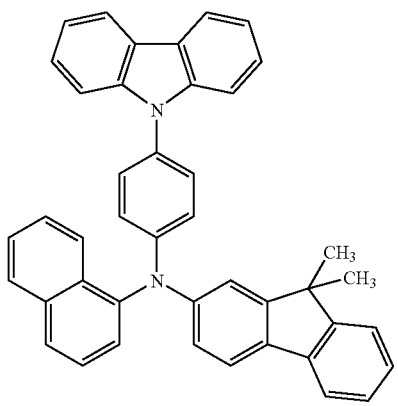
(23)
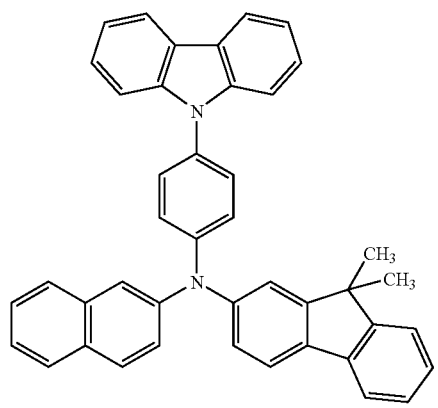
(24)
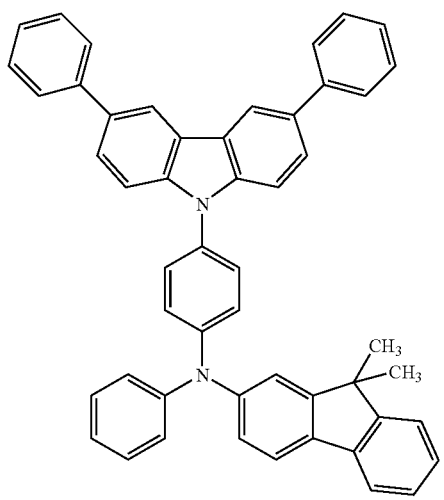
(25)
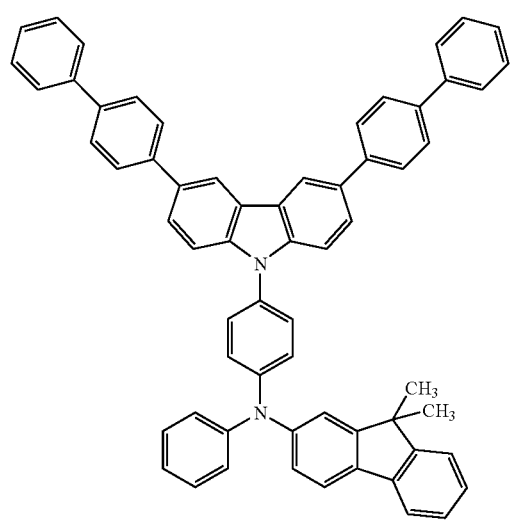
(26)
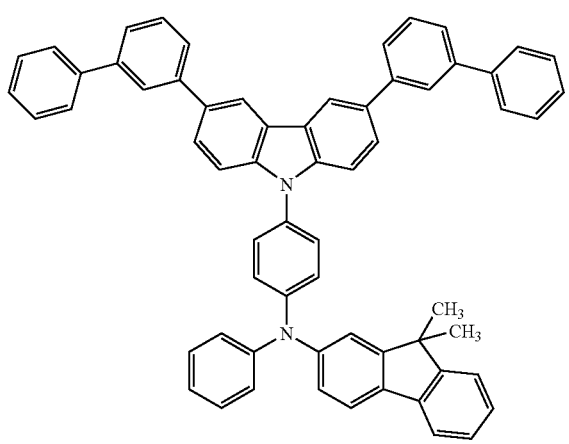

-continued
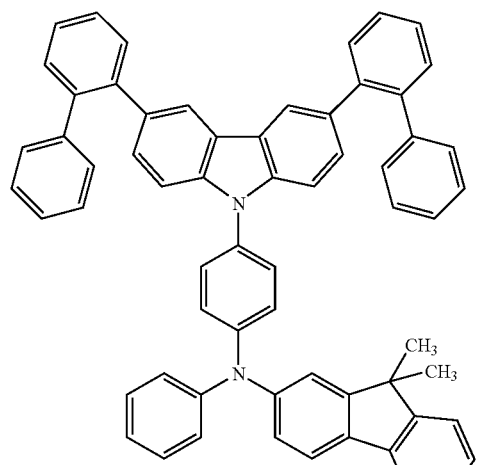
(27)
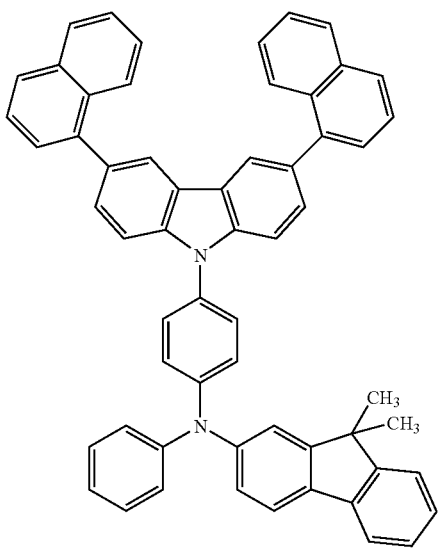
(28)
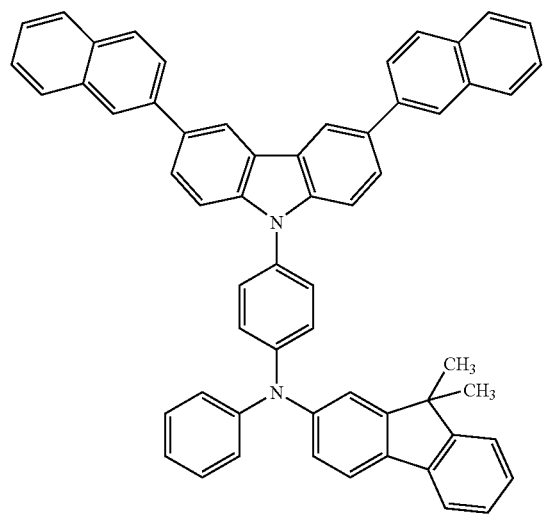
(29)
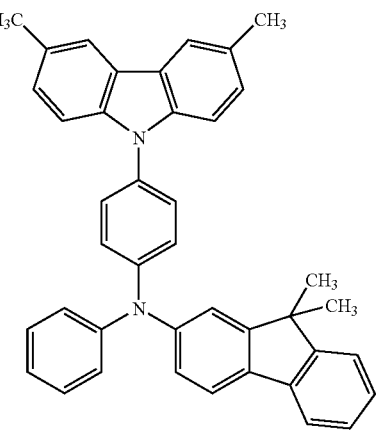
(30)
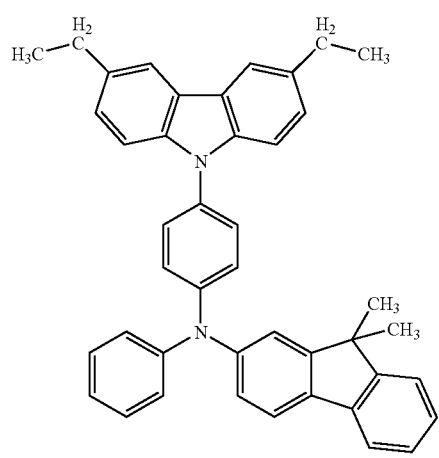
(31)
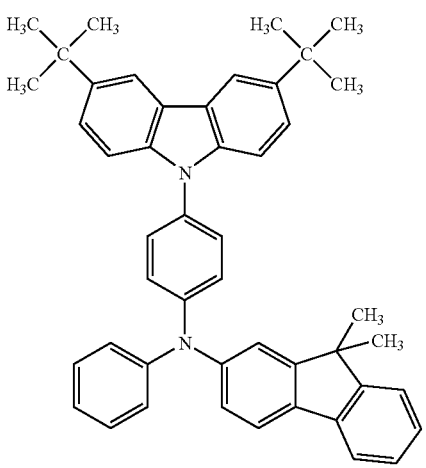
(32)

(33)
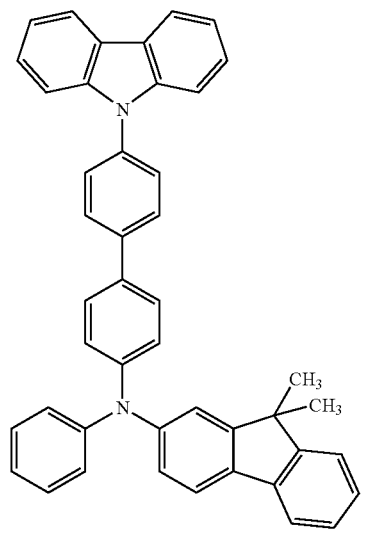
(34)
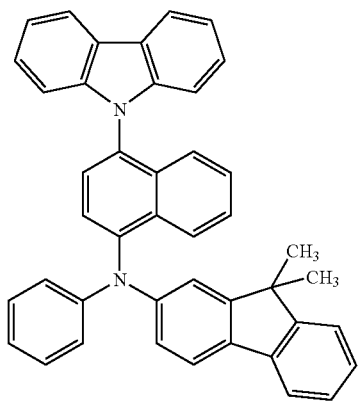
(35)
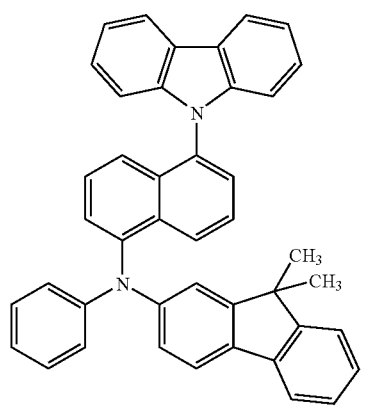
(36)
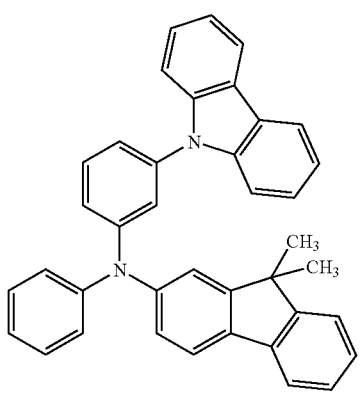
(37)
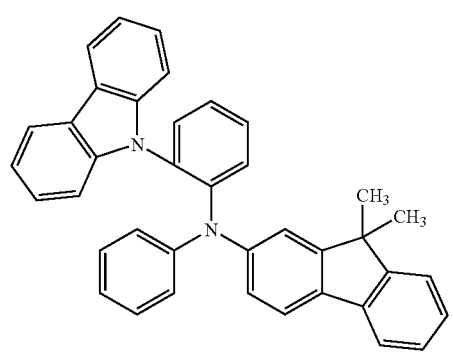
(38)
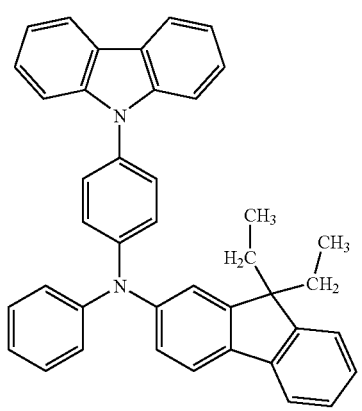

-continued
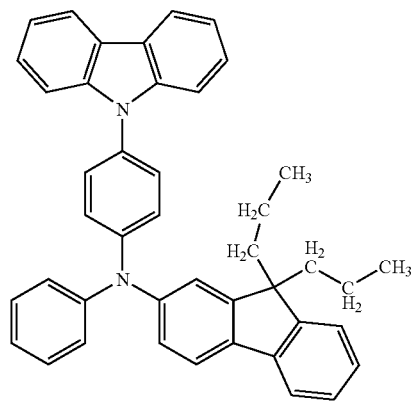
(39)
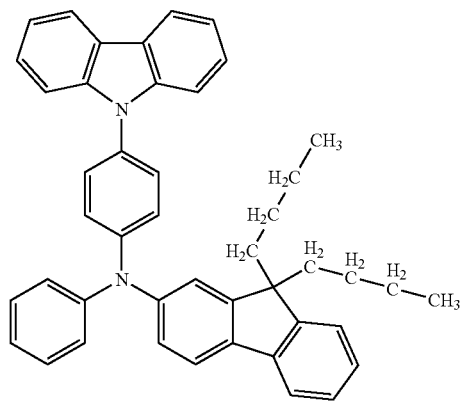
(40)
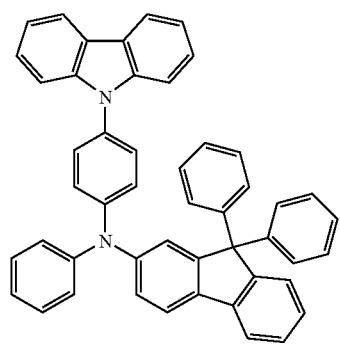
(41)
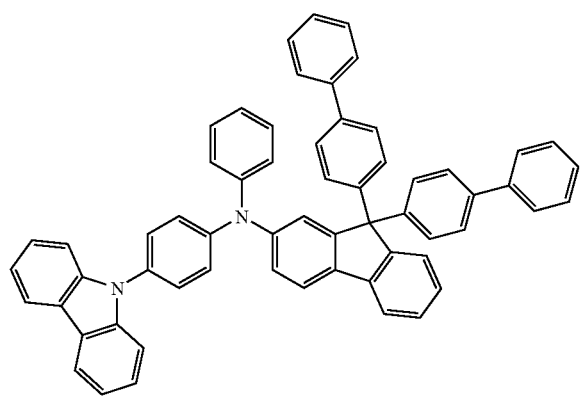
(42)
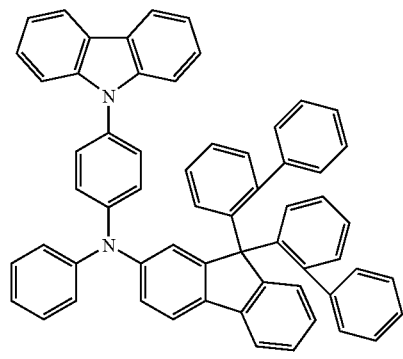
(43)
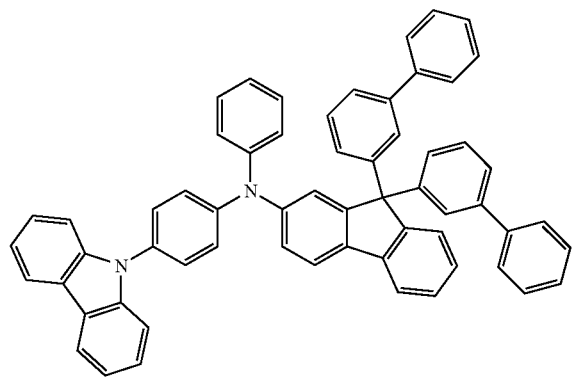
(44)

-continued
(45)
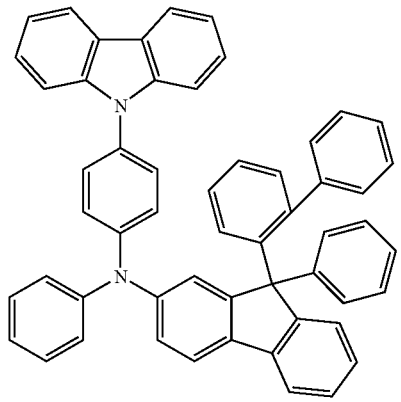
(46)
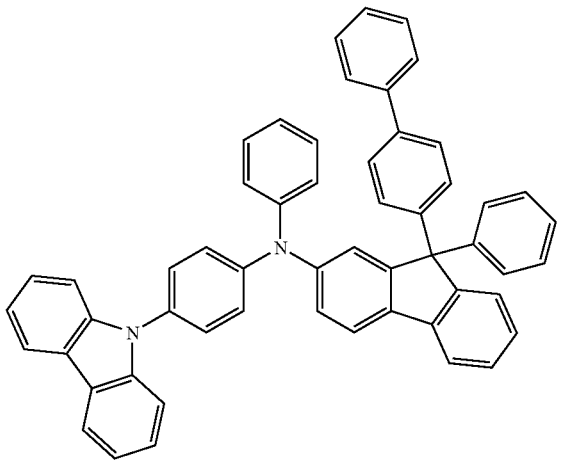
(47)
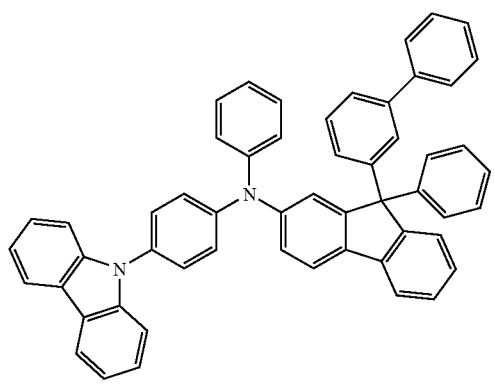
(48)
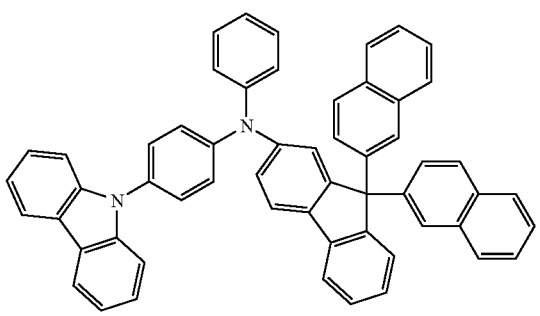
(49)
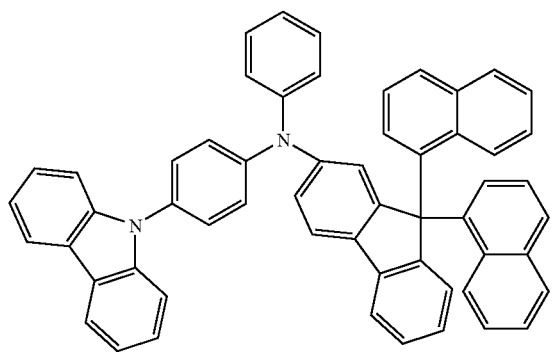
(50)
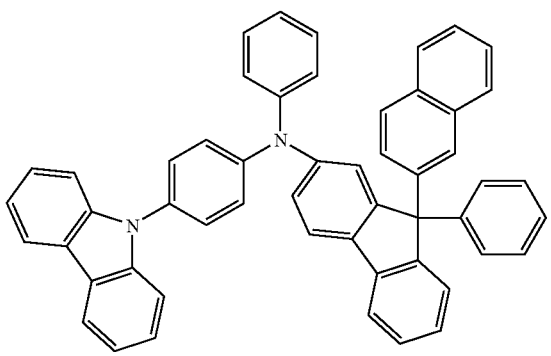

-continued
(51)
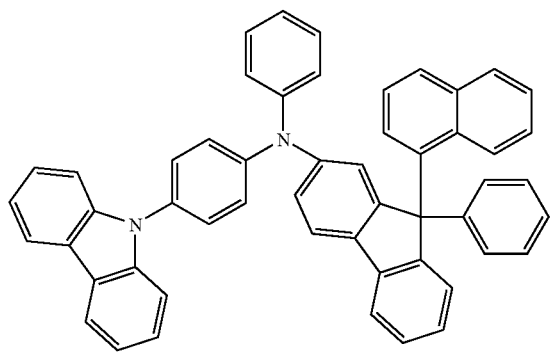
(52)
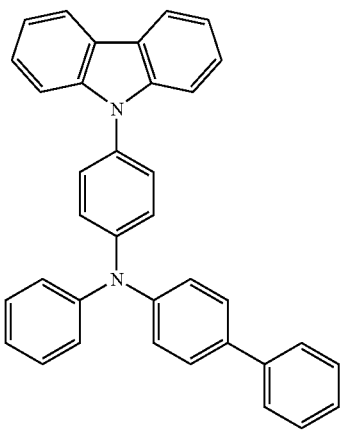
(53)
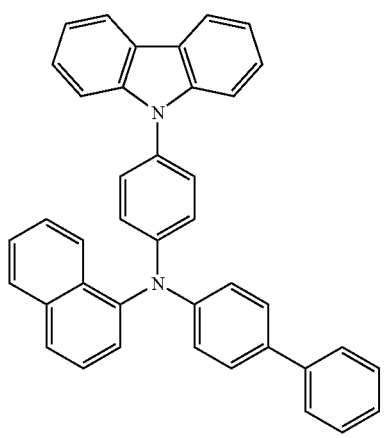
(54)
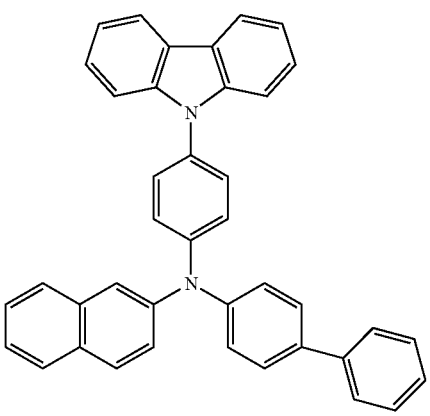
(55)
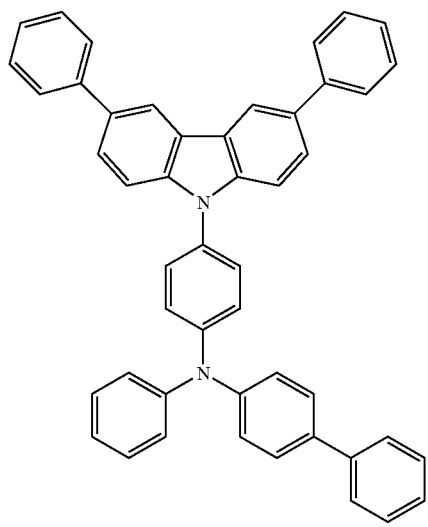

-continued
(56)
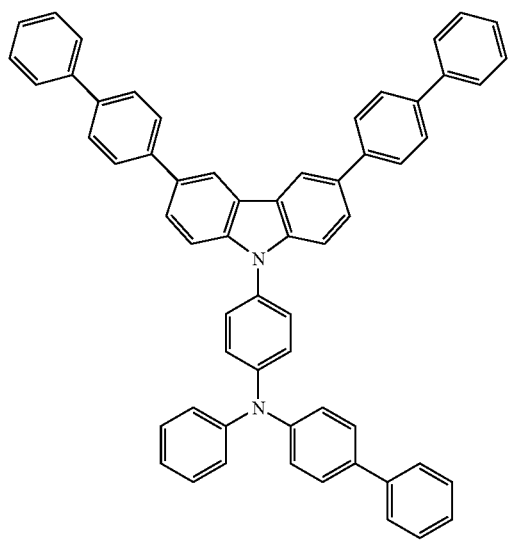
(57)
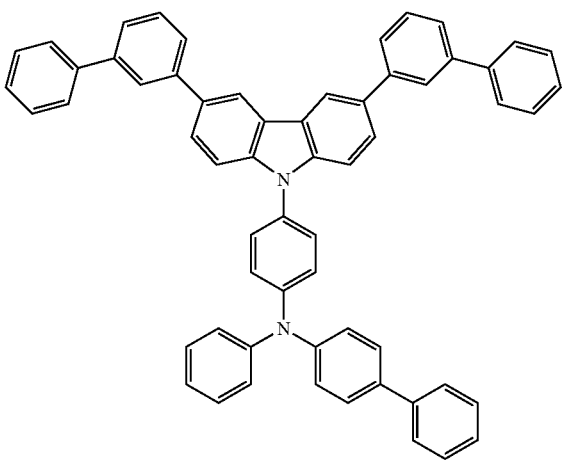
(58)
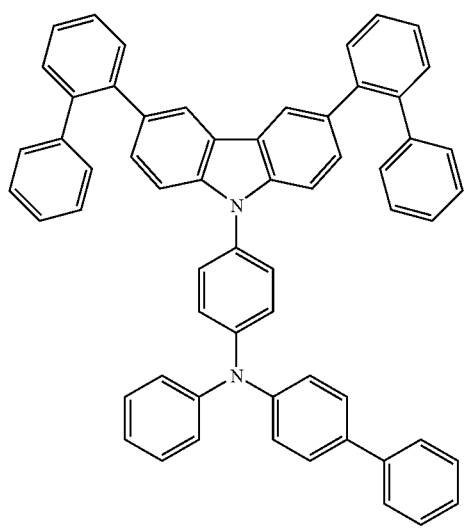
(59)
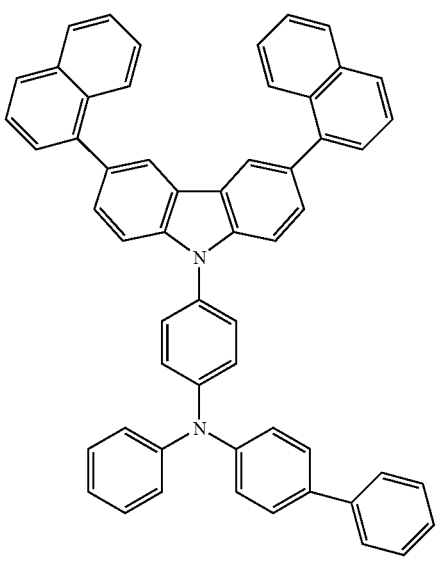
(60)
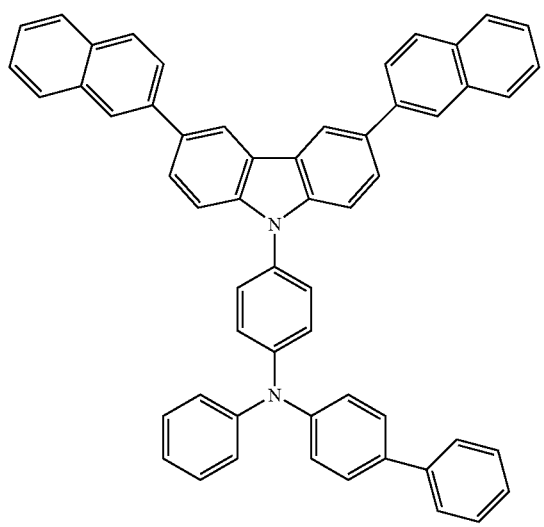
(61)
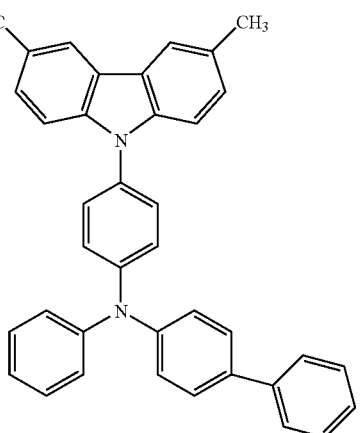

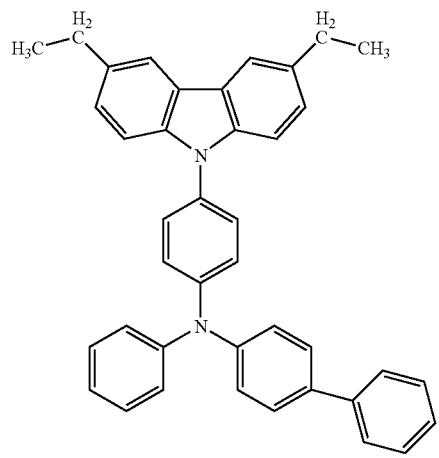
(62)
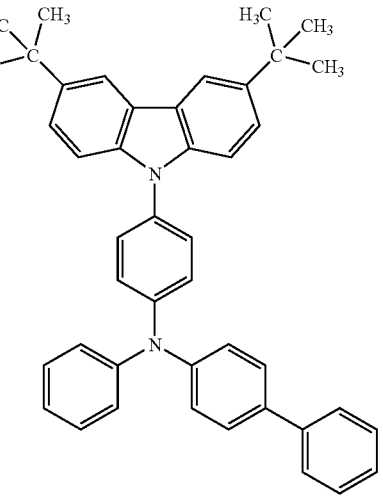
(63)
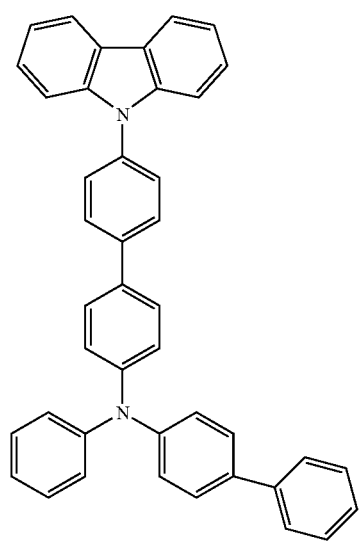
(64)
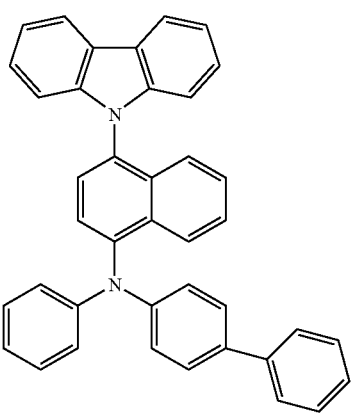
(65)
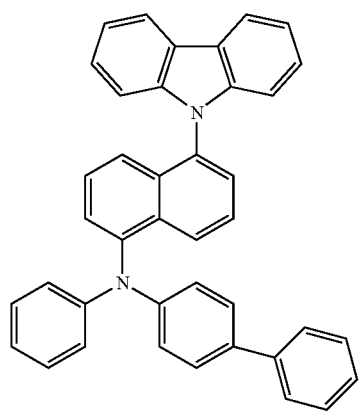
(66)
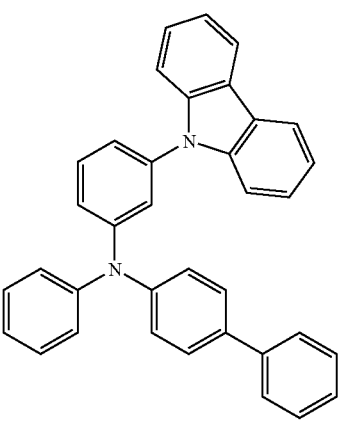
(67)

-continued
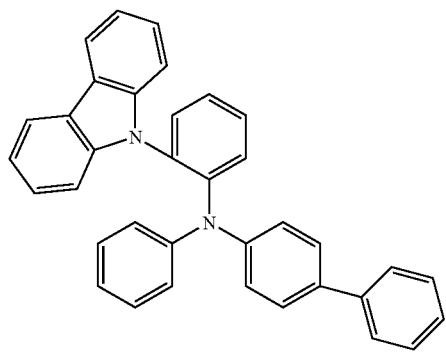
(68)
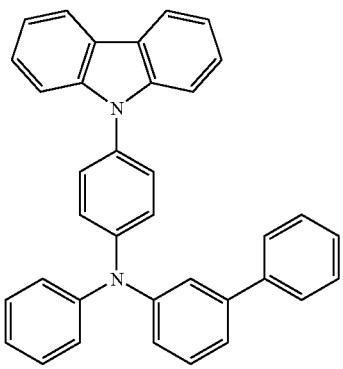
(69)
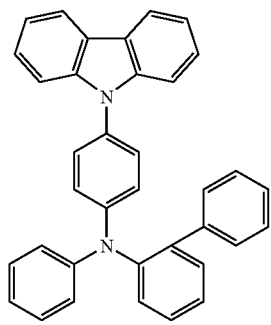
(70)
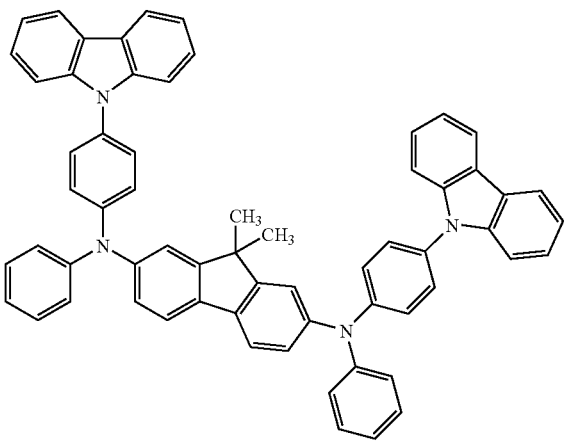
(71)
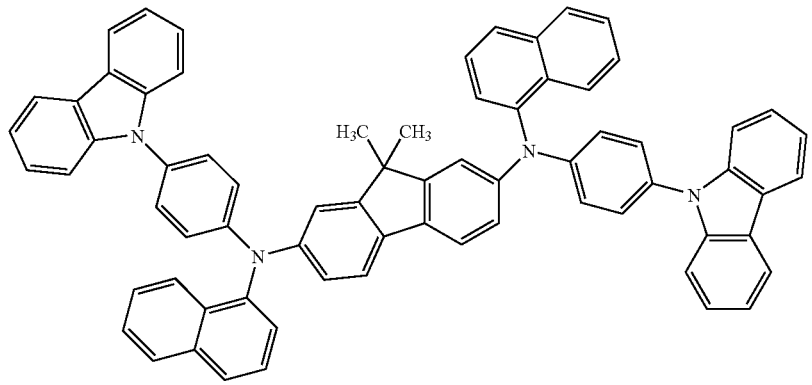
(72)
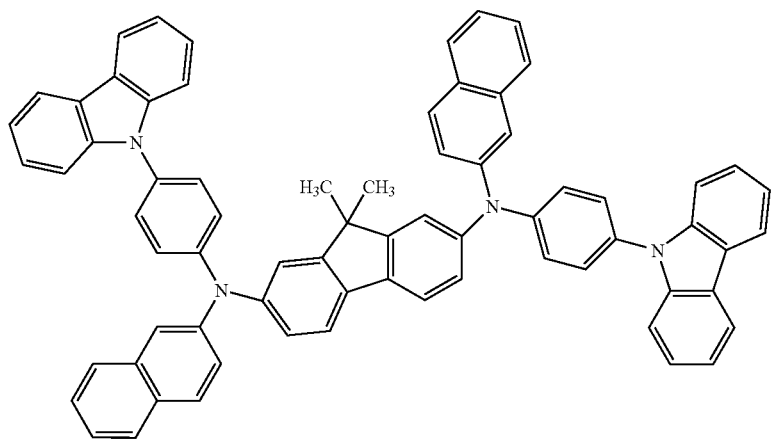
(73)

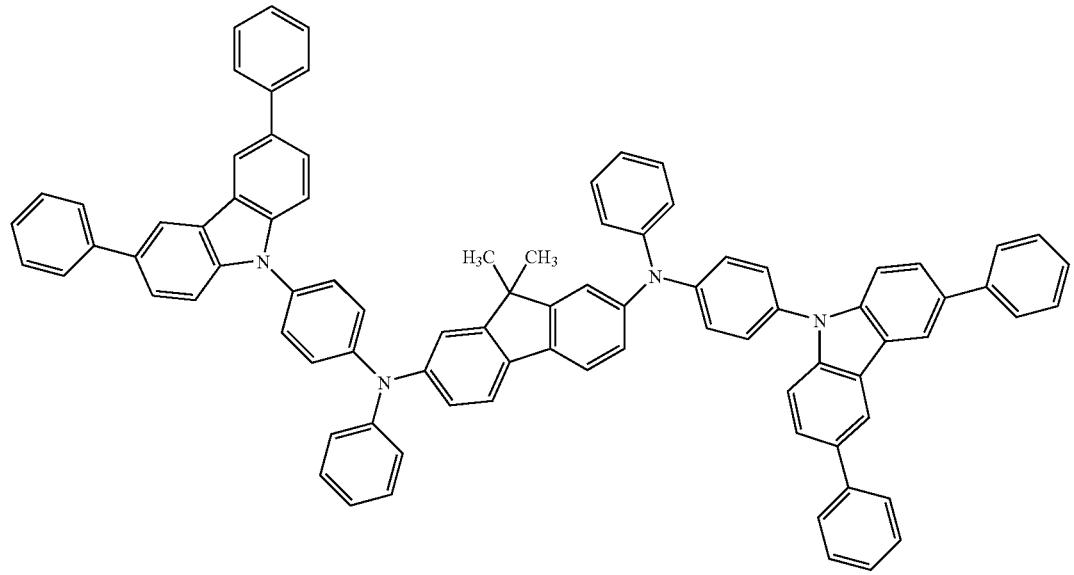
(74)
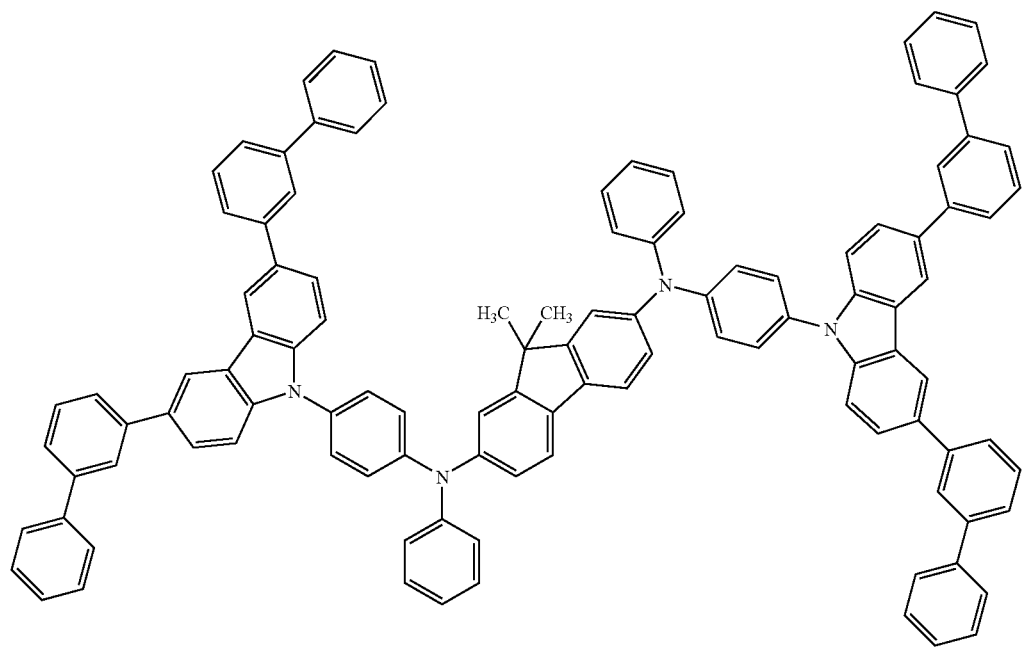
(75)

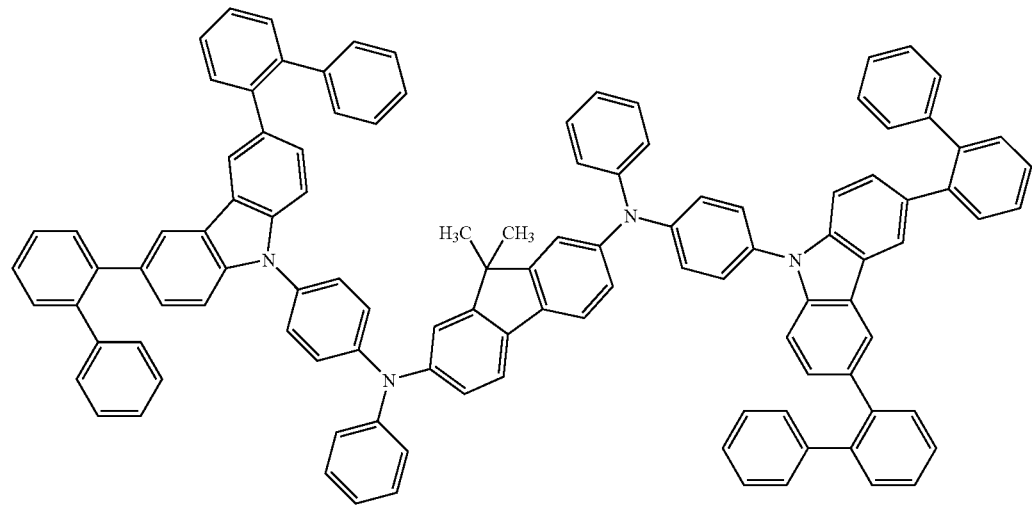
(76)
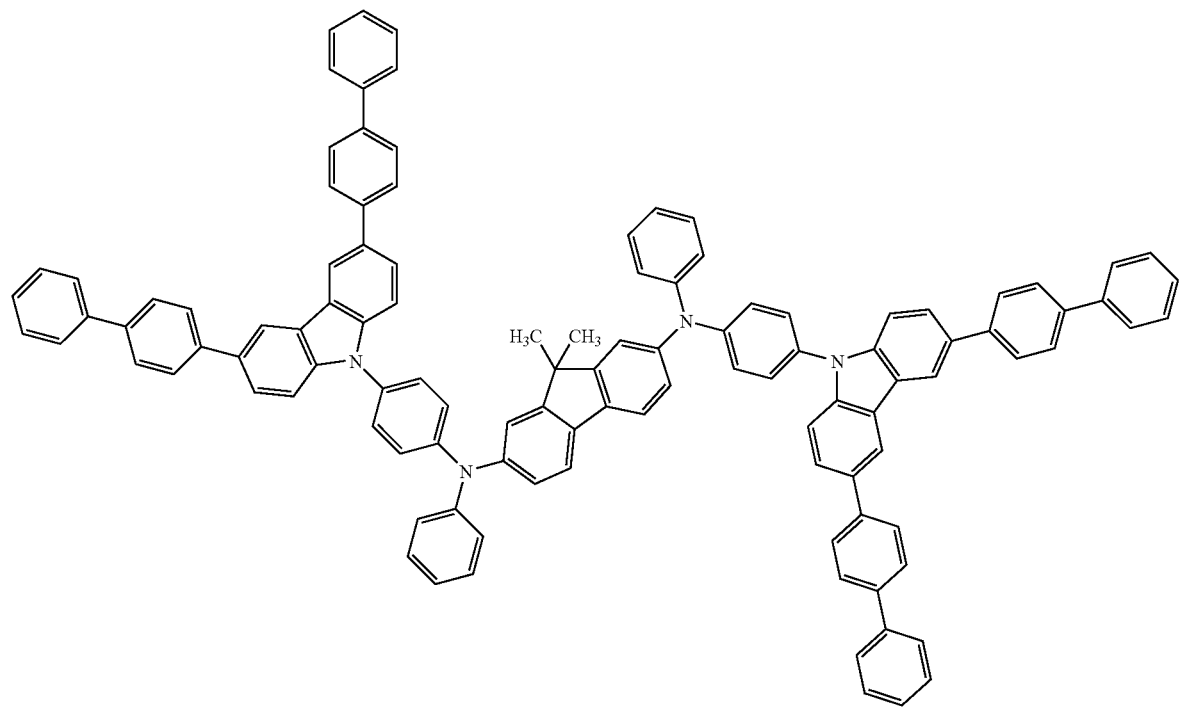
(77)

(78)
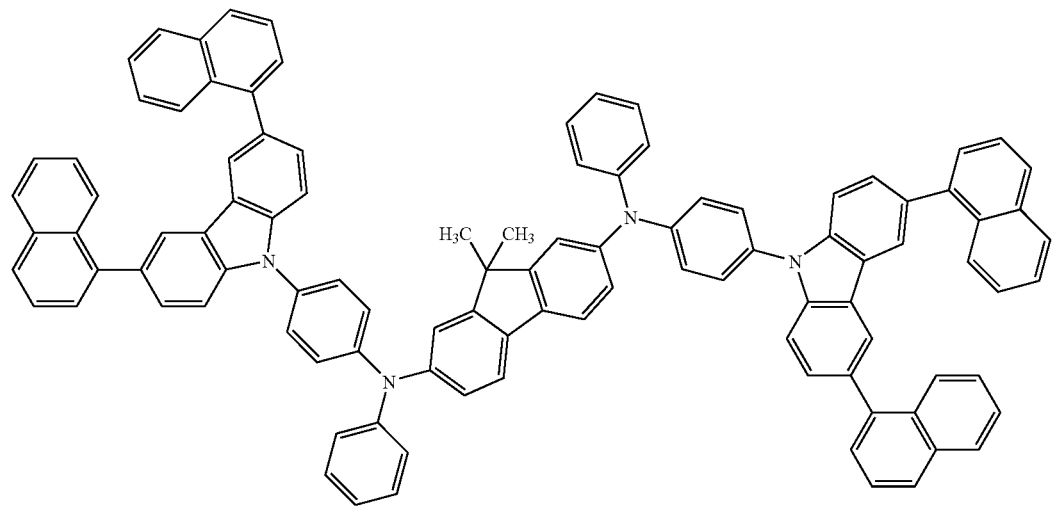
(79)
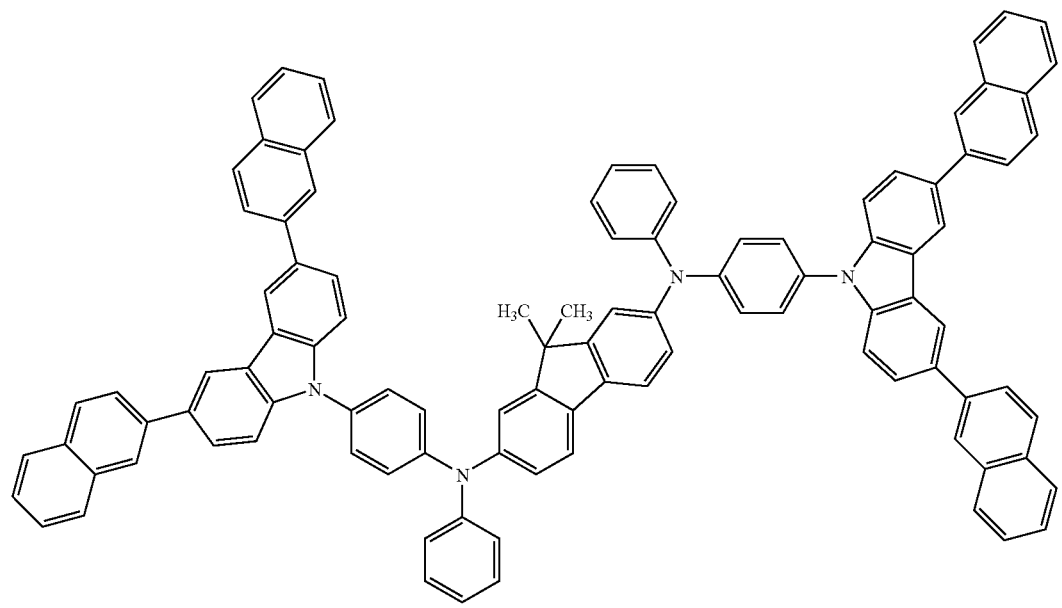
(80)
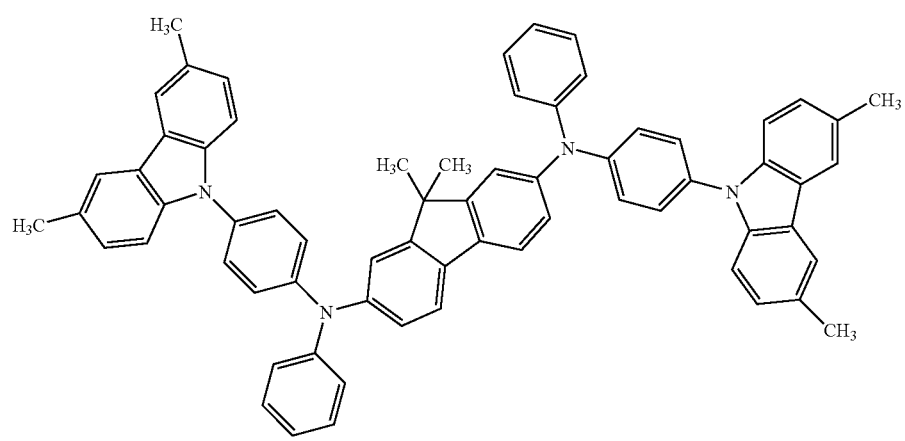

(81)
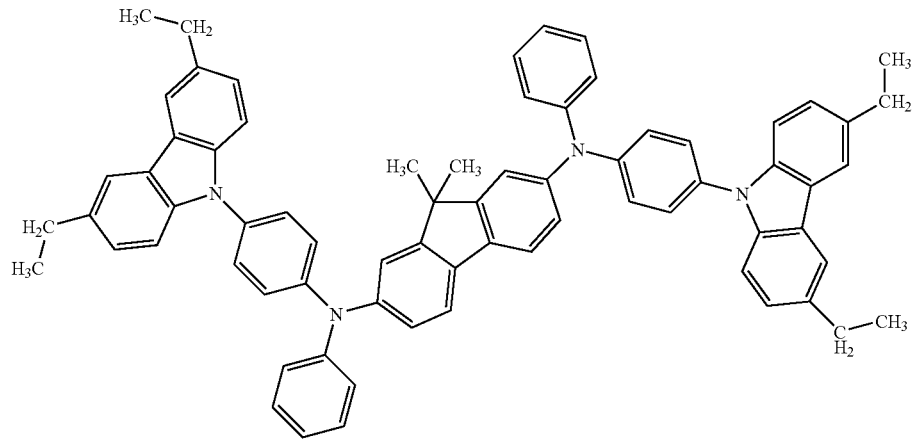
(82)
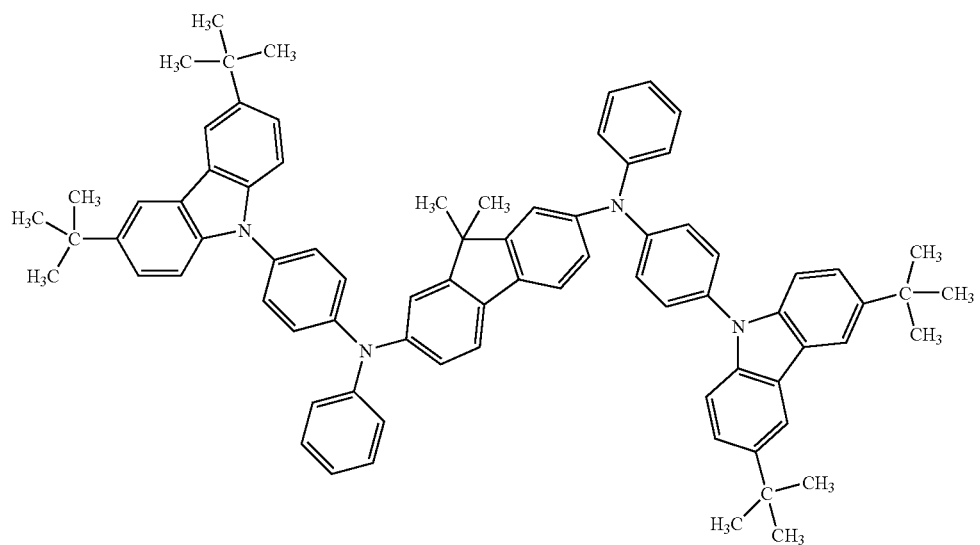
(83)
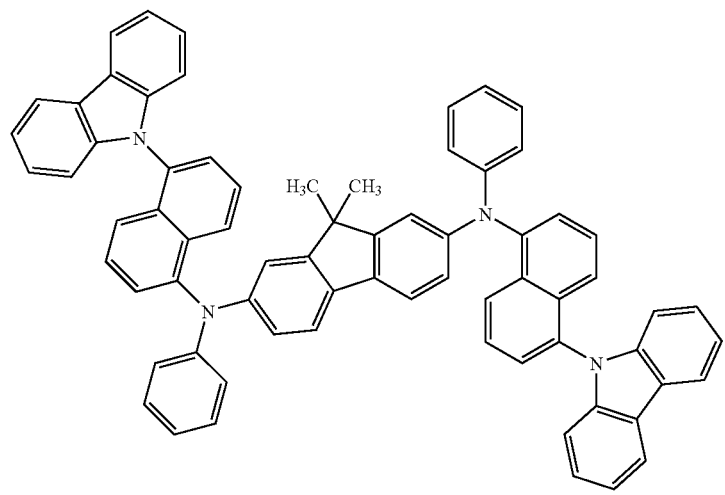

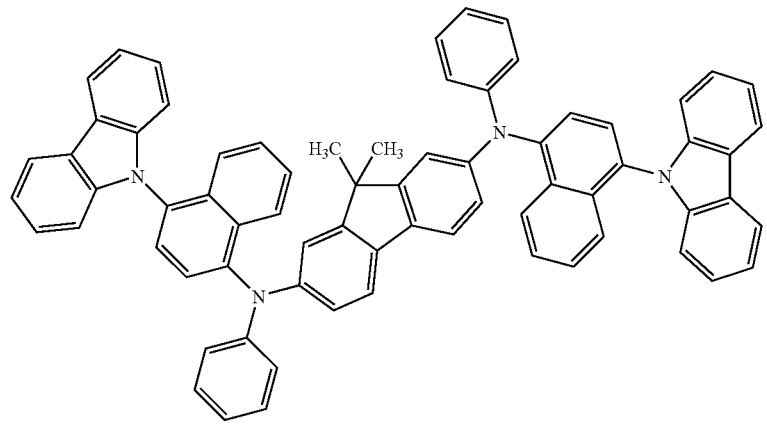
(84)
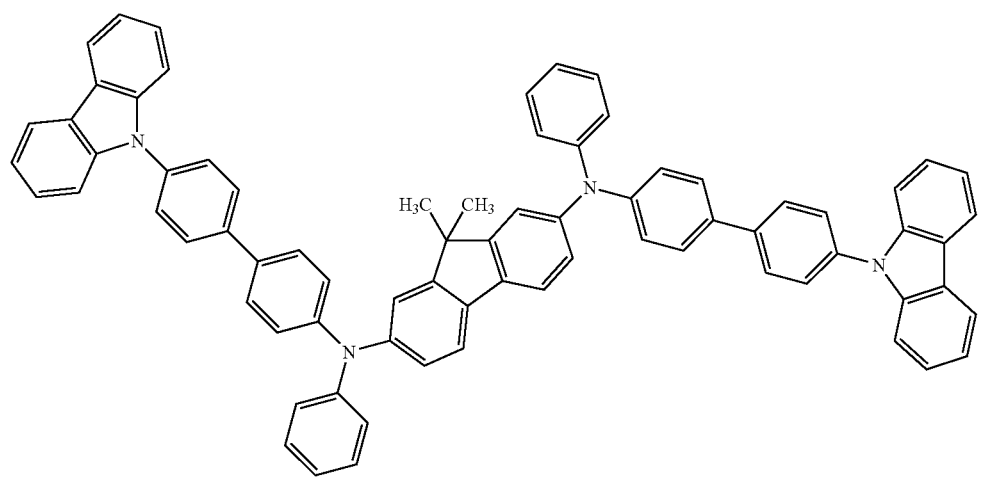
(85)
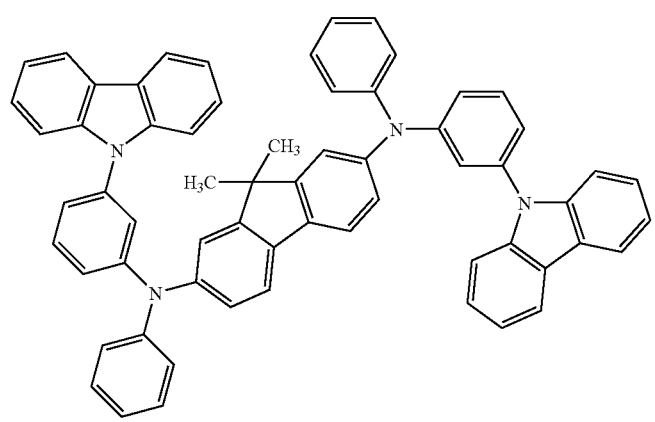
(86)

-continued
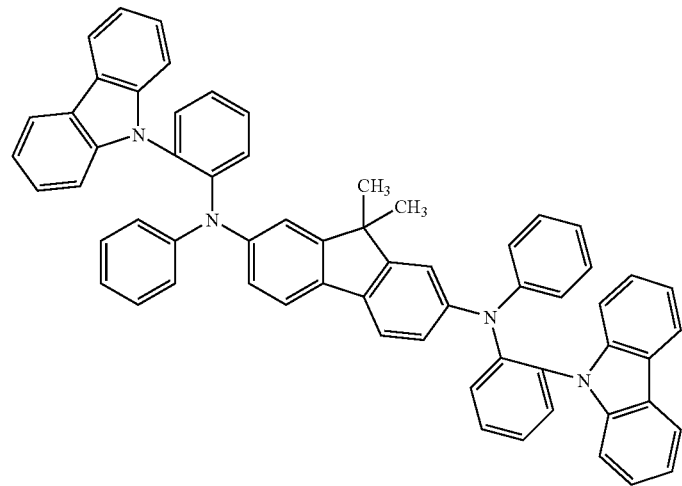
(87)
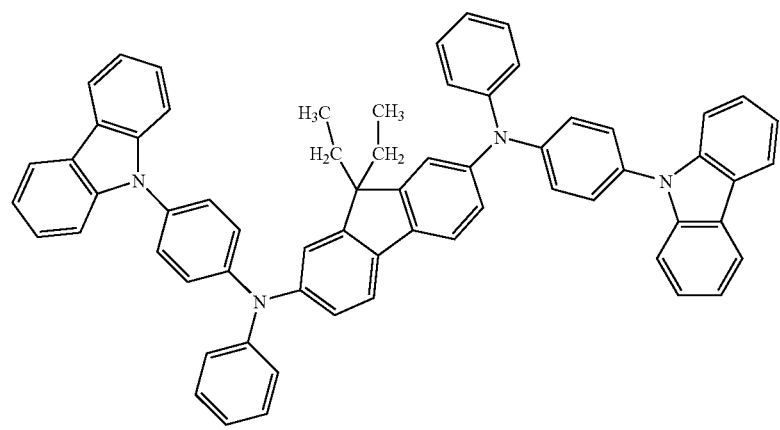
(88)
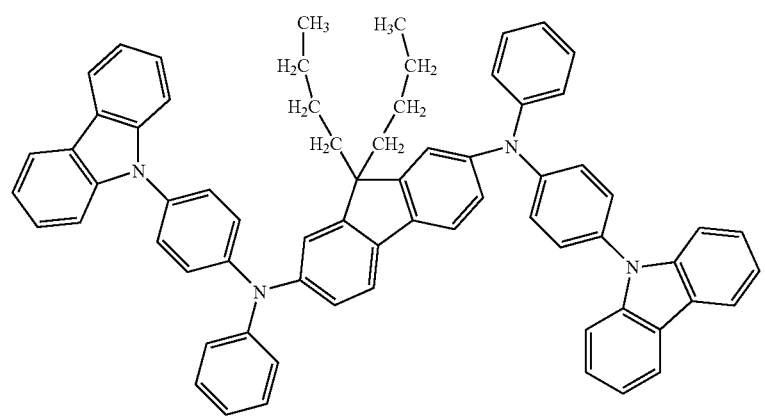
(89)

-continued
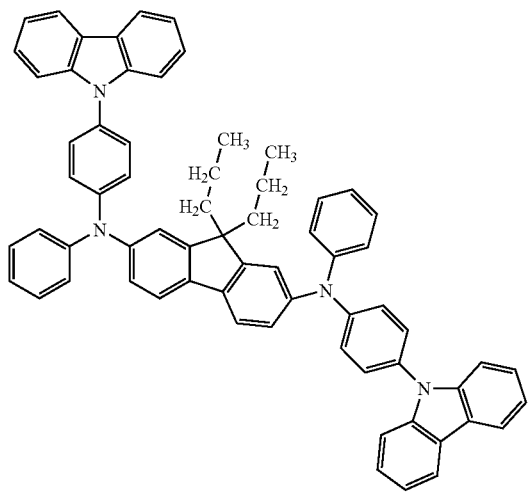
(90)
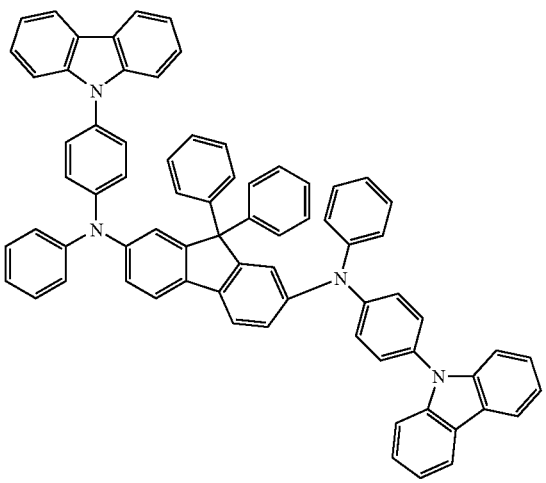
(91)
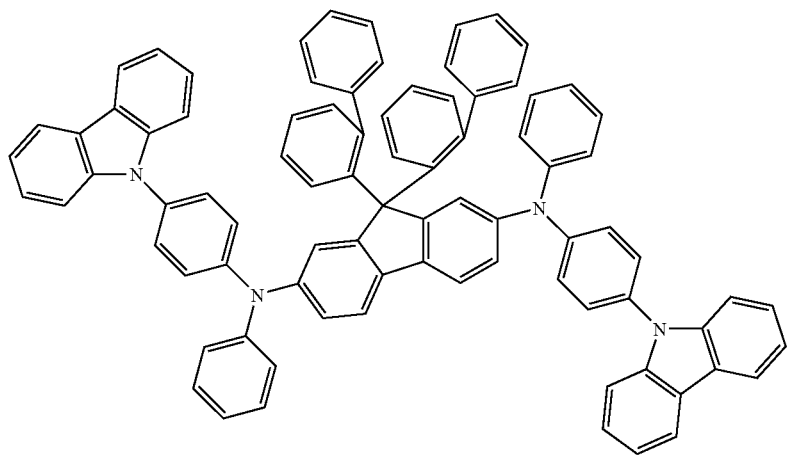
(92)
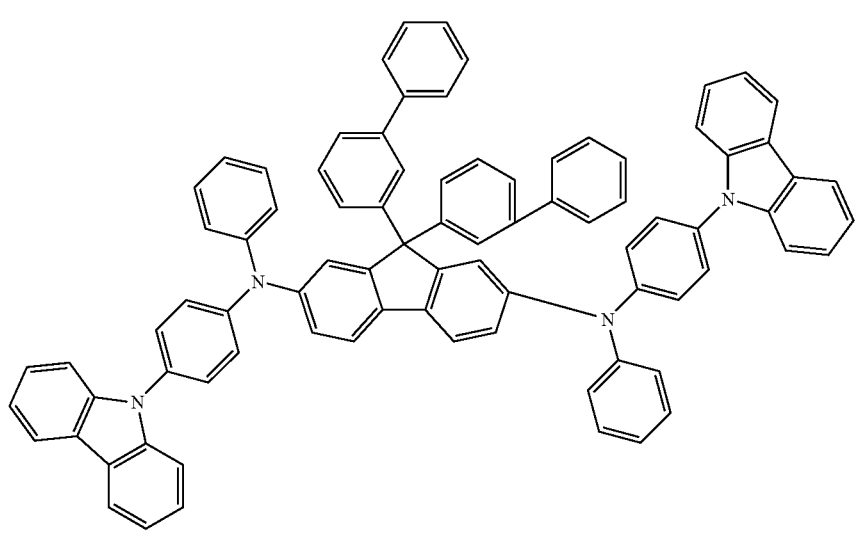
(93)

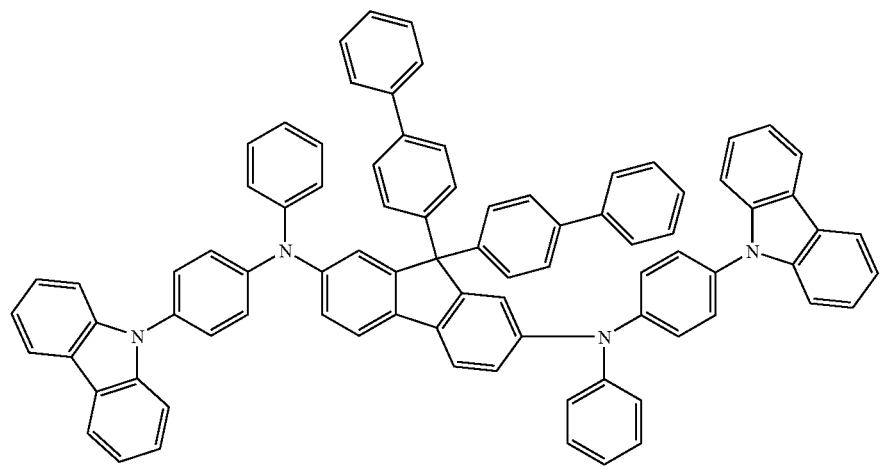
(94)
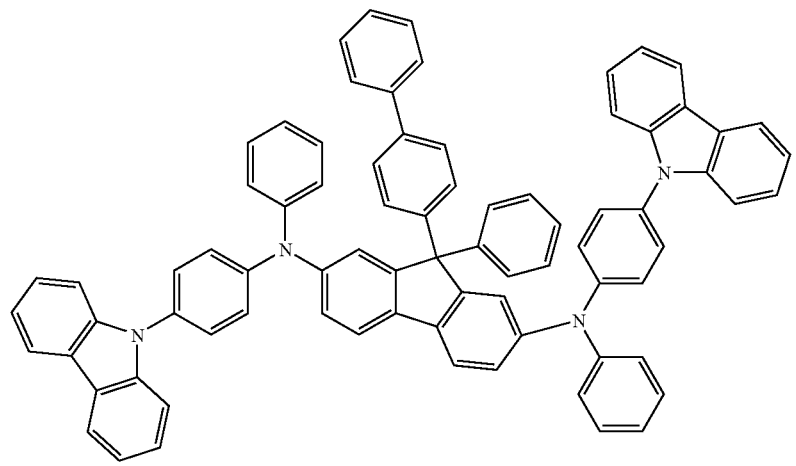
(95)
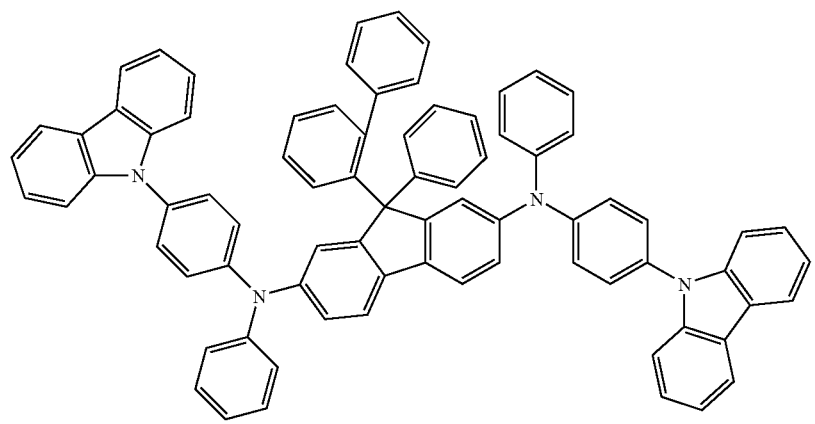
(96)

(97)
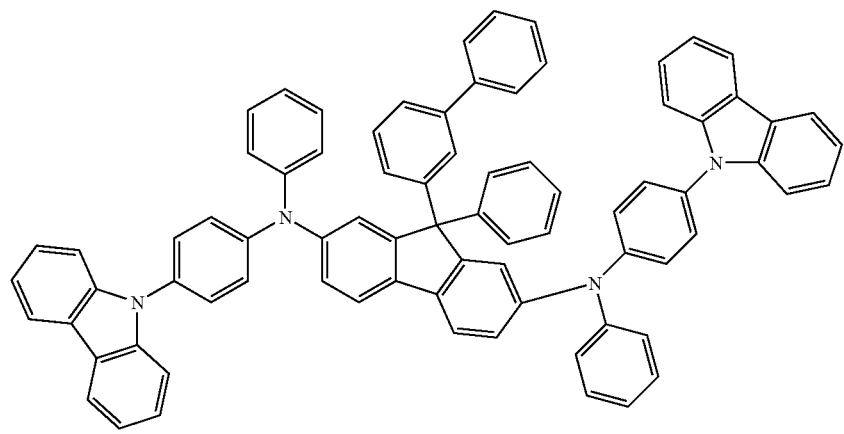
(98)
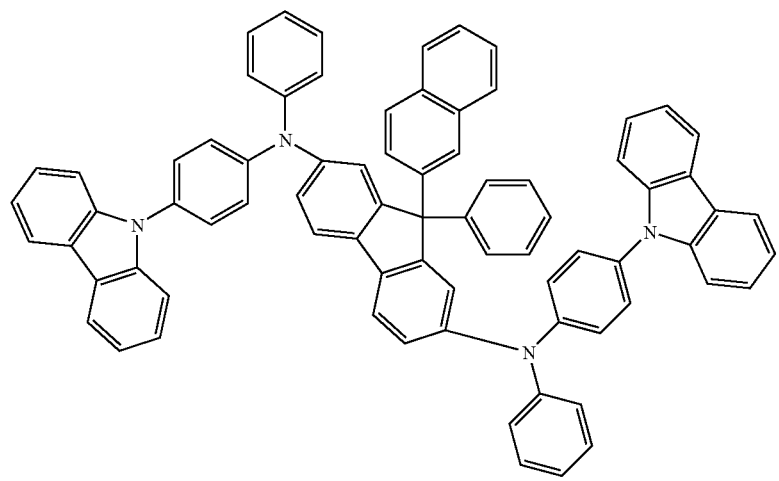
(99)
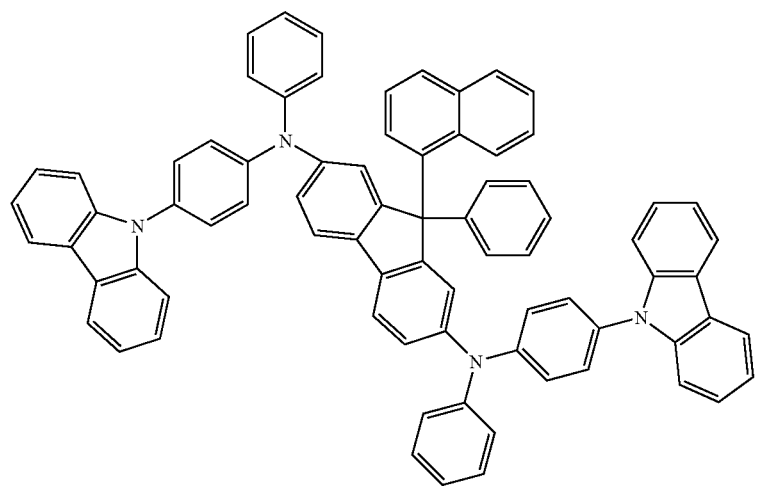

(100)
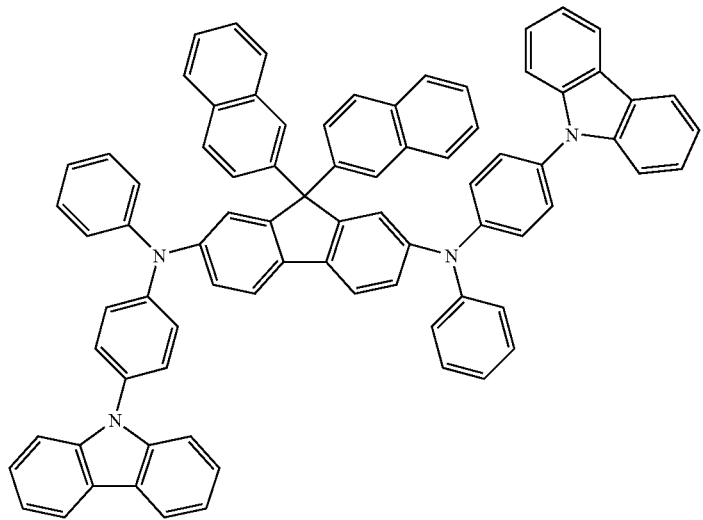
(101)
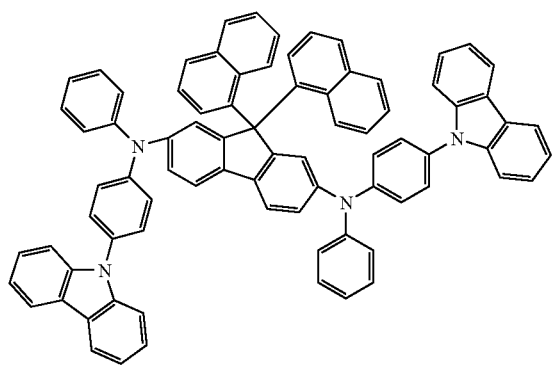
(102)
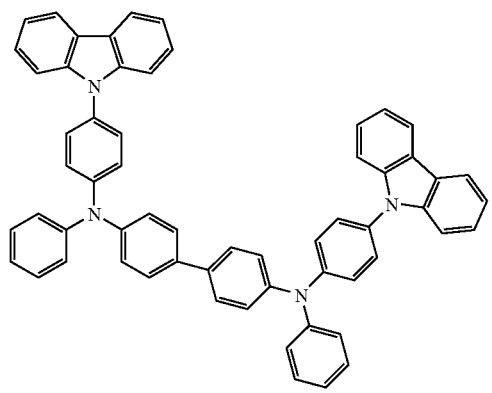
(103)
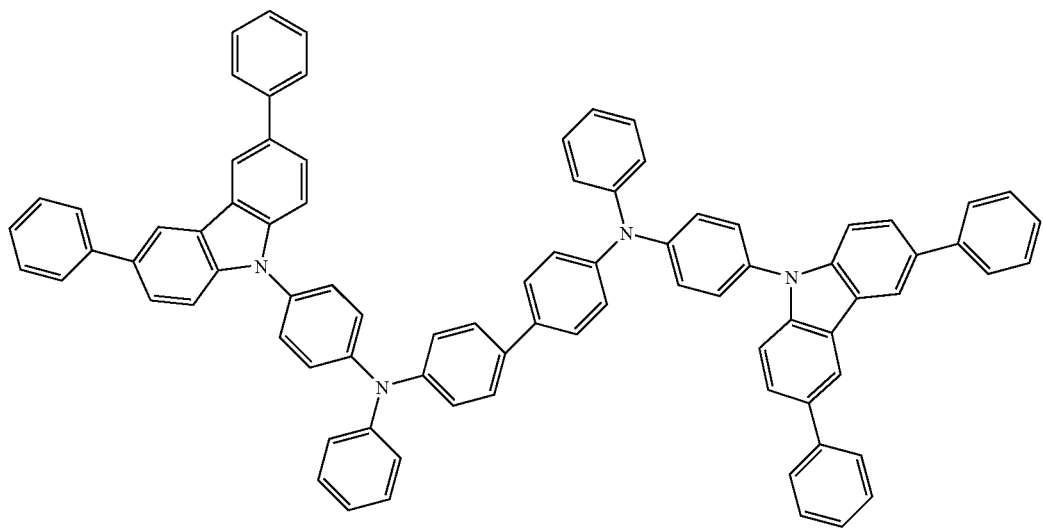

(104)
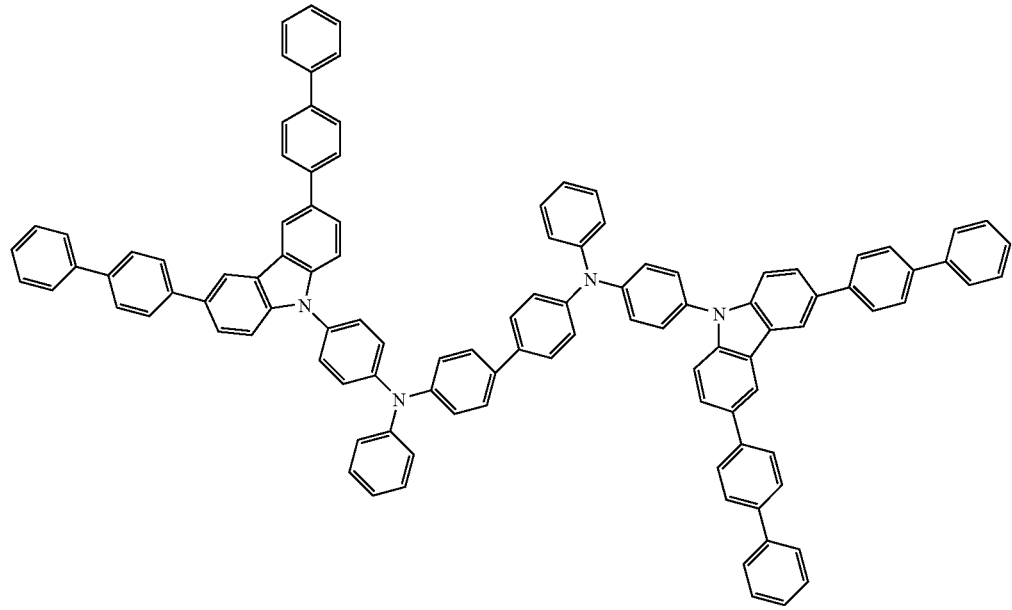
(105)
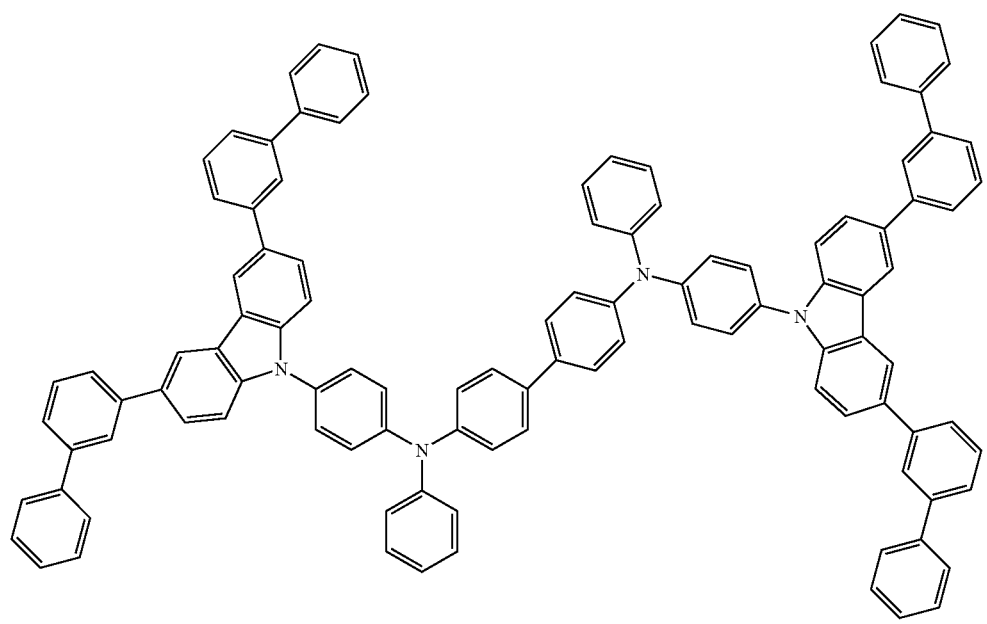

(106)
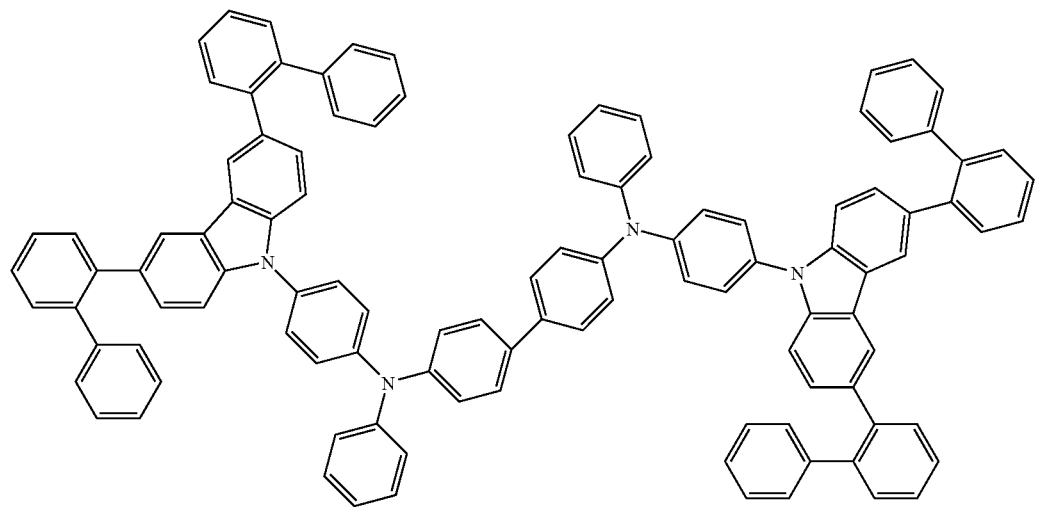
(107)
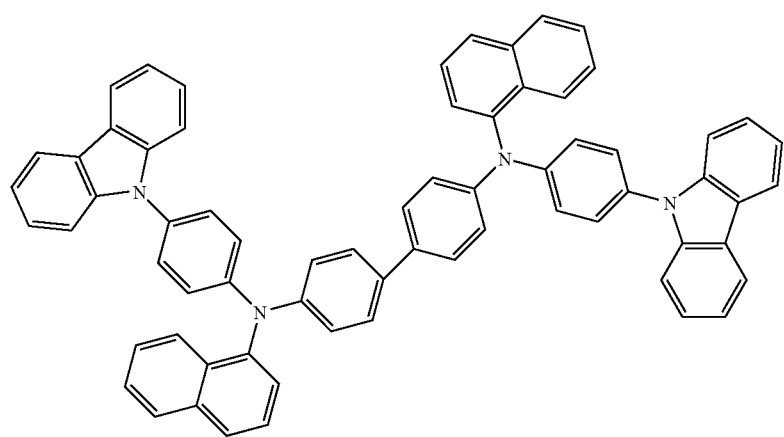
(108)
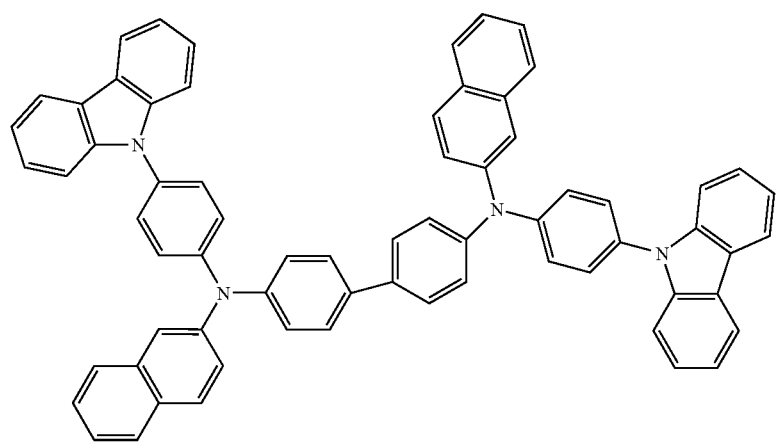

(109)
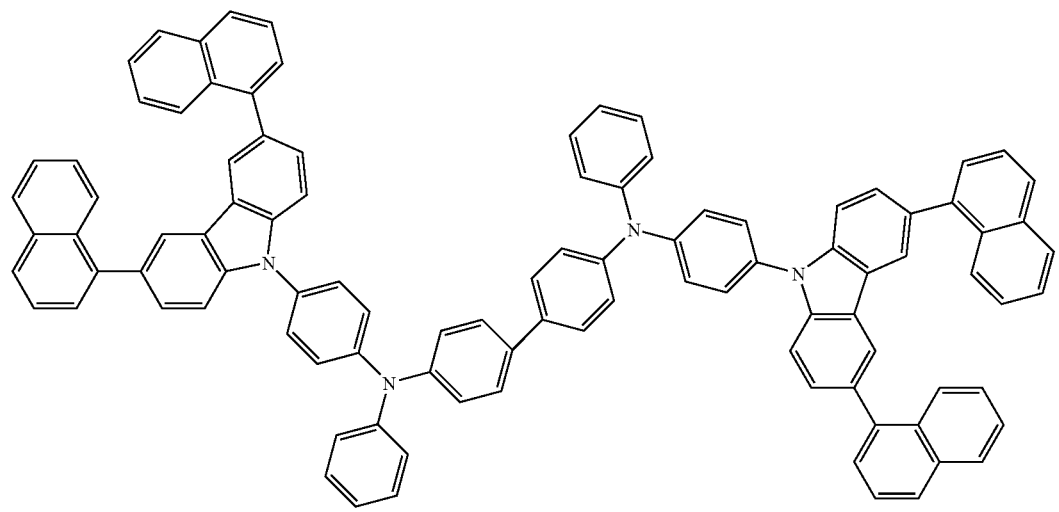
(110)
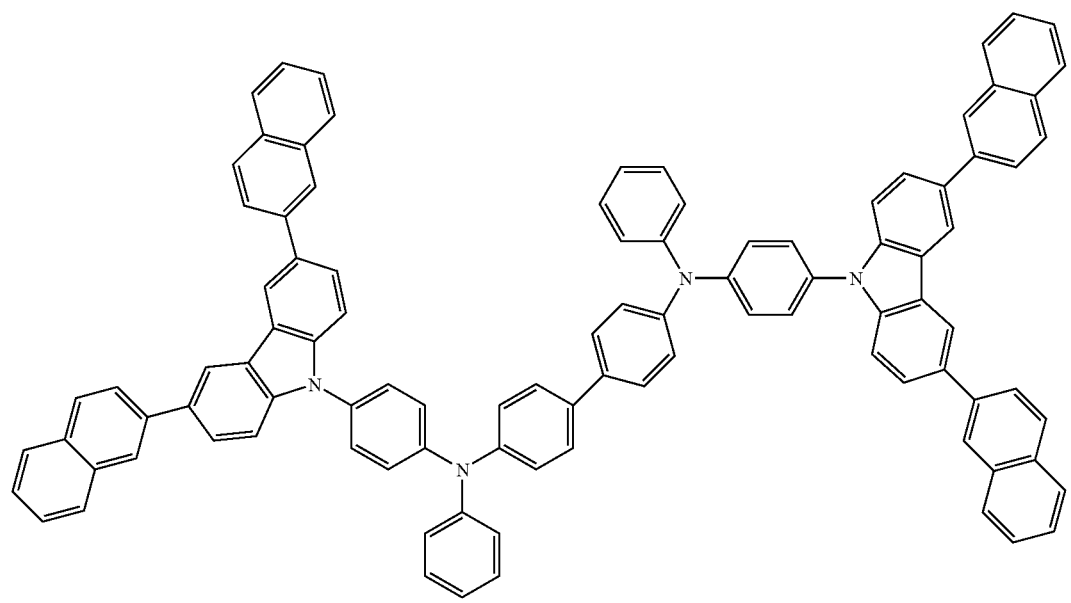
(111)
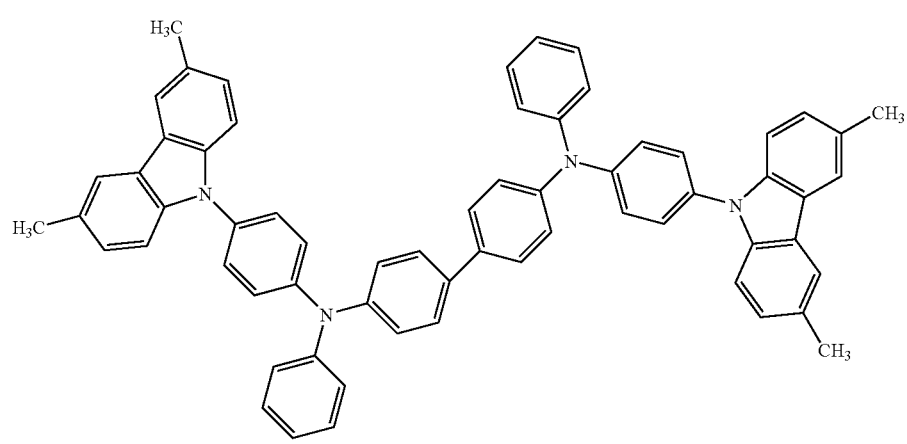

(112)
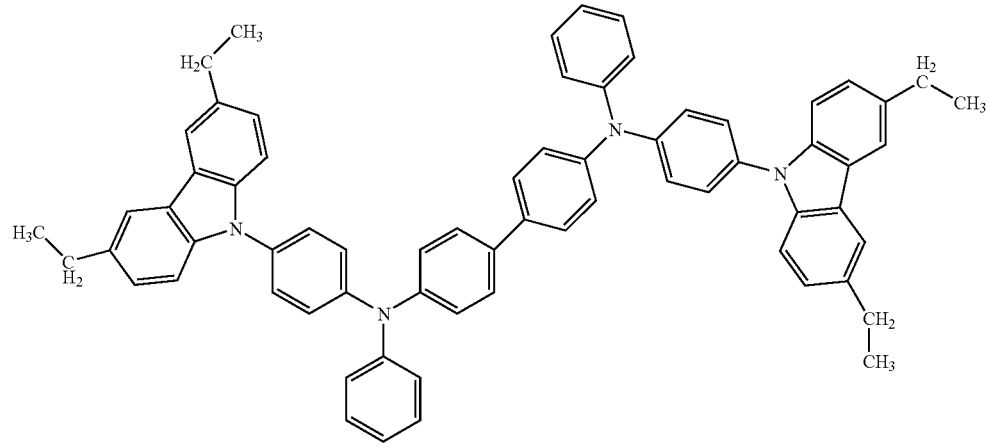
(113)
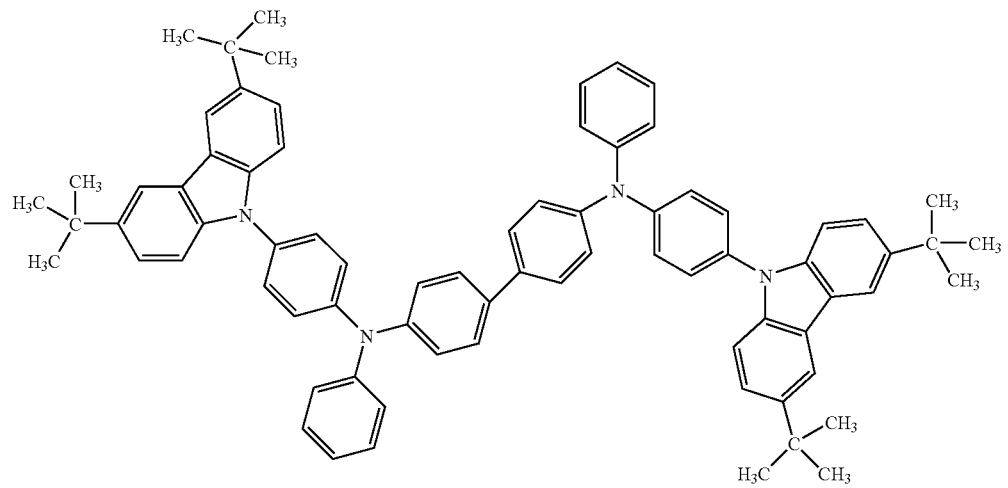
(114)
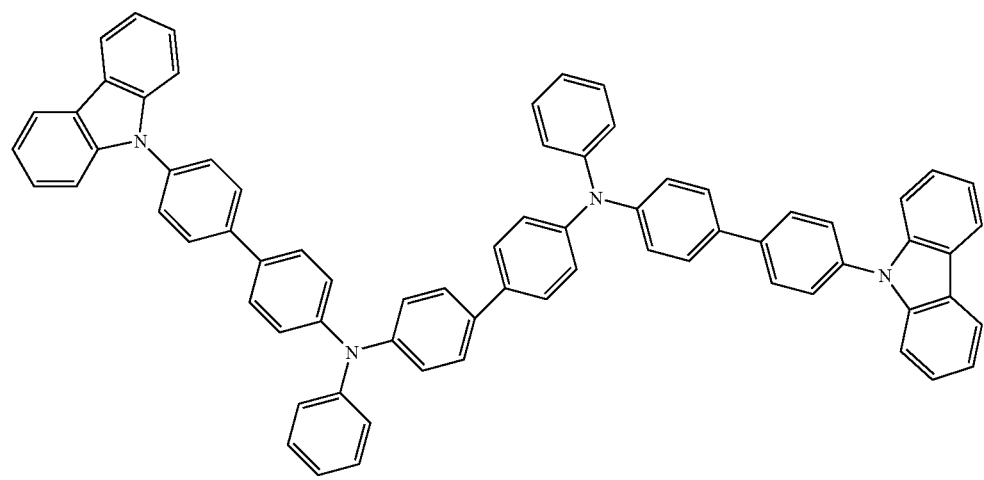

(115)
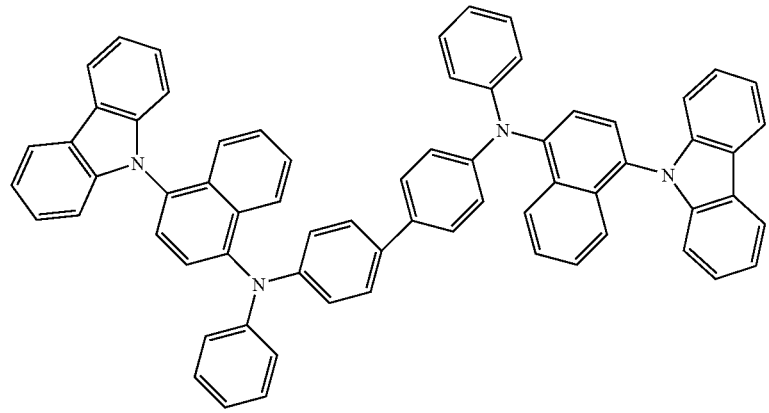
(116)
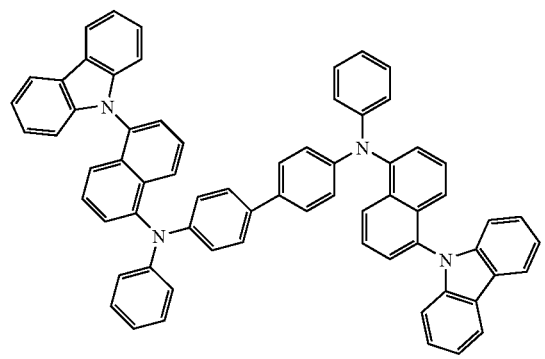
(117)
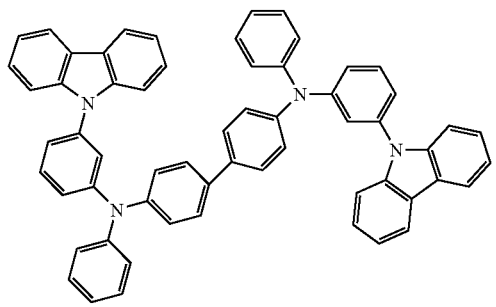
(118)
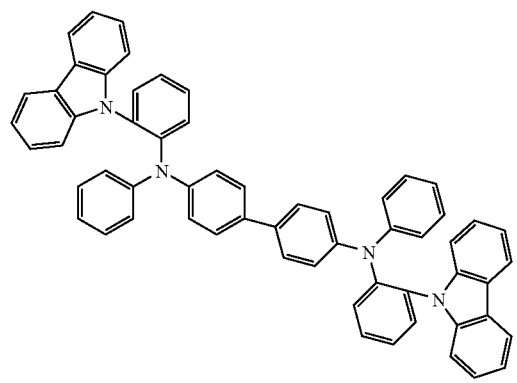
(119)
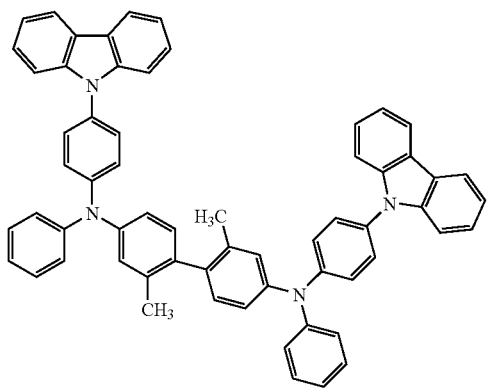

The aromatic amine compound of the present invention expressed by General Formula (1) can be synthesized by a synthesizing method expressed by Synthesis Scheme (A-1) and Synthesis Schemes (B-1) to (B-4).

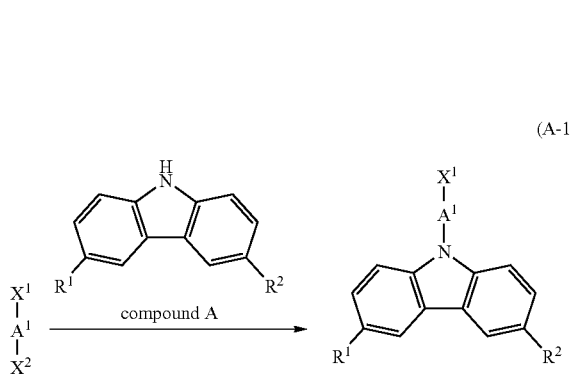

(A-1)

compound A compound B

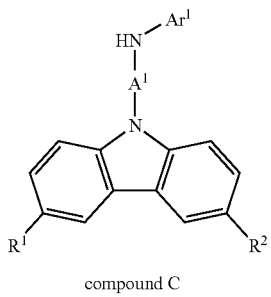

compound C

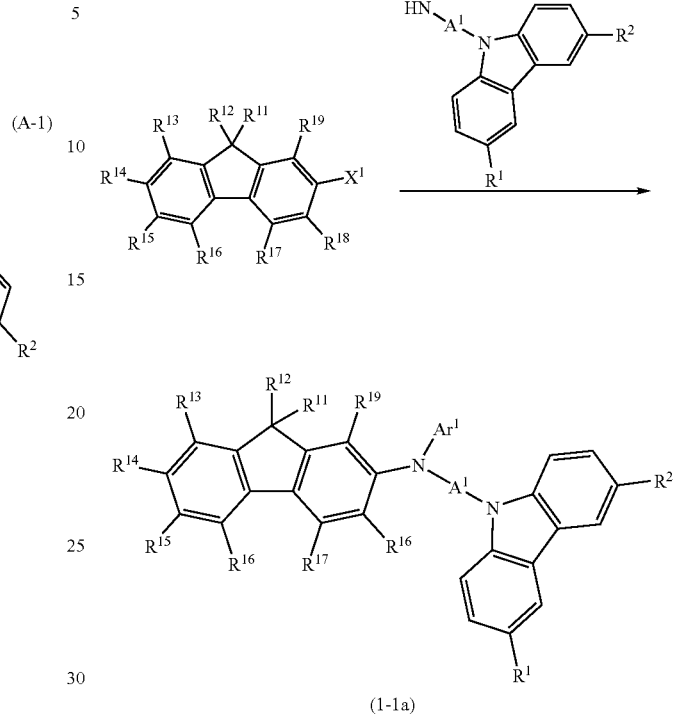

(B-1)

(1-1a)

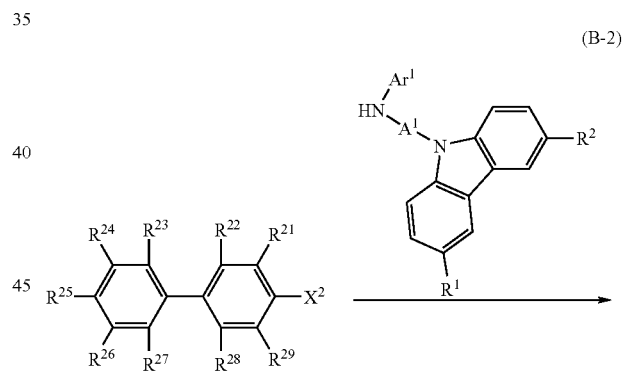

(B-2)

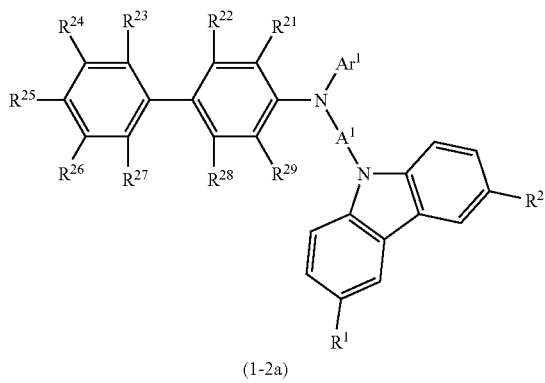

(1-2a)

First, a compound (Compound A) including carbazole in its skeleton is reacted with a dihalide of an aromatic compound by a coupling reaction using a metal catalyst to synthesize a compound (Compound B) including N-(arylhalide) carbazole in its skeleton; then, a coupling reaction with arylamine is carried out using a metal catalyst such as palladium to obtain Compound C. In Synthesis Scheme (A-1), a halogen element ($X^1$, $X^2$) of the dihalide of the aromatic compound is preferably iodine or bromine. Moreover, $X^1$ and $X^2$ may be either the same or different. Each of $R^1$ and $R^2$ represents any of a hydrogen atom, an alkyl group having 1 to 4 carbon atoms, and an aryl group having 6 to 25 carbon atoms. The aromatic amine compound is preferably a compound having 6 to 25 carbon atoms. The arylamine preferably has 6 to 25 carbon atoms.

Compound C can be reacted with a halide of a fluorene derivative or a halide of a biphenyl derivative by a coupling reaction using a palladium catalyst or an Ullmann reaction using copper, thereby synthesizing the aromatic amine compound of the present invention.

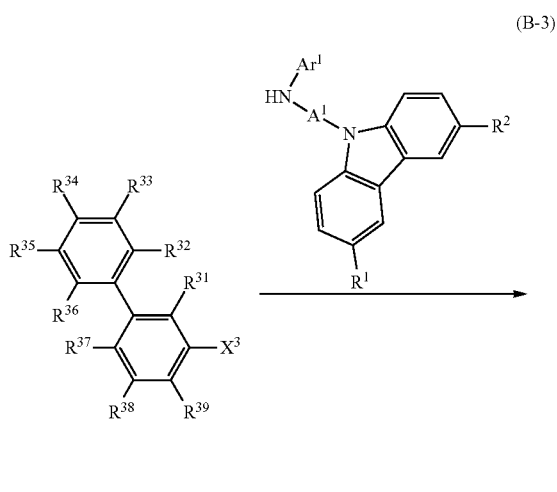

(B-3)

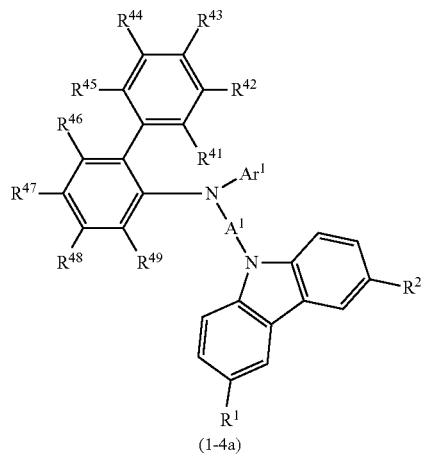

(1-4a)

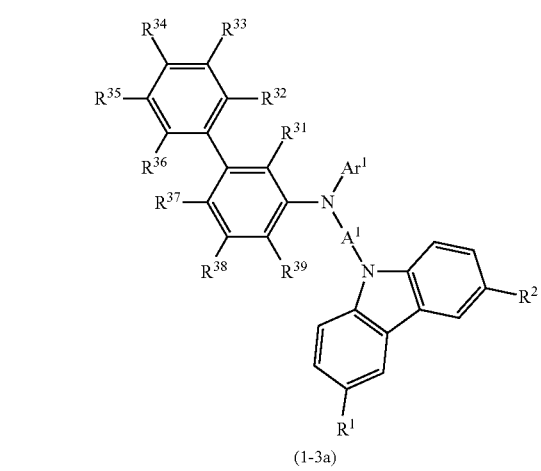

(1-3a)

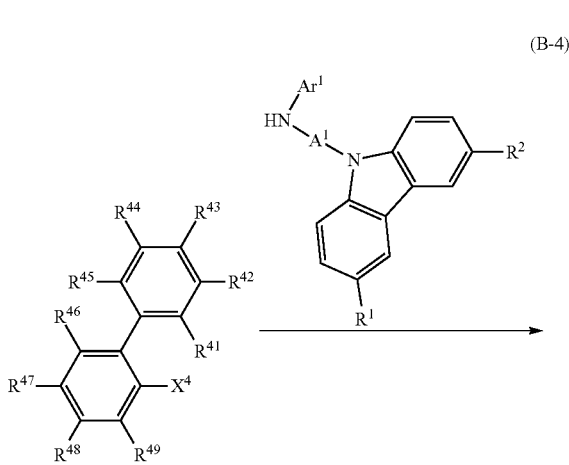

(B-4)

In Synthesis Schemes (B-1) to (B-4), $X^1$ to $X^4$ each represent a halogen atom. In addition, $R^1$ and $R^2$ each represent any of a hydrogen atom, an alkyl group having 1 to 4 carbon atoms, and an aryl group having 6 to 25 carbon atoms; $A^1$ represents an arylene group having 6 to 25 carbon atoms; and $Ar^1$ represents an aryl group having 6 to 25 carbon atoms. Moreover, $R^{11}$ and $R^{12}$ each represent any of a hydrogen atom, an alkyl group having 1 to 4 carbon atoms, and an aryl group having 6 to 12 carbon atoms. $R^{13}$ to $R^{19}$, $R^{21}$ to $R^{29}$, $R^{31}$ to $R^{39}$, and $R^{41}$ to $R^{49}$ each represent a hydrogen atom or an alkyl group having 1 to 4 carbon atoms.

In Synthesis Schemes (B-1) to (B-4), a compound expressed by General Formula (1-1a) corresponds to a case where α in the aforementioned General Formula (1) is General Formula (1-1), a compound expressed by General Formula (1-2a) corresponds to a case where α in the aforementioned General Formula (1) is General Formula (1-2), a compound expressed by General Formula (1-3a) corresponds to a case where α in the aforementioned General Formula (1) is General Formula (1-3), and a compound expressed by General Formula (1-4a) corresponds to a case where α in the aforementioned General Formula (1) is General Formula (1-4).

In Synthesis Scheme (B-1), the compound expressed by General Formula (1-1a) can be synthesized by coupling a halide of a fluorene derivative and Compound C in accordance with a coupling reaction using a palladium catalyst or an Ullumann reaction using copper. A halogen element of the halide of the fluorene derivative is preferably iodine or bromine.

Similarly, in Synthesis Schemes (B-2) to (B-4), the compounds expressed by General Formulae (1-2a) to (1-4a) can be synthesized by coupling a halide of a biphenyl derivative and Compound C in accordance with a coupling reaction using a palladium catalyst or an Ullumann reaction using copper. A halogen element of the halide of the biphenyl derivative is preferably iodine or bromine.

Moreover, the aromatic amine compound of the present invention expressed by General Formula (2) can be synthesized by a synthesizing method expressed by Synthesis Schemes (B-5) and (B-6).

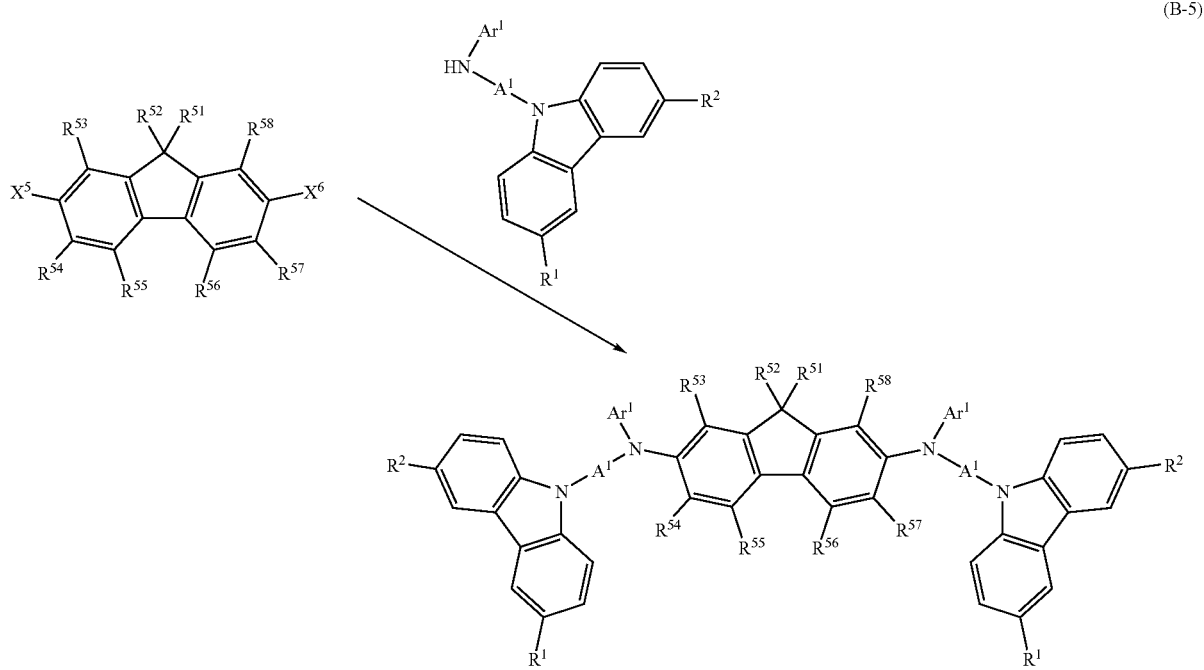

(B-5)

(2-1a)

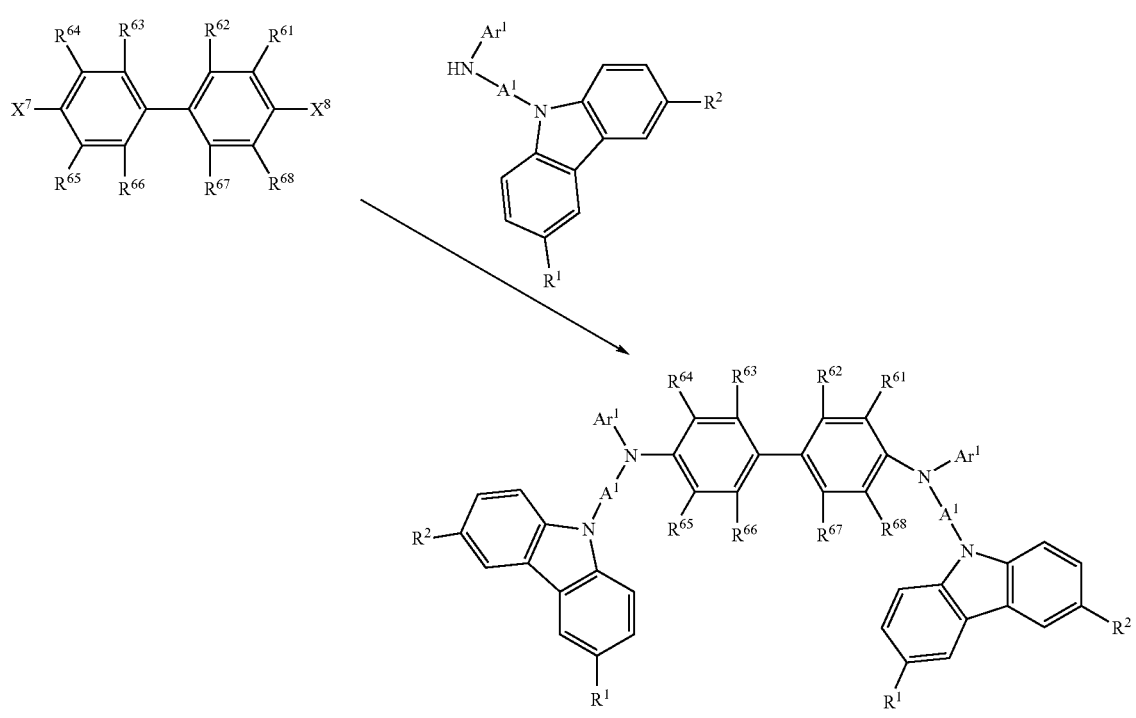

(B-6)

(2-2a)

In Synthesis Schemes (B-5) and (B-6), $X^5$ to $X^8$ each represent a halogen atom. Moreover, $R^1$ and $R^2$ each represent any of a hydrogen atom, an alkyl group having 1 to 4 carbon atoms, and an aryl group having 6 to 25 carbon atoms; $A^1$ represents an arylene group having 6 to 25 carbon atoms; and $Ar^1$ represents an aryl group having 6 to 25 carbon atoms. In addition, $R^{51}$ and $R^{52}$ each represent any of a hydrogen atom, an alkyl group having 1 to 4 carbon atoms, and an aryl group having 6 to 12 carbon atoms; and $R^{53}$ to $R^{58}$ and $R^{61}$ to $R^{68}$ each represent a hydrogen atom or an alkyl group having 1 to 4 carbon atoms.

In Synthesis Schemes (B-5) and (B-6), a compound expressed by General Formula (2-1a) corresponds to a case where α in the aforementioned General Formula (2) is General Formula (2-1), and a compound expressed by General Formula (2-2a) corresponds to a case where α in the aforementioned General Formula (2) is General Formula (2-2).

In Synthesis Scheme (B-5), the compound expressed by General Formula (2-1a) can be synthesized by coupling a halide of a fluorene derivative and Compound C in accordance with a coupling reaction using a palladium catalyst or an Ullumann reaction using copper. A halogen element of the halide of the fluorene derivative is preferably iodine or bromine.

Similarly, in Synthesis Scheme (B-6), the compound expressed by General Formula (2-2a) can be synthesized by coupling a halide of a biphenyl derivative and Compound C in accordance with a coupling reaction using a palladium catalyst or an Ullumann reaction using copper. A halogen element of the halide of the biphenyl derivative is preferably iodine or bromine.

Moreover, in Synthesis Schemes (B-5) and (B-6), the aromatic amine compound of the present invention of General Formula (2) can be obtained through one-stage reaction by reacting two equivalents of Compound C with respect to the halide.

In the above-described synthetic schemes, tri(tert-butyl) phosphine ((tert-Bu)$_3$P) can be used as a ligand for the coupling reaction using a palladium catalyst. As the Pd catalyst, a catalyst in which (tert-Bu)$_3$P is coordinated in bis(dibenzylideneacetone)palladium(0) (abbr.: Pd(dba)$_2$) by mixing bis(dibenzylideneacetone)palladium(0) and (tert-Bu)$_3$P can be used. It is to be noted that other ligands than (tert-Bu)$_3$P may be used as the ligand in the case of using the palladium catalyst. For example, DPPF can be used besides (tert-Bu)$_3$P. As the palladium catalyst, Pd(dba)$_2$, palladium diacetate (Pd(OAc)$_2$), or the like can be used. Preferably, Pd(dba)$_2$ is used. The reaction temperature is preferably in the range of room temperature to 130° C. It is more preferable to set the heating temperature in the range from 60° C. to 110° C. Note that dba refers to trans,trans-dibenzylideneacetone. In addition, DPPF refers to 1,1-bis(diphenylphosphino)ferrocene. As a solvent, toluene, xylene, or the like can be used. As a base, alkali metal alkoxide such as tert-BuONa; potassium carbonate (K$_2$CO$_3$); or the like can be used.

Since the aromatic amine compound of the present invention has a wide band gap, the aromatic amine compound can be used as a host material of a light-emitting material which emits light with a short wavelength, and moreover used for a layer which is in contact with a light-emitting material which emits light with a short wavelength.

More specifically, the aromatic amine compound of the present invention is effectively used as a host material for a fluorescent material which emits fluorescent light with a short wavelength, such as blue light, and moreover, effectively used for a layer which is in contact with a layer containing a fluorescent material which emits fluorescent light with a short wavelength because of the following reason. Since the aromatic amine compound of the present invention has high triplet level and singlet level, the energy transfer from an excited fluorescent material to the aromatic amine compound of the present invention does not easily occur. Therefore, the excited energy of the fluorescent material can be extracted efficiently as light emission. In addition, when the aromatic amine compound of the present invention is excited, the energy transfer from the triplet level or the singlet level of the excited aromatic amine compound to the fluorescent material becomes possible and the luminous efficiency of the light-emitting element can be improved. In the case of using the aromatic amine compound of the present invention for a layer which is in contact with a layer containing a fluorescent material, it is more effective to provide a light-emitting region close to a layer containing the aromatic amine compound of the present invention. In a case of a fluorescent material which emits light with a longer wavelength, the use of the aromatic amine compound of the present invention can offer a similar advantageous effect.

Specifically, the aromatic amine compound of the present invention is effectively used as a host material for a phosphorescent material which emits phosphorescent light with a relatively short wavelength such as green light, and moreover, effectively used for a layer which is in contact with a layer containing a phosphorescent material which emits phosphorescent light with a relatively short wavelength because of the following reason. Since the aromatic amine compound of the present invention has a high triplet level, the energy transfer from an excited phosphorescent material to the aromatic amine compound of the present invention does not easily occur. Therefore, the excited energy of the phosphorescent material can be extracted efficiently as light emission. In addition, when the aromatic amine compound of the present invention is excited, the energy transfer from the triplet level of the excited aromatic amine compound to the triplet level of the phosphorescent material becomes possible and the luminous efficiency of the light-emitting element can be improved. In the case of using the aromatic amine compound of the present invention for a layer which is in contact with a layer containing a phosphorescent material, it is more effective to provide a light-emitting region close to a layer containing the aromatic amine compound of the present invention. In a case of a phosphorescent material which emits light with a longer wavelength, the use of the aromatic amine compound of the present invention can offer a similar advantageous effect.

In particular, among the aromatic amine compounds of the present invention, the aromatic amine compound expressed by General Formula (1) with an asymmetrical structure is preferable because the band gap is wider and the triplet level is also high.

Moreover, the aromatic amine compound of the present invention is superior in a hole-transporting property; therefore, the aromatic amine compound can be used for a hole-transporting layer of a light-emitting element, thereby providing the light-emitting element with favorable characteristics.

Moreover, the aromatic amine compound expressed by General Formula (2) is superior in heat resistance. Therefore, by the use of the aromatic amine compound expressed by General Formula (2), a device superior in heat resistance can be obtained.

Embodiment Mode 2

An aspect of a light-emitting element using an aromatic amine compound of the present invention will be hereinafter described with reference to FIG. 1A.

A light-emitting element of the present invention has a plurality of layers between a pair of electrodes. The plurality of layers are formed by stacking a layer containing a substance with a high carrier-injecting property and a layer containing a substance with a high carrier-transporting property so that a light-emitting region is formed apart from the electrodes, i.e., so that carrier recombination is carried out in a portion apart from the electrodes.

In this embodiment mode, the light-emitting element includes a first electrode 102; a first layer 103, a second layer 104, a third layer 105, and a fourth layer 106 which are stacked in this order over the first electrode 102; and a second electrode 107 provided over them. In the explanation of this embodiment mode, the first electrode 102 functions as an anode and the second electrode 107 functions as a cathode.

The substrate 101 is used as a support for the light-emitting element. As the substrate 101, for example, a glass substrate, a plastic substrate, or the like can be used. Other substrates than these can also be used as long as the substrate functions as a support during a manufacturing process of the light-emitting element.

The first electrode 102 is preferably formed of a metal, alloy, conductive compound, mixture of these, or the like each having a high work function (specifically, 4.0 eV or higher). Specifically, for example, indium oxide-tin oxide (ITO: Indium Tin Oxide), indium oxide-tin oxide including silicon or silicon oxide, indium oxide-zinc oxide (IZO: Indium Zinc Oxide), indium oxide including tungsten oxide and zinc oxide (IWZO), or the like is given. Films of these conductive metal oxides are usually formed by sputtering; however, a sol-gel method or the like may also be used. For example, indium oxide-zinc oxide (IZO) can be formed by a sputtering method using a target in which 1 to 20 wt % of zinc oxide with respect to indium oxide is included. Moreover, indium oxide (IWZO) including tungsten oxide and zinc oxide can be formed by a sputtering method using a target in which 0.5 to 5 wt % of tungsten oxide and 0.1 to 1 wt % of zinc oxide with respect to indium oxide are included. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride (TiN)), or the like is given.

The first layer 103 includes a substance with a high hole-injecting property and can be formed of molybdenum oxide ($MoO_x$), vanadium oxide ($VO_x$), ruthenium oxide ($RuO_x$), tungsten oxide ($WO_x$), manganese oxide ($MnO_x$), or the like. In addition, phthalocyanine (abbr.: $H_2PC$), a phthalocyanine-based compound such as copper phthalocyanine (CuPC), a high-molecular material such as poly(ethylenedioxythiophene)/poly(styrenesulfonate) (PEDOT/PSS), or the like can also be used to form the first layer 103.

Moreover, the first layer 103 can be formed of a composite material including an organic compound and an inorganic compound. In particular, in a composite material including an organic compound and an inorganic compound exhibiting an electron-accepting property with respect to the organic compound, electrons are transported between the organic compound and the inorganic compound to increase carrier density; thus, the hole-injecting property and the hole-transporting property are excellent.

When the first layer 103 is formed of a composite material including an organic compound and an inorganic compound, since ohmic contact with the first electrode 102 becomes possible, the material for the first electrode can be selected regardless of its work function.

The inorganic compound used for the composite material is preferably an oxide of a transition metal. Moreover, an oxide of a metal belonging to any of Groups 4 to 8 in the periodic table can be used. Specifically, vanadium oxide, niobium oxide, tantalum oxide, chromium oxide, molybdenum oxide, tungsten oxide, manganese oxide, and rhenium oxide are preferable for their high electron-accepting property. Above all, molybdenum oxide is preferable because it is stable even in the air, it has a low moisture-absorption property, and it is easily handled.

The organic compound used for the composite material can be various kinds of compounds including an aromatic amine compound, a carbazole derivative, aromatic hydrocarbon, a high-molecular compound (such as oligomer, dendrimer, or polymer), and so on. The organic compound used for the composite material preferably has a high hole-transporting property. Specifically, a substance having a hole mobility of $10^{-6}$ $cm^2/Vs$ or higher is preferable. However, other materials than these can also be used as long as the hole-transporting property is higher than the electron-transporting property. The organic compound which can be used for the composite material will hereinafter be described specifically.

For example, the aromatic amine compound may be N,N'-di(p-tolyl)-N,N'-diphenyl-p-phenylenediamine (abbr.: DTD-PPA); 4,4'-bis[N-(4-diphenylaminophenyl)-N-phenylamino] biphenyl (abbr.: DPAB); 4,4'-bis(N-{4-[N-(3-methylphenyl)-N-phenylamino]phenyl}-N-phenylamino) biphenyl (abbr.: DNTPD); 1,3,5-tris[N-(4-diphenylaminophenyl)-N-phenylamino]benzene (abbr.: DPA3B); or the like.

As the carbazole derivative which can be used for the composite material, specifically, the following can be given: 3-[N-(9-phenylcarbazol-3-yl)-N-phenylamino]-9-phenyl-carbazole (abbr.: PCzPCA1); 3,6-bis[N-(9-phenylcarbazol-3-yl)-N-phenylamino]-9-phenylcarbazole (abbr.: PCz-PCA2); 3-[N-(1-naphthyl)-N-(9-phenylcarbazol-3-yl) amino]-9-phenylcarbazole (abbr.: PCzPCN1); or the like.

Moreover, 4,4'-di(N-carbazolyl)biphenyl (abbr.: CBP); 1,3,5-tris[4-(N-carbazolyl)phenyl]benzene (abbr.: TCPB); 9-[4-(N-carbazolyl)]phenyl-10-phenylanthracene (abbr.: CzPA); 1,4-bis[4-(N-carbazolyl)phenyl-2,3,5,6-tetraphenyl-benzene; or the like can be used.

As the aromatic hydrocarbon which can be used for the composite material, for example, the following can be given: 2-tert-butyl-9,10-di(2-naphthyl)anthracene (abbr.: t-BuDNA); 2-tert-butyl-9,10-di(1-naphthyl)anthracene; 9,10-bis(3,5-diphenylphenyl)anthracene (abbr.: DPPA); 2-tert-butyl-9,10-bis(4-phenylphenyl)anthracene (abbr.: t-BuDBA); 9,10-di(2-naphthyl)anthracene (abbr.: DNA); 9,10-diphenylanthracene (abbr.: DPAnth); 2-tert-butylan-thracene (abbr.: t-BuAnth); 9,10-bis(4-methyl-1-naphthyl) anthracene (abbr.: DMNA); 2-tert-butyl-9,10-bis[2-(1-naph-thyl)phenyl]anthracene; 9,10-bis[2-(1-naphthyl)phenyl] anthracene; 2,3,6,7-tetramethyl-9,10-di(1-naphthyl) anthracene; 2,3,6,7-tetramethyl-9,10-di(2-naphthyl) anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tet-racene; rubrene; perylene; 2,5,8,11-tetra(tert-butyl)perylene; or the like. In addition to these, pentacene, coronene, or the like can also be used. In this way, the aromatic hydrocarbon having a hole mobility of $1 \times 10^{-6}$ $cm^2/Vs$ or higher and 14 to 42 carbon atoms is more preferably used.

The aromatic hydrocarbon which can be used for the composite material may have a vinyl skeleton. As the aromatic hydrocarbon having a vinyl group, for example, 4,4'-bis(2,2-diphenylvinyl)biphenyl (abbr.: DPVBi); 9,10-bis[4-(2,2-diphenylvinyl)phenyl]anthracene (abbr.: DPVPA); or the like is given.

In addition, a high-molecular compound such as poly(N-vinylcarbazole) (abbr.: PVK) or poly(4-vinyltriphenylamine) (abbr.: PVTPA) can be used.

The second layer 104 includes a substance with a high hole-transporting property. The aromatic amine compound of the present invention shown in Embodiment Mode 1 can be suitably used for the second layer 104 for its excellent hole-transporting property. When the aromatic amine compound of the present invention is used for the second layer 104, a light-emitting element with favorable characteristics can be obtained.

The third layer 105 is a layer containing a substance with a light-emitting property. The substance with a light-emitting property is not particularly limited and various kinds of materials can be used. For example, as a fluorescent material which emits fluorescent light, the following can be given: coumarin derivatives such as coumarin 6 and coumarin 545T; quinacridone derivatives such as N,N'-dimethylquinacridone and N,N'-diphenylquinacridone; acridone derivatives such as N-phenylacridone and N-methylacridone; condensed aromatic compounds such as 2-tert-butyl-9,10-di(2-naphthyl) anthracene (abbr.: t-BuDNA), 9,10-diphenylanthracene (abbr.: DPhA), rubrene, periflanthene, and 2,5,8,11-tetra(tert-butyl)perylene (abbr.: TBP); pyran derivatives such as 4-dicyanomethylene-2-[p-(dimethylamino)styryl]-6-methyl-4H-pyran; amine derivatives such as 4-(2,2-diphenylvinyl) triphenylamine, 9-(4-{N-[4-(carbazol-9-yl)phenyl]-N-phenylamino}phenyl)-10-phenylanthracene (abbr.: YGAPA); and so on. As a phosphorescent material which emits phosphorescent light, the following can be given: iridium complexes such as tris(2-phenylpyridinato)iridium(III) (abbr.: Ir(ppy)$_3$), bis(2-phenylpyridinato)iridium(III)acetylacetonate (abbr.: Ir(ppy)$_2$(acac)), bis{2-(p-tolyl) pyridinato}iridium(III)acetylacetonate (abbr.: Ir(tpy)$_2$ (acac)), bis{2-(2'-benzothienyl)pyridinato}iridium(III) acetylacetonate (abbr.: Ir(btp)$_2$(acac)), and bis{2-(4,6-difluorophenyl)pyridinato}iridium(III)picolinate (abbr.: FIrpic); platinum complexes such as a 2,3,7,8,12,13,17,18-octaethyl-21H,23H-porphyrin-platinum complex (pt(OEP)); rare-earth complexes such as 4,7-diphenyl-1,10-phenanthrolinetris(2-tenoyltrifluoroacetonato)europium(III); and the like.

The present invention is effective when the substance with a light-emitting property included in the third layer 105 is a material which emits blue fluorescent light. Specifically, a fluorescent material which emits blue light, such as the aforementioned t-BuDNA, DPhA, TBP, or YGAPA, is preferably used.

Moreover, the present invention is effective when the substance with a light-emitting property included in the third layer 105 is a substance which emits green phosphorescent light. Specifically, a phosphorescent material which emits green light, such as the aforementioned Ir(ppy)$_3$, Ir(ppy)$_2$ (acac), or Ir(tpy)$_2$(acac), or a phosphorescent material which emits blue-green light such as the aforementioned FIrpic is preferably used.

The third layer 105 may be formed by dispersing the aforementioned substance with a light-emitting property. As a material for dispersing the substance with a light-emitting property, various kinds of materials can be used. In particular, a substance with a higher LUMO level and a lower HOMO level than the substance with a light-emitting property is preferable. Specifically, the following can be used: 4,4'-bis [N-(1-naphthyl)-N-phenylamino]biphenyl (abbr.: NPB), tris (8-quinolinolato)aluminum (abbr.: Alq), bis(2-methyl-8-quinolinolato)(4-phenylphenolato)aluminum (abbr.: BAlq), bis[2-(2-hydroxyphenyl)benzoxazolato]zinc (abbr.:Zn (BOX)$_2$), 2-tert-butyl-9,10-di(2-naphthyl)anthracene (abbr.: t-BuDNA), 9-[4-(N-carbazolyl)]phenyl-10-phenylanthracene (abbr.: CzPA), 2-(4-{N-[4-(carbazol-9-yl)phenyl]-N-phenylamino}phenyl)-5-phenyl-1,3,4-oxadiazole (abbr.: YGAO11), and the like. Moreover, plural kinds of materials may be employed to disperse the substance with a light-emitting property. For example, a substance which suppresses crystallization, such as rubrene, may be further added to suppress crystallization. In addition, NPB, Alq, or the like may be further added in order to transfer energy to the substance with a light-emitting property more efficiently.

The fourth layer 106 can be formed of a substance with a high electron-transporting property. For example, the fourth layer 106 includes the following metal complex having a quinoline skeleton or a benzoquinoline skeleton, or the like: tris(8-quinolinolato)aluminum (abbr.: Alq); tris(4-methyl-8-quinolinolato)aluminum (abbr.: Almq3); bis(10-hydroxybenzo[h]-quinolinato)beryllium (abbr: BeBq$_2$); bis(2-methyl-8-quinolinolato)(4-phenylphenolato)aluminum (BAlq); and the like. Besides those, the following metal complex having an oxazole-based ligand or a thiazole-based ligand, or the like can be used: bis[2-(2-hydroxyphenyl)benzoxazolato] zinc (abbreviation: Zn(BOX)$_2$); bis[2-(2-hydroxyphenyl) benzothiazolato]zinc (abbreviation: Zn(BTZ)$_2$); and the like. Furthermore, in addition to the metal complex, 2-(4-biphenylyl)-5-(4-tert-butylphenyl)-1,3,4-oxadiazole (abbreviation: PBD); 1,3-bis[5-(p-tert-butylphenyl)-1,3,4-oxadiazole-2-yl]benzene (abbreviation: OXD-7); 3-(4-biphenylyl)-4-phenyl-5-(4-tert-butylphenyl)-1,2,4-triazole (abbreviation: TAZ); bathophenanthroline (abbreviation: BPhen); bathocuproin (abbreviation: BCP); and the like can also be used. The substances mentioned here mainly have an electron mobility of $10^{-6}$ cm$^2$/Vs or higher. It is to be noted that the electron-transporting layer may include a substance other than those above as long as the substance has a higher electron-transporting property than hole-transporting property. Moreover, the electron-transporting layer may have not only a single-layer structure but also a stacked-layer structure including two or more layers formed of the above-mentioned substances.

The second electrode 107 can be formed of a metal, alloy, electrically conductive compound, or mixture of these, each having a low work function (specifically, 3.8 eV or lower). As a typical example of a cathode material, an element belonging to Group 1 or 2 in the periodic table, i.e., an alkali metal such as lithium (Li) or cesium (Cs), or an alkaline earth metal such as magnesium (Mg), calcium (Ca), or strontium (Sr); an alloy containing any of these (such as MgAg or AlLi); a rare earth metal such as europium (Er) or ytterbium (Yb); an alloy containing a rare earth metal; or the like can be used. However, when a layer having a function of promoting electron injection is provided between the second electrode 107 and the fourth layer 106 as a stack with the second electrode, the second electrode 107 can be formed of various conductive materials such as Al, Ag, ITO, or ITO including silicon regardless of its work function.

For the layer having a function of promoting electron injection, an alkali metal, an alkaline earth metal, or a compound of an alkali metal or an alkaline earth metal, such as lithium fluoride (LiF), cesium fluoride (CsF), or calcium fluoride (CaF$_2$) can be used. For example, a layer which includes a substance with an electron-transporting property and also includes an alkali metal, an alkaline earth metal, or a compound of an alkali metal or an alkaline earth metal can be used. Specifically, for example, Alq including magnesium (Mg), or the like can be used. It is to be noted that as the electron-injecting layer, an alkali metal or an alkaline earth metal is preferably included in the layer which includes a substance with an electron-transporting property because electron injection from the second electrode 107 is efficiently performed.

The first layer 103, the second layer 104, the third layer 105, and the fourth layer 106 can be formed by not only an evaporation method but also various methods such as an ink jet method or a spin coating method. Moreover, a different forming method may be used for each electrode or each layer.

In the light-emitting element of the present invention having the aforementioned structure, current flows by a potential difference generated between the first electrode 102 and the second electrode 107 and holes and electrons are recombined in the third layer 105, which is the layer containing a substance with a high light-emitting property; thus, light is emitted. In other words, in this structure, a light-emitting region is formed in the third layer 105.

Figure 1B:
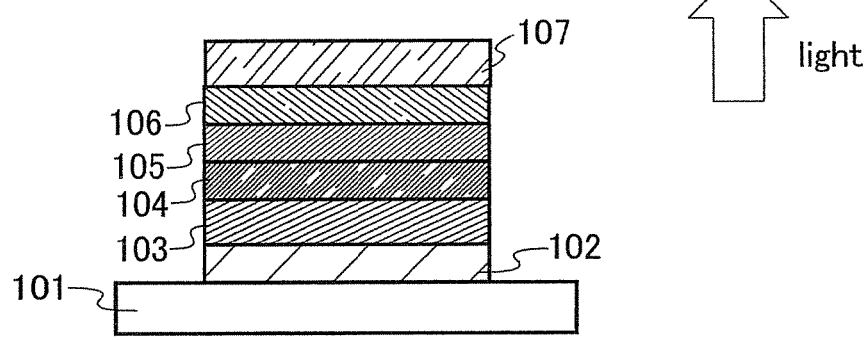
Figure 1C:
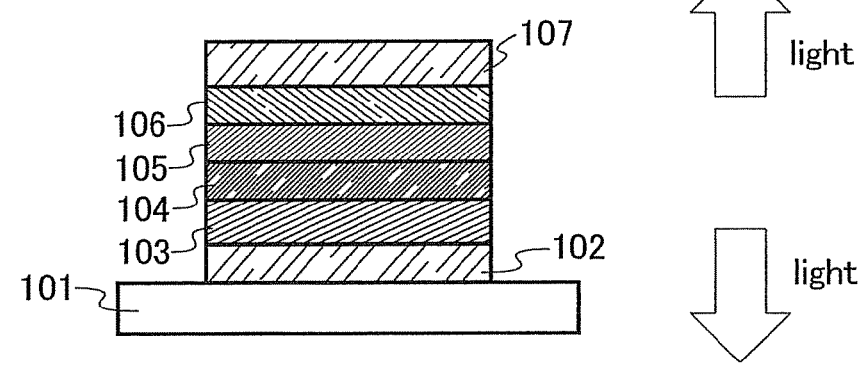

The emitted light is extracted to the outside through one or both of the first electrode 102 and the second electrode 107. Therefore, one or both of the first electrode 102 and the second electrode 107 is/are formed of a substance with a light-transmitting property. When only the first electrode 102 is formed of a substance with a light-transmitting property, the emitted light is extracted from the substrate side through the first electrode 102 as shown in FIG. 1A. Meanwhile, when only the second electrode 107 is formed of a substance with a light-transmitting property, the emitted light is extracted from the side opposite to the substrate side through the second electrode 107 as shown in FIG. 1B. When each of the first electrode 102 and the second electrode 107 is formed of a substance with a light-transmitting property, the emitted light is extracted from both the substrate side and the side opposite to the substrate side through the first electrode 102 and the second electrode 107 as shown in FIG. 1C.

The structure of the layers provided between the first electrode 102 and the second electrode 107 is not limited to the aforementioned one. A structure other than the aforementioned one may also be used as long as a light-emitting region in which holes and electrons are recombined is provided in a portion apart from the first electrode 102 and the second electrode 107 so that light disappearance caused by approximation between the light-emitting region and metal is suppressed.

That is to say, the stacked-layer structure is not particularly limited, and layers containing a substance with a high electron-transporting property, a substance with a high hole-transporting property, a substance with a high electron-injecting property, a substance with a high hole-injecting property, a substance with a bipolar property (a material with a high electron and hole transporting property), a substance with a hole-blocking property, and the like may be freely combined with the aromatic amine compound of the present invention.

Figure 2:
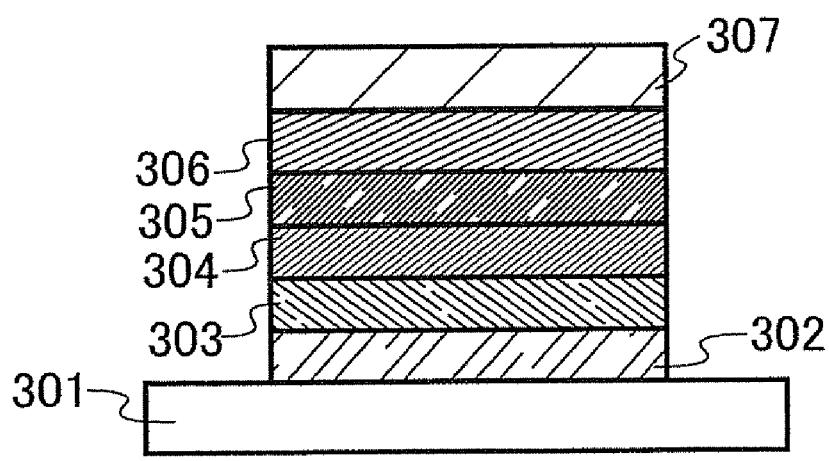
FIG. 2 explains a light-emitting element of the present invention.

In a structure of the light-emitting element shown in FIG. 2, a first layer 303 containing a substance with a high electron-transporting property, a second layer 304 containing a substance with a light-emitting property, a third layer 305 containing a substance with a high hole-transporting property, a fourth layer 306 containing a substance with a high hole-injecting property, and a second electrode 307 functioning as an anode are stacked in this order over a first electrode 302 functioning as a cathode. It is to be noted that reference numeral 301 denotes a substrate.

In this embodiment mode, the light-emitting element is manufactured over a substrate made of glass, plastic, or the like. When a plurality of such light-emitting elements are manufactured over one substrate, a passive light-emitting device can be manufactured. Moreover, for example, a thin film transistor (TFT) may be formed over a substrate made of glass, plastic, or the like so that a light-emitting element is manufactured over an electrode electrically connected to the TFT. Thus, an active matrix light-emitting device in which driving of the light-emitting element is controlled by the TFT can be manufactured. The structure of the TFT is not particularly limited. The TFT may be either a staggered type or an inverted staggered type. The crystallinity of a semiconductor used for the TFT is not limited in particular, and the semiconductor may be either amorphous or crystalline. Moreover, a driver circuit formed over the TFT substrate may include N-type and P-type TFTs or only one of N-type and P type TFTs.

Since the aromatic amine compound of the present invention has a wide band gap, a light-emitting element with the use of the aromatic amine compound of the present invention can have favorable characteristics.

The aromatic amine compound of the present invention is effectively used for a layer which is in contact with a layer containing a fluorescent material which emits fluorescent light with a short wavelength because of the following reason. Since the aromatic amine compound of the present invention has high triplet level and singlet level, the energy transfer from an excited fluorescent material to the aromatic amine compound of the present invention does not easily occur. Therefore, the excited energy of the fluorescent material can be extracted efficiently as light emission. In addition, when the aromatic amine compound of the present invention is excited, the energy transfer from the triplet level or the singlet level of the excited aromatic amine compound to the fluorescent material becomes possible and the luminous efficiency of the light-emitting element can be improved. In the case of using the aromatic amine compound of the present invention for a layer which is in contact with a layer containing a fluorescent material, it is more effective to provide a light-emitting region close to a layer containing the aromatic amine compound of the present invention. In a case of a fluorescent material which emits light with a longer wavelength, the use of the aromatic amine compound of the present invention can offer a similar advantageous effect.

Specifically, the aromatic amine compound of the present invention is effectively used for a layer which is in contact with a layer containing a phosphorescent material which emits phosphorescent light with a relatively short wavelength because of the following reason. Since the triplet level of the aromatic amine compound of the present invention is high, the energy transfer from an excited phosphorescent material to the aromatic amine compound of the present invention does not easily occur. Therefore, the excited energy of the phosphorescent material can be extracted effectively as light emission. In addition, when the aromatic amine compound of the present invention is excited, the energy transfer from the triplet level of the excited aromatic amine compound to the triplet level of the phosphorescent material becomes possible and the luminous efficiency of the light-emitting element can be improved. In the case of using the aromatic amine compound of the present invention for a layer which is in contact with a layer containing a phosphorescent material, it is more effective to provide a light-emitting region close to a layer containing the aromatic amine compound of the present invention. In a case of a phosphorescent material which emits light with a longer wavelength, the use of the aromatic amine compound of the present invention can offer a similar advantageous effect.

In particular, the aromatic amine compound of the present invention is preferably the aromatic amine compound expressed by General Formula (1), which has an asymmetrical structure, because the band gap is wider and moreover the triplet level is high.

In addition, since the light-emitting element of the present invention has high luminous efficiency, the power consumption can be reduced.

Further, the aromatic amine compound of the present invention is superior in a hole-transporting property. Therefore, the aromatic amine compound of the present invention can be used for the hole-transporting layer of the light-emitting element, which can provide a light-emitting element with favorable characteristics.

Moreover, the aromatic amine compound expressed by General Formula (2) is superior in heat resistance. Therefore, the use of the aromatic amine compound expressed by General Formula (2) can provide a device superior in heat resistance.

Embodiment Mode 3

Embodiment Mode 3 will explain a light-emitting element with a structure different from the structure shown in Embodiment Mode 2.

Since the aromatic amine compound of the present invention has a wide band gap and high triplet and singlet levels, the aromatic amine compound of the present invention can be used for a host for dispersing a material with a light-emitting property. That is to say, the aromatic amine compound of the present invention can be used for the third layer 105 shown in Embodiment Mode 2. As the material with a light-emitting property which is dispersed in the aromatic amine compound of the present invention, various fluorescent materials and phosphorescent materials can be used.

When the aromatic amine compound of the present invention is used for the third layer 105, the second layer 104 can be formed of various materials. For example, various aromatic amine compounds can be used. As the widely used materials, the following starburst aromatic amine compounds are given: 4,4'-bis[N-(3-methylphenyl)-N-phenylamino]biphenyl; its derivative, 4,4'-bis[N-(1-naphthyl)-N-phenylamino]biphenyl (hereinafter referred to as NPB); 4,4',4''-tris(N,N-diphenyl-amino)triphenylamine; 4,4',4''-tris[N-(3-methylphenyl)-N-phenylamino]triphenylamine; and the like. These are the substances mainly with a hole mobility of $10^{-6}$ cm$^2$/Vs or higher. However, other materials than these may also be used as long as the hole-transporting property is higher than the electron-transporting property. The second layer 104 may be not only a single layer, but also a mixed layer or a stack of two or more layers including any of the aforementioned substances.

Since the aromatic amine compound of the present invention has a wide band gap, the aromatic amine compound of the present invention can be used for a host material of a light-emitting material which emits light with a short wavelength.

The aromatic amine compound of the present invention is effectively used as a host material for a fluorescent material which emits fluorescent light with a short wavelength, such as blue light, because of the following reason. Since the aromatic amine compound of the present invention has high triplet level and singlet level, the energy transfer from an excited fluorescent material to the aromatic amine compound of the present invention does not easily occur. Therefore, the excited energy of the fluorescent material can be extracted efficiently as light emission. In addition, when the aromatic amine compound of the present invention is excited, the energy transfer from the triplet level or the singlet level of the excited aromatic amine compound to the phosphorescent material becomes possible and the luminous efficiency of the light-emitting element can be improved. In a case of a fluorescent material which emits light with a longer wavelength, the use of the aromatic amine compound of the present invention can offer a similar advantageous effect.

The aromatic amine compound of the present invention is effectively used as a host material for a phosphorescent material which emits phosphorescent light with a relatively short wavelength, such as green light, because of the following reason. Since the triplet level of the aromatic amine compound of the present invention is high, the energy transfer from an excited phosphorescent material to the aromatic amine compound of the present invention does not easily occur. Therefore, the excited energy of the phosphorescent material can be extracted efficiently as light emission. In addition, when the aromatic amine compound of the present invention is excited, the energy transfer from the triplet level of the excited aromatic amine compound to the triplet level of the phosphorescent material becomes possible and the luminous efficiency of the light-emitting element can be improved. In a case of a phosphorescent material which emits light with a longer wavelength, the use of the aromatic amine compound of the present invention can offer a similar advantageous effect.

In particular, the aromatic amine compound of the present invention is preferably the aromatic amine compound expressed by General Formula (1) which has an asymmetrical structure, because the band gap is wider and moreover the triplet level is also high.

Since the light-emitting element of the present invention has high luminous efficiency, the power consumption can be reduced.

In addition, the aromatic amine compound expressed by General Formula (2) is superior in heat resistance. Therefore, the use of the aromatic amine compound expressed by General Formula (2) can provide a device superior in heat resistance.

Embodiment Mode 4

Embodiment Mode 4 will explain a light-emitting element having a structure different from those shown in Embodiment Modes 2 and 3.

When the aromatic amine compound of the present invention is used for the third layer 105 shown in Embodiment Mode 2, light can be emitted from the aromatic amine compound of the present invention. Since the aromatic amine compound of the present invention emits violet to blue light, a light-emitting element emitting violet to blue light can be obtained.

The third layer 105 may include only the aromatic amine compound of the present invention or may include the aromatic amine compound of the present invention which is dispersed in another substance. As the substance in which the aromatic amine compound of the present invention is dispersed, various materials such as the following can be used in addition to the substance with a high hole-transporting property and the substance with a high electron-transporting property described in Embodiment Mode 2: 3-(4-biphenylyl)-4-phenyl-5-(4-tert-butylphenyl)-1,2,4-triazole (abbr.: TAZ), 4,4'-di(N-carbazolyl)biphenyl (abbr.: CBP), 2,2',2''-(1,3,5-benzenetri-yl)-tris[1-phenyl-1H-benzimidazole] (abbr.: TPBI), and the like.

Since the aromatic amine compound of the present invention has a high glass transition point, a light-emitting element with the use of the aromatic amine compound of the present invention can have excellent heat resistance.

The aromatic amine compound of the present invention is stable even after repetition of oxidation reactions and subsequent reduction reactions. That is to say, the aromatic amine compound of the present invention is stable against repeated oxidation reactions. Therefore, a light-emitting element with the use of the aromatic amine compound of the present invention can have a long lifetime.

The structure shown in Embodiment Mode 2 or 3 can be appropriately used except the third layer 105.

Embodiment Mode 5

Embodiment Mode 5 will explain a light-emitting element having a structure different from those described in Embodiment Modes 2 to 4.

Since the aromatic amine compound of the present invention has a hole-injecting property, the aromatic amine compound of the present invention can be used for the first layer 103 shown in Embodiment Mode 2. Moreover, a composite material including the aromatic amine compound of the present invention and an inorganic compound can be used for the first layer 103. The inorganic compound used for the composite material is preferably an oxide of a transition metal. In addition, an oxide of a metal belonging to any of Groups 4 to 8 in the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting property. Above all, molybdenum oxide is preferable because it is stable in the air, easily handled, and has a low moisture-absorption property.

In the composite material including the aromatic amine compound of the present invention and the inorganic compound, electrons are transported between the organic compound and the inorganic compound to increase carrier density; therefore, the hole-injecting property and the hole-transporting property are excellent. When the first layer 103 is formed of the composite material including the aromatic amine compound of the present invention and the inorganic compound, ohmic contact with the first electrode 102 is possible; thus, the material for forming the first electrode can be selected regardless of the work function.

When the aromatic amine compound of the present invention is used for the first layer 103, the second layer 104 can be formed of various materials. For example, an aromatic amine compound (i.e., having a bond of a benzene ring and nitrogen) can be used. As the widely used material, the following starburst aromatic amine compounds are given: 4,4'-bis[N-(3-methylphenyl)-N-phenylamino]biphenyl; its derivative, 4,4'-bis[N-(1-naphthyl)-N-phenylamino]biphenyl (hereinafter referred to as NPB); 4,4',4"-tris(N,N-diphenyl-amino)triphenylamine; 4,4',4"-tris[N-(3-methylphenyl)-N-phenylamino]triphenylamine; and the like. These are the substances mainly with a hole mobility of $10^{-6}$ cm$^2$/Vs or higher. However, other materials than these may also be used as long as the hole-transporting property is higher than the electron-transporting property. The second layer 104 may be not only a single layer, but also a mixed layer or a stack of two or more layers including any of the aforementioned substances.

The aromatic amine compound of the present invention may be used for the first layer 103 and the second layer 104.

Since the aromatic amine compound of the present invention has a hole-injecting property, the aromatic amine compound of the present invention can be used as the hole-injecting layer of the light-emitting element.

In addition, since the aromatic amine compound of the present invention has a high glass transition point, the light-emitting element with the use of the aromatic amine compound of the present invention can have excellent heat resistance.

The aromatic amine compound of the present invention is stable even after repetition of an oxidation reaction and a subsequent reduction reaction. That is to say, the aromatic amine compound of the present invention is stable against repeated oxidation reactions. Therefore, a light-emitting element with the use of the aromatic amine compound of the present invention can have a long lifetime.

The structure shown in any of Embodiment Modes 2 to 4 can be appropriately used except the first layer 103.

Embodiment Mode 6

In this embodiment mode, a mode of a light-emitting element in which a plurality of light-emitting units of the present invention are stacked (hereinafter this light-emitting element is referred to as a stacked-type element) will be described with reference to FIG. 9. The light-emitting element includes a plurality of light-emitting units between a first electrode and a second electrode. Each of the light-emitting units may have a similar structure to that of the layer containing a light-emitting substance shown in Embodiment Mode 2. That is, the light-emitting element shown in Embodiment Mode 2 is a light-emitting element having one light-emitting unit, whereas the light-emitting element described in this embodiment mode has a plurality of light-emitting units.

Figure 9:
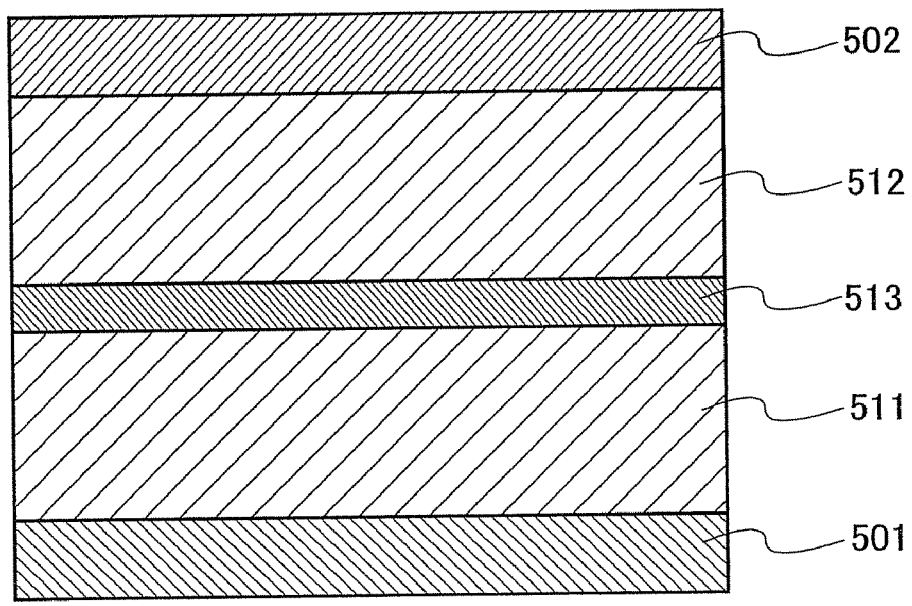
FIG. 9 explains a light-emitting element of the present invention.

In FIG. 9, a first light-emitting unit 511 and a second light-emitting unit 512 are stacked between a first electrode 501 and a second electrode 502. The first electrode 501 and the second electrode 502 may be similar to the electrodes shown in Embodiment Mode 2. The first light-emitting unit 511 and the second light-emitting unit 512 may have either the same structure or a different structure, which may be similar to those described in Embodiment Modes 2 to 5.

A charge-generating layer 513 includes a composite material of an organic compound and a metal oxide. The composite material of an organic compound and a metal oxide includes the organic compound shown in Embodiment Mode 2 and a metal oxide such as vanadium oxide, molybdenum oxide, or tungsten oxide. As the organic compound, various compounds such as an aromatic amine compound, a carbazole derivative, aromatic hydrocarbon, and a high molecular compound (oligomer, dendrimer, polymer, or the like) can be used. As the organic compound, it is preferable to use the organic compound which has a hole-transporting property and has a hole mobility of $10^{-6}$ cm$^2$/Vs or higher. However, other substances than these may also be used as long as the hole-transporting property is higher than the electron-transporting property. The composite material of the organic compound and the metal oxide can achieve low-voltage driving and low-current driving because of superior carrier-injecting property and carrier-transporting property.

Alternatively, the charge-generating layer 513 may be formed by combining the composite material of the organic compound and the metal oxide with another material. For example, a layer containing the composite material of the organic compound and the metal oxide may be combined with a layer containing a compound of a substance selected from substances with an electron-donating property and a compound with a high electron-transporting property. Moreover, a layer containing the composite material of the organic compound and the metal oxide may be combined with a transparent conductive film.

In any case, it is acceptable as long as the charge-generating layer 513 interposed between the first light-emitting unit 511 and the second light-emitting unit 512 injects electrons to one of these light-emitting units and holes to the other when voltage is applied to the first electrode 501 and the second electrode 502.

Although this embodiment mode describes the light-emitting element having two light-emitting units, the present invention can be similarly applied to a light-emitting element in which three or more light-emitting units are stacked. When the charge-generating layer is provided between the pair of electrodes so as to partition the plural light-emitting units like the light-emitting element of this embodiment mode, the element can have long lifetime in a high luminous region while keeping low current density. When the light-emitting element is applied for illumination, voltage drop due to resistance of an electrode material can be reduced, thereby achieving homogeneous light emission in a large area. Moreover, a light-emitting device of low power consumption, which can be driven at low voltage, can be achieved.

This embodiment mode can be appropriately combined with another embodiment mode.

Embodiment Mode 7

Embodiment Mode 7 will explain a light-emitting device manufactured by using an aromatic amine compound of the present invention.

In this embodiment mode, a light-emitting device manufactured by using an aromatic amine compound of the present invention is explained with reference to FIGS. 3A and 3B. FIG. 3A is a top view of the light-emitting device, while FIG. 3B is a cross-sectional view along a line A-A' and a line B-B'. This light-emitting device includes a driver circuit portion (source side driver circuit) 601, a pixel portion 602, and a driver circuit portion (gate side driver circuit) 603 which are shown by dashed lines in order to control the light emission of the light-emitting element. Moreover, reference numeral 604 denotes a sealing substrate; 605, a sealant; and 607, a space surrounded by the sealant 605.

A lead wiring 608 is to transmit signals to be inputted to the source side driver circuit 601 and the gate side driver circuit 603 and receive a video signal, a clock signal, a start signal, a reset signal, and the like from an FPC (Flexible Printed Circuit) 609 which is an external input terminal. Although only an FPC is shown here, this FPC may have a printed wiring board (PWB) attached. In this specification, the light-emitting device includes not only a light-emitting device alone but also a light-emitting device with an FPC or a PWB attached thereto.

Next, the cross-sectional structure is explained with reference to FIG. 3B. Although the driver circuit portion and the pixel portion are formed over an element substrate 610, the source side driver circuit 601 as the driver circuit portion and one pixel in the pixel portion 602 are shown here.

In the source side driver circuit 601, a CMOS circuit in which an n-channel TFT 623 and a p-channel TFT 624 are combined is formed. The driver circuit may be formed by various CMOS circuits, PMOS circuits, or NMOS circuits. Although this embodiment mode shows a driver-integrated type in which the driver circuit is formed over the substrate, the structure may be different. For example, the driver circuit may be formed not over the substrate but outside the substrate.

Moreover, the pixel portion 602 is formed by a plurality of pixels including a switching TFT 611, a current controlling TFT 612, and a first electrode 613 electrically connected to a drain of the current controlling TFT 612. An insulator 614 is formed covering an end portion of the first electrode 613. Here, the insulator 614 is formed using a positive photosensitive acrylic resin film.

In order to have favorable coverage, the insulator 614 is formed so as to have a curved surface with curvature at its upper end or lower end portion. For example, in a case of using a positive photosensitive acrylic for the insulator 614, only the upper end portion of the insulator 614 preferably has a curved surface with a radius of curvature of 0.2 to 3 μm. As the insulator 614, either a negative type which becomes insoluble in etchant by light irradiation or a positive type which becomes soluble in etchant by light irradiation can be used.

A layer 616 containing a light-emitting substance and a second electrode 617 are formed over the first electrode 613. Here, the first electrode 613 functioning as an anode is preferably formed of a material with a high work function. For example, a single-layer film of an ITO film, an indium tin oxide film including silicon, an indium oxide film containing 2 to 20 wt % of zinc oxide, a titanium nitride film, a chromium film, a tungsten film, a Zn film, a Pt film, or the like can be used. Besides these single-layer films, a stack of a film containing titanium nitride as its main component and a film containing aluminum as its main component, a stack of three layers of a titanium nitride film, a film containing aluminum as its main component, and a titanium nitride film, or the like can be used. When a stacked-layer structure is employed, the first conductive film 613 can have low resistance as wiring, obtain favorable ohmic contact, and moreover function as an anode.

The layer 616 containing a light-emitting substance is formed by various methods such as an evaporation method using an evaporation mask, an inkjet method, or a spin coating method. The layer 616 containing a light-emitting substance includes the aromatic amine compound of the present invention shown in Embodiment Mode 1. As another material for forming the layer 616 containing a light-emitting substance, a low molecular material or a high molecular material (including oligomer and dendrimer) may be used.

The second electrode 617 which is formed over the layer 616 containing a light-emitting substance and functions as a cathode is preferably formed of a material with a low work function (Al, Mg, Li, Ca, or an alloy or compound thereof such as MgAg, MgIn, AlLi, LiF, or $CaF_2$). When light generated in the layer 616 containing a light-emitting substance passes through the second electrode 617, the second electrode 617 is preferably formed by a stack of a thin metal film and a transparent conductive film (ITO, indium oxide including 2 to 20 wt % of zinc oxide, indium tin oxide including silicon, zinc oxide (ZnO), or the like).

When the sealing substrate 604 and the element substrate 610 are attached to each other with the sealant 605, the light-emitting element 618 is provided in the space 607 surrounded by the element substrate 610, the sealing substrate 604, and the sealant 605. The space 607 is filled with a filler, which may be an inert gas (such as nitrogen or argon) or the sealant 605.

The sealant 605 is preferably formed of an epoxy-based resin. It is desirable that the material of the sealant 605 preferably allows as little moisture and oxygen as possible to penetrate. As the sealing substrate 604, a plastic substrate formed of FRP (Fiberglass-Reinforced Plastics), PVF (polyvinyl fluoride), polyester, acrylic, or the like can be used besides a glass substrate or a quartz substrate.

As described above, the light-emitting device manufactured by the aromatic amine compound of the present invention can be obtained.

The light-emitting device of the present invention uses the aromatic amine compound shown in Embodiment Mode 1; therefore, the light-emitting device can have favorable characteristics. In specific, the light-emitting device can have high luminous efficiency.

The aromatic amine compound expressed by General Formula (2) is superior in heat resistance. Therefore, the light-emitting device using the aromatic amine compound expressed by General Formula (2) can have excellent heat resistance.

Figure 4:
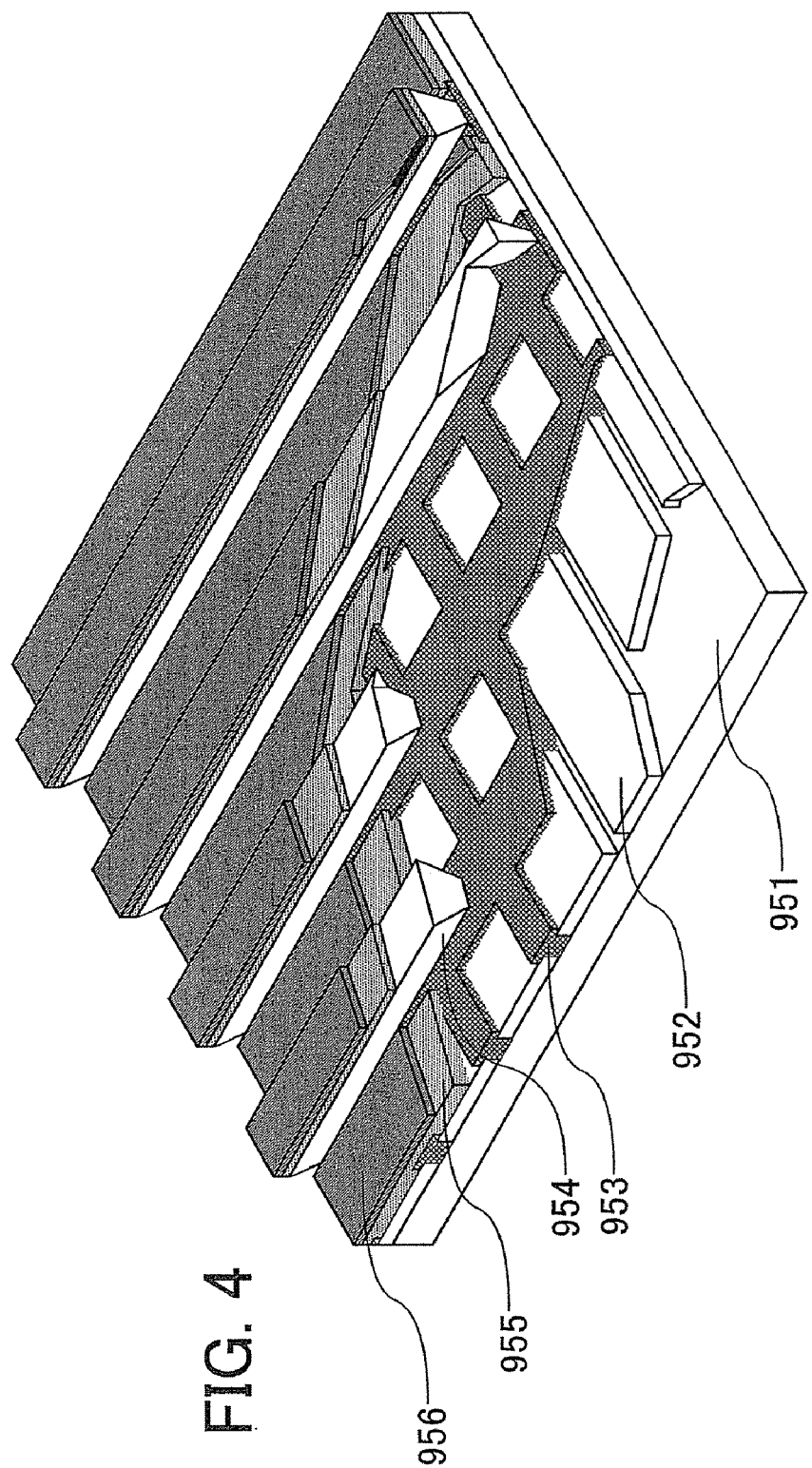
FIG. 4 explains a light-emitting device of the present invention.

This embodiment mode thus describes the active light-emitting device in which the driving of the light-emitting element is controlled by a transistor. However, the light-emitting device may be of passive type in which the light-emitting element is driven without particularly providing an element for driving, such as a transistor. FIG. 4 is a perspective view of a passive light-emitting device manufactured by applying the present invention. In FIG. 4, a layer 955 containing a light-emitting substance is provided over a substrate 951 and between an electrode 952 and an electrode 956. End portions of the electrode 952 are covered with an insulating layer 953. Then, a partition wall layer 954 is provided over the insulating layer 953. A side wall of the partition wall layer 954 slopes so that a distance between one side wall and the other side wall becomes narrow toward a substrate surface. In other words, a cross section of the partition wall layer 954 in the direction of a narrow side is trapezoidal, and a base (a side facing in a similar direction to a plane direction of the insulating layer 953 and being in contact with the insulating layer 953) is shorter than an upper side (a side facing in a similar direction to the plane direction of the insulating layer 953 and not being in contact with the insulating layer 953). A defect of the light-emitting element due to static electricity or the like can be prevented by providing the partition wall layer 954 in this manner. In addition, the passive-type light-emitting device can also have high luminous efficiency and excellent heat resistance when it includes the light-emitting element of the present invention with high luminous efficiency. Moreover, the high luminous efficiency leads to low power consumption.

Embodiment Mode 8

This embodiment mode explains an electronic appliance of the present invention which includes the light-emitting device described in Embodiment Mode 7 as its component. The electronic appliance of the present invention includes the aromatic amine compound of the present invention described in Embodiment Mode 1 and has a display portion with high heat resistance and high luminous efficiency. The high luminous efficiency leads to low power consumption.

Examples of the electronic appliance having the light-emitting element manufactured using the aromatic amine compound of the present invention include the following: a camera such as a video camera or a digital camera, a goggle type display, a navigation system, a sound reproducing device (a car audio system, an audio component, or the like), a computer, a game machine, a mobile information terminal (a mobile computer, a cellular phone, a mobile game machine, an electronic book, or the like), an image reproducing device having a recording medium (specifically, a device which reproduces a recording medium such as a digital versatile disc (DVD) and has a display device for displaying the image), and the like. Specific examples of these electronic appliances are shown in FIGS. 5A to 5D.

Figure 5A:
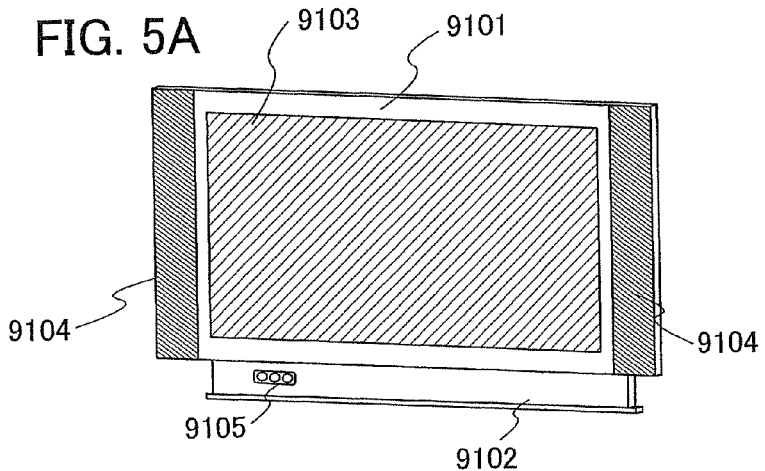
FIGS. 5A to 5D explain electronic appliances of the present invention.

FIG. 5A shows a television device according to the present invention, which includes a housing 9101, a support base 9102, a display portion 9103, speaker portions 9104, a video input terminal 9105, and the like. In this television device, the display portion 9103 includes light-emitting elements similar to those described in Embodiment Modes 2 to 6, which are arranged in matrix. The light-emitting element has features of high luminous efficiency and high heat resistance. The display portion 9103 which includes the light-emitting element also has a similar feature. Therefore, in this television device, image quality does not deteriorate much and power consumption is reduced. With such features, a deterioration compensation circuit and a power supply circuit can be significantly reduced or downsized in the television device, thereby achieving reduction in size and weight of the housing 9101 and the support base 9102. Since reduction in power consumption, improvement in image quality, and reduction in size and weight are achieved in the television device according to the present invention, a product which is suitable for a living environment can be provided.

Figure 5B:
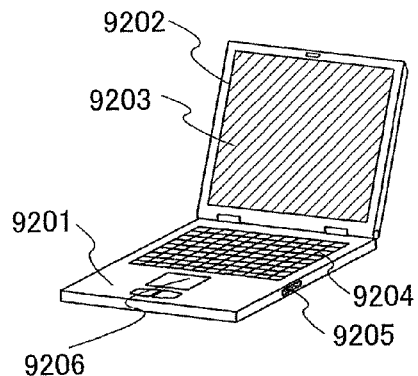

FIG. 5B shows a computer according to the present invention, which includes a main body 9201, a housing 9202, a display portion 9203, a keyboard 9204, an external connection port 9205, a pointing mouse 9206, and the like. In this computer, the display portion 9203 includes light-emitting elements similar to those described in Embodiment Modes 2 to 6, which are arranged in matrix. The light-emitting element has features of high luminous efficiency and high heat resistance. The display portion 9203 which includes the light-emitting element has a similar feature. Therefore, in this computer, image quality does not deteriorate much and power consumption is reduced. With such features, a deterioration compensation circuit and a power supply circuit can be significantly reduced or downsized in the computer, thereby achieving reduction in size and weight of the main body 9201 and the housing 9202. Since reduction in power consumption, improvement in image quality, and reduction in size and weight thereof are achieved in the computer according to the present invention, a product which is suitable for environment can be provided.

Figure 5C:
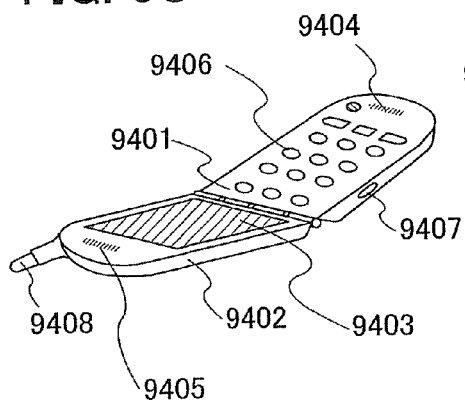

FIG. 5C shows a cellular phone according to the present invention, which includes a main body 9401, a housing 9402, a display portion 9403, an audio input portion 9404, an audio output portion 9405, operation keys 9406, an external connection port 9407, an antenna 9408, and the like. In this cellular phone, the display portion 9403 includes light-emitting elements similar to those described in Embodiment Modes 2 to 6, which are arranged in matrix. The light-emitting element has features of high luminous efficiency and high heat resistance. The display portion 9403 which includes the light-emitting element also has a similar feature. Therefore, in this cellular phone, image quality does not deteriorate much and power consumption is reduced. With such features, a deterioration compensation circuit and a power supply circuit can be significantly reduced or downsized in the cellular phone, thereby achieving reduction in size and weight of the main body 9401 and the housing 9402. Since reduction in power consumption, improvement in image quality, and reduction in size and weight thereof are achieved in the cellular phone according to the present invention, a product which is suitable for being carried can be provided.

Figure 5D:
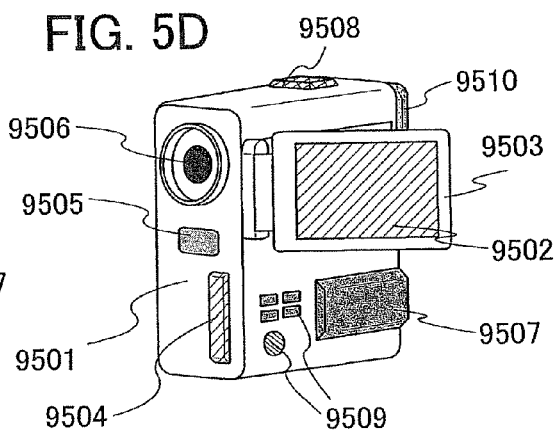

FIG. 5D shows a camera according to the present invention, which includes a main body 9501, a display portion 9502, a housing 9503, an external connection port 9504, a remote control receiving portion 9505, an image receiving portion 9506, a battery 9507, an audio input portion 9508, an operation key 9509, an eye piece portion 9510, and the like. In this camera, the display portion 9502 includes light-emitting elements similar to those described in Embodiment Modes 2 to 6, which are arranged in matrix. The light-emitting element has features of high luminous efficiency and high heat resistance. The display portion 9502 which includes the light-emitting element also has similar features. Therefore, in this camera, image quality does not deteriorate much and power consumption is reduced. With such features, a deterioration compensation circuit and a power supply circuit can be significantly reduced or downsized in the camera, thereby achieving reduction in size and weight of the main body 9501. Since reduction in power consumption, improvement in image quality, and reduction in size and weight thereof are achieved in the camera according to the present invention, a product which is suitable for being carried can be provided.

As described above, the applicable range of the light-emitting device of the present invention is so wide that the light-emitting device can be applied to electronic appliances of various fields. By the use of the aromatic amine compound of the present invention, an electronic appliance including a display portion with high luminous efficiency and high heat resistance can be provided.

In addition, the light-emitting device of the present invention can also be used as an illumination apparatus. One mode of using the light-emitting element of the present invention as an illumination apparatus is explained with reference to FIG. 6.

FIG. 6 shows an example of a liquid crystal display device using the light-emitting device of the present invention as a backlight. The liquid crystal display device shown in FIG. 6 includes a housing 901, a liquid crystal layer 902, a backlight 903, and a housing 904. The liquid crystal layer 902 is connected to a driver IC 905. The light-emitting device of the present invention is used as the backlight 903, to which current is supplied through a terminal 906.

By the use of the light-emitting device of the present invention as a backlight of the liquid crystal display device, the backlight can have high luminous efficiency. Since the light-emitting device of the present invention is a surface light-emitting illumination apparatus and can be formed to have a large area, a larger-area backlight can be obtained and a larger-area liquid crystal display device can also be obtained. Further, the light-emitting device of the present invention is thin and consumes less electric power; therefore, reduction in thickness and power consumption of the display device can also be achieved. Moreover, since the light-emitting device of the present invention is superior in heat resistance, the liquid crystal display device using the light-emitting device of the present invention is also superior in heat resistance.

Figure 7:
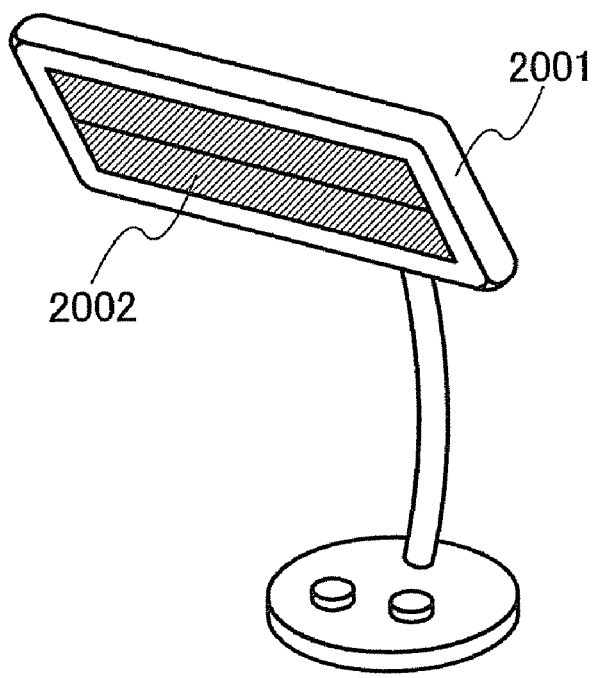
FIG. 7 explains a light-emitting device of the present invention.

FIG. 7 shows an example in which the light-emitting device of the present invention is used as a desk lamp, which is an illumination apparatus. The desk lamp shown in FIG. 7 includes a housing 2001 and a light source 2002. The light-emitting device of the present invention is used as the light source 2002. Since the light-emitting device of the present invention is capable of emitting light with high luminance, an elaborate operation and the like can be efficient by having the device at hand.

Figure 8:
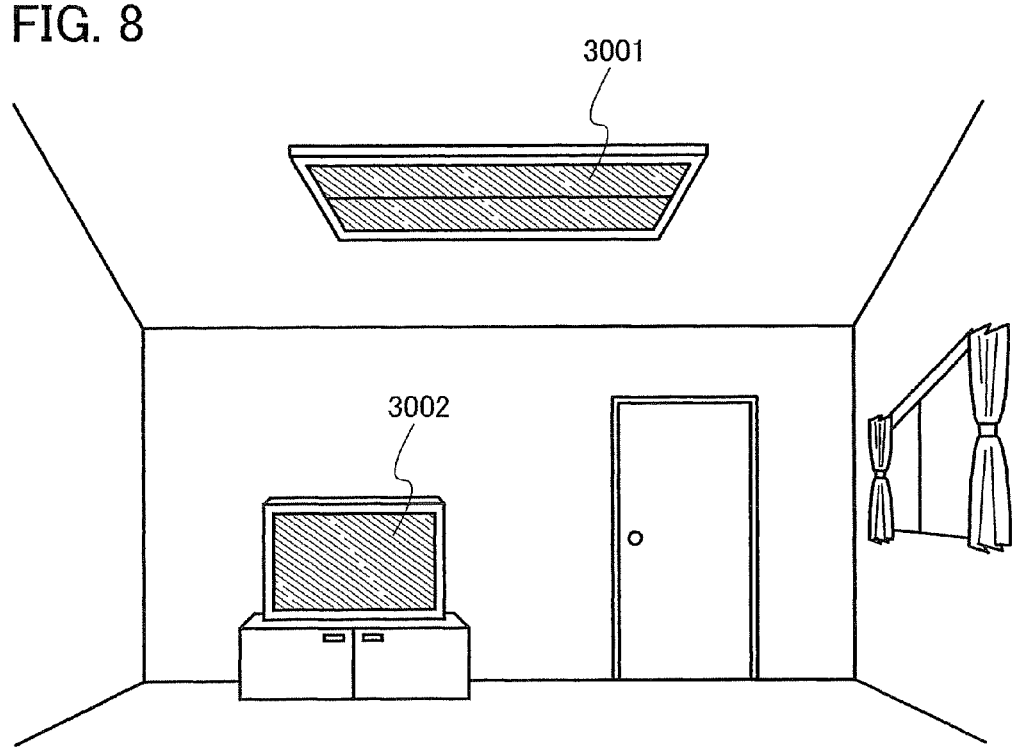
FIG. 8 explains light-emitting devices of the present invention.

FIG. 8 shows an example of using the light-emitting device of the present invention as an illumination apparatus 3001 in the room. Since the light-emitting device of the present invention can be enlarged, the light-emitting device can be used as a large-area illumination apparatus. Moreover, since the light-emitting device of the present invention is thin and consumes less electric power, the light-emitting device can be used as the thin illumination apparatus consuming less electric power. Thus, a television device 3002 of the present invention similar to the television device described with reference to FIG. 5A can be installed in the room using the light-emitting device of the present invention as the illumination apparatus 3001, so that pubic broadcasting and movies can be enjoyed. In such a case, since both of the television device and the illumination apparatus consume less electric power, it is possible to enjoy dynamic images in the bright room without worrying about electricity charges.

Embodiment 1

Embodiment 1 will explain a method of synthesizing N-[4-(carbazol-9-yl)phenyl]-N-phenyl-9,9-dimethylfluorenyl-2-amine (abbr: YGAF) expressed by Structure Formula (21).

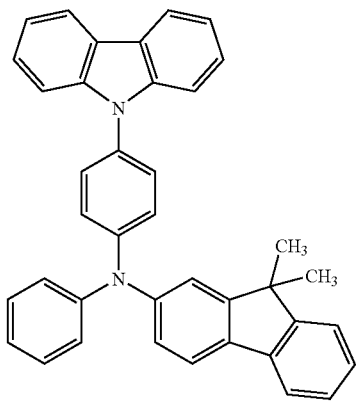

(21)

[Step 1]
A method of synthesizing 9-[4-(N-phenylamino)phenyl]carbazole (abbr.: YGA) is explained.

(i) Synthesis of N-(4-bromophenyl)carbazole

Synthesis Scheme (C-1) of N-(4-bromophenyl)carbazole is hereinafter shown.

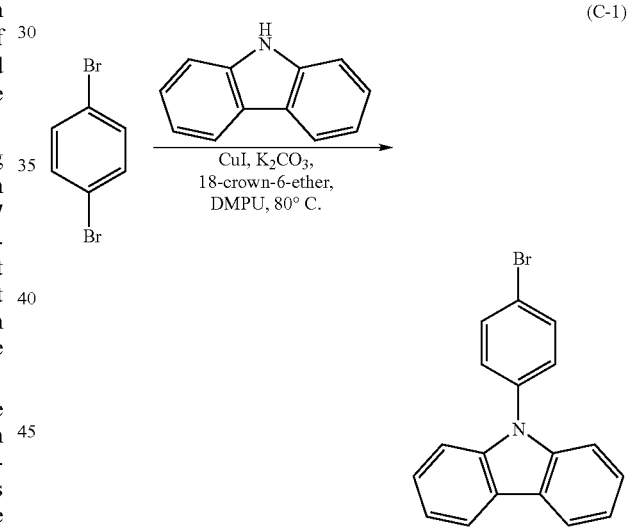

(C-1)

First, a method of synthesizing N-(4-bromophenyl)carbazole is explained. In a three-necked flask of 300 mL content, 56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were mixed and nitrogen substitution was carried out. Then, 8 mL of 1,3-dimethyl-3,4,5,6-tetrahydro-2(1H)-pyrimidinone (abbr.: DMPU) was added and stirred for six hours at 180° C. After the reaction mixture was cooled down to room temperature, the sediment was removed by suction filtration. The filtrate was washed with diluted hydrochloric acid, a saturated sodium hydrogen carbonate aqueous solution, and saturated saline in this order and then dried with magnesium sulfate. After the drying, the reaction mixture was naturally filtered and concentrated, and then the obtained oil-like substance was purified by silica gel column chromatography (hexane:ethyl acetate=9:1) and recrystallized by chloroform and hexane. Then, the target matter, i.e., a light-brown plate-like crystal of N-(4-bromophenyl)carbazole was obtained for 20.7 g with a yield of 35%. It was confirmed that this compound was N-(4-bromophenyl)carbazole by nuclear magnetic resonance spectroscopy (NMR).

The $^1$H-NMR data on this compound is shown. A $^1$H-NMR (300 MHz, CDCl$_3$): δ=8.14 (d, J=7.8 Hz, 2H), δ=7.73 (d, J=8.7 Hz, 2H), δ=7.46 (d, J=8.4 Hz, 2H), and δ=7.42-7.26 (m, 6H).

(ii) Synthesis of 9-[4-(N-phenylamino)phenyl]carbazole (abbr.: YGA)

Synthesis Scheme (C-2) of YGA is hereinafter shown.

maography (hexane:ethyl acetate=9:1), whereby 9-[4-(N-phenylamino)phenyl]carbazole (abbr.: YGA) as the target matter is obtained for 4.1 g with a yield of 73%. By the use of nuclear magnetic resonance spectroscopy (NMR), it was confirmed that this compound was 9-[4-(N-phenylamino)phenyl]carbazole (abbr.: YGA).

Figure 10A:
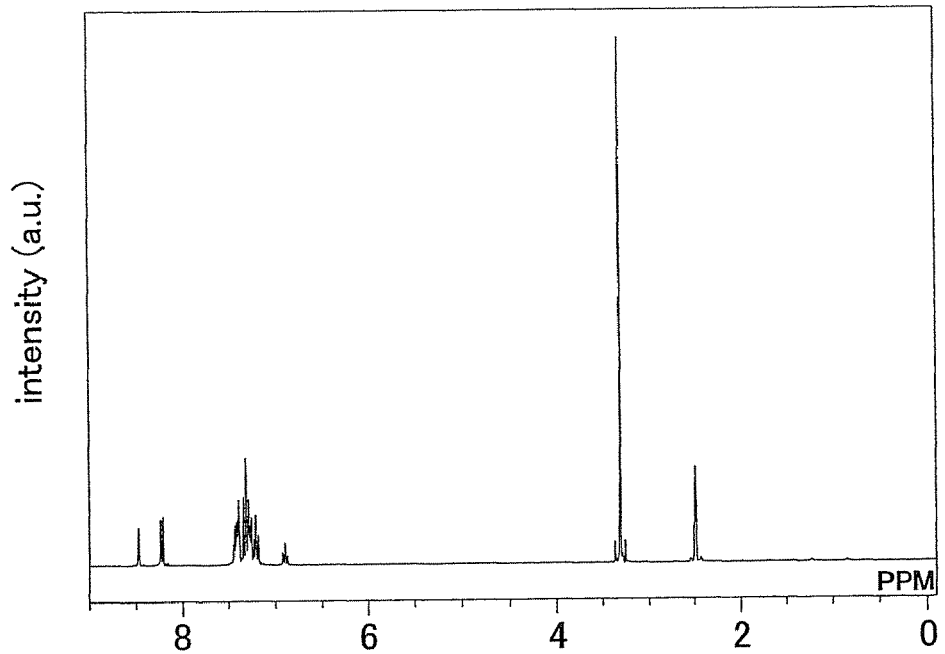
FIGS. 10A and 10B each show a $^1$H-NMR chart of 9-[4-(N-phenylamino)phenyl]carbazole.
Figure 10B:
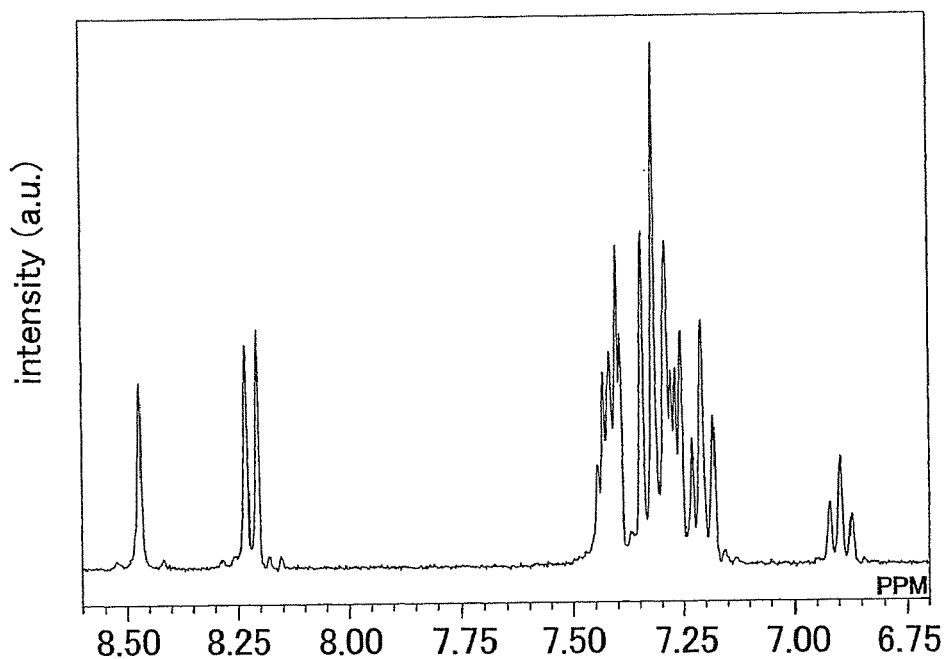

The $^1$H-NMR data on the compound is shown. A $^1$H-NMR (300 MHz, DMSO-d$_6$): δ=8.47 (s, 1H), δ=8.22 (d, J=7.8 Hz, 2H), δ=7.44-7.16 (m, 14H), and δ=6.92-6.87 (m, 1H). In addition, a $^1$H-NMR chart is also shown in FIGS. 10A and 10B. FIG. 10B is a chart showing an enlarged part in the range of 6.7 ppm to 8.6 ppm of FIG. 10A.

[Step 2]

A method of synthesizing N-[4-(carbazol-9-yl)phenyl]-N-phenyl-9,9-dimethylfluorenyl-2-amine (abbr.: YGAF) expressed by Structure Formula (21) is explained. Synthesis Scheme (D-1) is shown below.

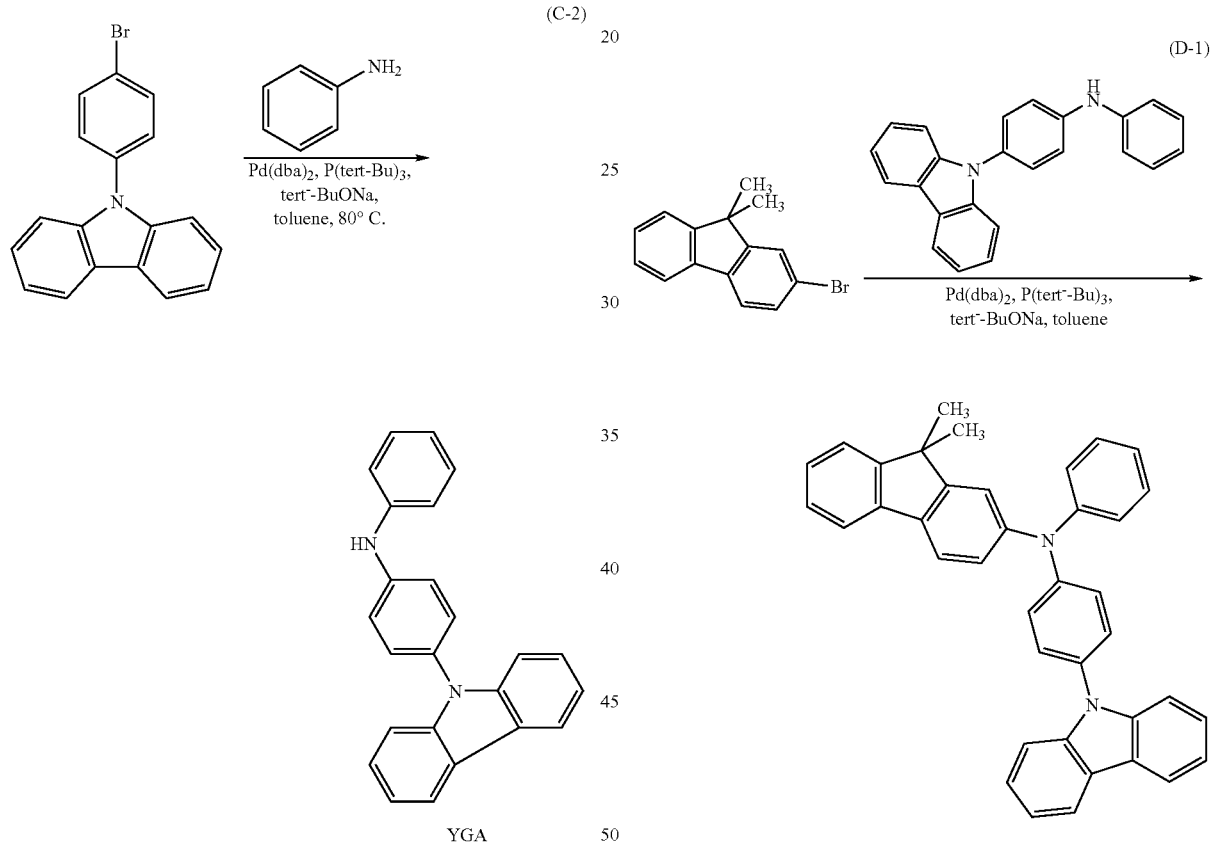

In a three-necked flask of 200 mL content, 5.4 g (17.0 mmol) of N-(4-bromophenyl)carbazole obtained by the aforementioned step (i), 1.8 mL (20.0 mmol) of aniline, 100 mg (0.17 mmol) of bis(dibenzylideneacetone)palladium(0), and 3.9 g (40 mmol) of sodium tert-butoxide were mixed and nitrogen substitution was carried out. Then, 0.1 mL of tri(tert-butyl)phosphine (10 wt % hexane solution) and 50 mL of toluene were added and stirred for six hours at 80° C. After the reaction mixture was filtered through Florisil, celite, and alumina, the filtrate was washed with water or saturated saline and then dried with magnesium sulfate. The reaction mixture was naturally filtered and concentrated, and then the obtained oil-like substance was purified by silica gel column chro- In a three-necked flask of 300 mL content, 2.9 g (10 mmol) of 2-bromo-9,9-dimethylfluorene, 3.34 g (10 mmol) of 4-(carbazol-9-yl)diphenylamine, 115 mg (0.2 mmol) of bis(dibenzylideneacetone)palladium(0), and 3.0 g (31.2 mmol) of tert-butoxysodium were mixed and nitrogen substitution was carried out. Then, 100 mL of toluene and 0.2 mL of tri(tert-butyl)phosphine (10 wt % hexane solution) were added and stirred for five hours at 80° C. After the reaction, the reaction solution was filtered through celite, Florisil, and alumina, the filtrate was washed with water, and a water layer was abstracted with toluene. The abstracted solution was washed with saturated saline together with an organic layer and then dried with magnesium sulfate. After the obtained reaction mixture was naturally filtered, the filtrate was concentrated to obtain a solid. When the solid was purified with silica gel column chromatography (hexane:toluene=7:3), 3.6 g of a white solid, which is a target matter, was obtained with a yield of 64%. It was confirmed by nuclear magnetic resonance spectroscopy (NMR) that this compound was N-[4-(carbazol-9-yl)phenyl]-N-phenyl-9,9-dimethylfluorenyl-2-amine (abbr.: YGAF) expressed by Structure Formula (21).

Figure 11A:
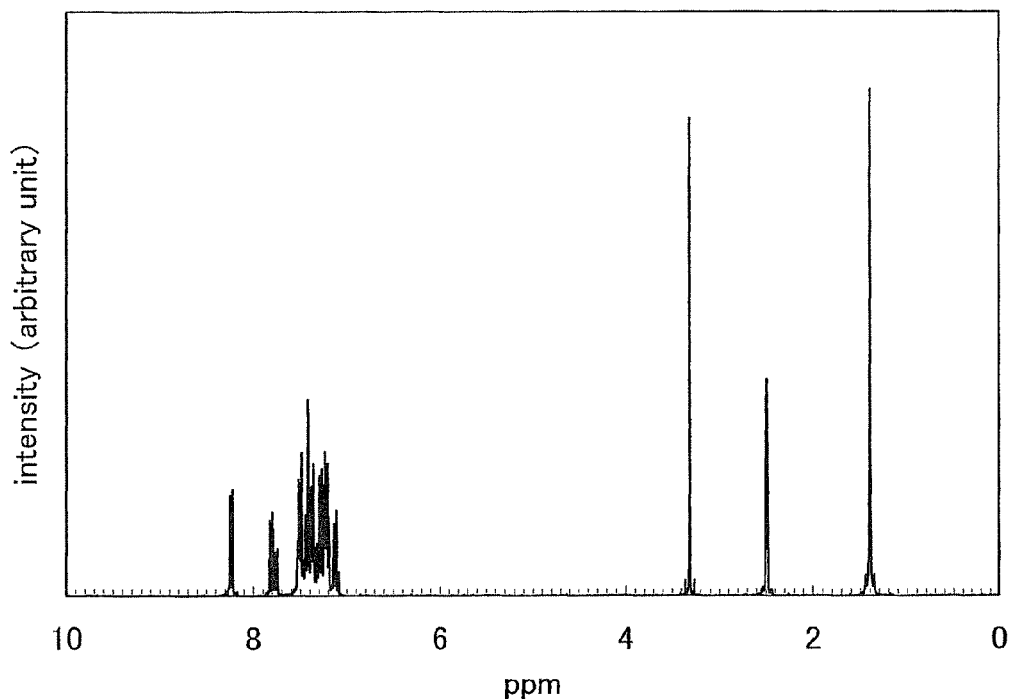
FIGS. 11A and 11B each show a $^1$H-NMR chart of N-[4-(carbazol-9-yl)phenyl]-N-phenyl-9,9-dimethylfluorenyl-2-amine.
Figure 11B:
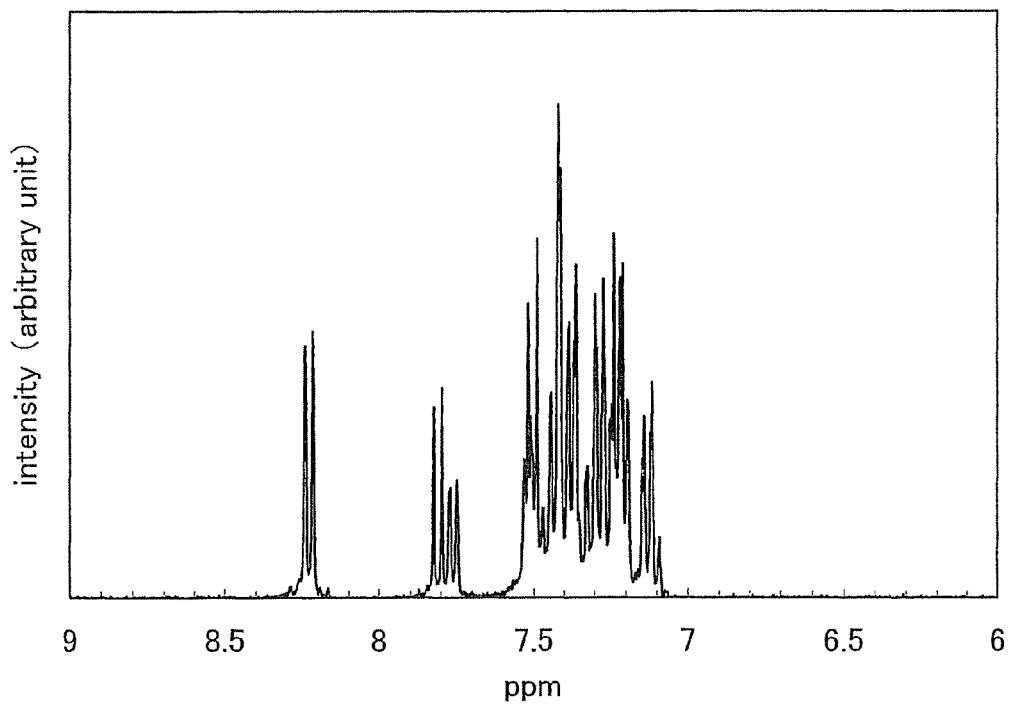

The $^1$H-NMR data on this compound are shown. The $^1$H-NMR (300 MHz, DMSO-d$_6$): δ=1.40 (s, 6H), 7.09-7.53 (m, 20H), 7.75-7.77 (m, 1H), 7.81 (d, J=8.4 Hz, 1H), and 8.23 (d, J=7.5 Hz, 2H). A $^1$H-NMR chart is also shown in FIGS. 11A and 11B. Further, FIG. 11B is a chart showing an enlarged part in the range of 6.0 ppm to 9.0 ppm of FIG. 11A.

The obtained YGAF with an amount of 635 mg was then purified by sublimation for 12 hours at 230° C. under 200 Pa in the flow of argon gas at a rate of 20.0 mL/min; thus, 485 mg of a light yellow solid of YGAF was obtained with a yield of 76%.

Further, when a decomposition temperature ($T_d$) of the thus obtained YGAF was measured by a thermo-gravimetric/differential thermal analyzer (TG/DTA 320, manufactured by Seiko Instruments Inc.), the $T_d$ was 313° C.

Figure 12:
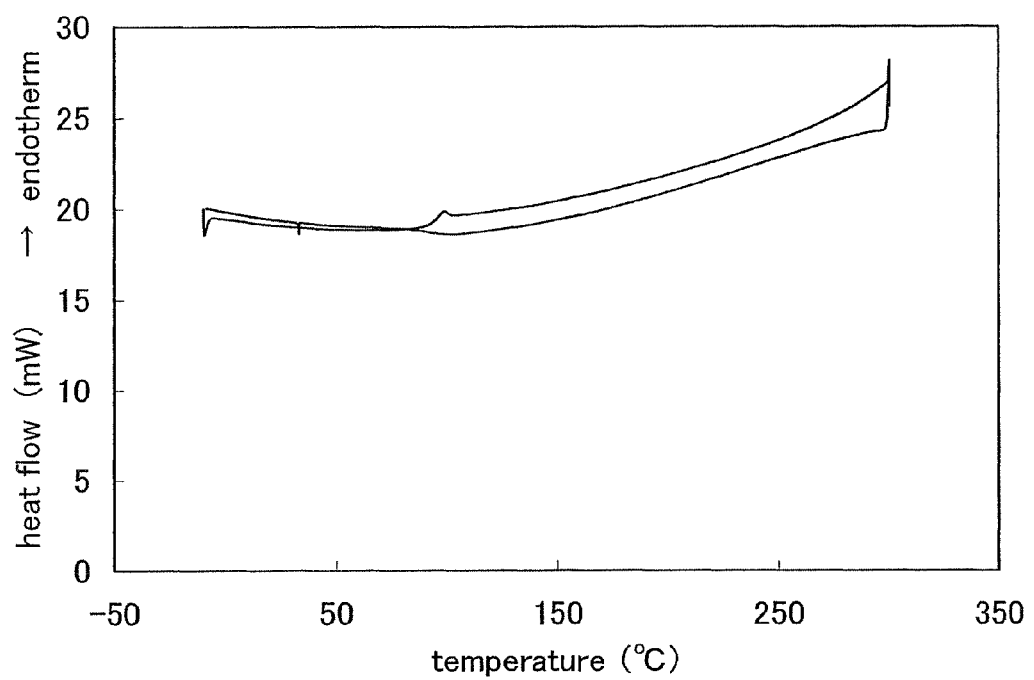
FIG. 12 shows a DSC chart of N-[4-(carbazol-9-yl)phenyl]-N-phenyl-9,9-dimethylfluorenyl-2-amine.

In addition, the glass transition point was measured by a differential scanning calorimeter (DSC, manufactured by PerkinElmer, Inc., Pyris 1). First, a sample was heated up to 300° C. at 40° C./min, and then it was cooled down to room temperature at 40° C./min. After that, the temperature was raised to 300° C. at 10° C./min and then lowered to room temperature at 10° C./min, thereby obtaining the DSC chart shown in FIG. 12. In FIG. 12, the X axis shows temperature and the Y axis shows heat flow. The Y axis shows endotherm in an upward direction. It was understood from this chart that the glass transition point ($T_g$) of YGAF was 91° C.

Figure 13:
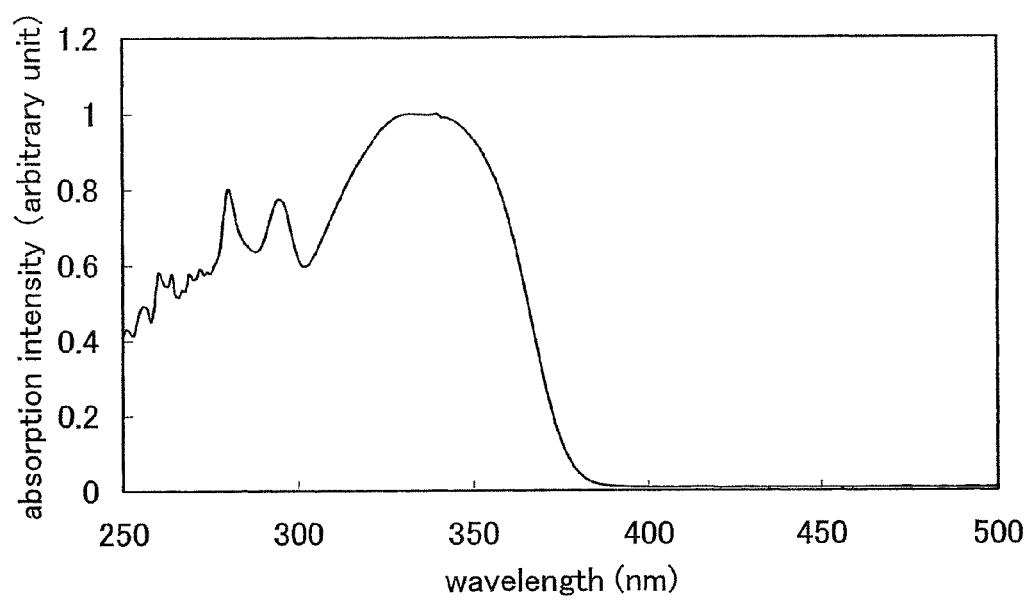
FIG. 13 shows an absorption spectrum of a toluene solution of N-[4-(carbazol-9-yl)phenyl]-N-phenyl-9,9-dimethylfluorenyl-2-amine.
Figure 14:
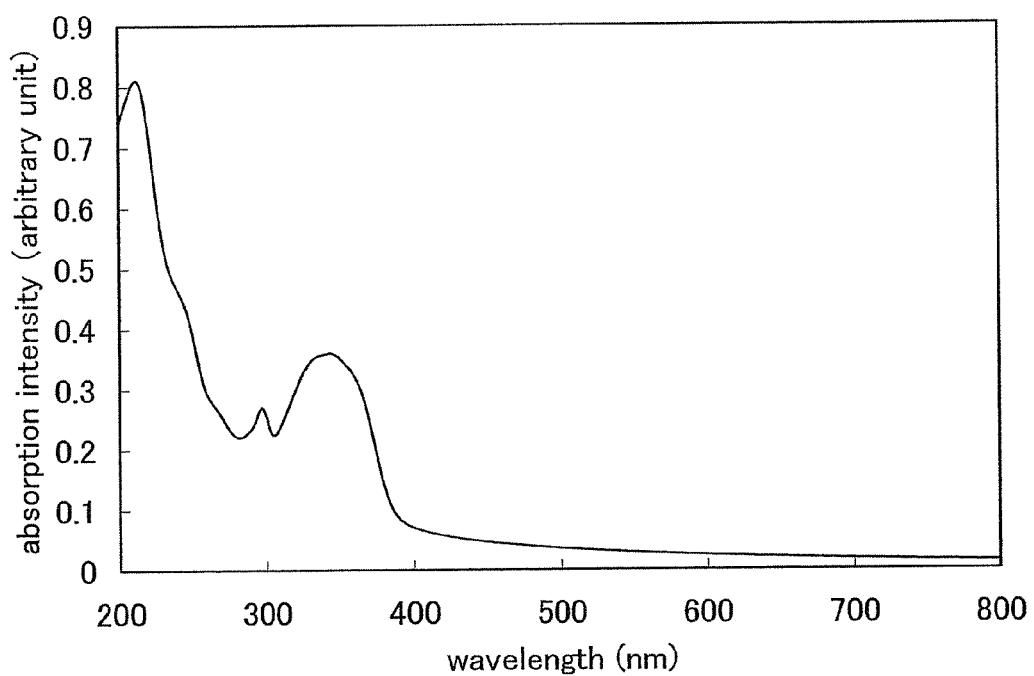
FIG. 14 shows an absorption spectrum of a thin film of N-[4-(carbazol-9-yl)phenyl]-N-phenyl-9,9-dimethylfluorenyl-2-amine.
Figure 15:
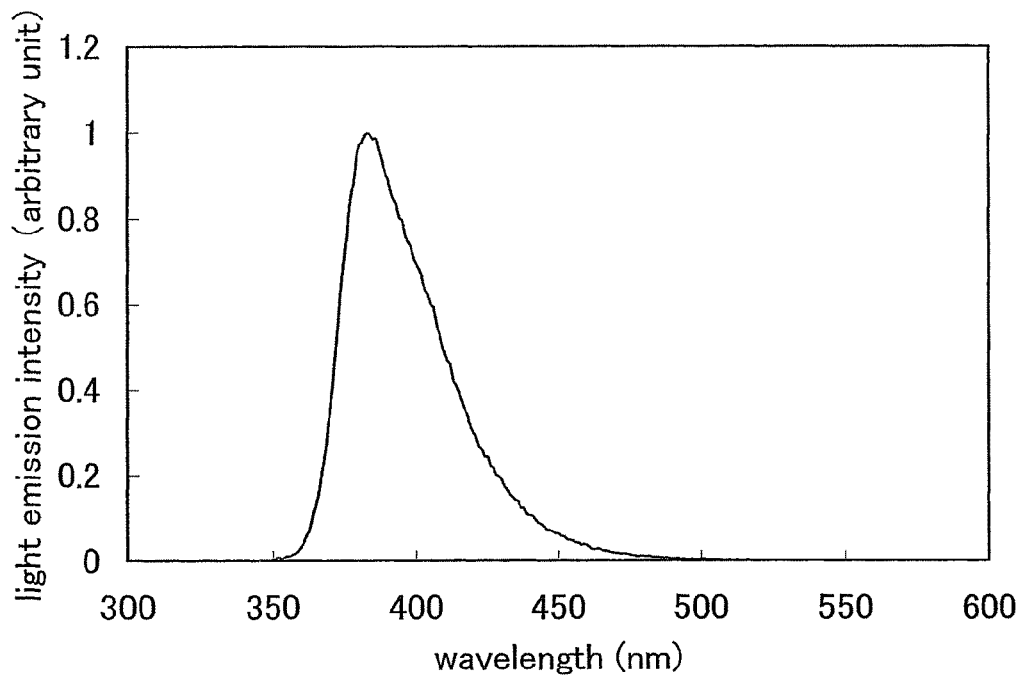
FIG. 15 shows a light emission spectrum of a toluene solution of N-[4-(carbazol-9-yl)phenyl]-N-phenyl-9,9-dimethylfluorenyl-2-amine.
Figure 16:
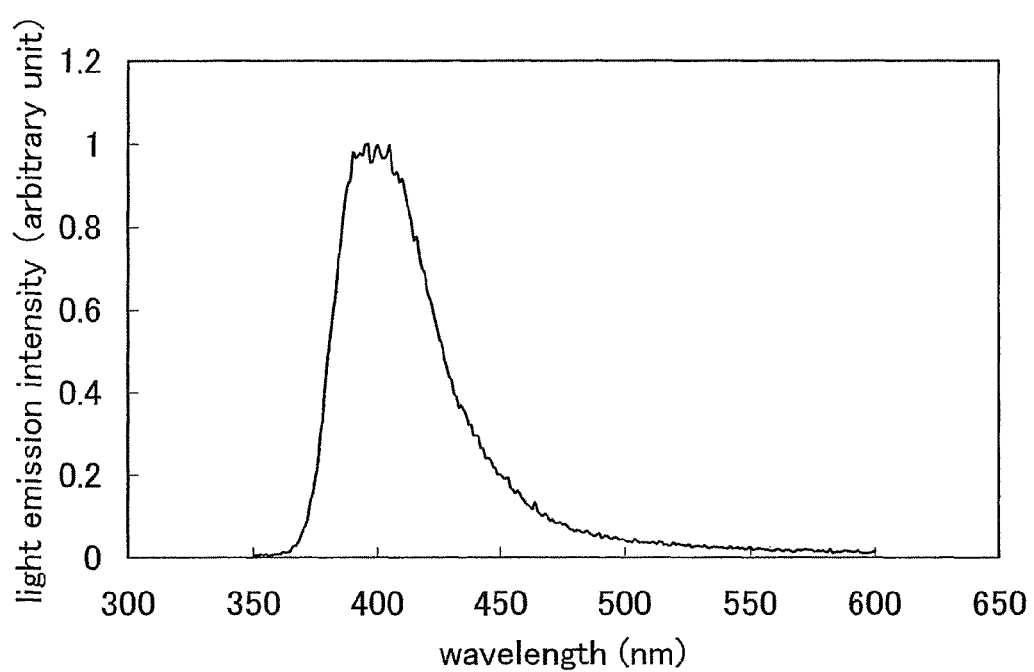
FIG. 16 shows a light emission spectrum of a thin film of N-[4-(carbazol-9-yl)phenyl]-N-phenyl-9,9-dimethylfluorenyl-2-amine.

FIG. 13 shows an absorption spectrum of a toluene solution of YGAF. FIG. 14 shows an absorption spectrum of a thin film of YGAF. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIGS. 13 and 14. In FIGS. 13 and 14, the horizontal axis shows a wavelength (nm) while the vertical axis shows absorption intensity (arbitrary unit). In the case of the toluene solution, absorption was observed at around 326 to 362 nm, and in the case of the thin film, it was observed at around 343 nm. The light emission spectrum of the toluene solution of YGAF (excitation wavelength: 340 nm) is shown in FIG. 15, while that of the thin film of YGAF (excitation wavelength: 343 nm) is shown in FIG. 16. In FIGS. 15 and 16, the horizontal axis shows a wavelength (nm) and the vertical axis shows light emission intensity (arbitrary unit). The maximum light emission wavelength was 384 nm in the case of the toluene solution (excitation wavelength: 340 nm), and 396 nm in the case of the thin film (excitation wavelength: 343 nm).

In addition, the HOMO level of YGAF in the thin film state was −5.39 eV, which was measured by photoelectron spectrometer (AC-2, manufactured by Riken Keiki Co., Ltd.) in the air. Moreover, the absorption edge was obtained from Tauc plot using data on the absorption spectrum of the thin film of YGAF in FIG. 14. When the absorption edge was estimated as an optical energy gap, the energy gap was 3.25 eV. Therefore, the LUMO level was −2.14 eV.

Moreover, the oxidation reaction characteristic of YGAF was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode. It is to be noted that the measurement was conducted at room temperature.

The oxidation reaction characteristic of YGAF was measured as follows. A scan for changing the potential of the work electrode with respect to the reference electrode from 0.8 V to −0.12 V after changing the potential from −0.12 V to 0.8 V was set as one cycle, and 100 cycles were measured. Further, the scanning speed of the CV measurement was set to be 0.1 V/s.

Figure 17:
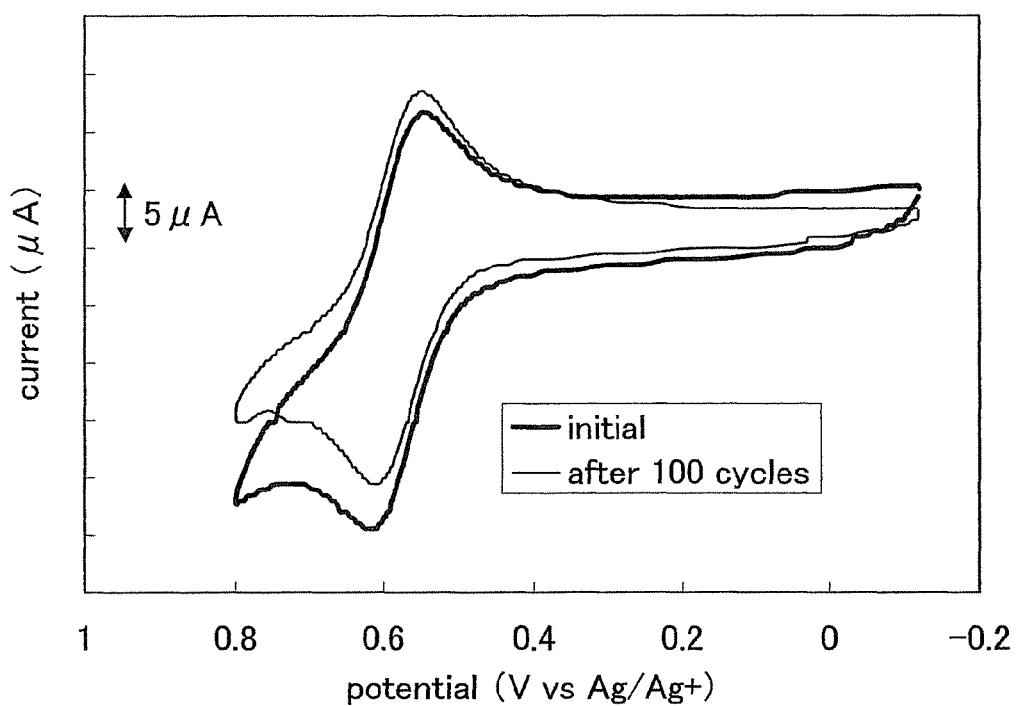
FIG. 17 shows a CV measurement result of N-[4-(carbazol-9-yl)phenyl]-N-phenyl-9,9-dimethylfluorenyl-2-amine.

A result of the measurement on the oxidation reaction characteristic of YGAF is shown in FIG. 17, in which the horizontal axis shows the potential (V) of the work electrode with respect to the reference electrode, while the vertical axis shows a value (μA) of current flowing between the work electrode and the auxiliary electrode.

In FIG. 17, a current indicating oxidation was observed at around 0.62 V (vs. Ag/Ag$^+$ electrode). Regardless of the repetition of 100-cycle scans, the peak position and the peak intensity at the CV curve hardly changes in the oxidation reaction. Based on this fact, it was understood that the aromatic amine compound of the present invention is quite stable against the oxidation reaction and the subsequent reduction reaction (that is, repetition of oxidation).

An optimal molecular structure of YGAF in a ground state was calculated with B3LYP/6-311 (d, p) of density functional theory (DFT). The accuracy of calculation of the DFT is higher than that of Hartree-Fock (HF) which does not consider electron correlation. In addition, the calculation cost of the DFT is lower than that of a method of perturbation (MP) which has the same level accuracy of calculation as the DFT. Therefore, the DFT was employed in the present calculation. The calculation was performed using a high-performance computer (HPC) (manufactured by SGI Japan, Ltd., Altix3700 DX).

In addition, the triplet-excitation energy (energy gap) of YGAF was calculated by employing B3LYP/6-311 (d, p) of time-dependent density functional theory (TDDFT) for the molecular structure whose structure was optimized by the DFT. The triplet-excitation energy was calculated to be 2.70 eV. Thus, it was understood from the calculation result that the aromatic amine compound of the present invention has high triplet-excitation energy.

Embodiment 2

This embodiment will explain a method of synthesizing 4-(carbazol-9-yl)phenyl-4'-phenyltriphenylamine (abbr.: YGA1BP) expressed by Structure Formula (52). Synthesis Scheme (D-2) is shown below.

(52)

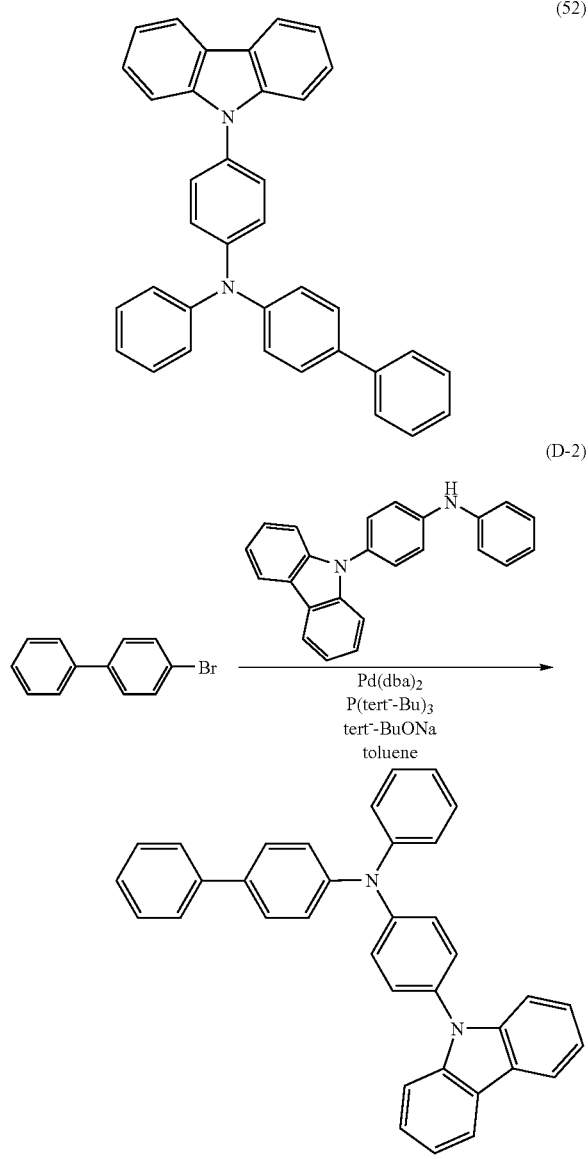

(D-2)

In a three-necked flask of 300 mL content, 2.33 g (10 mmol) of 4-bromobiphenyl, 3.30 g (10 mmol) of 4-(carbazol-9-yl)diphenylamine, 56 mg (0.1 mmol) of bis(dibenzylideneacetone)palladium(0), and 3.0 g (31.2 mmol) of tert-butoxysodium were put and nitrogen substitution was carried out. Then, 20 mL of toluene and 0.1 mL of tri(tert-butyl)phosphine (10 wt % hexane solution) were added and stirred for five hours at 80° C. After the reaction, the reaction mixture was filtered through celite, Florisil, and alumina, the filtrate was washed with water, and a water layer was abstracted with toluene. The abstracted solution was washed with saturated saline together with an organic layer and then dried with magnesium sulfate. After the obtained reaction mixture was naturally filtered, the filtrate was concentrated to obtain a solid. When the solid was purified with silica gel column chromatography (hexane:toluene=7:3) and the obtained solid was recrystallized by toluene and hexane, 4.2 g of a white powder-like solid, which is a target matter, was obtained with a yield of 86%. It was confirmed by nuclear magnetic resonance spectroscopy (NMR) that this compound was 4-(9-carbazol-9-yl)phenyl-4'-phenyltriphenylamine (abbr.: YGA1BP) expressed by Structure Formula (52).

Figure 18A:
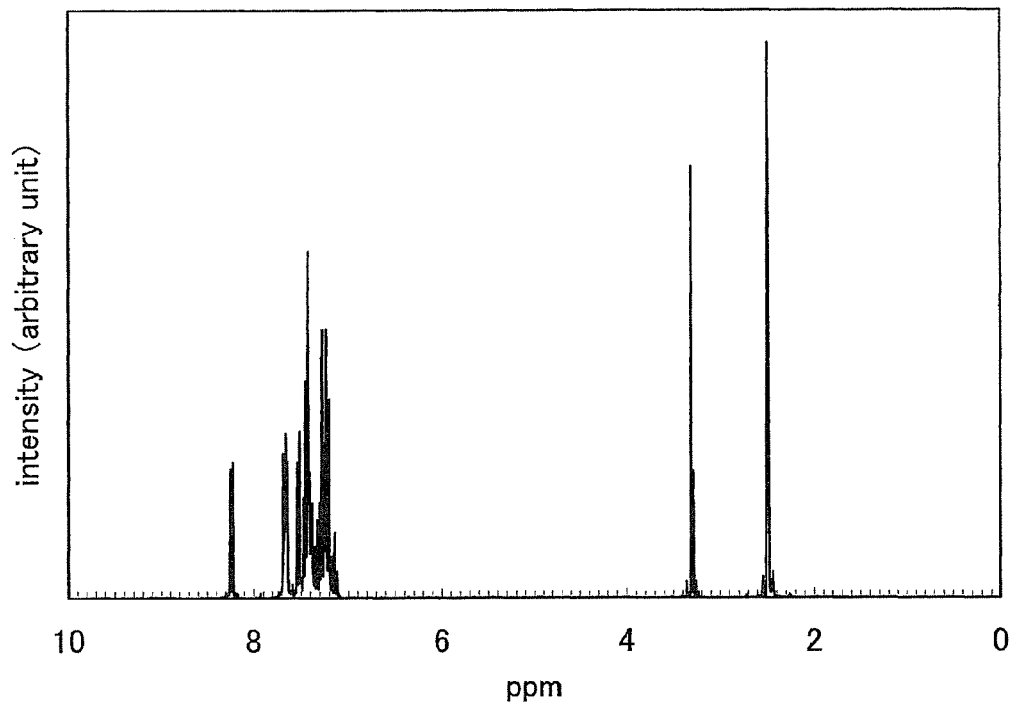
FIGS. 18A and 18B each show a $^1$H-NMR chart of 4-(carbazol-9-yl)phenyl-4'-phenyltriphenylamine.
Figure 18B:
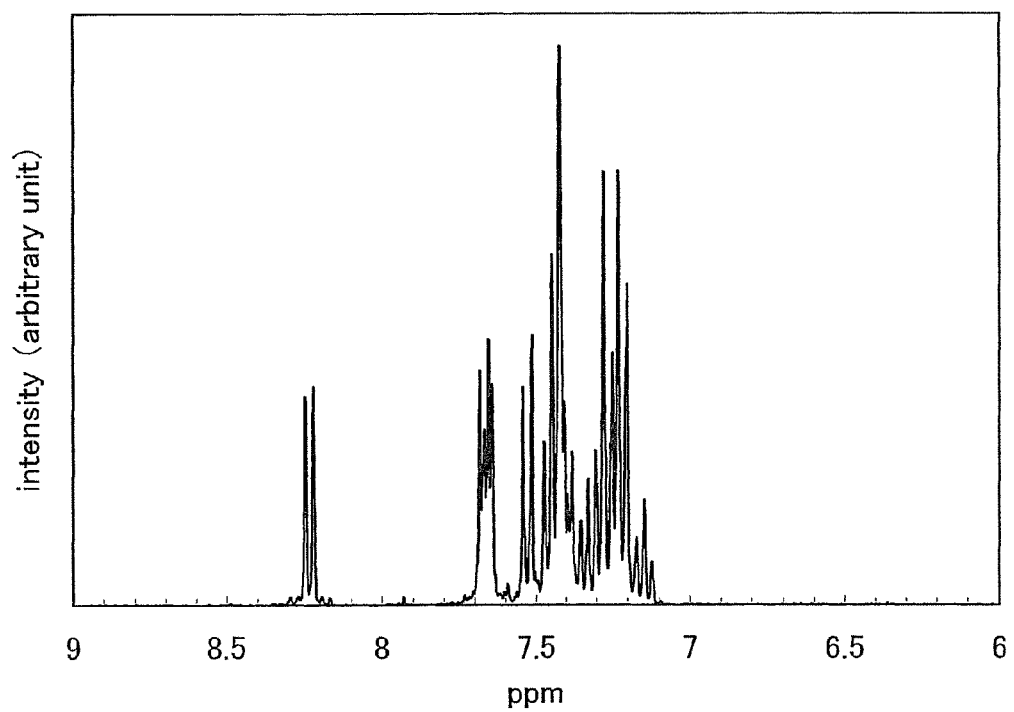

The $^1$H-NMR data on this compound are shown. The $^1$H-NMR (300 MHz, DMSO-$d_6$) $\delta$=7.12-7.47 (m, 18H), 7.53 (d, J=8.7 Hz, 2H), 7.68-7.64 (m, 4H), and 8.23 (d, J=7.8 Hz, 2H). A $^1$H-NMR chart is also shown in FIGS. 18A and 18B. Further, FIG. 18B is a chart showing an enlarged part in the range of 6.0 ppm to 9.0 ppm of FIG. 18A.

The obtained YGA1BP with an amount of 694 mg was then purified by sublimation for five hours at 280° C. under 200 Pa in the flow of argon gas at a rate of 20.0 mL/min; thus, 544 mg of an achromatous solid of YGA1BP was obtained with a yield of 78%.

A thermogravimetry-differential thermal analysis (TG-DTA) of YGA1BP was conducted by using a high vacuum differential type differential thermal balance (manufactured by Bruker AXS K.K., DTA2410SA). When the measurement was conducted under normal pressure with a temperature-rising speed of 10° C./min, the temperature at which the weight becomes 95% or lower of the weight at the start of the measurement was 398° C. from the relation between the weight and temperature (thermogravimetry).

Figure 19:
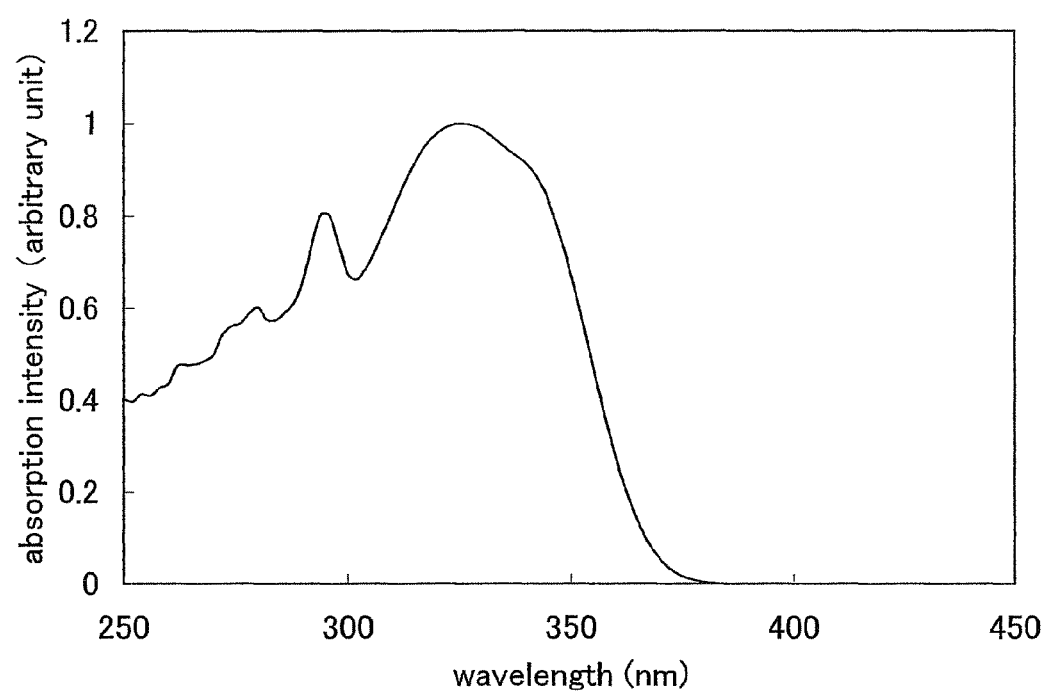
FIG. 19 shows a DSC chart of 4-(carbazol-9-yl)phenyl-4'-phenyltriphenylamine.
Figure 20:
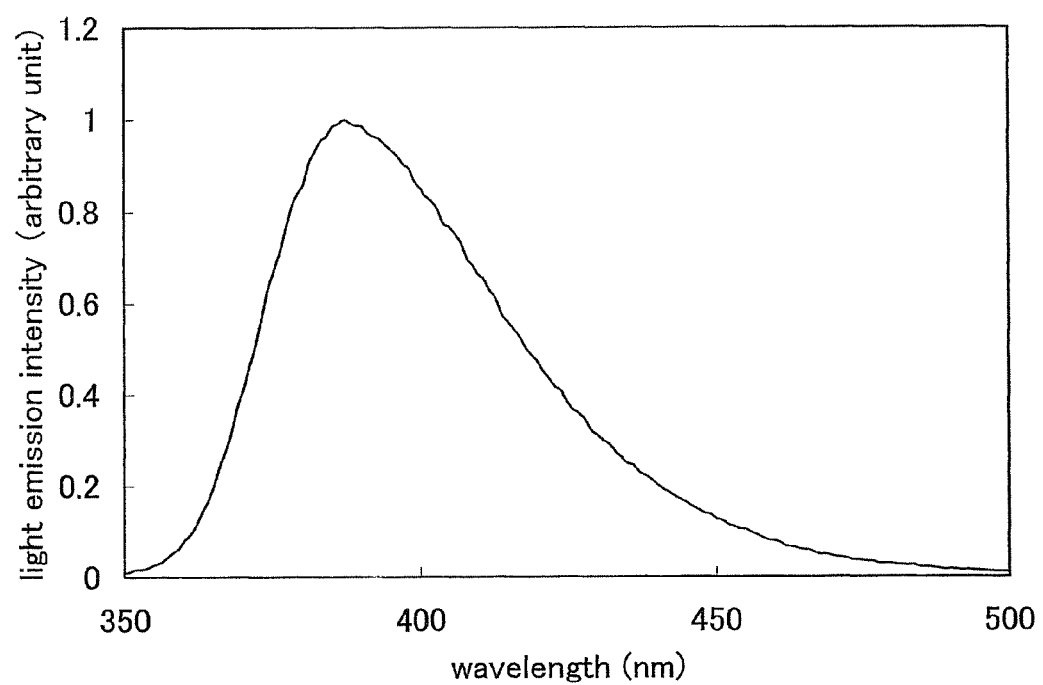
FIG. 20 shows a light emission spectrum of a toluene solution of 4-(carbazol-9-yl)phenyl-4'-phenyltriphenylamine.

FIG. 19 shows an absorption spectrum of a toluene solution of YGA1BP. The measurement was conducted by using a UV-visible spectrophotometer (V-550, manufactured by Japan Spectroscopy Corporation). The solution was put in a quartz cell. The absorption spectrum from which the absorption spectrum of quartz is subtracted is shown in FIG. 19. In FIG. 19, the horizontal axis shows a wavelength (nm) while the vertical axis shows absorption intensity (arbitrary unit). In the case of the toluene solution, absorption was observed at around 324 nM. The light emission spectrum of the toluene solution of YGA1BP (excitation wavelength: 340 nm) is shown in FIG. 20. In FIG. 20, the horizontal axis shows a wavelength (nm) and the vertical axis shows light emission intensity (arbitrary unit). The maximum light emission wavelength was 387 nm in the case of the toluene solution (excitation wavelength: 340 nm).

An optimal molecular structure of YGA1BP in a ground state was calculated with B3LYP/6-311 (d, p) of density functional theory (DFT). The accuracy of calculation of the DFT is higher than that of Hartree-Fock (HF) which does not consider electron correlation. In addition, the calculation cost of the DFT is lower than that of a method of perturbation (MP) which has the same level accuracy of calculation as the DFT. Therefore, the DFT was employed in the present calculation. The calculation was performed using a high-performance computer (HPC) (manufactured by SGI Japan, Ltd., Altix3700 DX).

In addition, the triplet-excitation energy (energy gap) of YGA1BP was calculated by employing B3LYP/6-311 (d, p) of time-dependent density functional theory (TDDFT) for the molecular structure whose structure was optimized by the DFT. The triplet-excitation energy was calculated to be 2.87 eV. Thus, it was understood from the calculation result that the aromatic amine compound of the present invention has high triplet-excitation energy.

Embodiment 3

This embodiment will explain a method of synthesizing N,N'-bis[4-(carbazol-9-yl)phenyl]-N,N'-diphenyl-9,9-dimethylfluorene-2,7-diamine (abbr.: YGA2F) expressed by Structure Formula (71). Synthesis Scheme (D-3) is shown below.

(71)

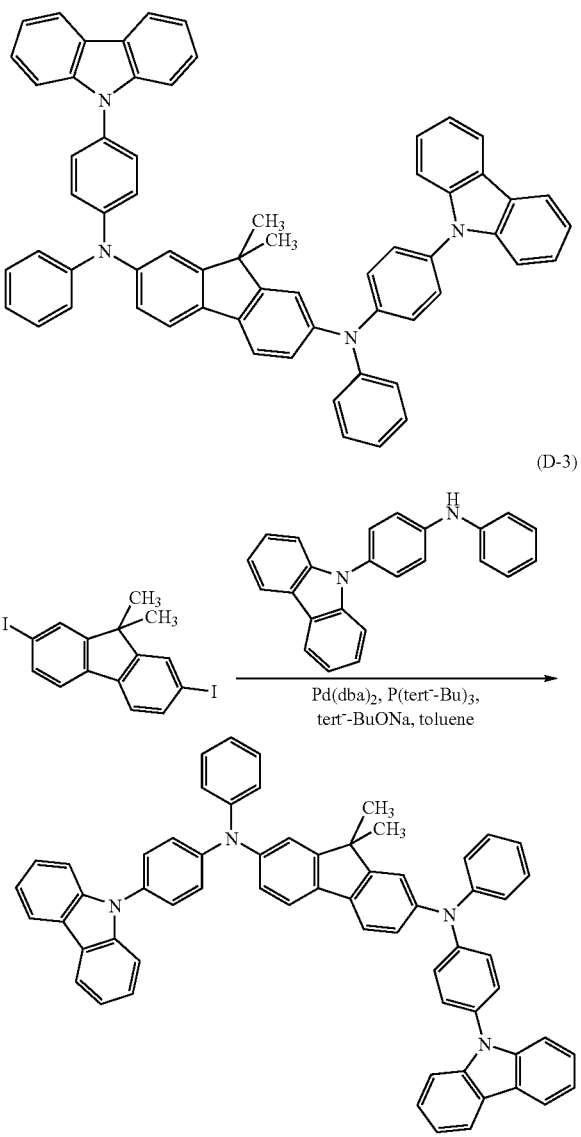

(D-3)

In a three-necked flask of 300 mL content, 1.7 g (3.8 mmol) of 2,7-diiodo-9,9-dimethylfluorene, 2.5 g (7.6 mmol) of 4-(carbazol-9-yl)diphenylamine, 44 mg (0.2 mmol) of bis(dibenzylideneacetone)palladium(0), and 2.0 g (20 mmol) of tert-butoxysodium were put and nitrogen substitution was carried out. Then, 30 mL of toluene and 0.1 mL of tri(tert-butyl)phosphine (10 wt % hexane solution) were added and stirred for 12 hours at 80° C. After the reaction, the reaction mixture was filtered through celite, Florisil, and alumina, the filtrate was washed with water, and a water layer was abstracted with toluene. The abstracted solution was washed with saturated saline together with an organic layer and then dried with magnesium sulfate. After the obtained reaction mixture was naturally filtered, the filtrate was concentrated to obtain a solid. When the solid was purified with silica gel column chromatography (hexane:toluene=6:4) and the obtained compound was recrystallized by toluene and hexane, 2.9 g of a light yellow powder-like solid, which is a target matter, was obtained with a yield of 89%. It was confirmed by nuclear magnetic resonance spectroscopy (NMR) that this compound was N,N'-bis[4-(carbazol-9-yl)phenyl]-N,N'-diphenyl-9,9-dimethylfluorene-2,7-diamine (abbr.: YGA2F) expressed by Structure Formula (71).

Figure 21A:
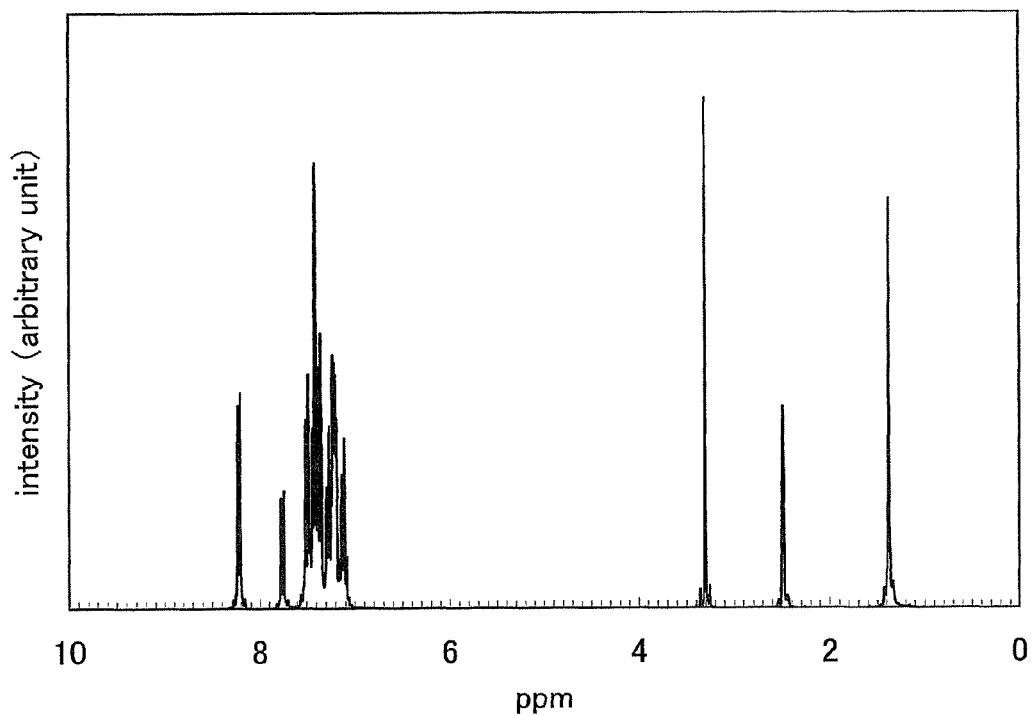
FIGS. 21A and 21B each show a $^1$H-NMR chart of N,N'-bis[4-(carbazol-9-yl)phenyl]-N,N'-diphenyl-9,9-dimethylfluorene-2,7-diamine.
Figure 21B:
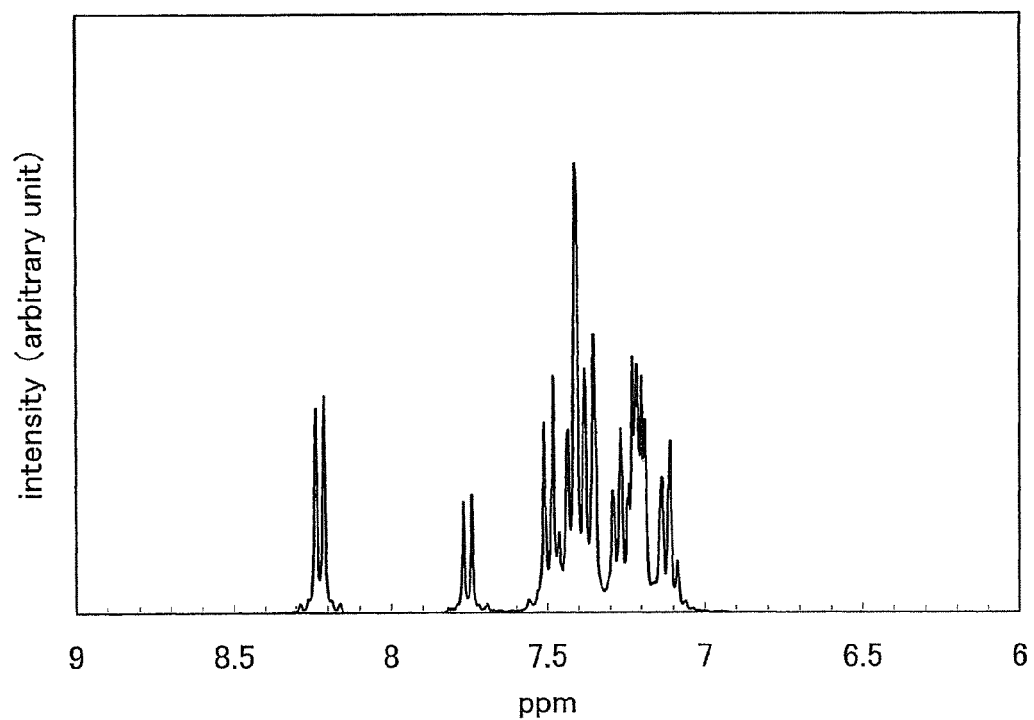

The $^1$H-NMR data on this compound are shown. The $^1$H-NMR (300 MHz, DMSO-$d_6$): δ=1.37 (s, 6H), 7.06-7.51 (m, 34H), 7.76 (d, J=8.4 Hz, 2H), and 8.22 (d, J=7.8 Hz, 4H). A $^1$H-NMR chart is also shown in FIGS. 21A and 21B. Further, FIG. 21B is a chart showing an enlarged part in the range of 6.0 ppm to 9.0 ppm of FIG. 21A.

The obtained YGA2F with an amount of 670 mg was then purified by sublimation for 15 hours at 420° C. under 200 Pa in the flow of argon gas at a rate of 3.0 mL/min; thus, 511 g of a light yellow solid of YGA2F was obtained with a yield of 76%.

Further, when a decomposition temperature ($T_d$) of the thus obtained YGA2F was measured by a thermo-gravimetric/differential thermal analyzer (TG/DTA 320, manufactured by Seiko Instruments Inc.), the $T_d$ was 500° C. or more, and it was understood that YGA2F has high $T_d$.

Figure 22:
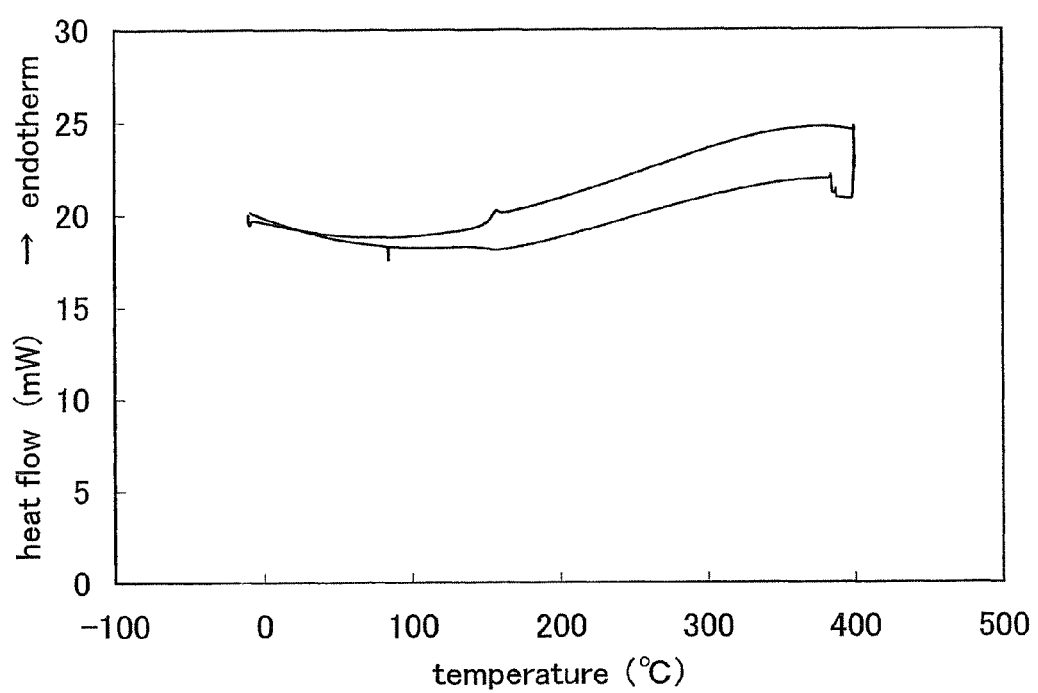
FIG. 22 shows a DSC chart of N,N'-bis[4-(carbazol-9-yl)phenyl]-N,N'-diphenyl-9,9-dimethylfluorene-2,7-diamine.

In addition, the glass transition point was measured by a differential scanning calorimeter (DSC, manufactured by PerkinElmer, Inc., Pyris 1). First, a sample was heated up to 400° C. at 40° C./min, and then it was cooled down to room temperature at 40° C./min. After that, the temperature was raised to 400° C. at 10° C./min and then lowered to room temperature at 10° C./min, thereby obtaining the DSC chart shown in FIG. 22. In FIG. 22, the X axis shows temperature and the Y axis shows heat flow. The Y axis shows endothermin an upward direction. It was understood from this chart that the glass transition point ($T_g$) of YGA2F was 150° C., and moreover that the aromatic amine compound of the present invention has excellent heat resistance.

Figure 23:
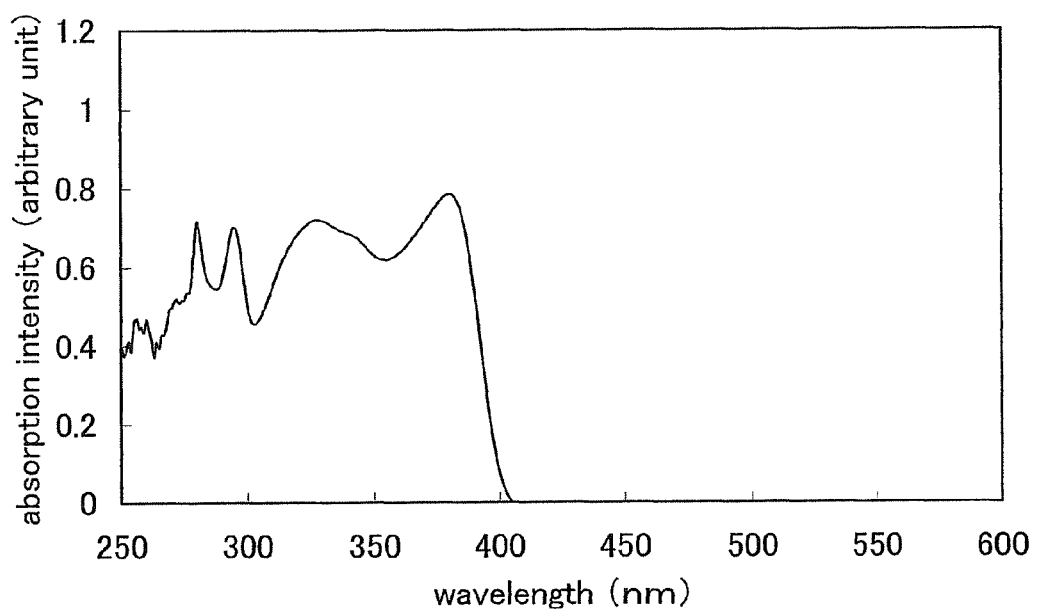
FIG. 23 shows an absorption spectrum of a toluene solution of N,N'-bis[4-(carbazol-9-yl)phenyl]-N,N'-diphenyl-9,9-dimethylfluorene-2,7-diamine.
Figure 24:
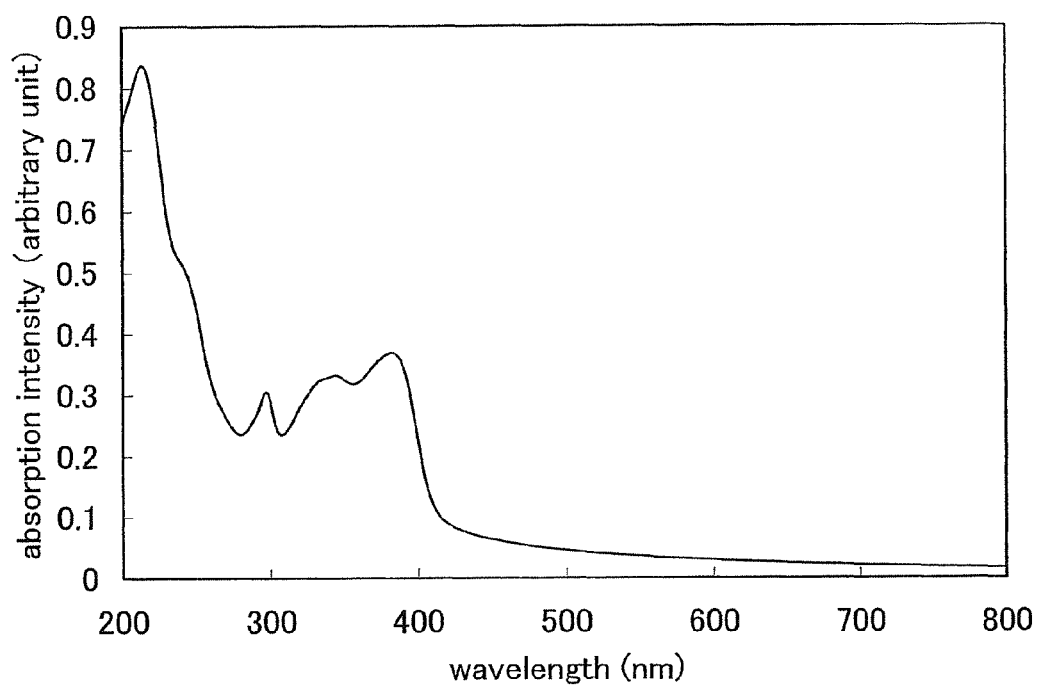
FIG. 24 shows an absorption spectrum of a thin film of N,N'-bis[4-(carbazol-9-yl)phenyl]-N,N'-diphenyl-9,9-dimethylfluorene-2,7-diamine.
Figure 25:
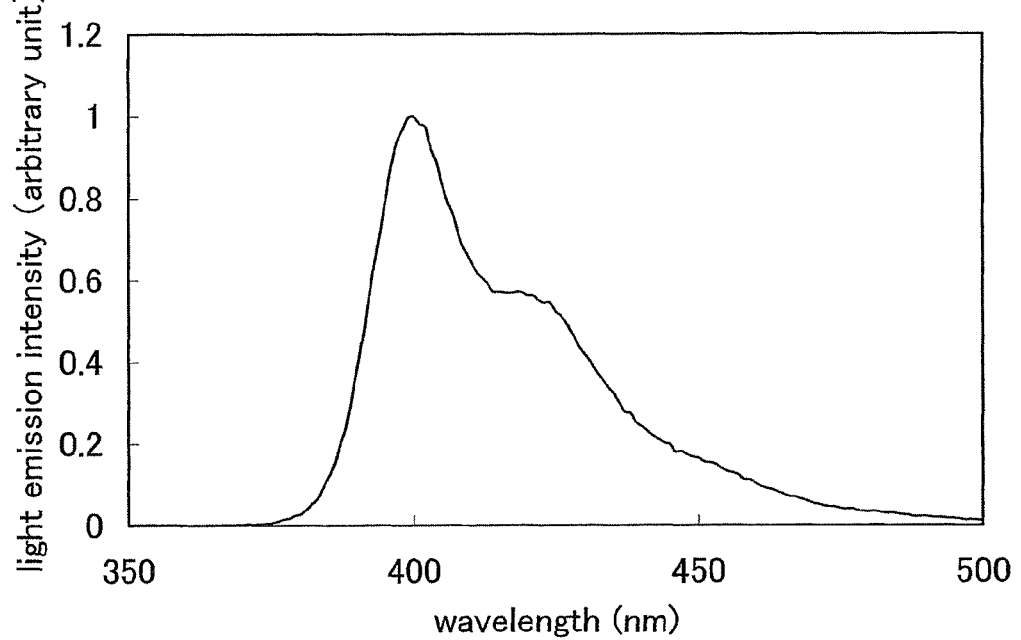
FIG. 25 shows a light emission spectrum of a toluene solution of N,N'-bis[4-(carbazol-9-yl)phenyl]-N,N'-diphenyl-9,9-dimethylfluorene-2,7-diamine.
Figure 26:
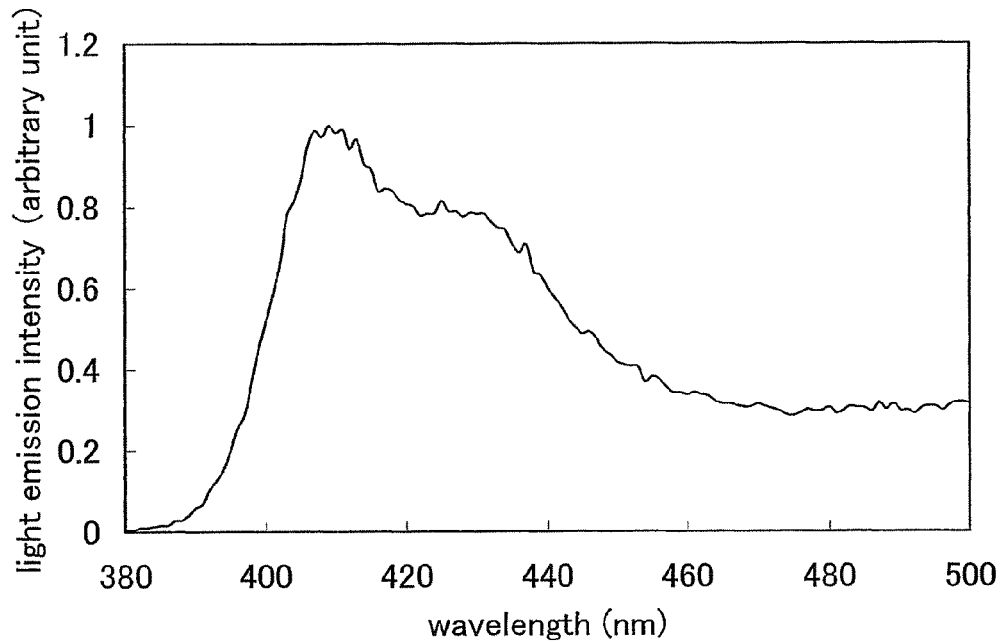
FIG. 26 shows a light emission spectrum of a thin film of N,N'-bis[4-(carbazol-9-yl)phenyl]-N,N'-diphenyl-9,9-dimethylfluorene-2,7-diamine.

FIG. 23 shows an absorption spectrum of a toluene solution of YGA2F. Moreover, FIG. 24 shows an absorption spectrum of a thin film of YGA2F. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIGS. 23 and 24. In FIGS. 23 and 24, the horizontal axis shows a wavelength (nm) while the vertical axis shows absorption intensity (arbitrary unit). In the case of the toluene solution, absorption was observed at around 327 nm and 377 nm, and in the case of the thin film, it was observed at around 383 nm. The light emission spectrum of the toluene solution of YGA2F (excitation wavelength: 340 nm) is shown in FIG. 25, while that of the thin film of YGA2F (excitation wavelength: 383 nm) is shown in FIG. 26. In FIGS. 25 and 26, the horizontal axis shows a wavelength (nm) and the vertical axis shows light emission intensity (arbitrary unit). The peak of the light emission spectrum was observed at 400 nm and 422 nm in the case of the toluene solution (excitation wavelength: 340 nm), and 410 nm, 430 nm, and 537 nm in the case of the thin film (excitation wavelength: 383 nm).

In addition, the HOMO level of YGA2F in the thin film state was −5.27 eV, which was measured by photoelectron spectrometer (AC-2, manufactured by Riken Keiki Co., Ltd.) in the air. Moreover, the absorption edge was obtained from Tauc plot using data on the absorption spectrum of the thin film of YGA2F in FIG. 24. When the absorption edge was estimated as an optical energy gap, the energy gap was 3.05 eV. Therefore, the LUMO level was −2.22 eV.

Moreover, the oxidation reaction characteristic of YGA2F was measured by cyclic voltammetry (CV) measurement.

Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode. It is to be noted that the measurement was conducted at room temperature.

The oxidation reaction characteristic of YGA2F was measured as follows. A scan for changing the potential of the work electrode with respect to the reference electrode from 1.0 V to −0.31 V after changing the potential from −0.31 V to 1.0 V was set as one cycle, and 100 cycles were measured. Further, the scanning speed of the CV measurement was set to be 0.1 V/s.

Figure 27:
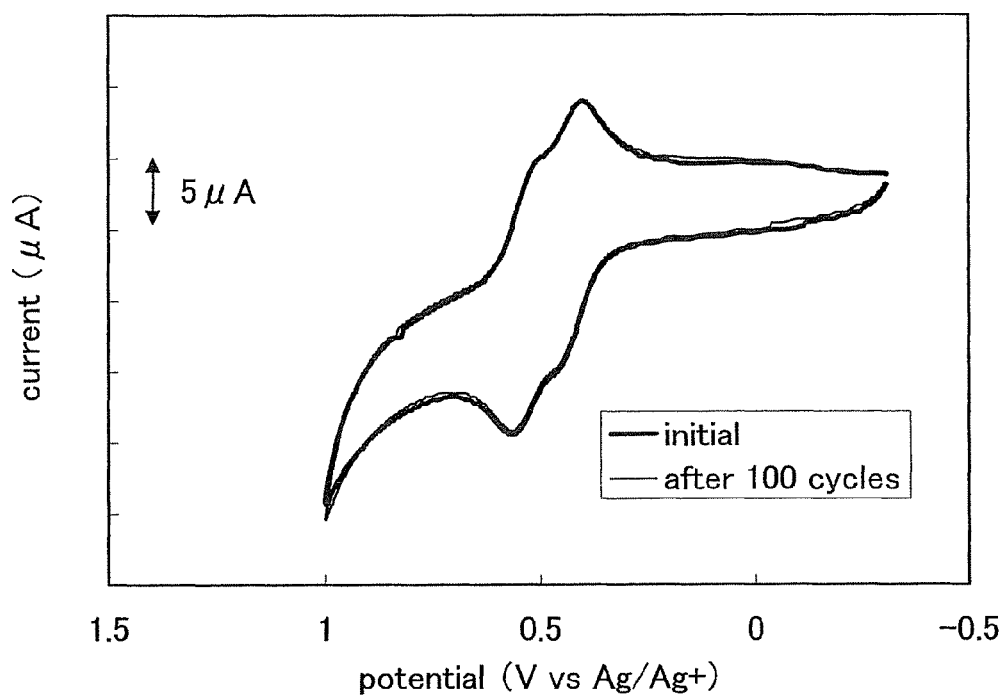
FIG. 27 shows a CV measurement result of N,N'-bis[4-(carbazol-9-yl)phenyl]-N,N'-diphenyl-9,9-dimethylfluorene-2,7-diamine.

A result of the measurement on the oxidation reaction characteristic of YGA2F is shown in FIG. 27, in which the horizontal axis shows the potential (V) of the work electrode with respect to the reference electrode, while the vertical axis shows a value (µA) of current flowing between the work electrode and the auxiliary electrode.

In FIG. 27, a current indicating oxidation was observed at around 0.40 V (vs. Ag/Ag$^+$ electrode). Regardless of the repetition of 100-cycle scans, the peak position and the peak intensity at the CV curve hardly changes in the oxidation reaction. Based on this fact, it was understood that the aromatic amine compound of the present invention is quite stable against the oxidation reaction and the subsequent reduction reaction (that is, repetition of oxidation).

Embodiment 4

This embodiment will explain a method of synthesizing N,N'-bis[4-(carbazol-9-yl)phenyl]-N,N'-diphenylbiphenyl-4,4'-diamine (abbr.: YGABP) expressed by Structure Formula (102). Synthesis Scheme (D-4) is shown below.

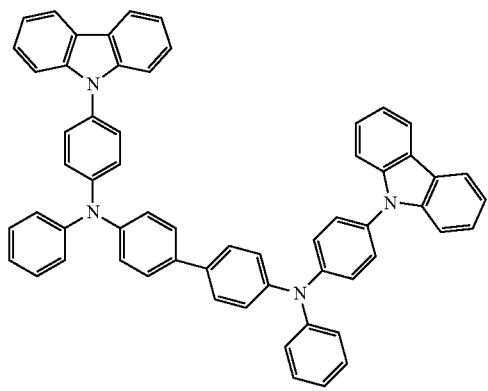

(102)

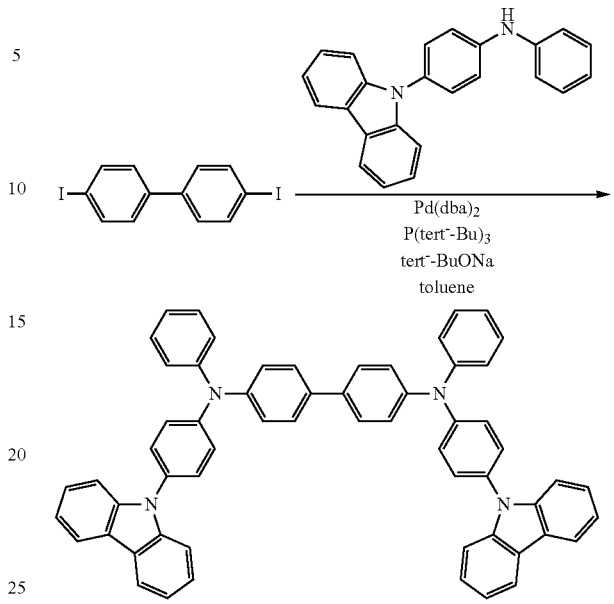

In a three-necked flask of 200 mL content, 2.0 g (5.0 mmol) of 4,4-diiodo-1,1'-biphenyl, 3.3 g (10.0 mmol) of 4-(carbazol-9-yl)diphenylamine, 65 mg (0.1 mmol) of bis(dibenzylideneacetone)palladium(0), and 2.0 g (21.0 mmol) of tert-butoxysodium were put and nitrogen substitution was carried out. Then, 50 mL of toluene and 0.1 mL of tri(tert-butyl)phosphine (10 wt % hexane solution) were added and stirred for six hours at 80° C. After the reaction mixture was cooled down to room temperature, the mixture was filtered through celite, Florisil, and alumina. The filtrate was then washed with water or saturated saline. The mixture was washed naturally and magnesium sulfate was removed. The filtrate was concentrated to obtain a white solid, which was then recrystallized by chloroform and hexane; thus, 1.8 g of a white powder-like solid, which is a target matter, was obtained with a yield of 45%. It was confirmed that this compound was N,N'-bis[4-(carbazol-9-yl)phenyl]-N,N'-diphenylbiphenyl-4,4'-diamine (abbr.: YGABP) expressed by Structure Formula (102).

Figure 28A:
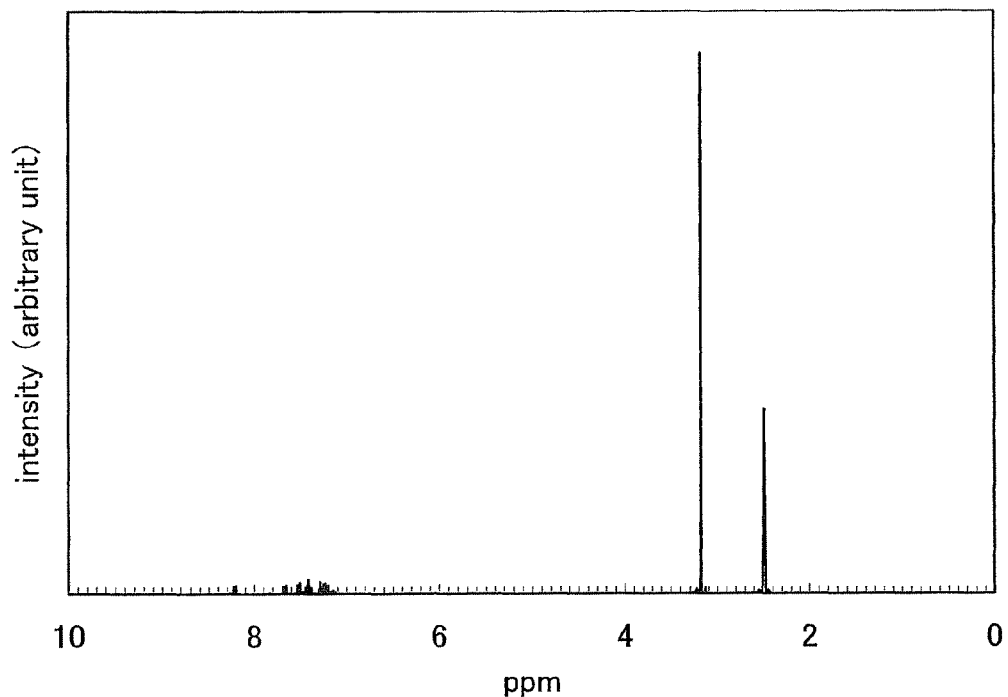
FIGS. 28A and 28B each show a $^1$H-NMR chart of N,N'-bis[4-(carbazol-9-yl)phenyl]-N,N'-diphenyl-4,4'-biphenyl-diamine.
Figure 28B:
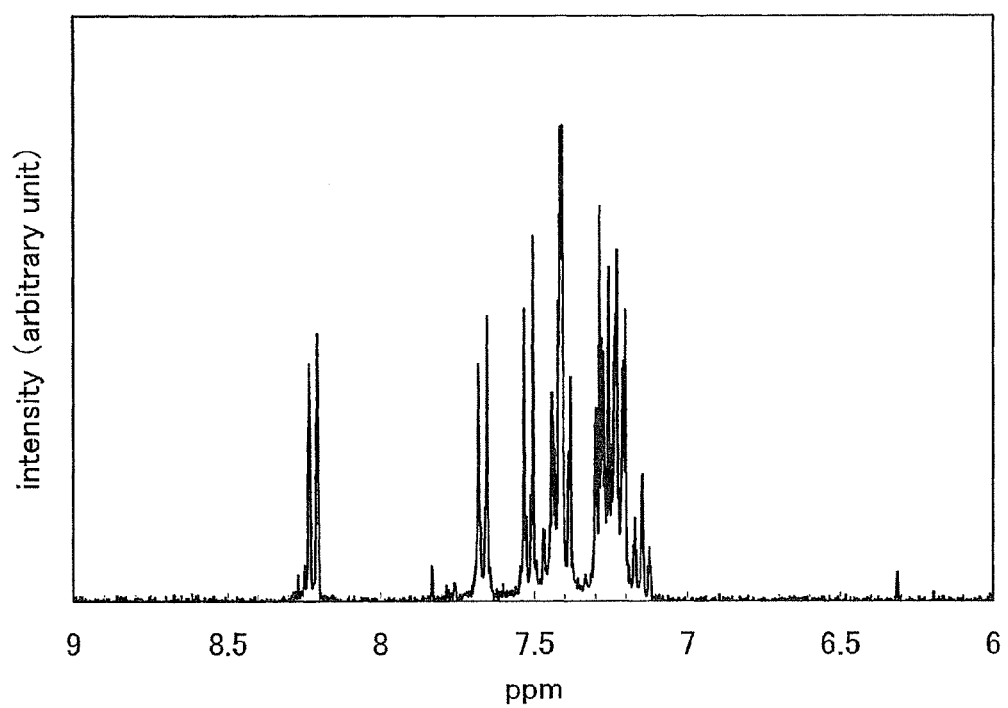

The $^1$H-NMR data on this compound are shown. The $^1$H-NMR (300 MHz, DMSO-d$_6$): δ=7.12-7.17 (m, 2H), 7.20-7.30 (m, 16H), 7.38-7.47 (m, 12H), 7.5 (d, J=8.7 Hz, 4H), 7.67 (d, J=9.0 Hz, 4H), and 8.22 (d, J=7.8 Hz, 4H). A $^1$H-NMR chart is also shown in FIGS. 28A and 28B. Further, FIG. 28B is a chart showing an enlarged part in the range of 6.0 ppm to 9.0 ppm of FIG. 28A.

The obtained YGABP1 with an amount of 1.8 g was then purified by sublimation for 15 hours at 300° C. under 7.8 Pa in the flow of argon gas at a rate of 3.0 mL/min; thus, 1.6 g of a light yellow solid of YGABP was obtained with a yield of 89%.

Further, when a decomposition temperature (T$_d$) of the thus obtained YGABP was measured by a thermo-gravimetric/differential thermal analyzer (TG/DTA 320, manufactured by Seiko Instruments Inc.), the T$_d$ was 500° C. or more, and it was understood that YGABP has high T$_d$.

Figure 29:
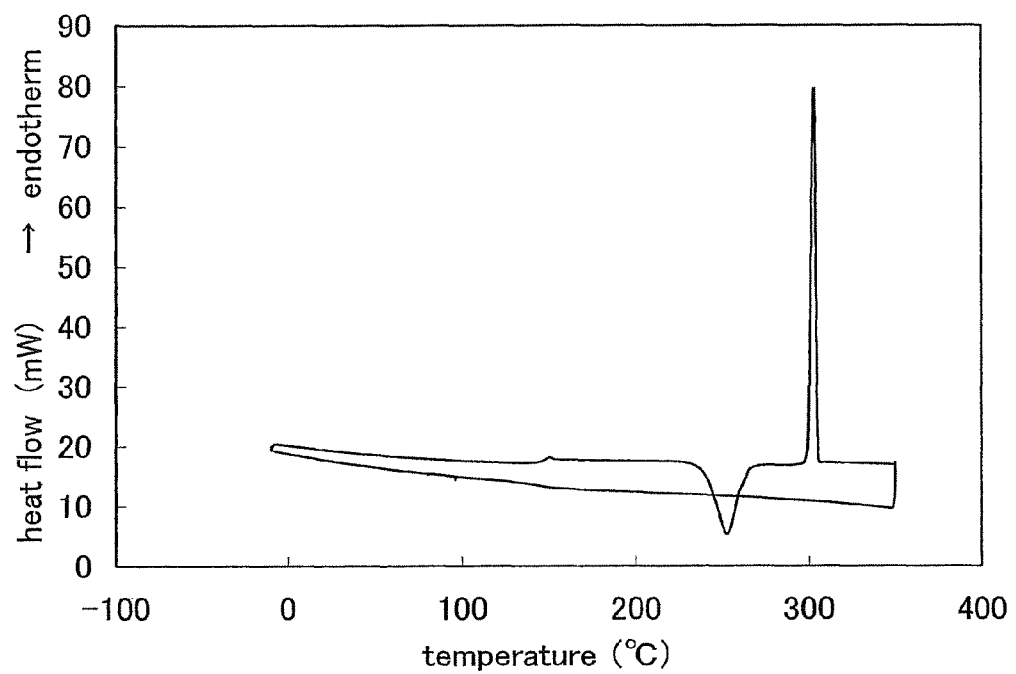
FIG. 29 shows a DSC chart of N,N'-bis[4-(carbazol-9-yl)phenyl]-N,N'-diphenyl-4,4'-biphenyl-diamine.

In addition, the glass transition point was measured by a differential scanning calorimeter (DSC, manufactured by PerkinElmer, Inc., Pyris 1). First, a sample was heated up to 350° C. at 40° C./min, and then it was cooled down to room temperature at 40° C./min. After that, the temperature was raised to 350° C. at 10° C./min and then lowered to room temperature at 10° C./min, thereby obtaining the DSC chart shown in FIG. 29. In FIG. 29, the X axis shows temperature and the Y axis shows heat flow. The Y axis shows endothermin an upward direction. It was understood from this chart that the glass transition point ($T_g$) of YGABP was 144° C., and moreover that the aromatic amine compound of the present invention has excellent heat resistance.

Figure 30:
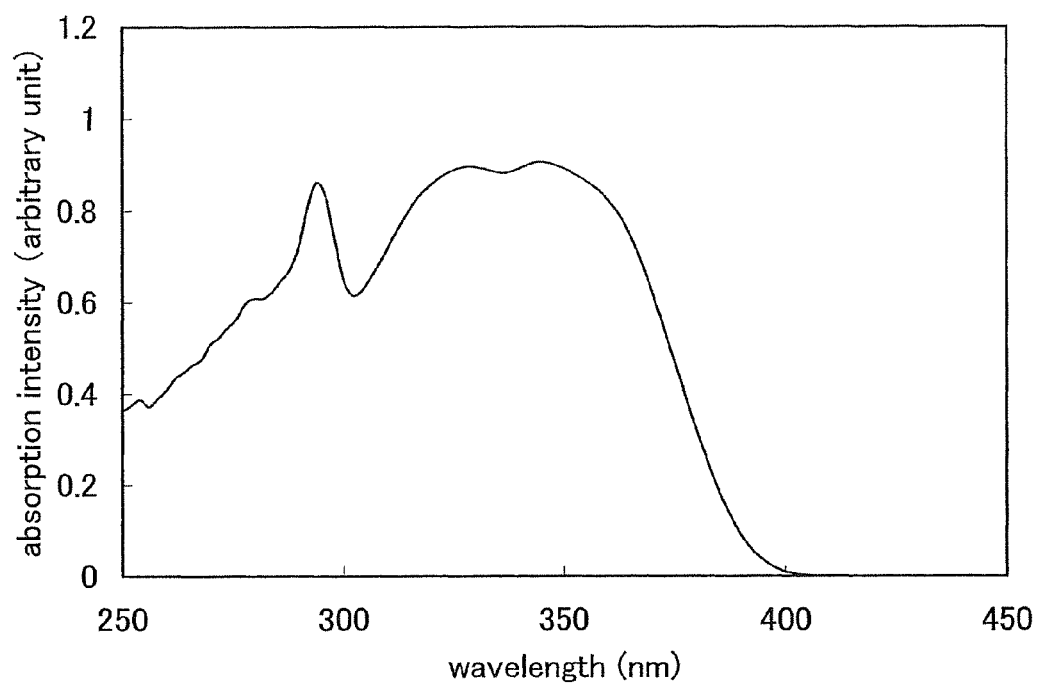
FIG. 30 shows an absorption spectrum of a toluene solution of N,N'-bis[4-(carbazol-9-yl)phenyl]-N,N'-diphenyl-4,4'-biphenyl-diamine.
Figure 31:
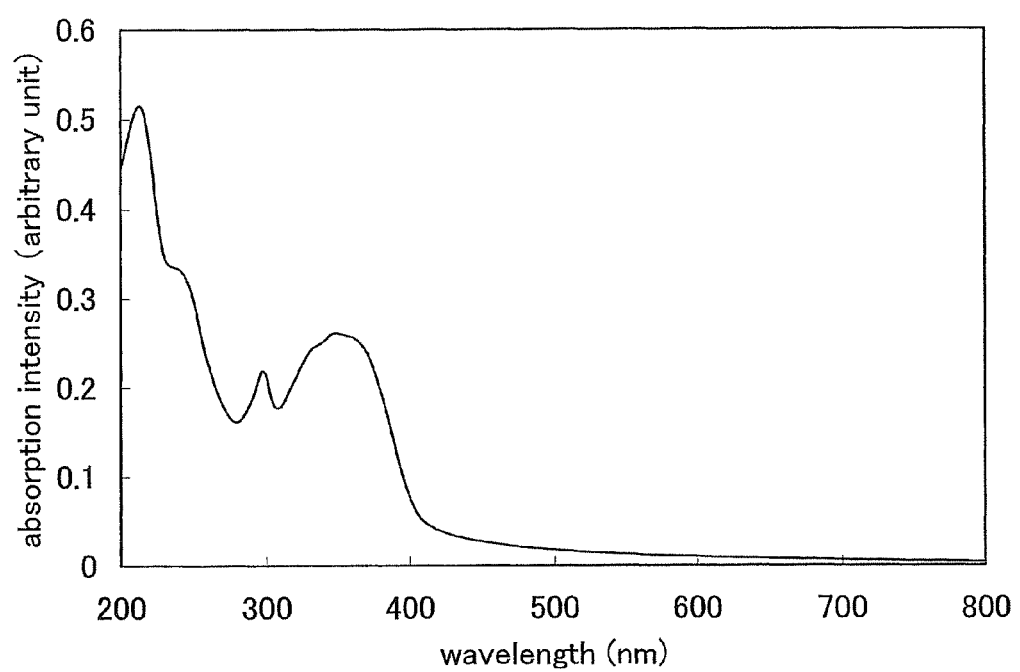
FIG. 31 shows an absorption spectrum of a thin film of N,N'-bis[4-(carbazol-9-yl)phenyl]-N,N'-diphenyl-4,4'-biphenyl-diamine.
Figure 32:
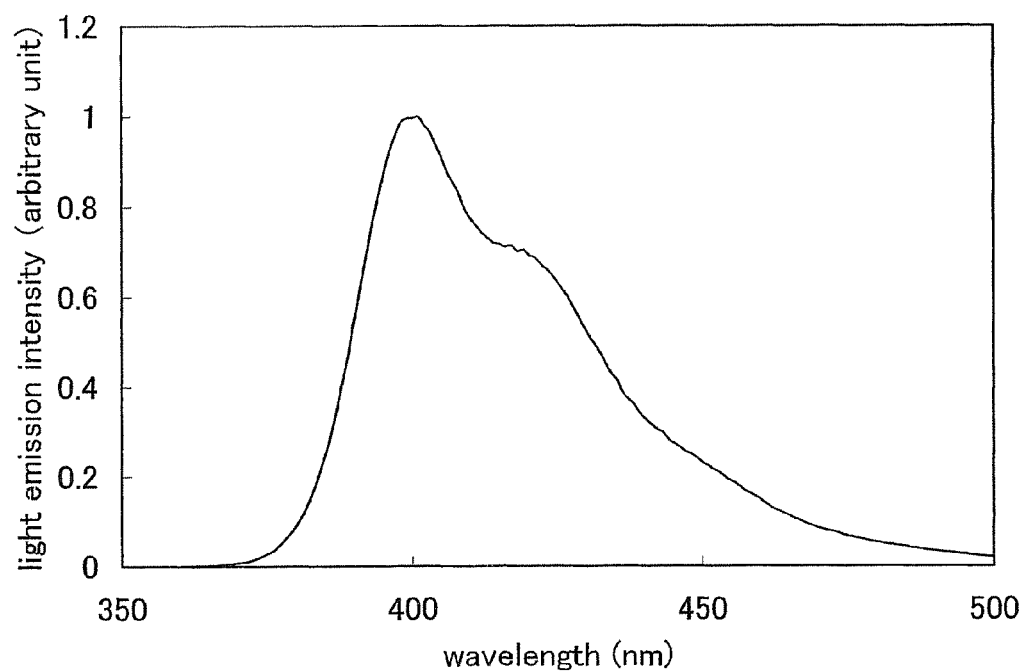
FIG. 32 shows a light emission spectrum of a toluene solution of N,N'-bis[4-(carbazol-9-yl)phenyl]-N,N'-diphenyl-4,4'-biphenyl-diamine.
Figure 33:
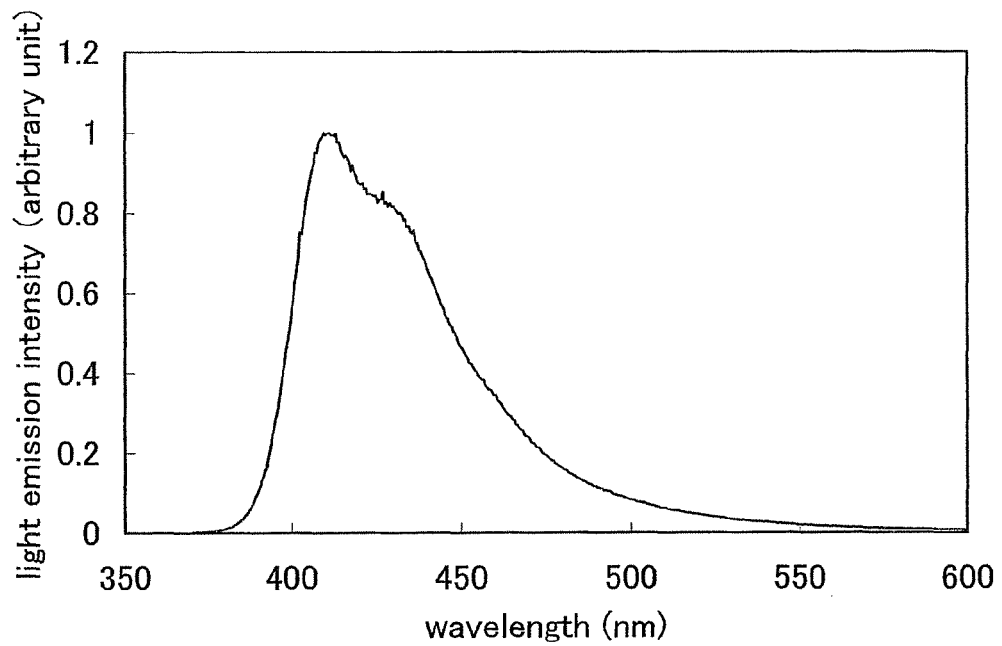
FIG. 33 shows a light emission spectrum of a thin film of N,N'-bis[4-(carbazol-9-yl)phenyl]-N,N'-diphenyl-4,4'-biphenyl-diamine.

FIG. 30 shows an absorption spectrum of a toluene solution of YGABP. FIG. 31 shows an absorption spectrum of a thin film of YGABP. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIGS. 30 and 31. In FIGS. 30 and 31, the horizontal axis shows a wavelength (nm) while the vertical axis shows absorption intensity (arbitrary unit). In the case of the toluene solution, absorption was observed at around 328 nm and 346 nm, and in the case of the thin film, it was observed at around 349 nm. The light emission spectrum of the toluene solution of YGABP (excitation wavelength: 350 nm) is shown in FIG. 32, while that of the thin film of YGABP (excitation wavelength: 350 nm) is shown in FIG. 33. In FIGS. 32 and 33, the horizontal axis shows a wavelength (nm) and the vertical axis shows light emission intensity (arbitrary unit). The maximum light emission wavelength was 400 nm in the case of the toluene solution (excitation wavelength: 350 nm), and 410 nm in the case of the thin film (excitation wavelength: 350 nm).

In addition, the HOMO level of YGABP in the thin film state was −5.41 eV, which was measured by photoelectron spectrometer (AC-2, manufactured by Riken Keiki Co., Ltd.) in the air. Moreover, the absorption edge was obtained from Tauc plot using data on the absorption spectrum of the thin film of YGABP in FIG. 31. When the absorption edge was estimated as an optical energy gap, the energy gap was 3.13 eV. Therefore, the LUMO level was −2.28 eV.

Moreover, the oxidation reaction characteristic of YGABP was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n-butylammonium perchlorate (n-$Bu_4NClO_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An $Ag/Ag^+$ electrode (an RE5 nonaqueous solvent reference electrode, manufactured by BAS Inc.) was used as a reference electrode. It is to be noted that the measurement was conducted at room temperature.

The oxidation reaction characteristic of YGABP was measured as follows. A scan for changing the potential of the work electrode with respect to the reference electrode from 1.0 V to −0.2 V after changing the potential from −0.2 V to 1.0 V was set as one cycle, and 100 cycles were measured. Further, the scanning speed of the CV measurement was set to be 0.1 V/s.

Figure 34:
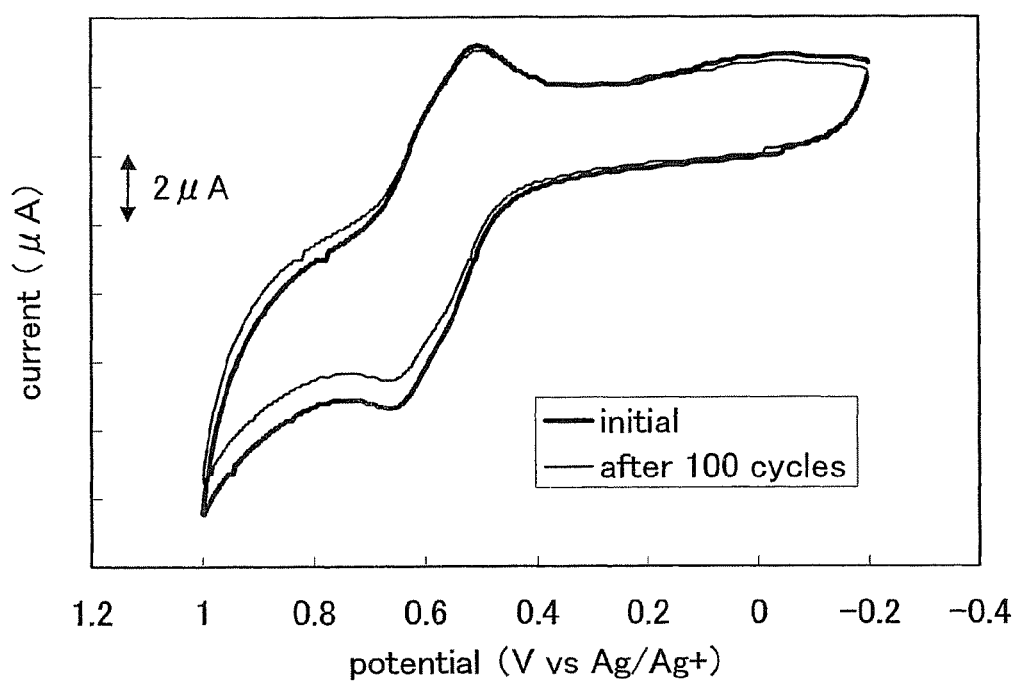
FIG. 34 shows a CV measurement result of N,N'-bis[4-(carbazol-9-yl)phenyl]-N,N'-diphenyl-4,4'-biphenyl-diamine.

A result of the measurement on the oxidation reaction characteristic of YGABP is shown in FIG. 34, in which the horizontal axis shows the potential (V) of the work electrode with respect to the reference electrode, while the vertical axis shows a value (μA) of current flowing between the work electrode and the auxiliary electrode.

In FIG. 34, a current indicating oxidation was observed at around 0.66 V (vs. $Ag/Ag^+$ electrode). Regardless of the repetition of 100-cycle scans, the peak position and the peak intensity at the CV curve hardly changes in the oxidation reaction. Based on this fact, it was understood that the aromatic amine compound of the present invention is quite stable against the oxidation reaction and the subsequent reduction reaction (that is, repetition of oxidation).

Embodiment 5

Figure 35:
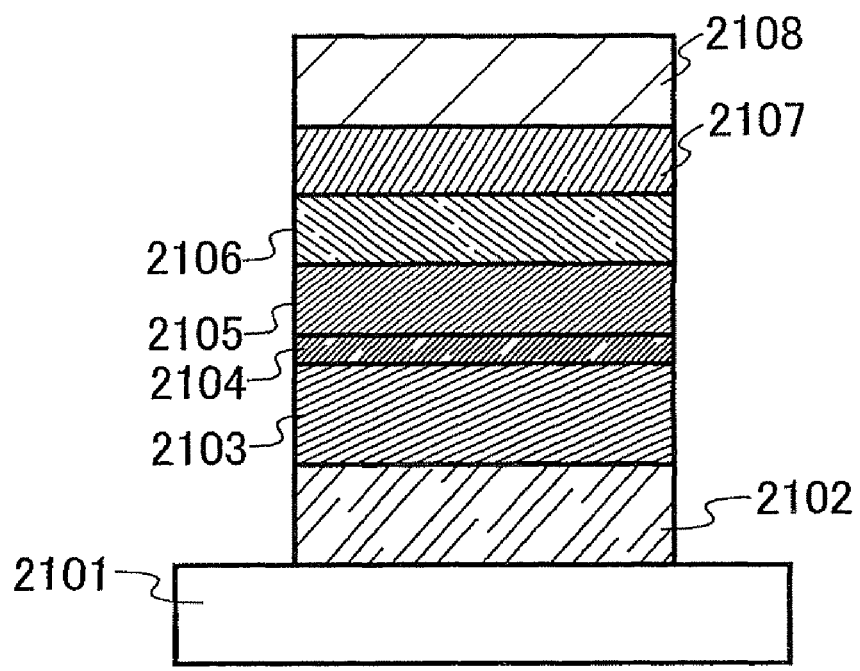
FIG. 35 explains a light-emitting element of Embodiment 5.

This embodiment will explain a light-emitting element of the present invention with reference to FIG. 35. A chemical formula of a material used in this embodiment is shown below.

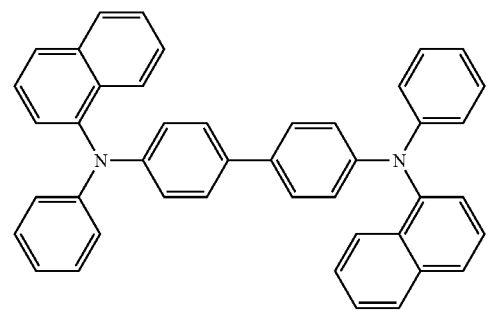

NPB

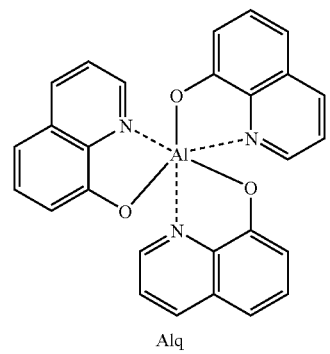

Alq

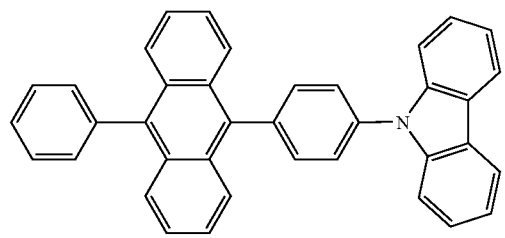

CzPA

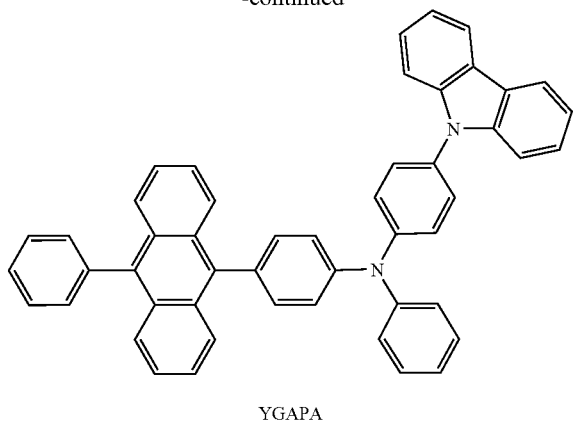

YGAPA (Light-Emitting Element 1)

First, indium tin oxide including silicon oxide was formed over a glass substrate 2101 by a sputtering method, thereby forming a first electrode 2102. The first electrode 2102 has a film thickness of 110 nm and an electrode area of 2 mm∴2 mm.

Next, the substrate over which the first electrode was formed was fixed to a substrate holder provided in a vacuum evaporation apparatus in such a way that a surface of the substrate having the first electrode faced downward. The pressure was reduced to be about $10^{-4}$ Pa and then, NPB and molybdenum oxide (VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide (VI) was set 4:1(=NPB:molybdenum oxide). It is to be noted that the co-evaporation method is an evaporation method in which evaporation is performed from plural evaporation sources in one process chamber.

Subsequently, a hole-transporting layer 2104 was formed in 10 nm thick over the layer 2103 containing a composite material by using N-[4-(carbazol-9-yl)phenyl]-N-phenyl-9,9-dimethylfluorenyl-2-amine (abbr.: YGAF) expressed by Structure Formula (21) by an evaporation method using resistance heating.

Further, a light-emitting layer 2105 of 30 nm thick was formed over the hole-transporting layer 2104 by co-evaporating 9-[4-(N-carbazolyl)]phenyl-10-phenylanthracene (abbr.: CzPA) and 9-(4-{N-[4-(carbazol-9-yl)phenyl]-N-phenylamino}phenyl)-10-phenylanthracene (abbr.: YGAPA). Here, the weight ratio between CzPA and YGAPA was adjusted so as to be 1:0.04(=CzPA:YGAPA).

After that, an electron-transporting layer 2106 was formed in 10 nm thick using tris(8-quinolinolato)aluminum (abbr.: Alq) over the light-emitting layer 2105 by an evaporation method using resistance heating.

Moreover, an electron-injecting layer 2107 was formed in 20 nm thick by co-evaporating Alq and lithium over the electron-transporting layer 2106. Here, the weight ratio between Alq and lithium was adjusted so as to be 1:0.01 (=Alq:lithium).

Then, a second electrode 2108 was formed of aluminum in 200 nm thick over the electron-injecting layer 2107 by an evaporation method using resistance heating. Thus, the light-emitting element 1 was manufactured.

(Light-Emitting Element 2)

The hole-transporting layer 2104 was formed in 10 nm thick by N,N'-bis[4-(carbazol-9-yl)phenyl]-N,N'-diphenyl-9,9-dimethylfluorene-2,7-diamine (abbr.: YGA2F) expressed by Structure Formula (71). The structure other than the hole-transporting layer is similar to that of the light-emitting element 1.

(Light-Emitting Element 3)

The hole-transporting layer 2104 was formed in 10 nm thick by N,N'-bis[4-(carbazol-9-yl)phenyl]-N,N'-diphenyl-biphenyl-4,4'-diamine (abbr.: YGABP) expressed by Structure Formula (102). The structure other than the hole-transporting layer is similar to that of the light-emitting element 1.

(Comparative Light-Emitting Element 4)

The hole-transporting layer 2104 was formed of NPB in 10 nm thick. The structure other than the hole-transporting layer is similar to that of the light-emitting element 1.

Figure 36:
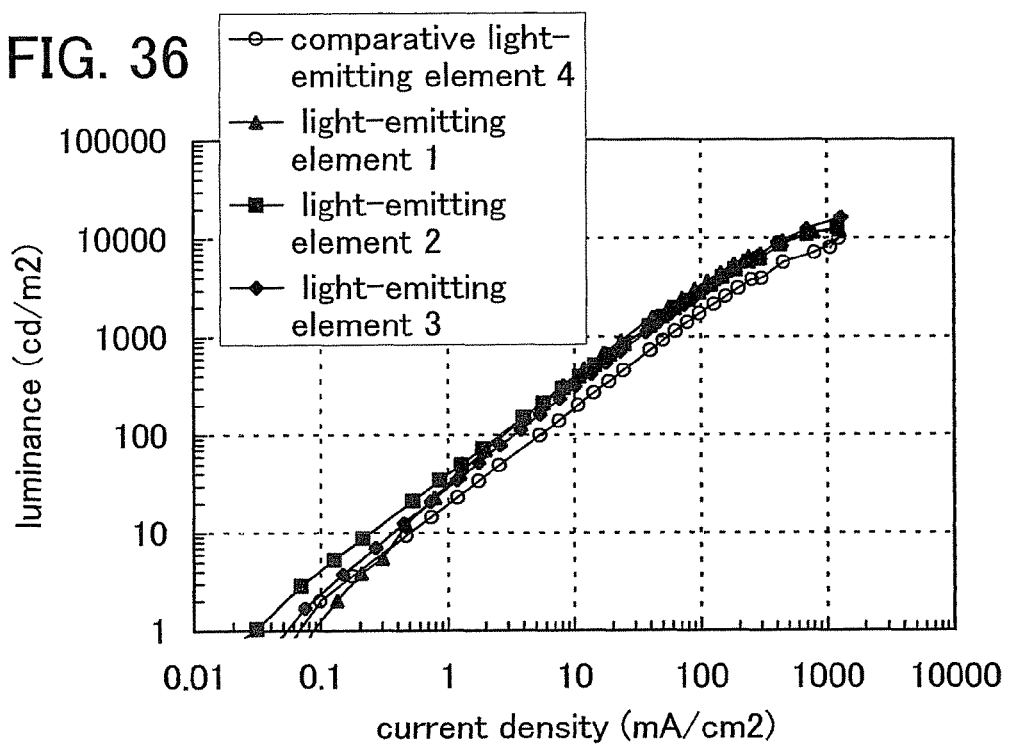
FIG. 36 shows current density-luminance characteristics of a light-emitting element manufactured in accordance with Embodiment 5.
Figure 37:
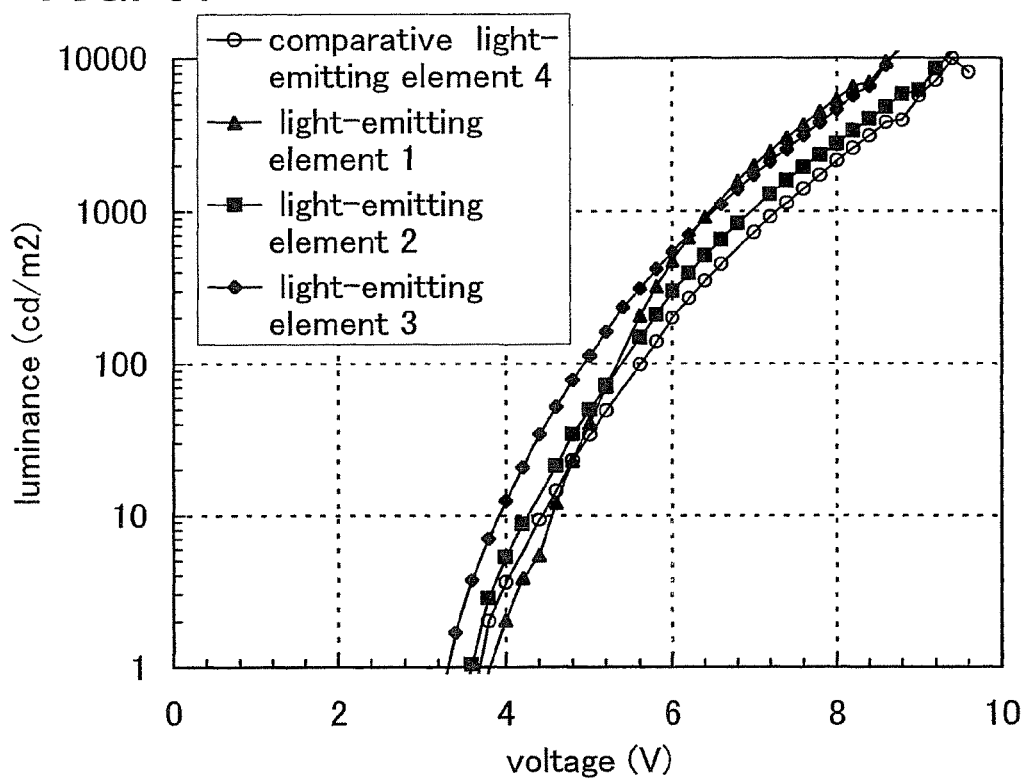
FIG. 37 shows voltage-luminance characteristics of a light-emitting element manufactured in accordance with Embodiment 5.
Figure 38:
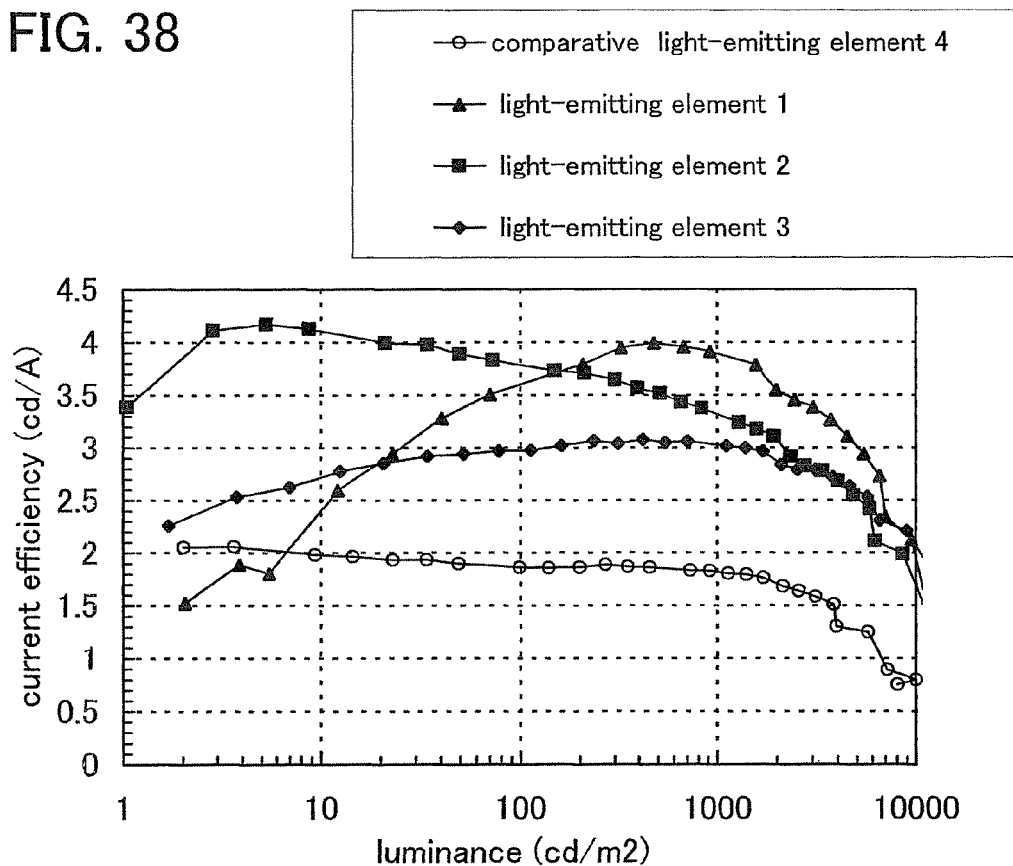
FIG. 38 shows luminance-current efficiency characteristics of a light-emitting element manufactured in accordance with Embodiment 5.

FIG. 36 shows a current density-luminance characteristic of the light-emitting elements 1 to 3 and the comparative light-emitting element 4. FIG. 37 shows a voltage-luminance characteristic thereof, and FIG. 38 shows luminance-current efficiency characteristics thereof. As can be seen from FIG. 38, the light-emitting element using the aromatic amine compound of the present invention shows high current efficiency. Moreover, as shown in FIG. 37, a voltage necessary to obtain a certain luminance can be reduced in the light-emitting element of the present invention. That is to say, the drive voltage can be reduced. Therefore, the power consumption of the light-emitting element can be reduced.

In this way, the light-emitting element with the use of the aromatic amine compound of the present invention for the hole-transporting layer can have favorable characteristics.

Embodiment 6

This embodiment will explain a light-emitting element of the present invention with reference to FIG. 35. A chemical formula of a material used in this embodiment is shown below.

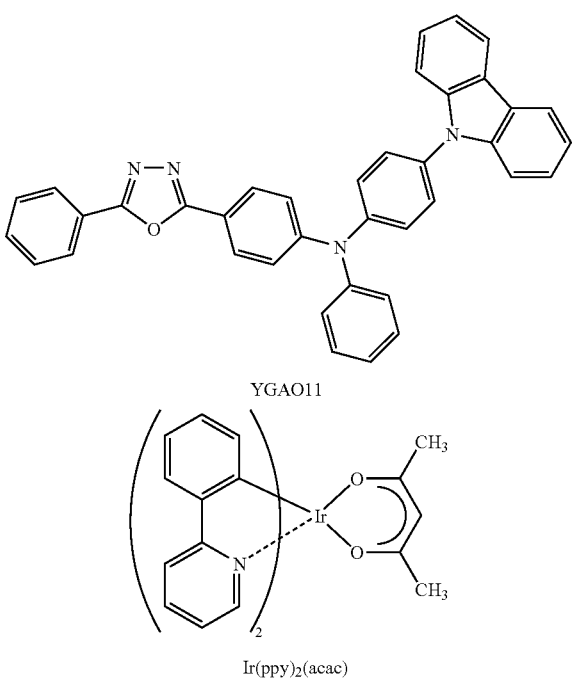

YGAO11

Ir(ppy)₂(acac)

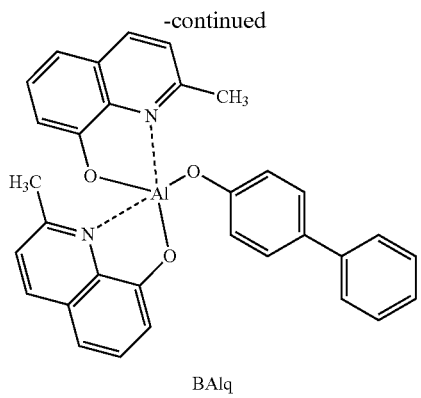

BAlq (Light-Emitting Element 5)

First, indium tin oxide including silicon oxide was formed over the glass substrate 2101 by a sputtering method, thereby forming the first electrode 2102. The first electrode 2102 has a film thickness of 110 nm and an electrode area of 2 mm×2 mm.

Next, the substrate over which the first electrode was formed was fixed to a substrate holder provided in a vacuum evaporation apparatus in such a way that a surface of the substrate having the first electrode faced downward. The pressure was reduced to be about $10^{-4}$ Pa and then, NPB and molybdenum oxide (VI) were co-evaporated on the first electrode 2102, thereby forming the layer 2103 containing a composite material of an organic compound and an inorganic compound. The film thickness of the layer 2103 was 50 nm, and the weight ratio between NPB and molybdenum oxide (VI) was set 4:1(=NPB:molybdenum oxide). It is to be noted that the co-evaporation method is an evaporation method in which evaporation is performed from plural evaporation sources in one process chamber.

Subsequently, the hole-transporting layer 2104 was formed in 10 nm thick over the layer 2103 containing a composite material by using N-[4-(carbazol-9-yl)phenyl]-N-phenyl-9,9-dimethylfluorenyl-2-amine (abbr.: YGAF) expressed by Structure Formula (21) by an evaporation method using resistance heating.

Further, the light-emitting layer 2105 of 30 nm thick was formed over the hole-transporting layer 2104 by co-evaporating 2-(4-{N-[4-(carbazol-9-yl)phenyl]-N-phenylamino}phenyl)-5-phenyl-1,3,4-oxadiazole (abbr.: YGAO11) and bis(2-phenylpyridinato)iridium(III)acetylacetonate (abbr.: Ir(ppy)$_2$(acac)). Here, the weight ratio between YGAO11 and Ir(ppy)$_2$(acac) was adjusted so as to be 1:0.05(=YGAO11:Ir(ppy)$_2$(acac)).

After that, the electron-transporting layer 2106 was formed in 10 nm thick using bis(2-methyl-8-quinolinolato)(4-phenylphenolato)aluminum (abbr.: BAlq) over the light-emitting layer 2105 by an evaporation method using resistance heating.

Moreover, the electron-injecting layer 2107 was formed in 20 nm thick by co-evaporating Alq and lithium over the electron-transporting layer 2106. Here, the weight ratio between Alq and lithium was adjusted so as to be 1:0.01 (=Alq:lithium).

Then, the second electrode 2108 was formed of aluminum in 200 nm thick over the electron-injecting layer 2107 by an evaporation method using resistance heating. Thus, the light-emitting element 5 was manufactured.

(Comparative Light-Emitting Element 6)

The hole-transporting layer 2104 was formed of NPB in 10 nm thick. The structure other than the hole-transporting layer is similar to that of the light-emitting element 5.

Figure 39:
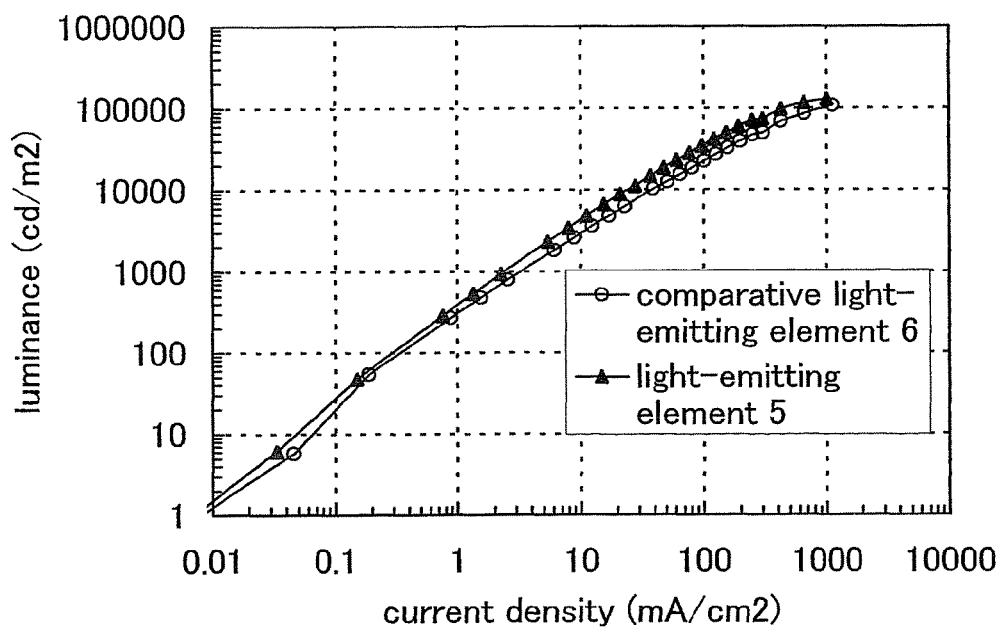
FIG. 39 shows current density-luminance characteristics of a light-emitting element manufactured in accordance with Embodiment 6.
Figure 40:
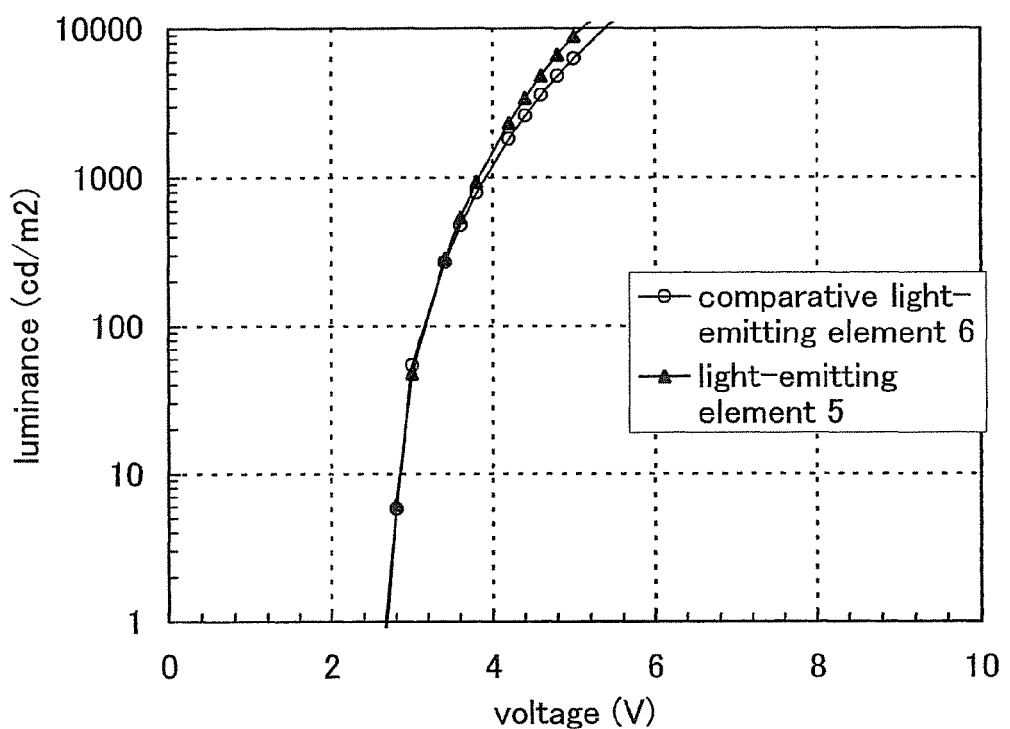
FIG. 40 shows voltage-luminance characteristics of a light-emitting element manufactured in accordance with Embodiment 6.
Figure 41:
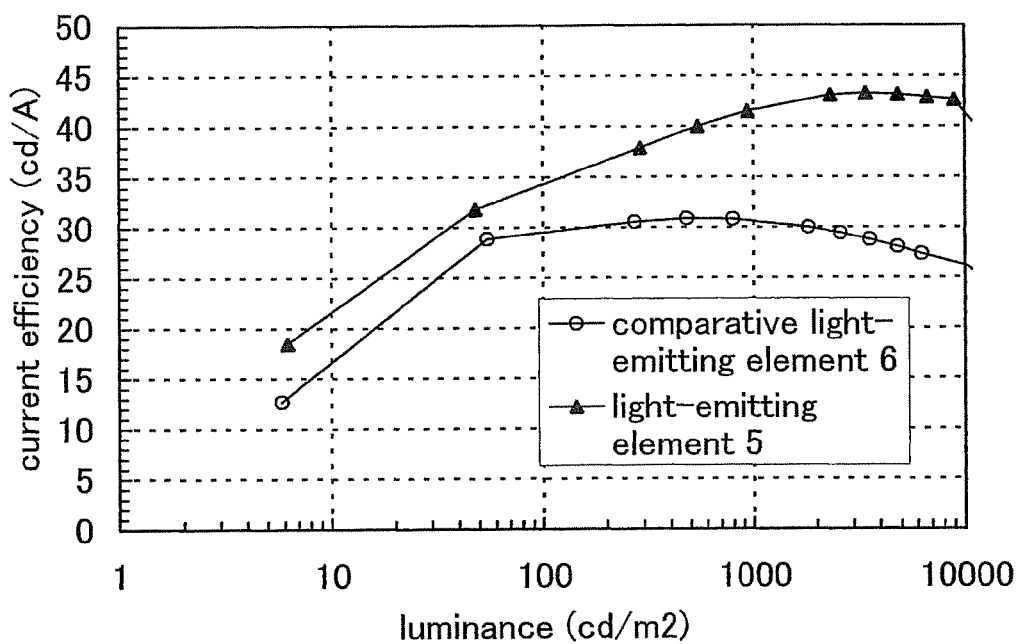
FIG. 41 shows luminance-current efficiency characteristics of a light-emitting element manufactured in accordance with Embodiment 6.

FIG. 39 shows a current density-luminance characteristic of the light-emitting element 5 and the comparative light-emitting element 6. FIG. 40 shows a voltage-luminance characteristic thereof, and FIG. 41 shows luminance-current efficiency characteristics thereof. As can be seen from FIG. 41, the light-emitting element using the aromatic amine compound of the present invention shows high current efficiency. As shown in FIG. 40, the light-emitting element of the present invention has almost the same drive voltage as the comparative light-emitting element 6.

In addition, the triplet-excitation energy (energy gap) of each of YGAF and YGA1BP, which are the aromatic amine compounds of the present invention, and NPB used for the comparative light-emitting element 6 was calculated. The calculation was performed in such a way that an optimal molecular structure thereof in a ground state was calculated with B3LYP/6-311 (d, p) of density functional theory (DFT). The accuracy of calculation of the DFT is higher than that of Hartree-Fock (HF) which does not consider electron correlation. In addition, the calculation cost of the DFT is lower than that of a method of perturbation (MP) which has the same level accuracy of calculation as the DFT. Therefore, the DFT was employed in the present calculation. The calculation was performed using a high-performance computer (HPC) (manufactured by SGI Japan, Ltd., Altix3700 DX). After that, the triplet-excitation energy (energy gap) of each of these compounds was calculated with the application of B3LYP/6-311 (d, p) of a time-dependent density functional theory (TDDFT) for the molecular structure whose structure was optimized by the DFT. Further, the corresponding wavelength was calculated from the triplet-excitation energy (energy gap). The results are shown in Table 1 and FIG. 42.

TABLE 1

| material | triplet-excitation energy (eV) | wavelength corresponding to triplet-excitation energy (nm) |
|---|---|---|
| NPB | 2.48 | 501 |
| YGA1BP | 2.87 | 432 |
| YGAF | 2.70 | 458 |

Figure 42:
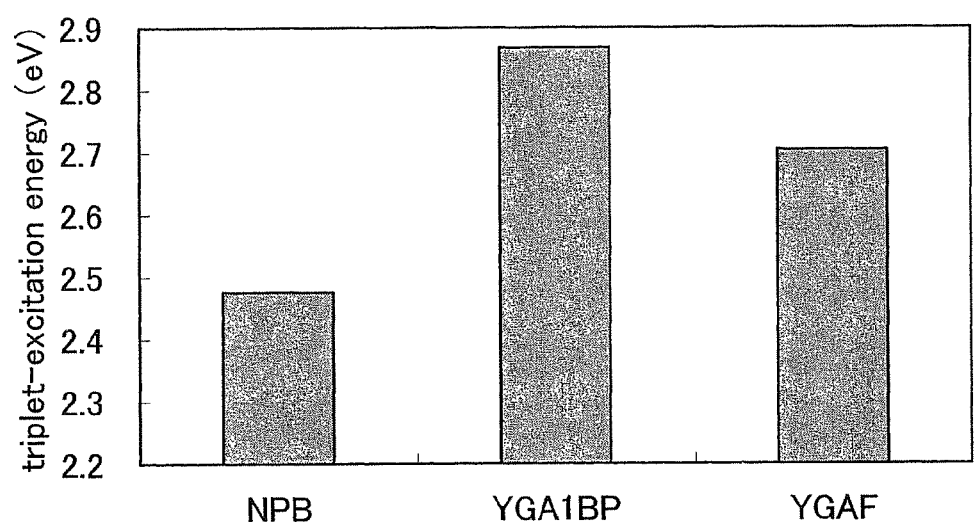
FIG. 42 shows triplet-excitation energy of an aromatic amine compound of the present invention.

As can be seen from Table 1 and FIG. 42, YGAF and YGA1BP which are the aromatic amine compounds of the present invention have higher triplet-excitation energy than NPB used for the comparative light-emitting element 6. In particular, YGA1BP has high triplet-excitation energy. The wavelength corresponding to the triplet-excitation energy of the aromatic amine compound of the present invention is about 450 nm, which corresponds to blue color. On the other hand, the wavelength corresponding to the triplet-excitation energy of NPB used for the comparative light-emitting element 6 is 500 nm, which corresponds to green color. Therefore, in a case of using NPB for a layer which is in contact with a green phosphorescent material, even when the green phosphorescent material is excited, the energy may transfer to NPB. Accordingly, light is not emitted from the phosphorescent material, which lowers the luminous efficiency. In contrast, in a case of using the aromatic amine compound of the present invention for a layer which is in contact with a phosphorescent material emitting green phosphorescent light, the energy does not transfer from the excited green phosphorescent material to the aromatic amine compound of the present invention. Moreover, when the aromatic amine compound of the present invention is excited, the energy can transfer to the green phosphorescent material. Therefore, high luminous efficiency can be achieved.

Moreover, singlet-excitation energy is higher than triplet-excitation energy. Therefore, a similar effect can also be obtained from a fluorescent material as well as the phosphorescent material. Specifically, since the wavelength for the aromatic amine compound of the present invention with respect to the triplet-excitation energy corresponds to blue color, the wavelength corresponding to the singlet-excitation energy is shorter than that of blue color. Therefore, in a case of using the aromatic amine compound for a layer which is in contact with a blue fluorescent material, the energy does not transfer from the excited blue fluorescent material to the aromatic amine compound of the present invention. In a case of the aromatic amine compound of the present invention being excited, the energy can transfer to the fluorescent material. Accordingly, high luminous efficiency can be achieved.

In this manner, with the aromatic amine compound of the present invention used for the hole-transporting layer, the light-emitting element with favorable characteristics can be obtained.

Embodiment 7

Embodiment 7 will explain a method of synthesizing 4-(carbazol-9-yl)phenyl-3'-phenyltriphenylamine (abbr.: mYGA1BP) expressed by Structure Formula (69). The following shows Synthesis Scheme (J-1) of mYGA1BP.

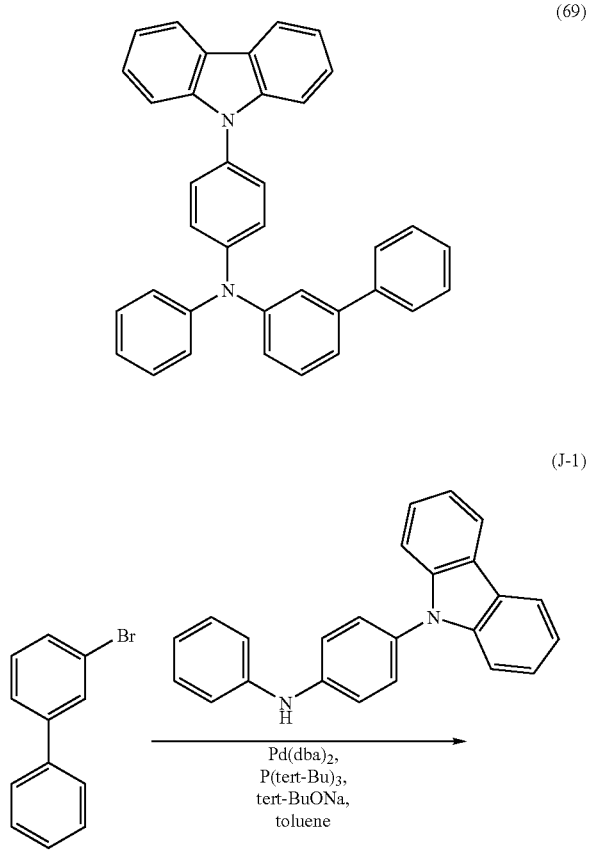

(69)

(J-1)

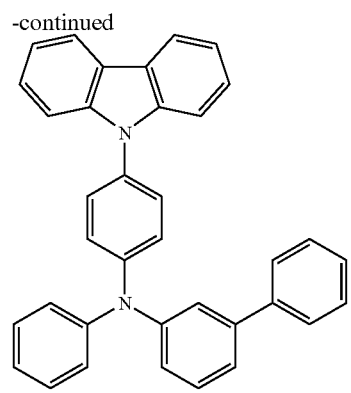

In a three-necked flask of 200 mL content, 1.9 g (5.8 mmol) of 4-(N-carbazolyl)diphenylamine and 2.0 g (21 mmol) of sodium tert-butoxide were put and nitrogen substitution in the flask was carried out. In this mixture, 30 mL of toluene, 0.1 mL of tri(tert-butyl)phosphine (10 wt % hexane solution), and 1.4 g (5.8 mmol) of 3-bromobiphenyl were added. The mixture was stirred under low pressure so as to be deaerated. After the deaeration, 33 mg (0.06 mmol) of bis(dibenzylideneacetone)palladium(0) was added. This mixture was stirred for five hours at 80° C. After the reaction, the reaction mixture was subjected to suction filtration through Florisil, celite, and alumina and the filtrate was concentrated, thereby obtaining a white solid. When this solid was recrystallized by dichloromethane and hexane, 2.1 g of a white powder-like solid, which is a target matter, was obtained with a yield of 98%. It was confirmed by nuclear magnetic resonance spectroscopy (NMR) that this compound was 4-(carbazol-9-yl)phenyl-3'-phenyltriphenylamine (abbr.: mYGA1BP) expressed by Structure Formula (69).

Figure 46A:
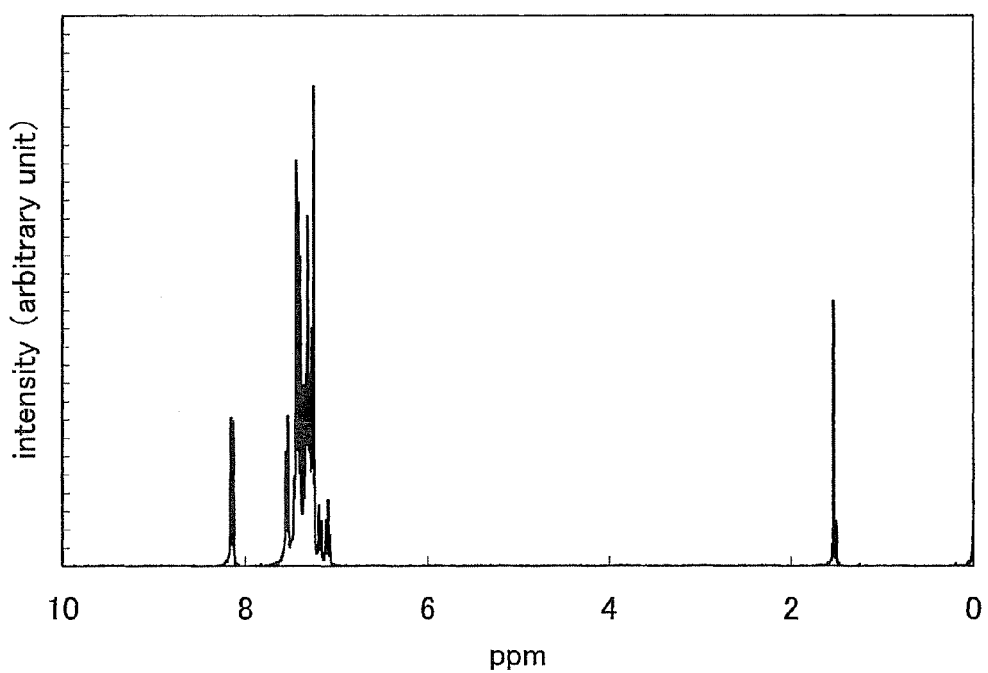
FIGS. 46A and 46B each show a $^1$H-NMR chart of 4-(carbazol-9-yl)phenyl-3'-phenyltriphenylamine (abbr.: mYGA1BP)
Figure 46B:
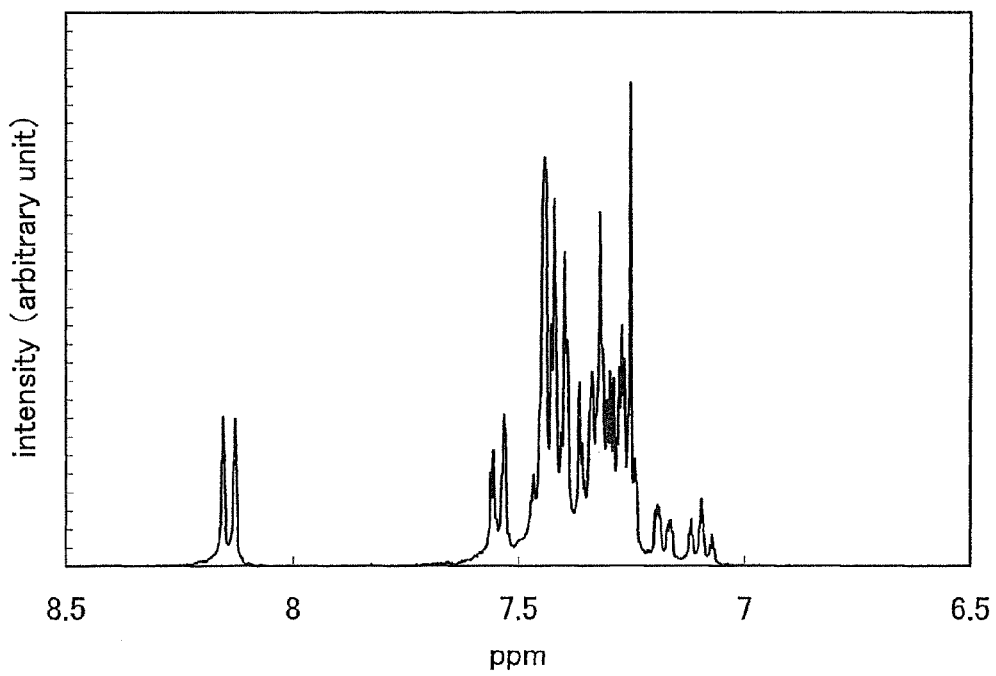

The $^1$H-NMR data on this compound are shown. The $^1$H-NMR (300 MHz, CDCl$_3$): δ=7.07-7.12 (m, 1H), 7.17-7.20 (m, 1H), 7.27-7.47 (m, 20H), 7.53-7.56 (m, 2H), and 8.14 (d, J=7.8 Hz, 2H). A $^1$H-NMR chart is also shown in FIGS. 46A and 46B. Further, FIG. 46B is a chart showing an enlarged part in the range of 6.5 ppm to 8.5 ppm of FIG. 46A.

The obtained mYGA1BP with an amount of 1.9 g was purified by sublimation for 15 hours at a heating temperature of 225° C. under a pressure of 5.9 Pa in the flow of argon gas at a flow rate of 3.0 ml/min; thus, 1.7 g of a white (achromatous) needle-like crystal as a target matter was obtained with a yield of 90%.

A thermogravimetry-differential thermal analysis (TG-DTA) of mYGA1BP was conducted by using a high vacuum differential type differential thermal balance (manufactured by Bruker AXS K.K., DTA2410SA). When the measurement was conducted under a low pressure of 10 Pa, the temperature at which the weight becomes 95% or lower of the weight at the start of the measurement was 224° C. from the relation between the weight and temperature (thermogravimetry). When the measurement was conducted at normal pressure, the temperature at which the weight becomes 95% or lower of the weight at the start of the measurement was 391° C. It is to be noted that the temperature-rising speed was 10° C./min in either measurement.

Figure 47:
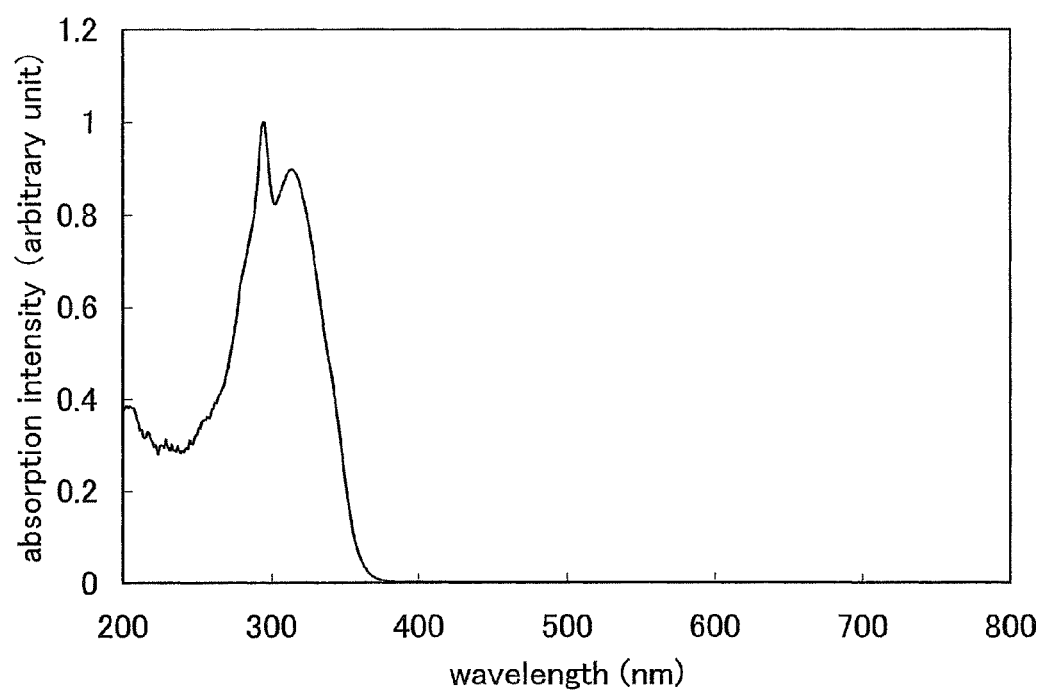
FIG. 47 shows an absorption spectrum of a toluene solution of 4-(carbazol-9-yl)phenyl-3'-phenyltriphenylamine (abbr.: mYGA1BP)
Figure 48:
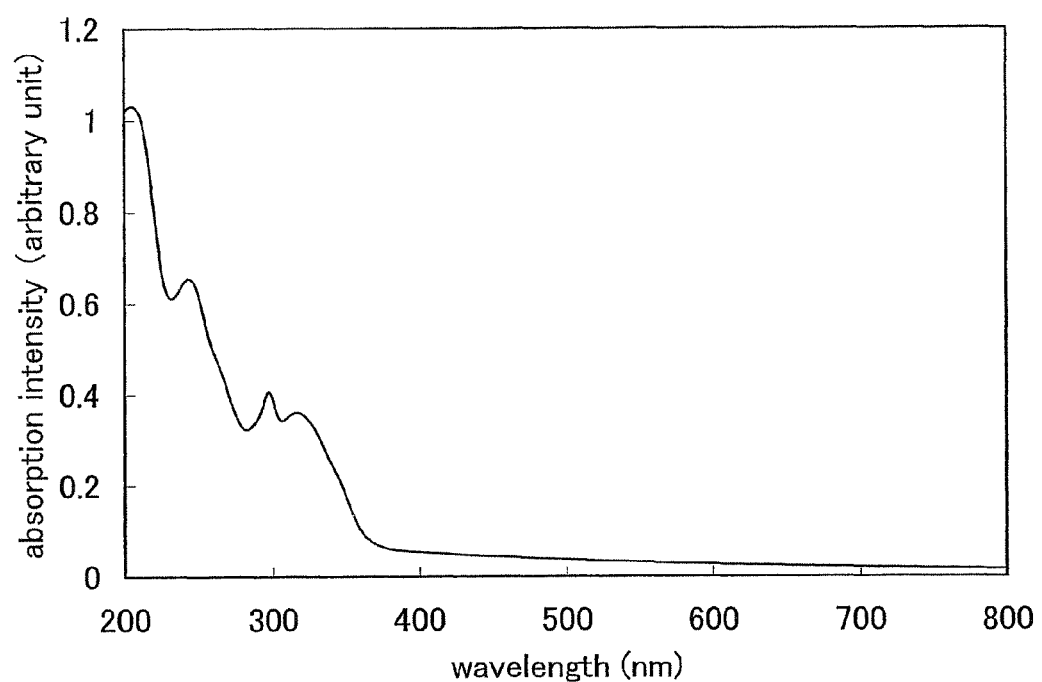
FIG. 48 shows an absorption spectrum of a thin film of 4-(carbazol-9-yl)phenyl-3'-phenyltriphenylamine (abbr.: mYGA1BP)
Figure 49:
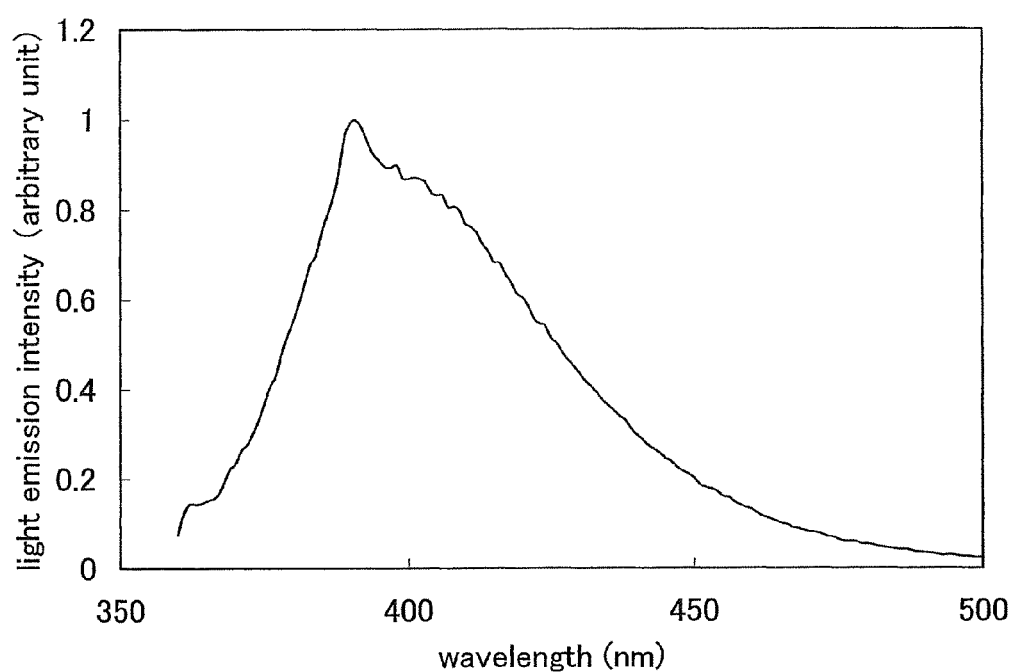
FIG. 49 shows a light emission spectrum of a toluene solution of 4-(carbazol-9-yl)phenyl-3'-phenyltriphenylamine (abbr.: mYGA1BP)
Figure 50:
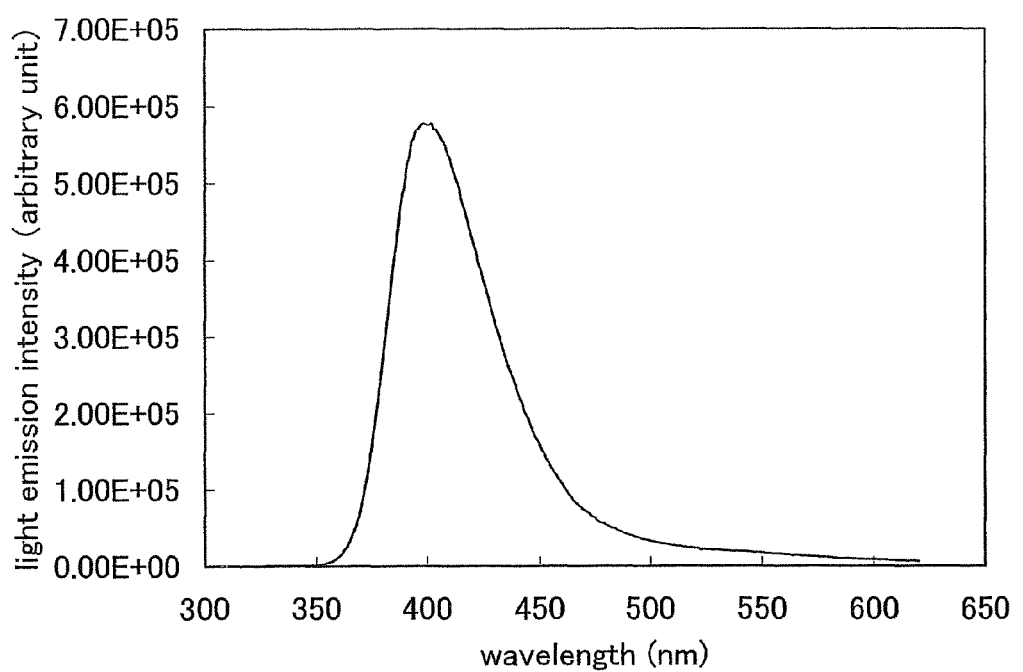
FIG. 50 shows a light emission spectrum of a thin film of 4-(carbazol-9-yl)phenyl-3'-phenyltriphenylamine (abbr.: mYGA1BP)

FIG. 47 shows an absorption spectrum of a toluene solution of mYGA1BP. FIG. 48 shows an absorption spectrum of a thin film of mYGA1BP. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIGS. 47 and 48. In FIGS. 47 and 48, the horizontal axis shows a wavelength (nm) while the vertical axis shows absorption intensity (arbitrary unit). In the case of the toluene solution, absorption was observed at around 294 nm and 313 nm, and in the case of the thin film, it was observed at around 317 nm. The light emission spectrum of the toluene solution of mYGA1BP (excitation wavelength: 350 nm) is shown in FIG. 49, while that of the thin film of mYGA1BP (excitation wavelength: 317 nm) is shown in FIG. 50. In FIGS. 49 and 50, the horizontal axis shows a wavelength (nm) and the vertical axis shows light emission intensity (arbitrary unit). The peak of the light emission spectrum was observed at 392 nm in the case of the toluene solution (excitation wavelength: 350 nm), and 402 nm in the case of the thin film (excitation wavelength: 317 nm).

In addition, the HOMO level of mYGA1BP in the thin film state was −5.57 eV, which was measured by photoelectron spectrometer (AC-2, manufactured by Riken Keiki Co., Ltd.) in the air. Moreover, the absorption edge was obtained from Tauc plot using data on the absorption spectrum of the thin film of mYGA1BP in FIG. 48. When the absorption edge was estimated as an optical energy gap, the energy gap was 3.45 eV. Therefore, the LUMO level was −2.12 eV.

Embodiment 8

Embodiment 8 will explain a method of synthesizing 4-(carbazol-9-yl)phenyl-2'-phenyltriphenylamine (abbr.: oYGA1BP) expressed by Structure Formula (70). The following shows Synthesis Scheme (K-1) of oYGA1BP.

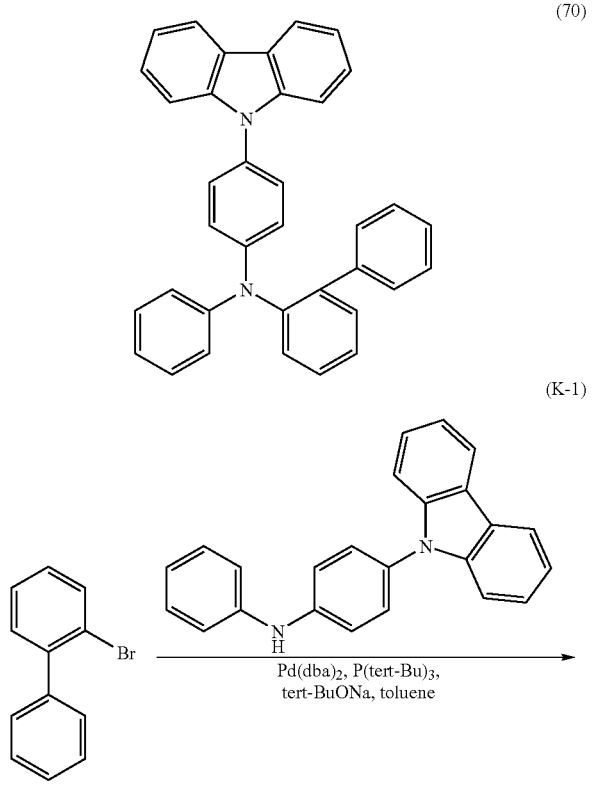

(70)

(K-1)

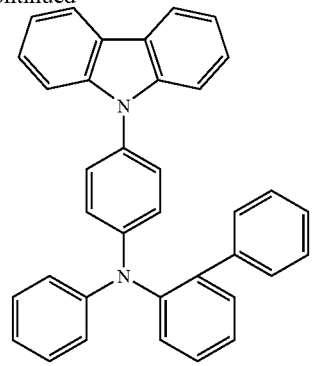

In a three-necked flask of 200 mL content, 1.9 g (5.8 mmol) of 4-(N-carbazolyl)diphenylamine and 2.0 g (21 mmol) of sodium tert-butoxide were put and nitrogen substitution in the flask was carried out. In this mixture, 30 mL of toluene, 0.1 mL of tri(tert-butyl)phosphine (10 wt % hexane solution), and 1.4 g (5.8 mmol) of 2-bromobiphenyl were added. The mixture was stirred under low pressure so as to be deaerated. After the deaeration, 33 mg (0.06 mmol) of bis(dibenzylideneacetone)palladium(0) was added. This mixture was stirred for five hours at 80° C. After the reaction, the reaction mixture was subjected to suction filtration through Florisil, celite, and alumina and the filtrate was concentrated, thereby obtaining a white solid. When this solid was recrystallized by dichloromethane and hexane, 2.3 g of a white powder-like solid as a target matter was obtained with a yield of 82%. It was confirmed by nuclear magnetic resonance spectroscopy (NMR) that this compound was 4-(carbazol-9-yl)phenyl-2'-phenyltriphenylamine (abbr.: oYGA1BP) expressed by Structure Formula (70).

Figure 51A:
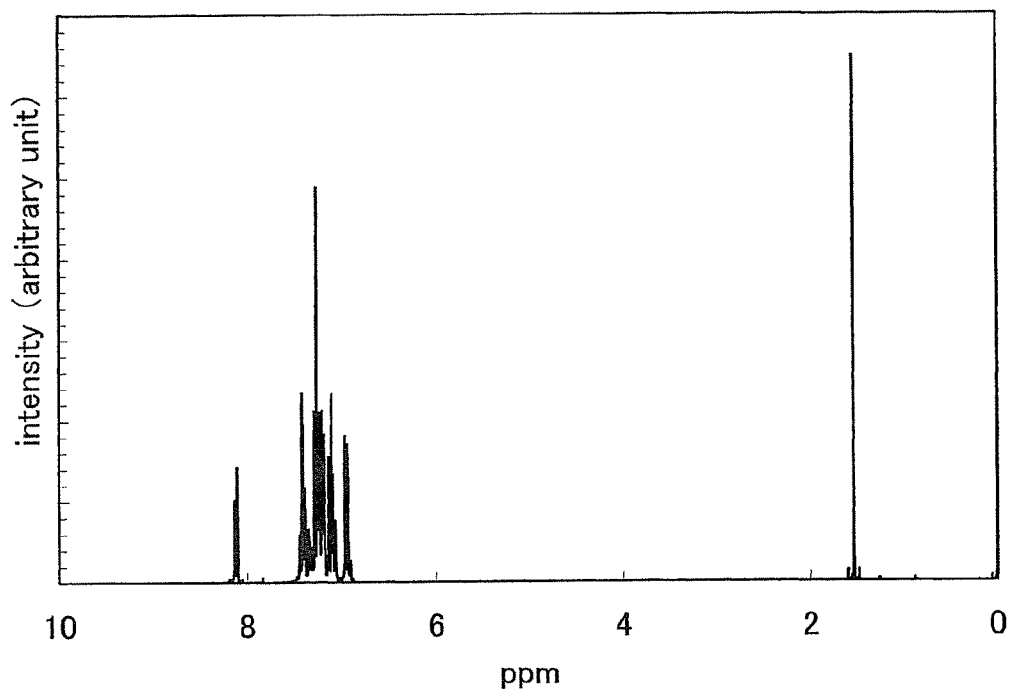
FIGS. 51A and 51B each show a $^1$H-NMR chart of 4-(carbazol-9-yl)phenyl-2'-phenyltriphenylamine (abbr.: oYGA1BP)
Figure 51B:
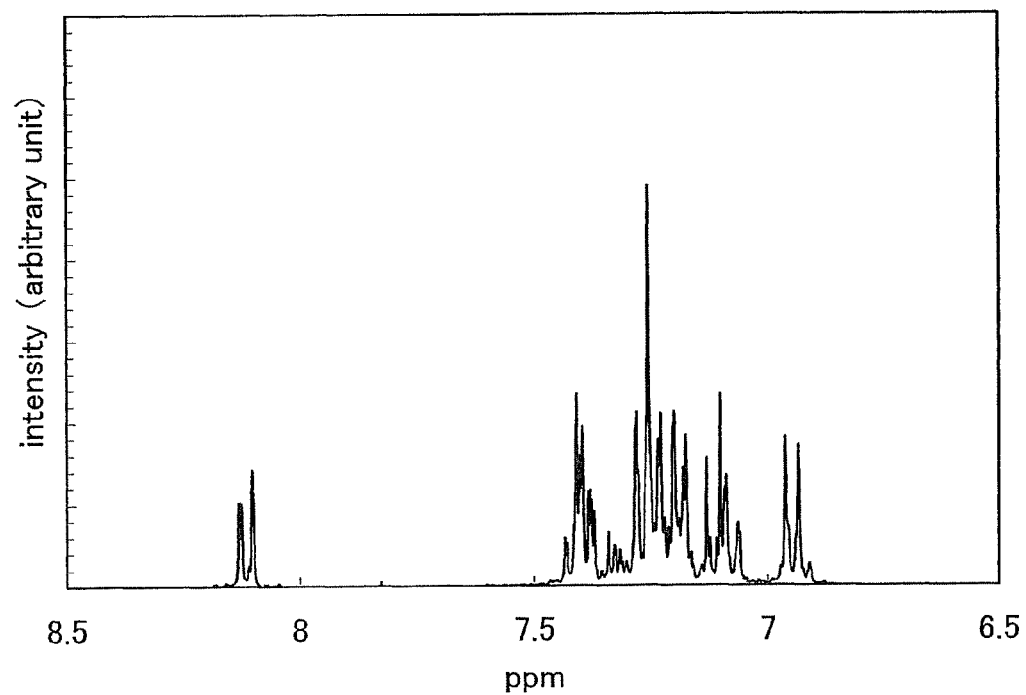

The $^1$H-NMR data on this compound are shown. The $^1$H-NMR (300 MHz, CDCl$_3$); δ=6.91-6.96 (m, 3H), 7.06-7.09 (m, 2H), 7.12 (d, 8.7 Hz, 2H), 7.18-7.44 (m, 17H), and 8.10-8.13 (m, 2H). A $^1$H-NMR chart is also shown in FIGS. 51A and 51B. Further, FIG. 51B is a chart showing an enlarged part in the range of 6.5 ppm to 8.5 ppm of FIG. 51A.

The obtained oYGA1BP with an amount of 2.0 g was purified by sublimation for 15 hours at a heating temperature of 210° C. under a pressure of 5.9 Pa in the flow of argon gas at a flow rate of 3.0 mL/min; thus, 1.9 g of a white (achromatous) needle-like crystal as a target matter was obtained with a yield of 87%.

A thermogravimetry-differential thermal analysis (TG-DTA) of oYGA1BP was conducted by using a high vacuum differential type differential thermal balance (manufactured by Bruker AXS K.K., DTA2410SA). When the measurement was conducted under a low pressure of 10 Pa, the temperature at which the weight becomes 95% or lower of the weight at the start of the measurement was 208° C. from the relation between the weight and temperature (thermogravimetry). When the measurement was conducted at normal pressure, the temperature at which the weight becomes 95% or lower of the weight at the start of the measurement was 370° C. It is to be noted that the temperature-rising speed was 10° C./min in either measurement.

Figure 52:
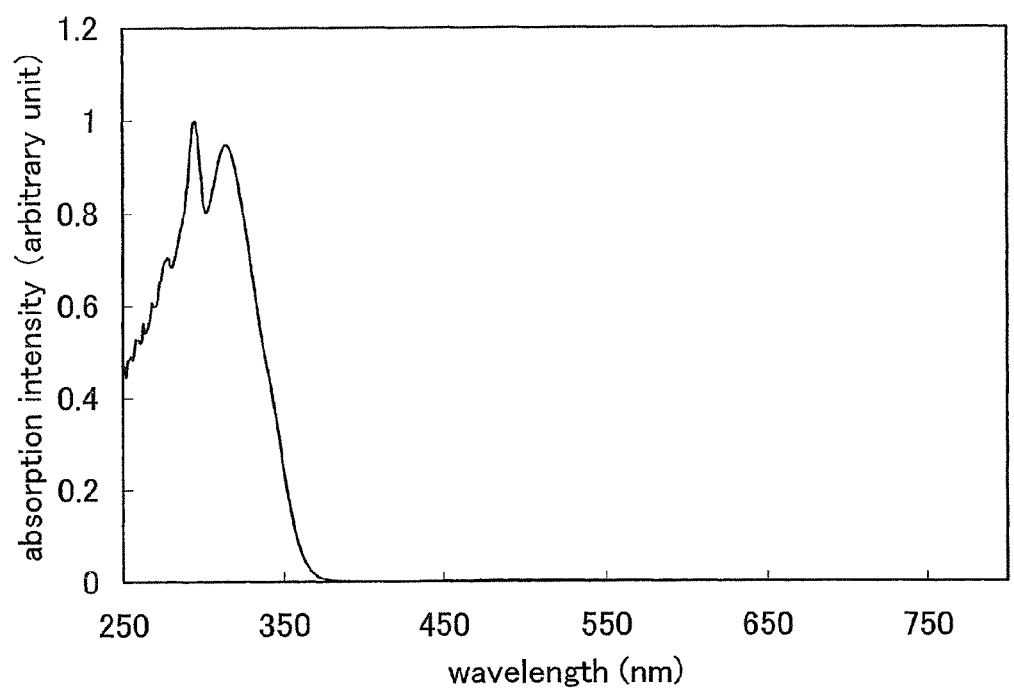
FIG. 52 shows an absorption spectrum of a toluene solution of 4-(carbazol-9-yl)phenyl-2'-phenyltriphenylamine (abbr.: oYGA1BP)
Figure 53:
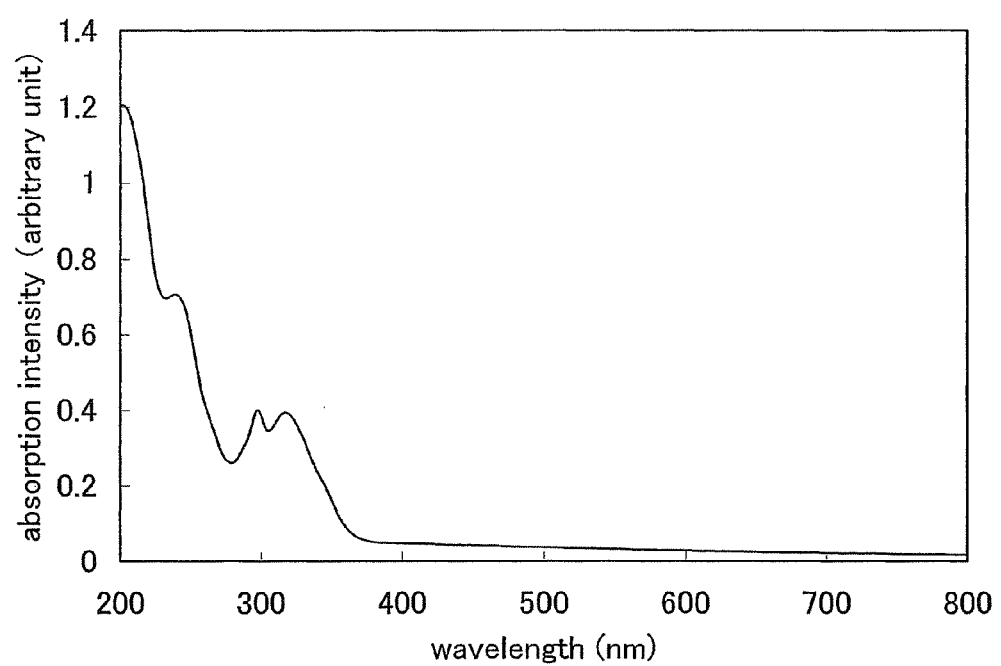
FIG. 53 shows an absorption spectrum of a thin film of 4-(carbazol-9-yl)phenyl-2'-phenyltriphenylamine (abbr.: oYGA1BP)
Figure 54:
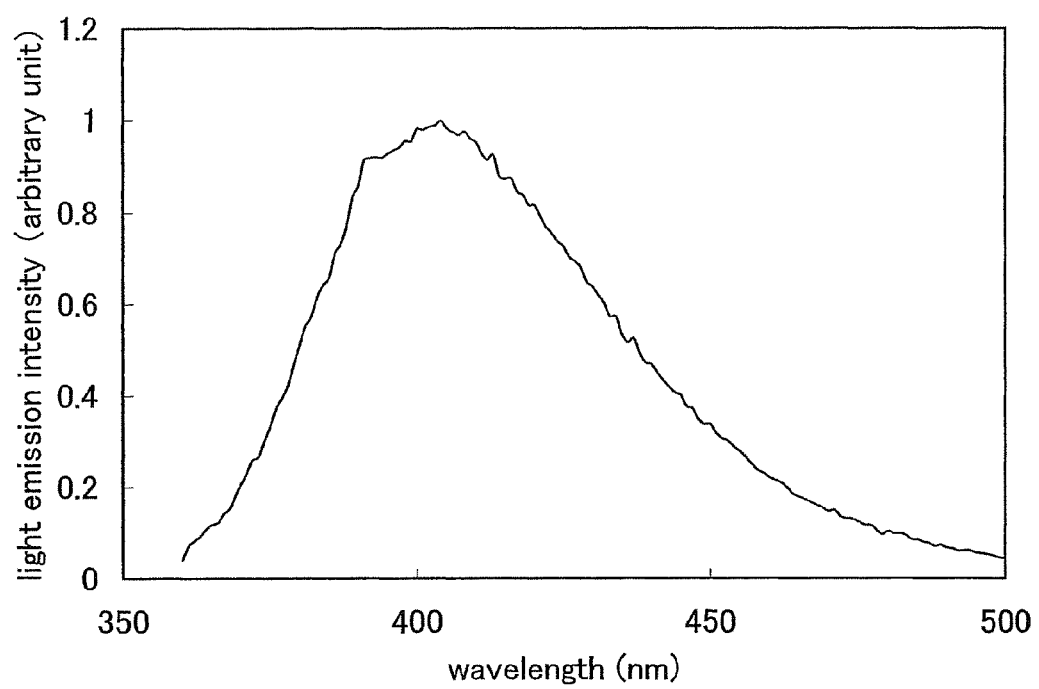
FIG. 54 shows a light emission spectrum of a toluene solution of 4-(carbazol-9-yl)phenyl-2'-phenyltriphenylamine (abbr.: oYGA1BP)
Figure 55:
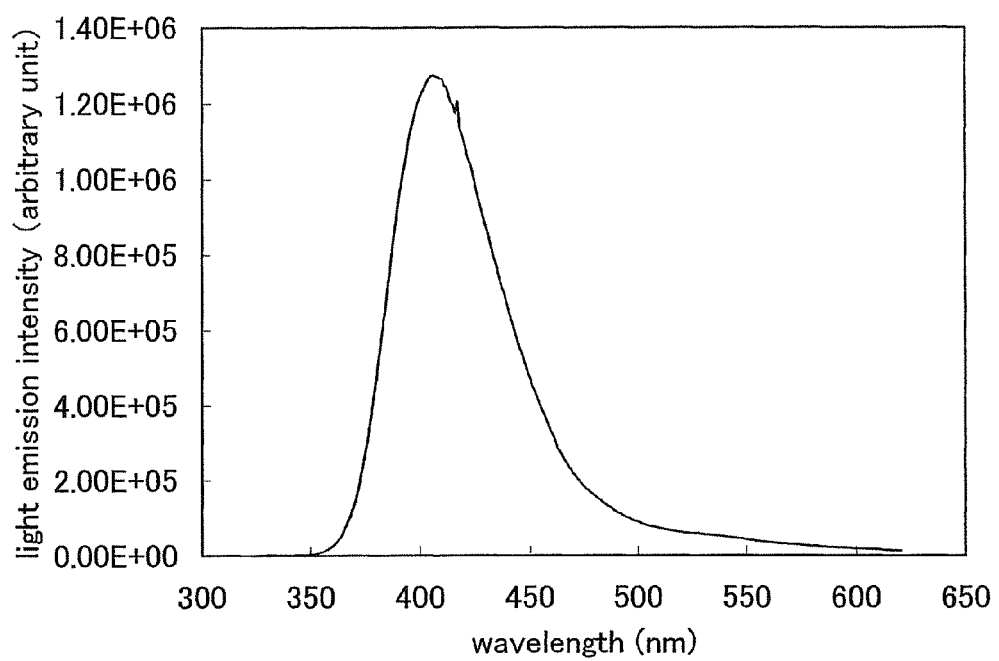
FIG. 55 shows a light emission spectrum of a thin film of 4-(carbazol-9-yl)phenyl-2'-phenyltriphenylamine (abbr.: oYGA1BP)

FIG. 52 shows an absorption spectrum of a toluene solution of oYGA1BP. FIG. 53 shows an absorption spectrum of a thin film of oYGA1BP. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIGS. 52 and 53. In FIGS. 52 and 53, the horizontal axis shows a wavelength (nm) while the vertical axis shows absorption intensity (arbitrary unit). In the case of the toluene solution, absorption was observed at around 294 nm and 311 nm, and in the case of the thin film, it was observed at around 317 nm. The light emission spectrum of the toluene solution of oYGA1BP (excitation wavelength: 350 nm) is shown in FIG. 54, while that of the thin film of oYGA1BP (excitation wavelength: 317 nm) is shown in FIG. 55. In FIGS. 54 and 55, the horizontal axis shows a wavelength (.nm) and the vertical axis shows light emission intensity (arbitrary unit). The peak of the light emission spectrum was observed at 404 nm in the case of the toluene solution (excitation wavelength: 350 nm), and 407 nm in the case of the thin film (excitation wavelength: 317 nm).

In addition, the HOMO level of oYGA1BP in the thin film state was −5.56 eV, which was measured by photoelectron spectrometer (AC-2, manufactured by Riken Keiki Co., Ltd.) in the air. Moreover, the absorption edge was obtained from Tauc plot using data on the absorption spectrum of the thin film of oYGA1BP in FIG. 53. When the absorption edge was estimated as an optical energy gap, the energy gap was 3.46 eV. Therefore, the LUMO level was −2.10 eV.

Embodiment 9

Embodiment 9 will explain a method of synthesizing N,N'-bis[4-(carbazol-9-yl)phenyl]-N,N'-di(1-naphthyl)biphenyl-4,4'-diamine (abbr.: YGNBP) expressed by Structure Formula (107).

(107)

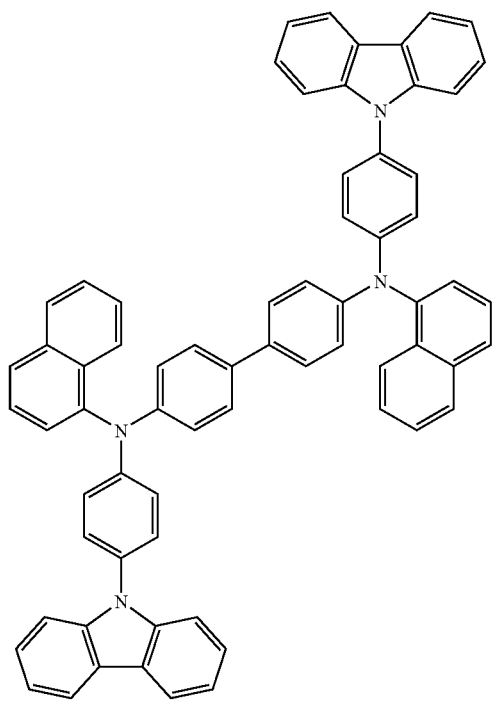

[Step 1]
A method of synthesizing N,N'-di(1-naphthyl)benzidine is explained. The following shows Synthesis Scheme (L-1) of N,N'-di(1-naphthyl)benzidine.

(L-1)

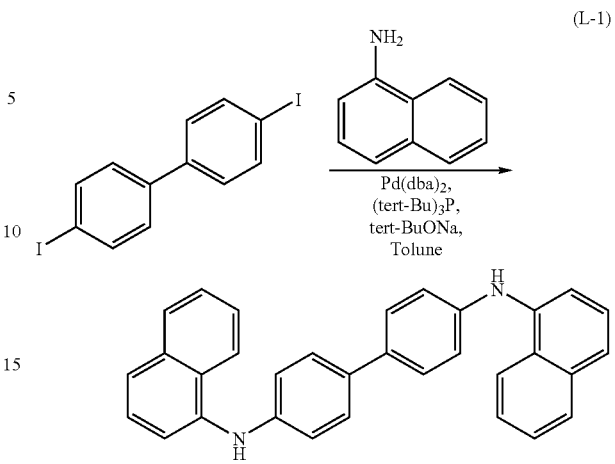

In a three-necked flask of 500 mL content, 20 g (50 mmol) of 4,4'-diiodobiphenyl, 14 g (100 mmol) of 1-naphthylamine, 580 mg (1 mmol) of bis(dibenzylideneacetone)palladium(0), and 12 g (12 mmol) of sodium tert-butoxide were put and 100 mL of dehydrated toluene was added. Then, the pressure in the three-necked flask was reduced for three minutes to perform deaeration until no bubbles came out. In this mixture, 6.0 mL (3.0 mmol) of tri(tert-butyl)phosphine (10 wt % hexane solution) was added and stirred while heated at 100° C. in a nitrogen atmosphere. The heating was stopped after three hours, and about 700 mL of a mixture solution of hot toluene and ethyl acetate was added to this reaction suspension and the suspension was filtered through Florisil, alumina, and celite. The obtained filtrate was washed with water and dried by adding magnesium sulfate to an organic layer. This suspension was further filtered and the obtained filtrate was concentrated. After adding hexane to this concentrated solution, recrystallization was performed by applying ultrasonic waves. The produced solid was filtered off and dried. Thus, 13 g of a white powder-like target matter was obtained with a yield of 57%. An Rf value of the target matter by a silicagel thin layer chromatography (TLC) (developing solution was hexane:ethyl acetate=2:1) was 0.53 and that of 1-naphthylamine was 0.36.

[Step 2]

A method of synthesizing N,N'-bis[4-(carbazol-9-yl)phenyl]-N,N'-di(1-naphthyl)biphenyl-4,4'-diamine (abbr.: YGNBP) is explained. The following shows Synthesis Scheme (L-2) of YGNBP.

(L-2)

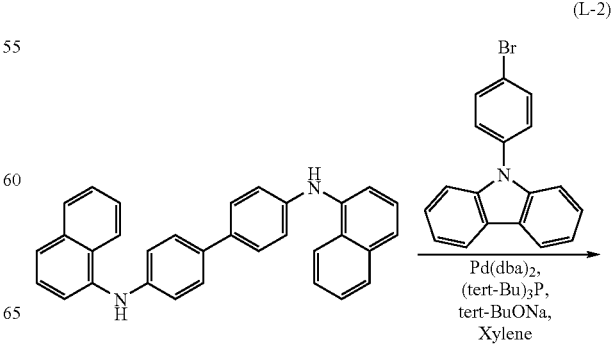

-continued

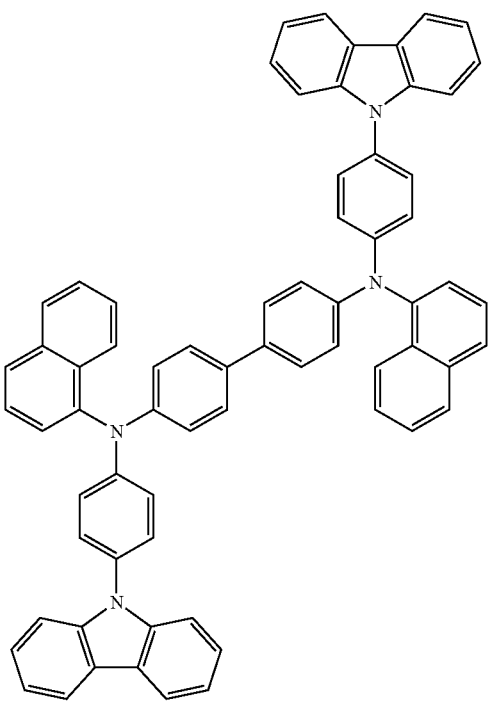

In a three-necked flask of 100 mL content, 3.5 g (11 mmol) of 4-bromophenylcarbazole, 2.2 g (5.0 mmol) of N,N'-di(1-naphthyl)benzidine, 30 mg (0.1 mmol) of bis(dibenzylideneacetone)palladium(0), and 1.5 g (15 mmol) of sodium tert-butoxide were put, and 20 mL of dehydrated xylene was added. Then, the pressure in the three-necked flask was reduced for three minutes to perform deaeration until no bubbles came out. In this mixture, 0.6 mL (0.3 mmol) of tri(tert-butyl)phosphine (10 wt % hexane solution) was added and stirred while heated at 130° C. in a nitrogen atmosphere. The heating was stopped after four hours, and about 200 mL of toluene was added to this reaction suspension and filtration was performed through Florisil, alumina, and celite. The obtained filtrate was washed with water and dried by adding magnesium sulfate to an organic layer. This suspension was further filtered through Florisil, alumina, and celite, and the obtained filtrate was concentrated. After adding acetone and hexane to this concentrated solution, recrystallization was performed by applying ultrasonic waves. The produced solid was filtered off and dried. Thus, 2.0 g of a light-yellow powder as a target matter was obtained with a yield of 43%. It was confirmed by nuclear magnetic resonance spectroscopy (NMR) that this compound was N,N'-bis[4-(carbazol-9-yl)phenyl]-N,N'-di(1-naphthyl)biphenyl-4,4'-diamine (abbr.: YGNBP) expressed by Structure Formula (107).

Figure 56A:
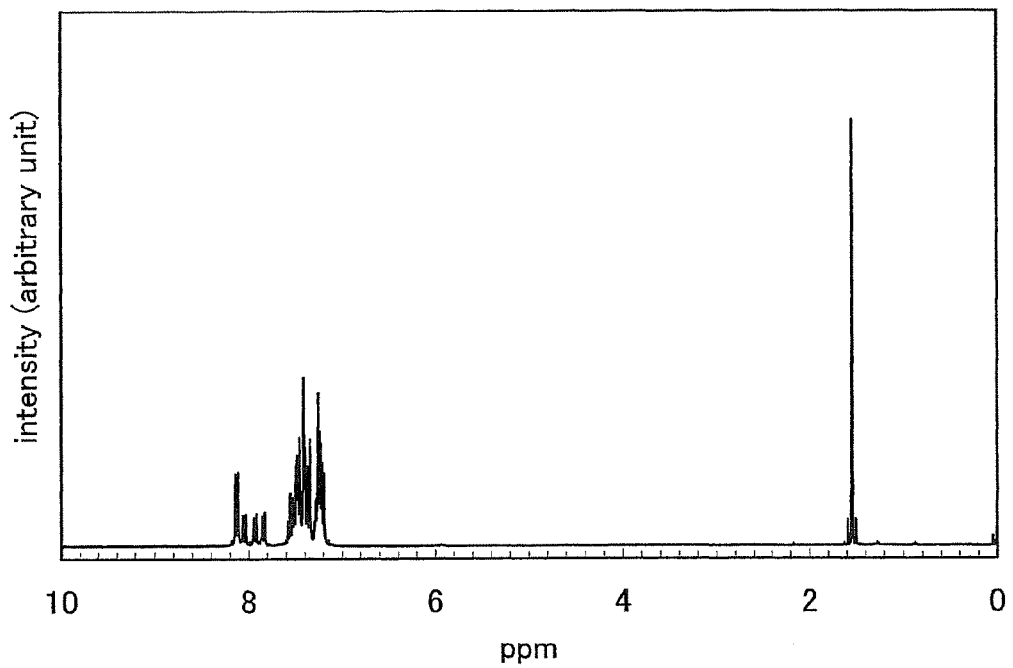
FIGS. 56A and 56B each show a $^1$H-NMR chart of N,N'-bis[4-(carbazol-9-yl)phenyl]-N,N'-di(1-naphthyl)biphenyl-4,4'-diamine (abbr.: YGNBP)
Figure 56B:
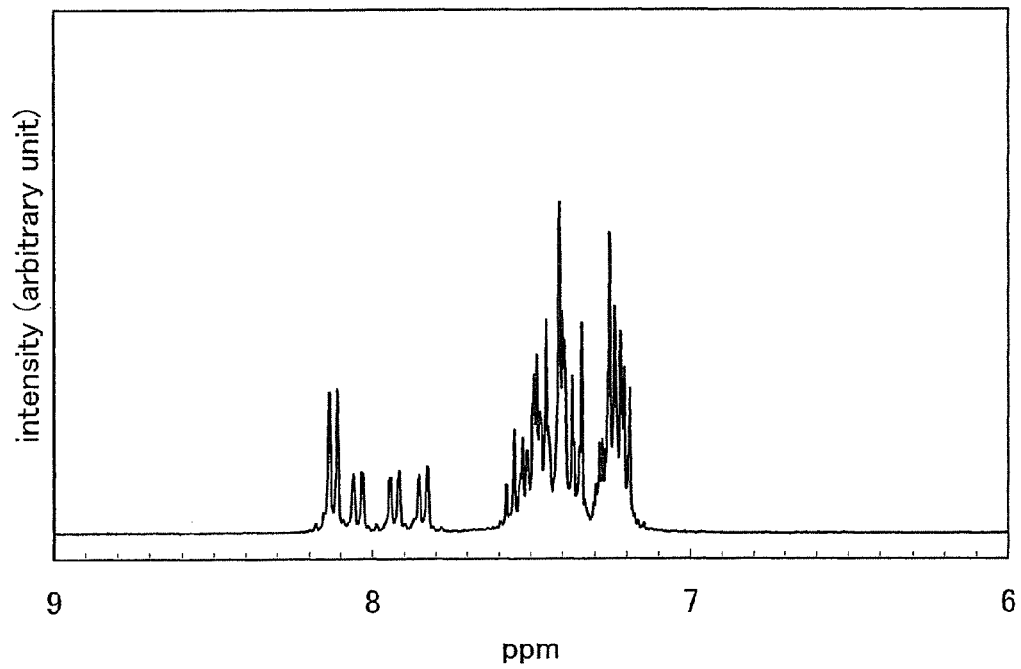

The $^1$H-NMR data on this compound are shown. The $^1$H-NMR (300 MHz, CDCl$_3$): δ (ppm)=7.19-7.58 (m, 36H), 7.84 (d, J=7.8, 2H), 7.93 (d, J=7.8, 2H), 8.05 (d, J=8.1, 2H), and 8.12 (d, J=7.2, 4H). A $^1$H-NMR chart is also shown in FIGS. 56A and 56B. Further, FIG. 56B is a chart showing an enlarged part in the range of 6.0 ppm to 9.0 ppm of FIG. 56A.

Figure 57A:
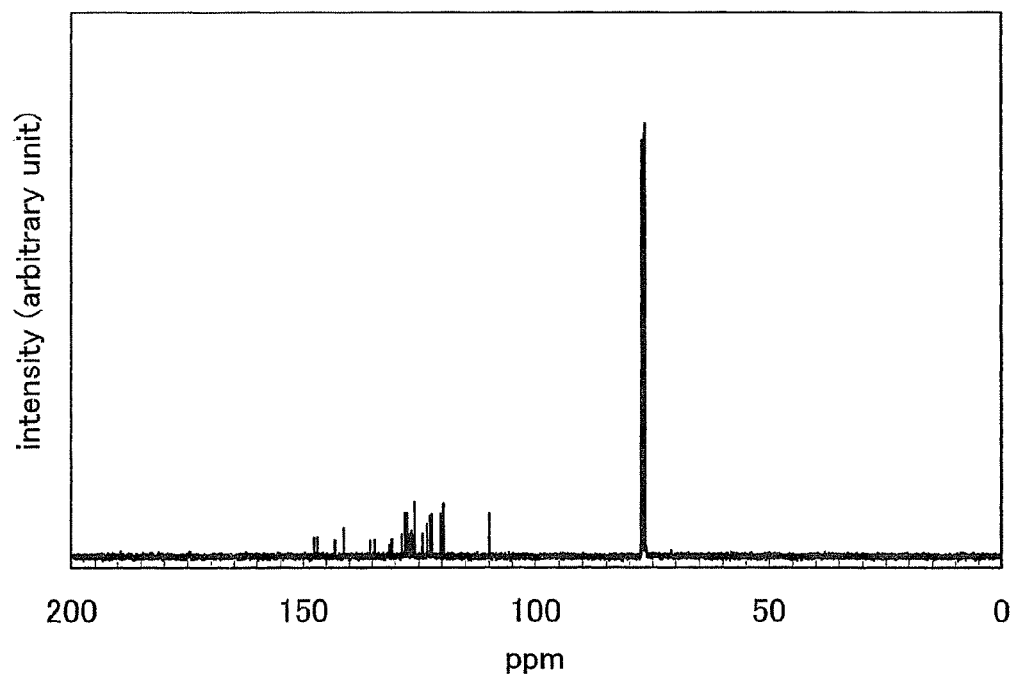
FIGS. 57A and 57B each show a $^{13}$C-NMR chart of N,N'-bis[4-(carbazol-9-yl)phenyl]-N,N'-di(1-naphthyl)biphenyl-4,4'-diamine (abbr.: YGNBP)
Figure 57B:
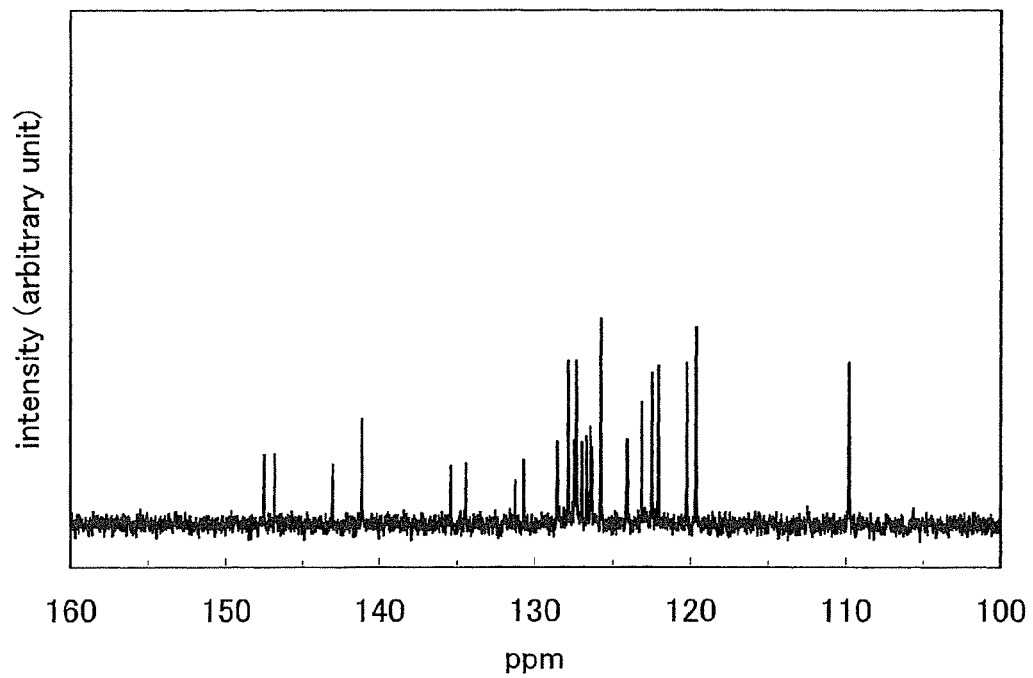

Moreover, the $^{13}$C-NMR data on this compound are shown. The $^{13}$C-NMR (75.5 MHz, CDCl$_3$): δ (ppm)=109.82, 119.65, 120.23, 122.06, 122.47, 123.15, 124.10, 125.78, 126.34, 126.45, 126.69, 126.99, 127.36, 127.47, 127.86, 128.55, 130.69, 131.26, 134.41, 135.40, 141.12, 143.02, 146.85, 147.53. A $^{13}$C-NMR chart is also shown in FIGS. 57A and 57B. Further, FIG. 57B is a chart showing an enlarged part in the range of 100 ppm to 160 ppm of FIG. 57A.

A thermogravimetry-differential thermal analysis (TG-DTA) of YGNBP was conducted by using a high vacuum differential type differential thermal balance (manufactured by Bruker AXS K.K., DTA2410SA). When the measurement was conducted under a low pressure of 10 Pa, the temperature at which the weight becomes 95% or lower of the weight at the start of the measurement was 390° C. from the relation between the weight and temperature (thermogravimetry). When the measurement was conducted at normal pressure, the weight was 99% of the weight at the start of the measurement at 500° C., and the heat resistance was excellent. It is to be noted that the temperature-rising speed was 10° C./min in either measurement.

Figure 72:
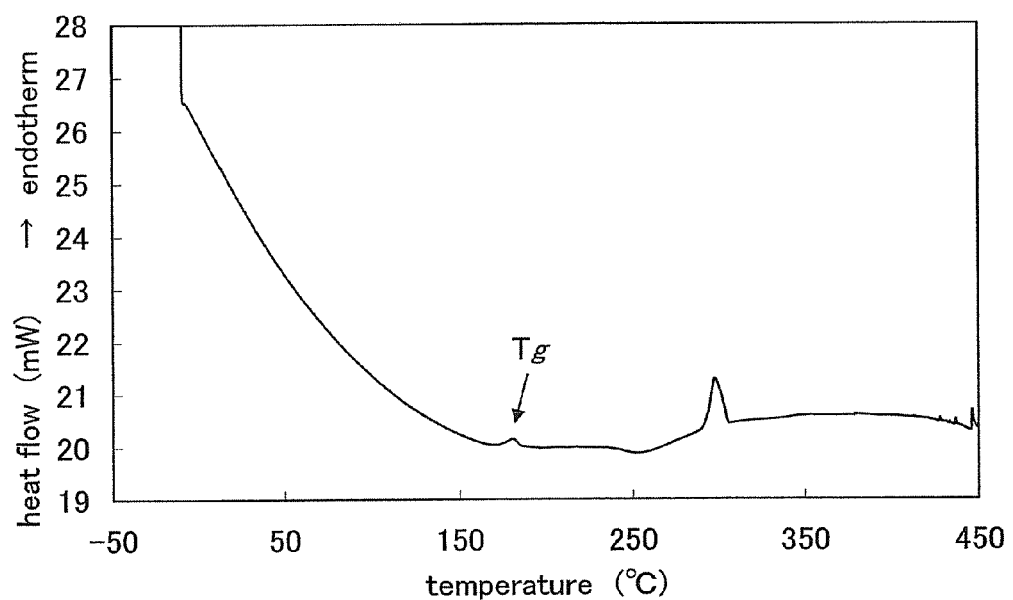
FIG. 72 shows a DSC chart of N,N'-bis[4-(carbazol-9-yl)phenyl]-N,N'-di-(1-naphthyl)biphenyl-4,4'-diamine (abbr.: YGNBP)

In addition, the glass transition point of YGNBP was measured by a differential scanning calorimeter (DSC, manufactured by PerkinElmer, Inc., Pyris 1). As shown in a DSC chart of FIG. 72, the temperature was raised to 500° C. at 10° C./min. In FIG. 72, the X axis shows temperature and the Y axis shows heat flow. The Y axis shows endotherm in an upward direction. It was understood from this chart that the glass transition point (T$_g$) of YGNBP was as high as 171° C.

Figure 58:
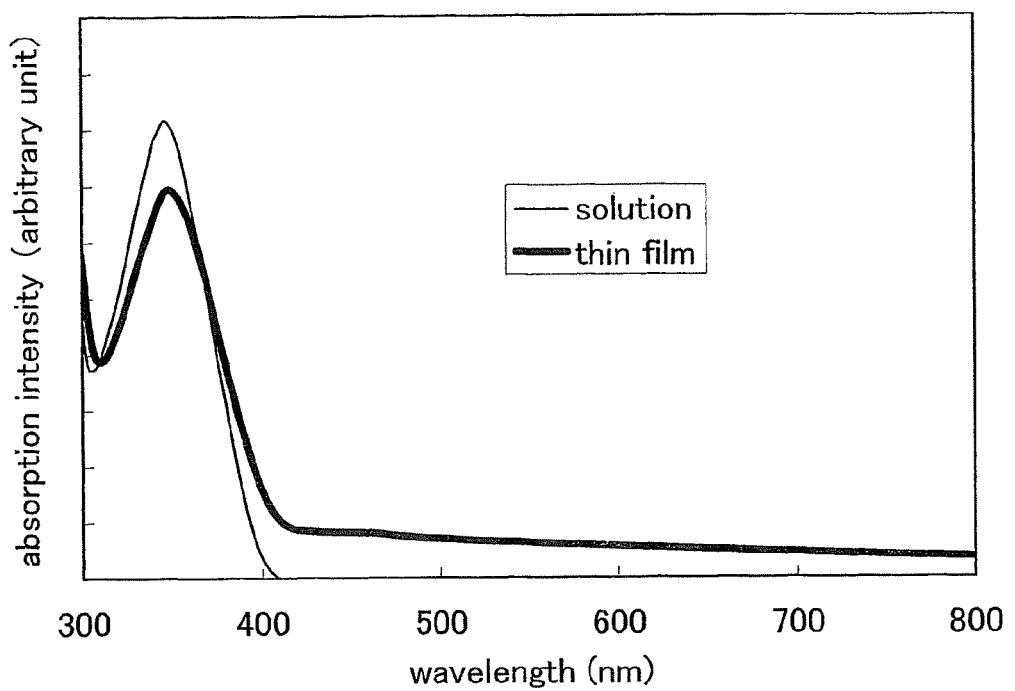
FIG. 58 shows an absorption spectrum of N,N'-bis[4-(carbazol-9-yl)phenyl]-N-di(1-naphthyl)biphenyl-4,4'-diamine (abbr.: YGNBP)
Figure 59:
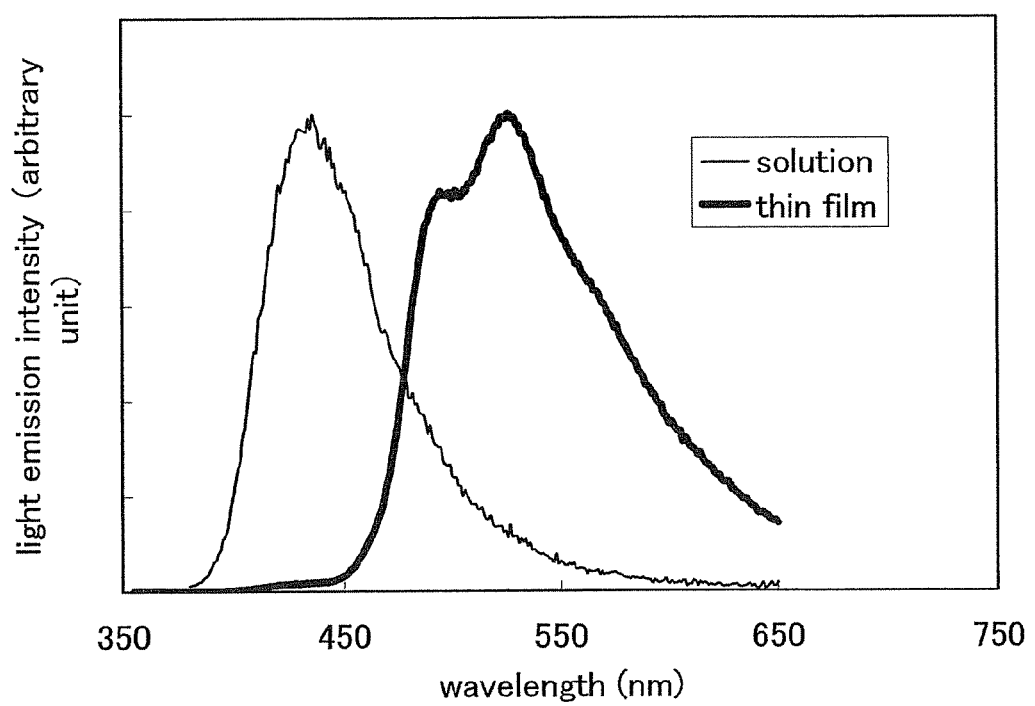
FIG. 59 shows a light emission spectrum of N,N'-bis[4-(carbazol-9-yl)phenyl]-N,N'-di(1-naphthyl)biphenyl-4,4'-diamine (abbr.: YGNBP)

FIG. 58 shows an absorption spectrum of a toluene solution of YGNBP and an absorption spectrum of a thin film of YGNBP. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIG. 58. In FIG. 58, the horizontal axis shows a wavelength (nm) while the vertical axis shows absorption intensity (arbitrary unit). In the case of the toluene solution, absorption was observed at around 345 nm, and in the case of the thin film, it was observed at around 349 nm. The light emission spectrum of the toluene solution of YGNBP (excitation wavelength: 350 nm) and that of the thin film of YGNBP (excitation wavelength: 349 nm) are shown in FIG. 59. In FIG. 59, the horizontal axis shows a wavelength (nm) and the vertical axis shows light emission intensity (arbitrary unit). The peak of the light emission spectrum was observed at 435 nm in the case of the toluene solution (excitation wavelength: 350 nm), and 526 nm in the case of the thin film (excitation wavelength: 349 nm).

In addition, the HOMO level of YGNBP in the thin film state was −5.34 eV, which was measured by photoelectron spectrometer (AC-2, manufactured by Riken Keiki Co., Ltd.) in the air. Moreover, the absorption edge was obtained from Tauc plot using data on the absorption spectrum of the thin film of YGNBP in FIG. 58. When the absorption edge was estimated as an optical energy gap, the energy gap was 3.19 eV. Therefore, the LUMO level was −2.15 eV.

Embodiment 10

Embodiment 10 will explain a method of synthesizing N,N'-bis[4-(carbazol-9-yl)-1-naphthyl]-N,N'-diphenylbiphenyl-4,4'-diamine (abbr.: CNABP) expressed by Structure Formula (115).

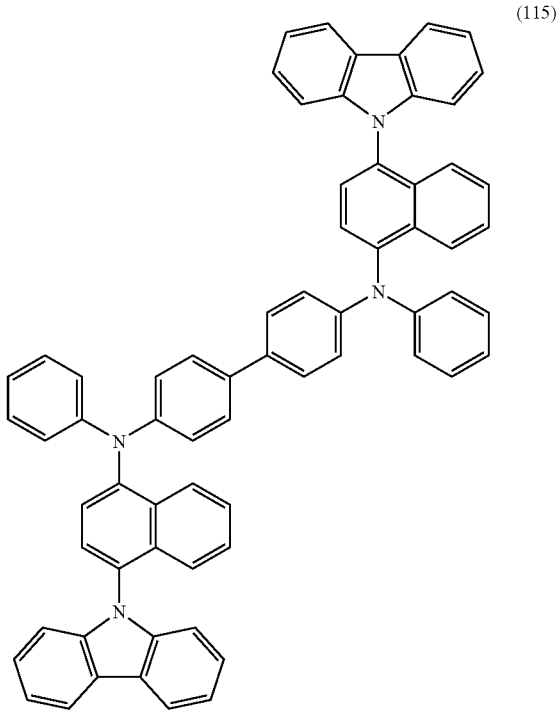

(115)

[Step 1]

A method of synthesizing 9-(4-bromo-1-naphthyl)carbazole will be explained. The following shows Synthesis Scheme (M-1) of 9-(4-bromo-1-naphthyl)carbazole.

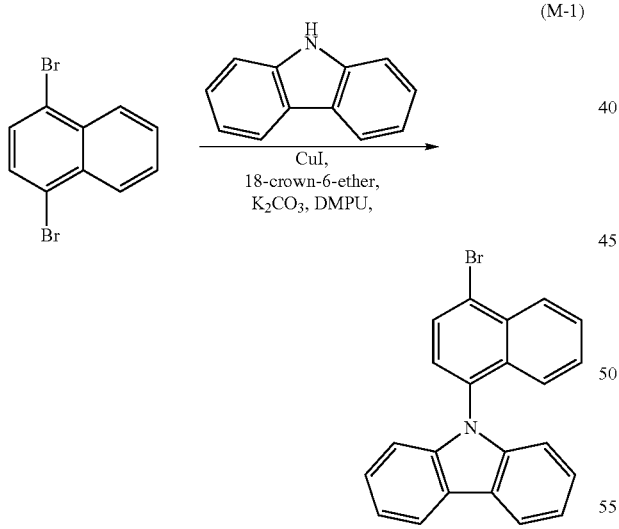

(M-1)

In a three-necked flask of 300 mL content, 14 g (50 mmol) of 1,4-dibromonaphthalene, 6.7 g (40 mmol) of carbazole, 1.9 g (10 mmol) of copper iodide(I), 1.3 g (5.0 mmol) of 18-crown-6-ether, 10 g (72 mmol) of potassium carbonate, and 8 mL of 1,3-dimethyl-3,4,5,6-tetrahydro-2(1H)-pyrimidinone (abbr.: DMPU) were put and heated at 170° C. for about 30 hours in a nitrogen atmosphere. After this reaction suspension was cooled down to room temperature, 300 mL of hot toluene was added to this reaction suspension and filtration was performed through celite. The obtained filtrate was washed with water, dilute hydrochloric acid, water, a sodium hydrogen carbonate aqueous solution, and water in this order, and dried by adding magnesium sulfate to an organic layer. This suspension was filtered through Florisil and celite, and the obtained filtrate was concentrated. This concentrated solution was sorted by silicagel chromatography (toluene: hexane=1:1). Thus, 7.5 g of a white powder as a target matter was obtained with a yield of 50%. It was confirmed by nuclear magnetic resonance spectroscopy (NMR) that this compound was 9-(4-bromo-1-naphthyl)carbazole.

Figure 60A:
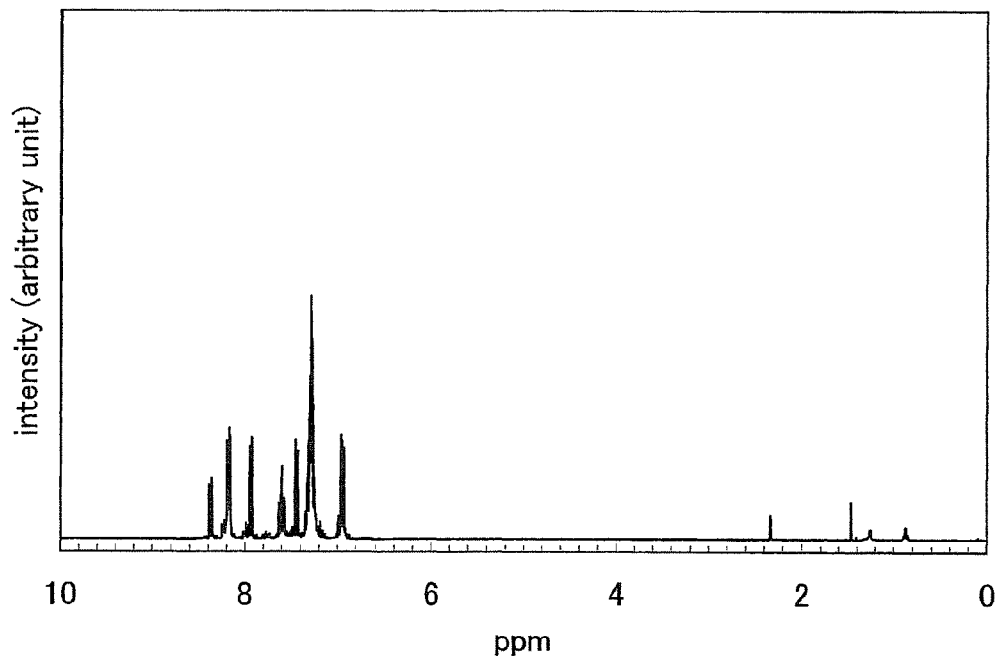
FIGS. 60A and 60B each show a $^1$H-NMR chart of 9-(4-bromo-1-naphthyl)carbazole.
Figure 60B:
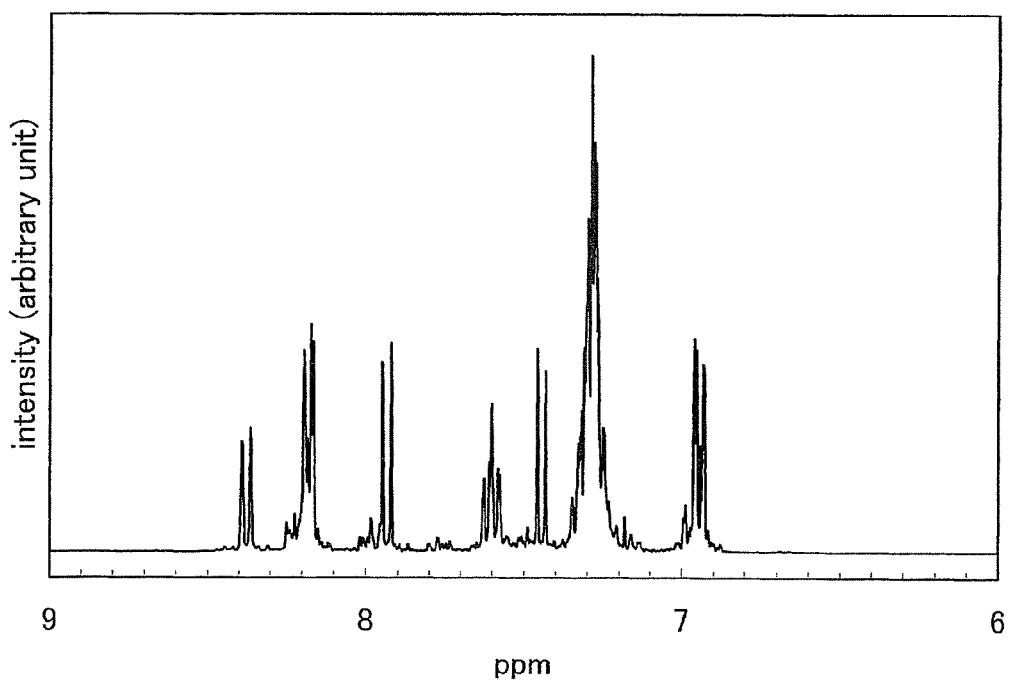

The $^1$H-NMR data on this compound are shown. The $^1$H-NMR (300 MHz, CDCl$_3$): δ (ppm)=6.93-6.96 (m, 2H), 7.25-7.33 (m, 6H), 7.45 (d, J=7.8, 1H), 7.60 (t, J=6.9, 1H), 7.94 (d, J=7.8, 1H), 8.16-8.19 (m, 2H), and 8.38 (d, J=8.7, 1H). A $^1$H-NMR chart is also shown in FIGS. 60A and 60B. Further, FIG. 60B is a chart showing an enlarged part in the range of 6.0 ppm to 9.0 ppm of FIG. 60A.

[Step 2]

A method of synthesizing N,N'-bis[4-(carbazol-9-yl)naphthyl]-N,N'-diphenylbiphenyl-4,4'-diamine (abbr.: CNABP) will be explained. The following shows Synthesis Scheme (M-2) of CNABP.

(M-2)

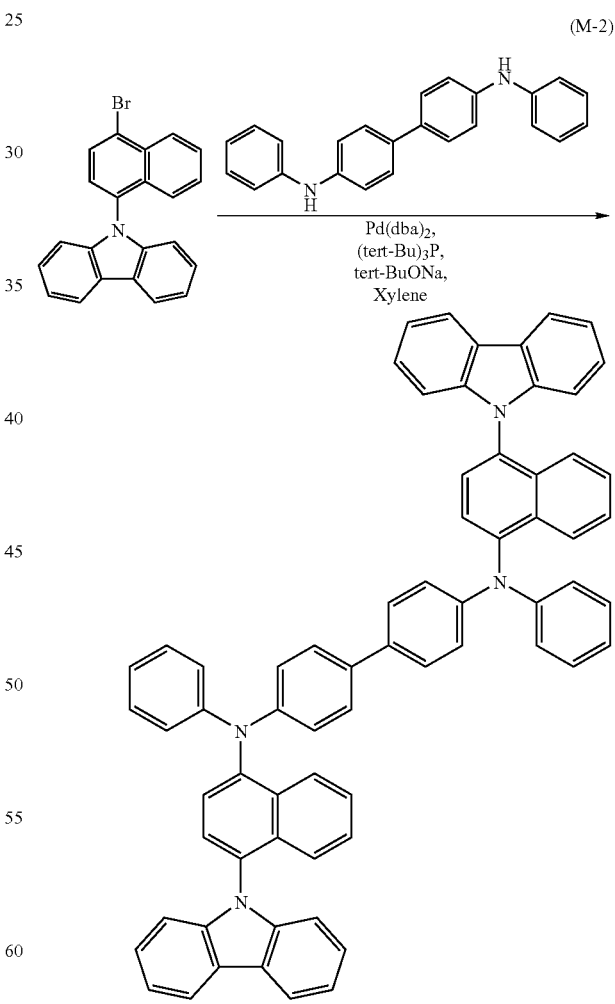

In a three-necked flask of 100 mL content, 3.4 g (9 mmol) of 9-(4-bromo-1-naphthyl)carbazole, 1.4 g (4 mmol) of N,N'-diphenylbenzidine, 60 mg (0.1 mmol) of bis(dibenzylideneacetone)palladium(0), and 1.5 g (15 mmol) of sodium tert-butoxide were put, and 20 mL of dehydrated xylene was added. Then, the pressure in the three-necked flask was reduced for three minutes to perform deaeration until no bubbles came out. In this mixture, 0.6 mL (0.3 mmol) of tri(tert-butyl)phosphine (10 wt % hexane solution) was added and stirred while heated at 120° C. in a nitrogen atmosphere. The heating was stopped after four hours, and about 200 mL of toluene was added to this reaction suspension and filtration was performed through Florisil, alumina, and celite. The obtained filtrate was washed with water and dried by addition of magnesium sulfate. This suspension was further filtered through Florisil, alumina, and celite, and the obtained filtrate was concentrated. After adding acetone and hexane to this concentrated filtrate, recrystallization was performed by applying ultrasonic waves. The produced solid was filtered off and dried. Thus, 2.7 g of a light-yellow powder as a target matter was obtained with a yield of 73%. It was confirmed by nuclear magnetic resonance spectroscopy (NMR) that this compound was N,N'-bis[4-(carbazol-9-yl)naphthyl]-N,N'-diphenylbiphenyl-4,4'-diamine (abbr.: CNABP) expressed by Structure Formula (115).

Figure 61A:
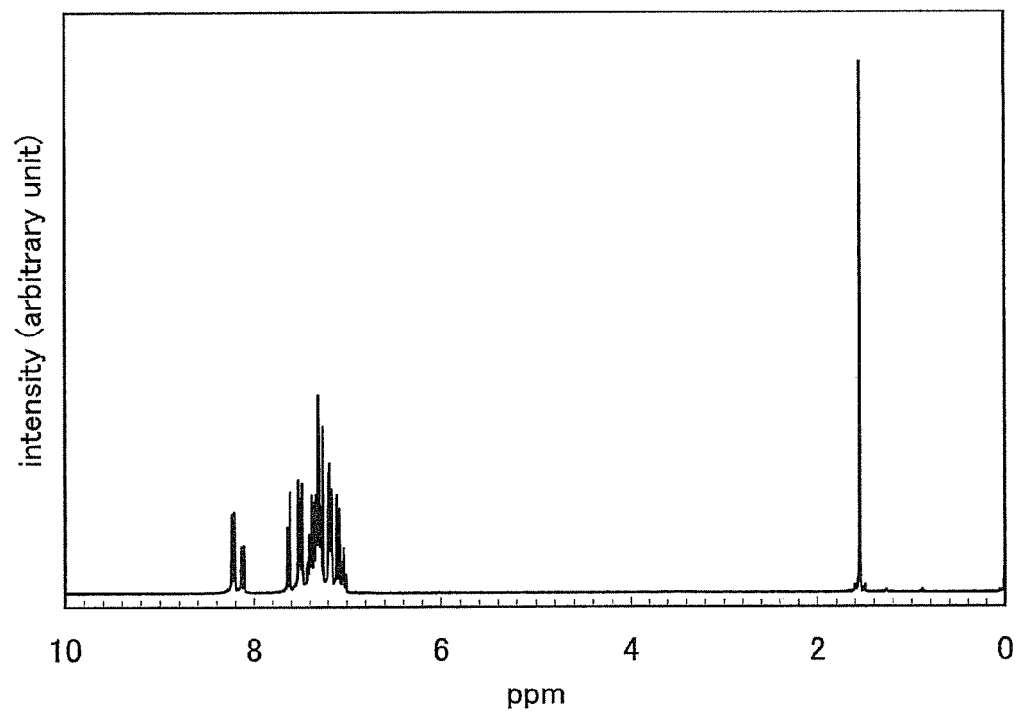
FIGS. 61A and 61B each show a $^1$H-NMR chart of N,N'-bis[4-(carbazol-9-yl)-1-naphthyl]-N,N'-diphenylbiphenyl-4,4'-diamine (abbr.: CNABP)
Figure 61B:
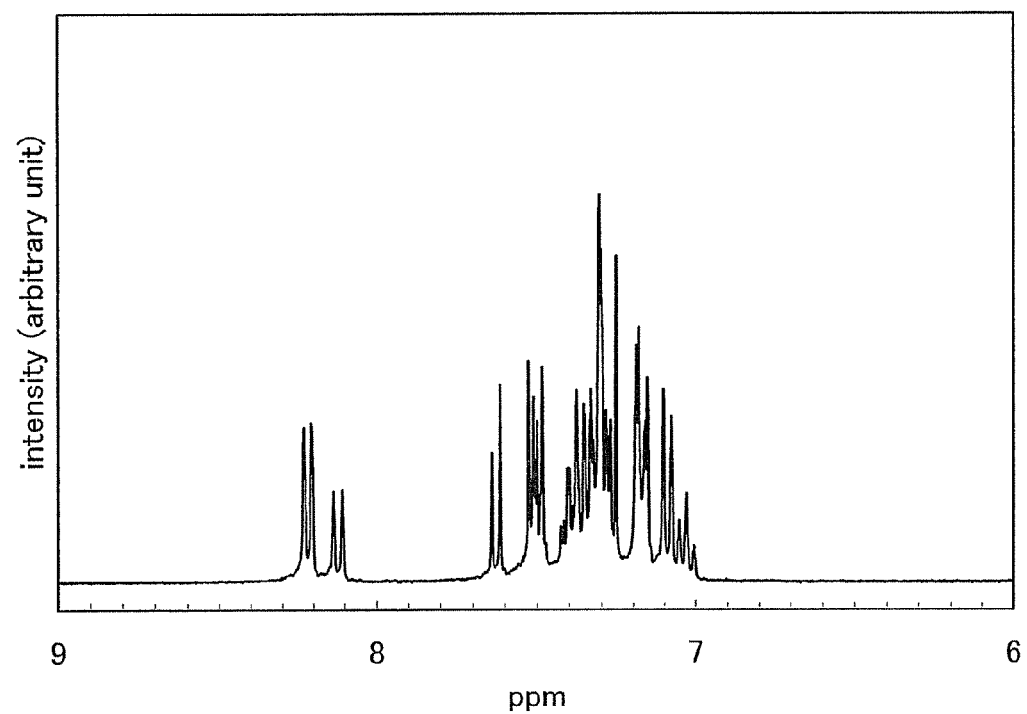

The $^1$H-NMR data on this compound are shown. The $^1$H-NMR (300 MHz, CDCl$_3$): δ (ppm)=7.03 (t, J=7.2, 2H), 7.09 (d, J=7.8, 4H), 7.15-7.19 (m, 8H), 7.25-7.43 (m, 18H), 7.48-7.53 (m, 6H), 7.63 (d, J=7.8, 2H), 8.12 (d, J=8.4, 2H), and 8.22 (d, J=6.9, 4H). A $^1$H-NMR chart is also shown in FIGS. 61A and 61B. Further, FIG. 61B is a chart showing an enlarged part in the range of 6.0 ppm to 9.0 ppm of FIG. 61A.

A thermogravimetry-differential thermal analysis (TG-DTA) of CNABP was conducted by using a high vacuum differential type differential thermal balance (manufactured by Bruker AXS K.K., DTA2410SA). When the measurement was conducted under a low pressure of 10 Pa, the temperature at which the weight becomes 95% or lower of the weight at the start of the measurement was 380° C. from the relation between the weight and temperature (thermogravimetry). When the measurement was conducted at normal pressure, the weight was 94% of the weight at the start of the measurement at 500° C., and the heat resistance was excellent. It is to be noted that the temperature-rising speed was 10° C./min in either measurement.

Figure 73:
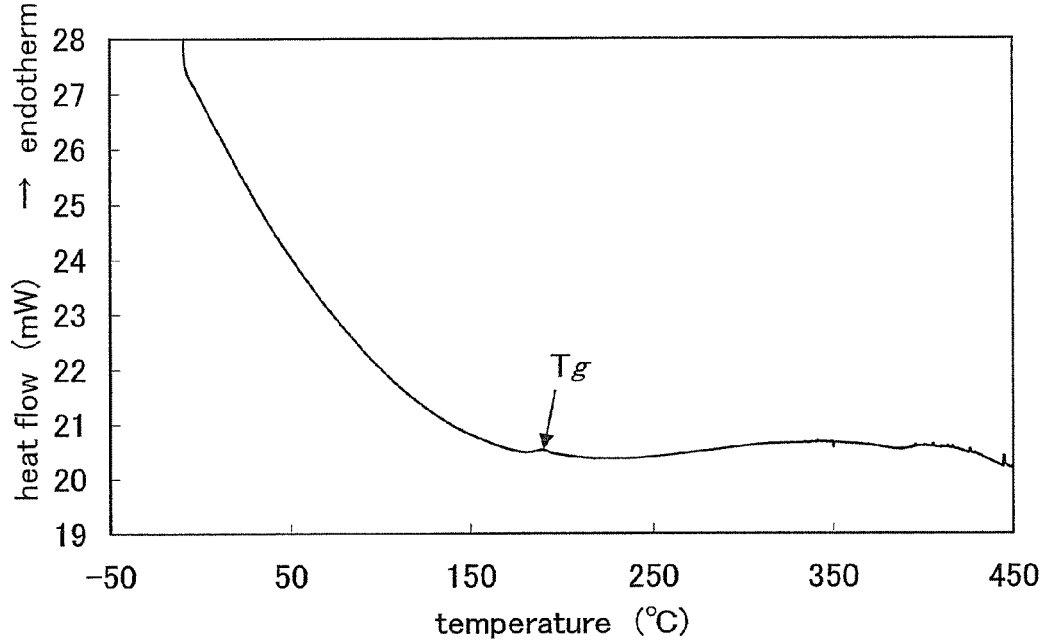
FIG. 73 shows a DSC chart of N,N'-bis[4-(carbazol-9-yl)-1-naphthyl]-N,N'-diphenylbiphenyl-4,4'-diamine (abbr.: CNABP)

In addition, the glass transition point of CNABP was measured by a differential scanning calorimeter (DSC, manufactured by PerkinElmer, Inc., Pyris 1). As shown in a DSC chart of FIG. 73, the temperature was raised to 500° C. at 10° C./min. In FIG. 73, the X axis shows temperature and the Y axis shows heat flow. The Y axis shows endotherm in an upward direction. It was understood from this chart that the glass transition point (T$_g$) of CNABP was as high as 183° C.

Figure 62:
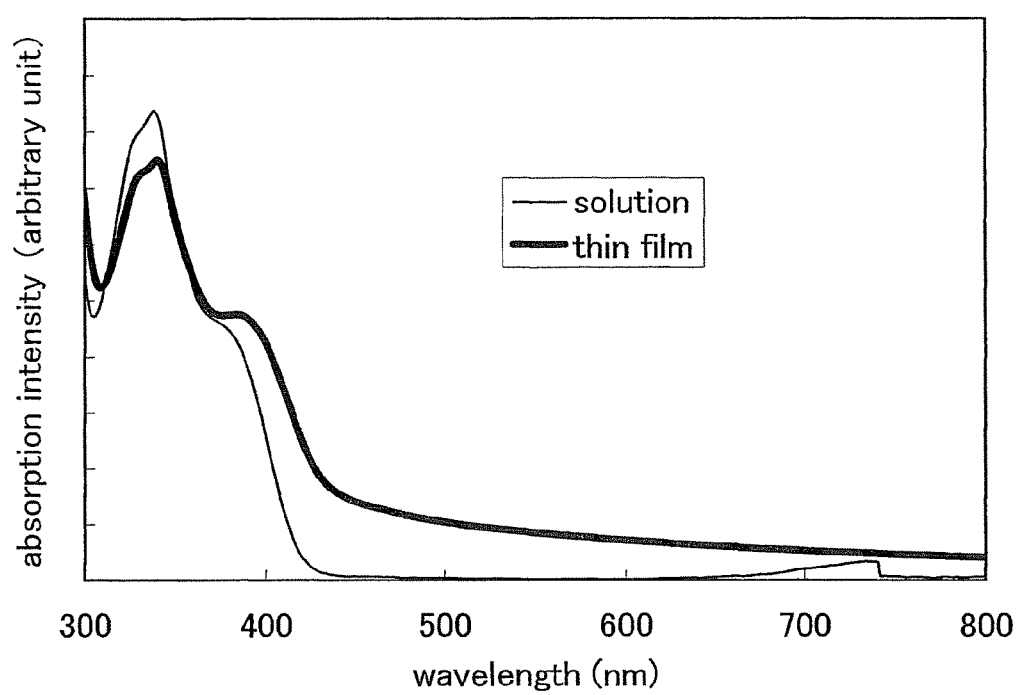
FIG. 62 shows an absorption spectrum of N,N'-bis[4-(carbazol-9-yl)-1-naphthyl]-N,N'-diphenylbiphenyl-4,4'-diamine (abbr.: CNABP)
Figure 63:
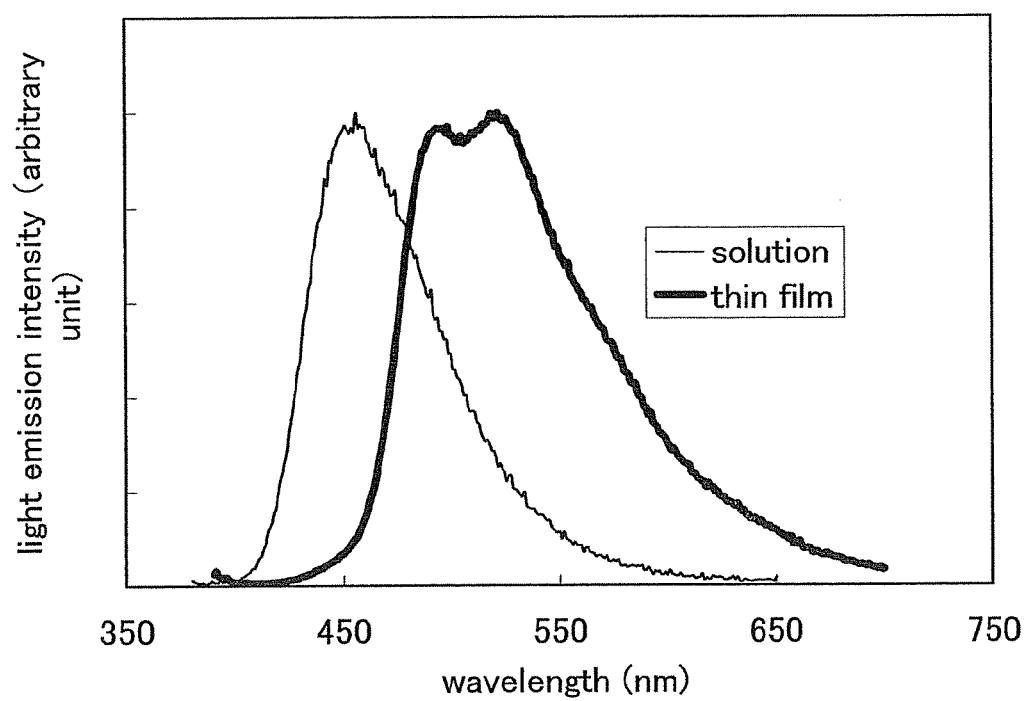
FIG. 63 shows a light emission spectrum of N,N'-bis[4-(carbazol-9-yl)-1-naphthyl]-N,N'-diphenylbiphenyl-4,4'-diamine (abbr.: CNABP)

FIG. 62 shows an absorption spectrum of a toluene solution of CNABP and an absorption spectrum of a thin film of CNABP. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIG. 62. In FIG. 62, the horizontal axis shows a wavelength (am) while the vertical axis shows absorption intensity (arbitrary unit). In the case of the toluene solution, absorption was observed at around 338 nm and 380 nm, and in the case of the thin film, it was observed at around 340 nm and 383 nm. The light emission spectrum of the toluene solution of CNABP (excitation wavelength: 340 nm) and that of the thin film of CNABP (excitation wavelength: 383 nm) are shown in FIG. 63. In FIG. 63, the horizontal axis shows a wavelength (nm) and the vertical axis shows light emission intensity (arbitrary unit). The peak of the light emission spectrum was observed at 455 nm in the case of the toluene solution (excitation wavelength: 340 nm), and 499 nm and 522 nm in the case of the thin film (excitation wavelength: 383 nm).

In addition, the HOMO level of CNABP in the thin film state was −5.43 eV, which was measured by photoelectron spectrometer (AC-2, manufactured by Riken Keiki Co., Ltd.) in the air. Moreover, the absorption edge was obtained from Tauc plot using data on the absorption spectrum of the thin film of CNABP in FIG. 62. When the absorption edge was estimated as an optical energy gap, the energy gap was 2.90 eV. Therefore, the LUMO level was −2.53 eV.

Embodiment 11

Embodiment 11 will explain a method of synthesizing N,N'-bis[4-(carbazol-9-yl)-1-naphthyl]-N,N'-di-1-naphthyl-biphenyl-4,4'-diamine (abbr.: CNNBP) expressed by Structure Formula (120). The following shows Synthesis Scheme (N-1) of CNNBP.

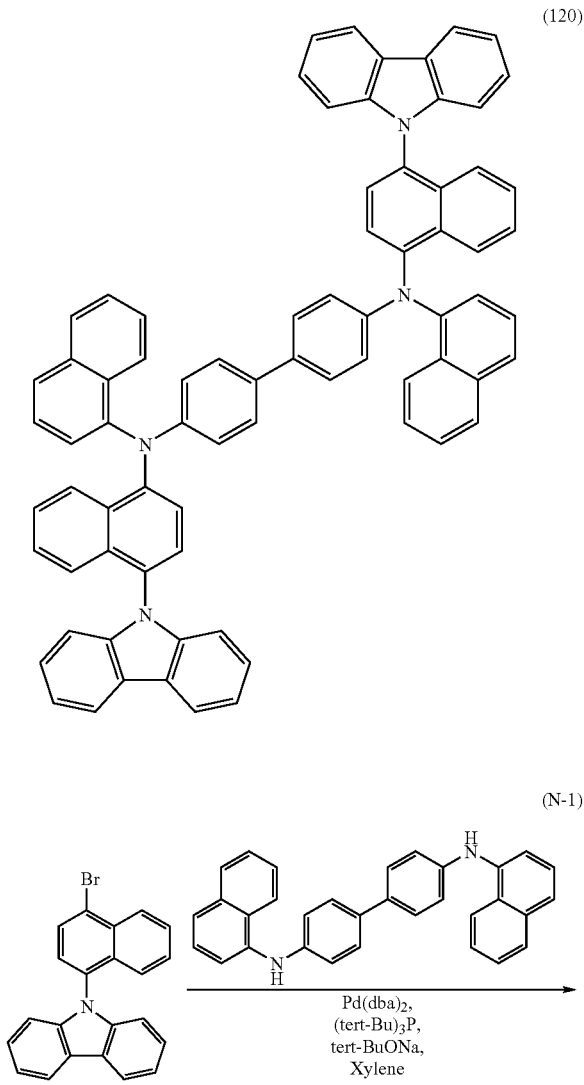

-continued

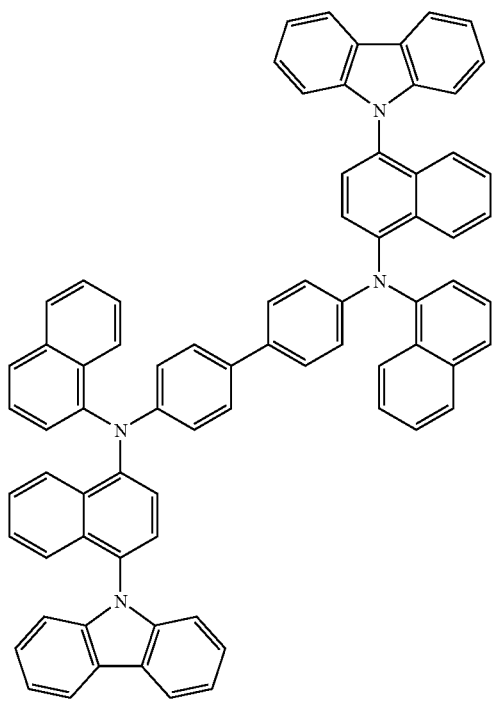

In a three-necked flask of 100 mL content, 3.4 g (9 mmol) of 9-(4-bromo-1-naphthyl)carbazole, 1.8 g (4 mmol) of N,N'-di(1-naphthyl)benzidine, 60 mg (0.1 mmol) of bis(dibenzylideneacetone)palladium(0), and 1.5 g (15 mmol) of sodium tert-butoxide were put, and 20 mL of dehydrated xylene was added. Then, the pressure in the three-necked flask was reduced for three minutes to perform deaeration until no bubbles came out. In this mixture, 0.6 mL (0.3 mmol) of tri(tert-butyl)phosphine (10 wt % hexane solution) was added and stirred while heated at 130° C. in a nitrogen atmosphere. The heating was stopped after four hours, and about 200 mL of toluene was added to this reaction suspension and filtration was performed through Florisil, alumina, and celite. The obtained filtrate was washed with water and dried by adding magnesium sulfate to an organic layer. This suspension was further filtered through Florisil, alumina, and celite, and the obtained filtrate was concentrated. After adding acetone and hexane to this concentrated filtrate, recrystallization was performed by applying ultrasonic waves. The produced solid was filtered off and dried. Thus, 0.8 g of a light-yellow powder as a target matter was obtained with a yield of 20%. It was confirmed by nuclear magnetic resonance spectroscopy (NMR) that this compound was N,N'-bis[4-(carbazol-9-yl)-1-naphthyl]-N,N'-di-1-naphthylbiphenyl-4,4'-diamine (abbr.: CNNBP).

The $^1$H-NMR data on this compound are shown. The $^1$H-NMR (300 MHz, CDCl$_3$): δ (ppm)=6.88 (d, J=8.1, 4H), 7.05 (d, J=7.8, 4H), 7.26-7.53 (m, 30H), 7.76 (d, J=7.8, 2H), 7.92 (d, J=8.4, 2H), 8.14 (d, J=7.8, 2H), and 8.19-8.23 (m, 6H). A $^1$H-NMR chart is also shown in FIGS. 64A and 64B.

Figure 64A:
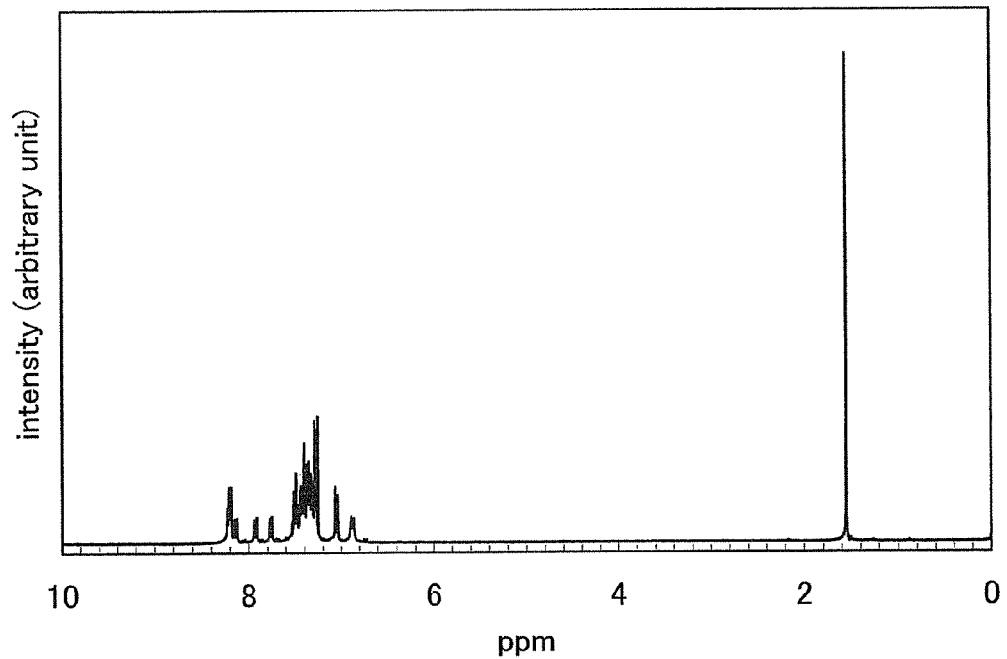
FIGS. 64A and 64B each show a $^1$H-NMR chart of N,N'-bis[4-(carbazol-9-yl)-1-naphthyl]-N,N'-di-1-naphthylbiphenyl-4,4'-diamine (abbr.: CNNBP)
Figure 64B:
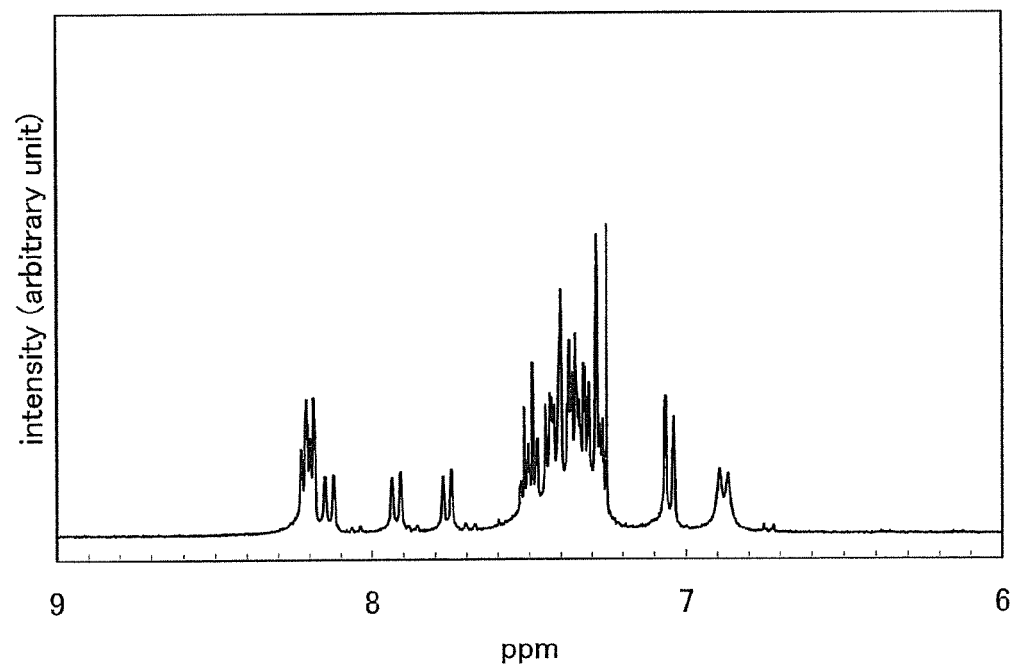

Further, FIG. 64B is a chart showing an enlarged part in the range of 6.0 ppm to 9.0 ppm of FIG. 64A.

A thermogravimetry-differential thermal analysis (TG-DTA) of CNNBP was conducted by using a high vacuum differential type differential thermal balance (manufactured by Bruker AXS K.K., DTA2410SA). When the measurement was conducted under a low pressure of 10 Pa, the temperature at which the weight becomes 95% or lower of the weight at the start of the measurement was 400° C. from the relation between the weight and temperature (thermogravimetry). When the measurement was conducted at normal pressure, the weight was 98% of the weight at the start of the measurement at 500° C., and the heat resistance was excellent. It is to be noted that the temperature-rising speed was 10° C./min in either measurement.

Figure 74:
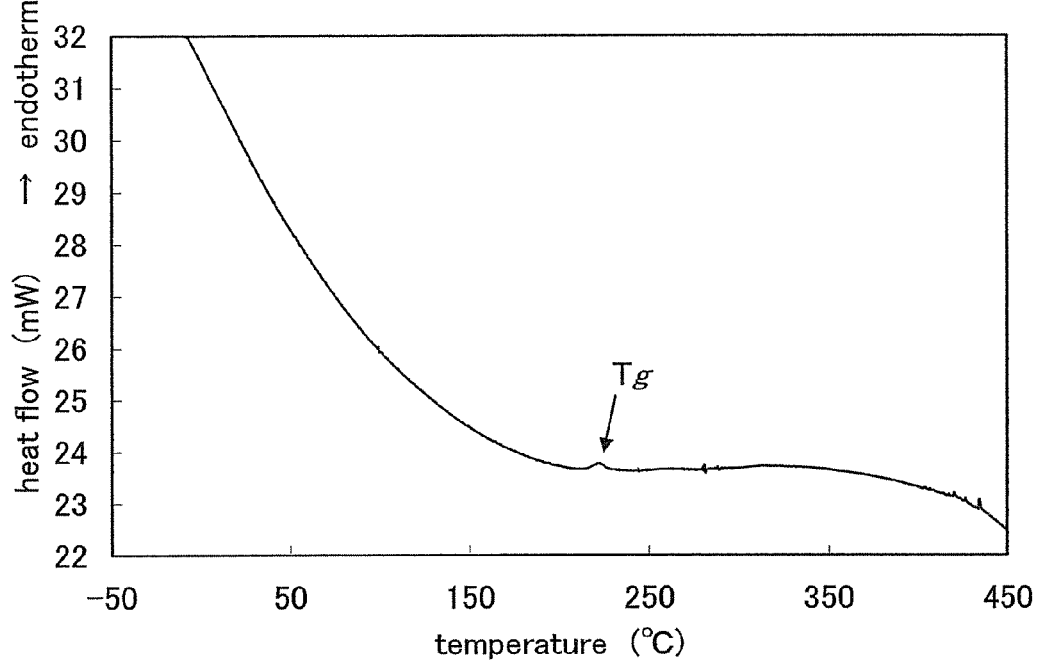
FIG. 74 shows a DSC chart of N,N'-bis[4-(carbazol-9-yl)-1-naphthyl]-N,N'-di-1-naphthylbiphenyl-4,4'-diamine (abbr.: CNNBP).

In addition, the glass transition point of CNNBP was measured by a differential scanning calorimeter (DSC, manufactured by PerkinElmer, Inc., Pyris 1). As shown in a DSC chart of FIG. 74, the temperature was raised to 500° C. at 10° C./min. In FIG. 74, the X axis shows temperature and the Y axis shows heat flow. The Y axis shows endotherm in an upward direction. It was understood from this chart that the glass transition point ($T_g$) of CNNBP was as high as 213° C.

Figure 65:
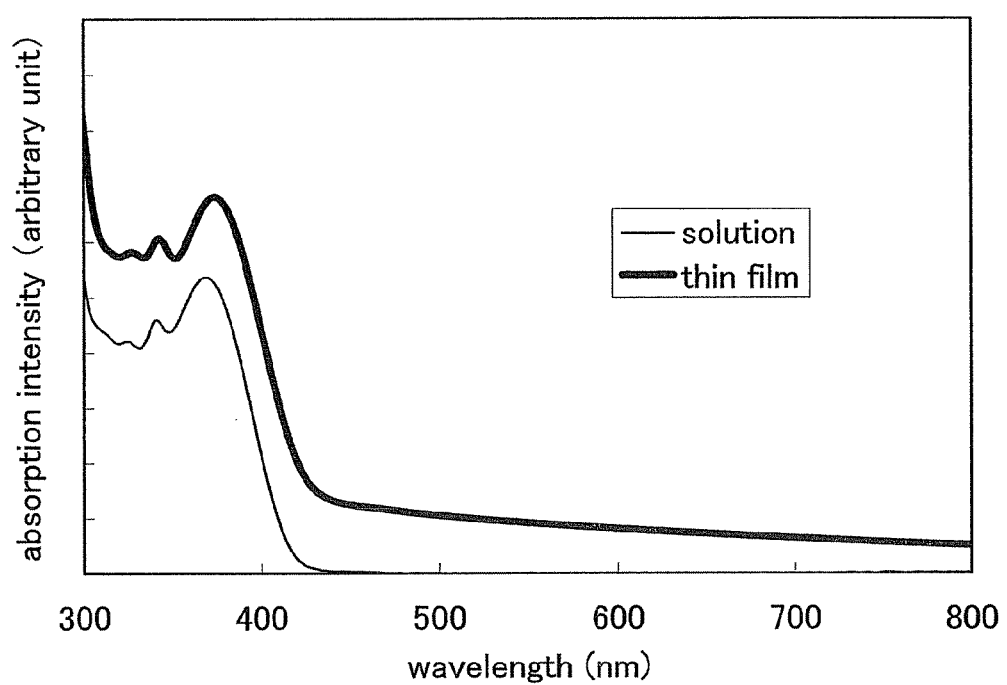
FIG. 65 shows an absorption spectrum of N,N'-bis[4-(carbazol-9-yl)-1-naphthyl]-N,N'-di-1-naphthylbiphenyl-4,4'-diamine (abbr.: CNNBP)
Figure 66:
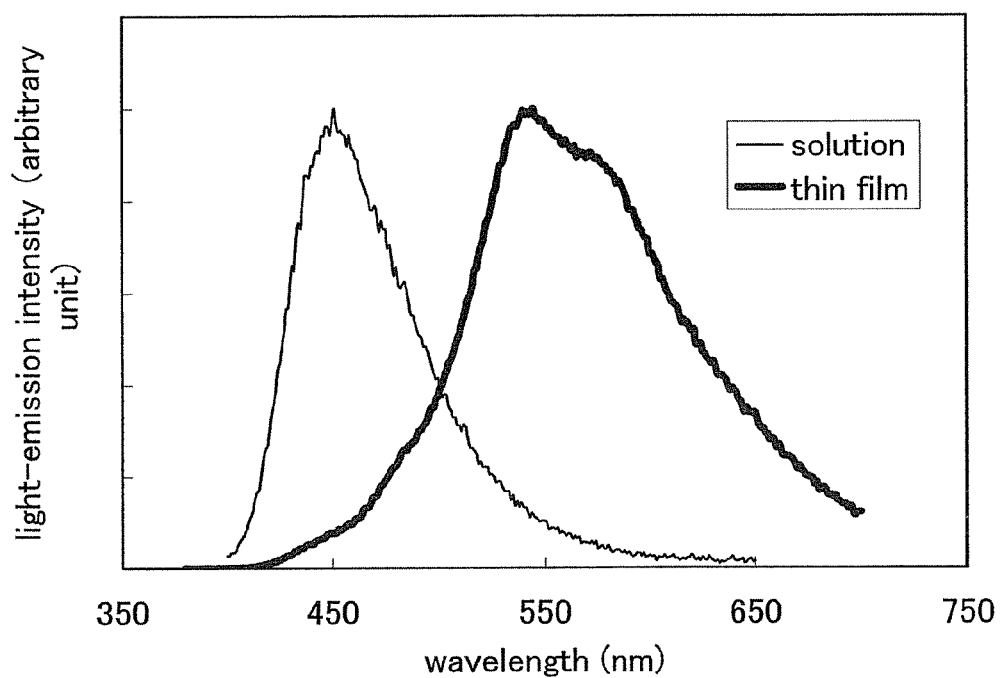
FIG. 66 shows a light emission spectrum of N,N'-bis[4-(carbazol-9-yl)-1-naphthyl]-N,N'-di-1-naphthylbiphenyl-4,4'-diamine (abbr.: CNNBP)

FIG. 65 shows an absorption spectrum of a toluene solution of CNNBP and an absorption spectrum of a thin film of CNNBP. The measurement was conducted by using a UV-visible spectrophotometer (V-550, manufactured by Japan Spectroscopy Corporation). The solution was put in a quartz cell, and the thin film was evaporated on a quartz substrate to form the samples. Their absorption spectra from each of which the absorption spectrum of quartz is subtracted are shown in FIG. 65. In FIG. 65, the horizontal axis shows a wavelength (nm) while the vertical axis shows absorption intensity (arbitrary unit). In the case of the toluene solution, absorption was observed at around 370 nm, and in the case of the thin film, it was observed at around 374 nm. The light emission spectrum of the toluene solution of CNNBP (excitation wavelength: 370 nm) and that of the thin film of CNNBP (excitation wavelength: 374 nm) are shown in FIG. 66. In FIG. 66, the horizontal axis shows a wavelength (nm) and the vertical axis shows light emission intensity (arbitrary unit). The peak of the light emission spectrum was observed at 450 nm in the case of the toluene solution (excitation wavelength: 370 nm), and 545 nm in the case of the thin film (excitation wavelength: 374 nm).

In addition, the HOMO level of CNNBP in the thin film state was −5.45 eV, which was measured by photoelectron spectrometer (AC-2, manufactured by Riken Keiki Co., Ltd.) in the air. Moreover, the absorption edge was obtained from Tauc plot using data on the absorption spectrum of the thin film of CNNBP in FIG. 65. When the absorption edge was estimated as an optical energy gap, the energy gap was 3.00 eV. Therefore, the LUMO level was −2.45 eV.

Embodiment 12

Figure 67:
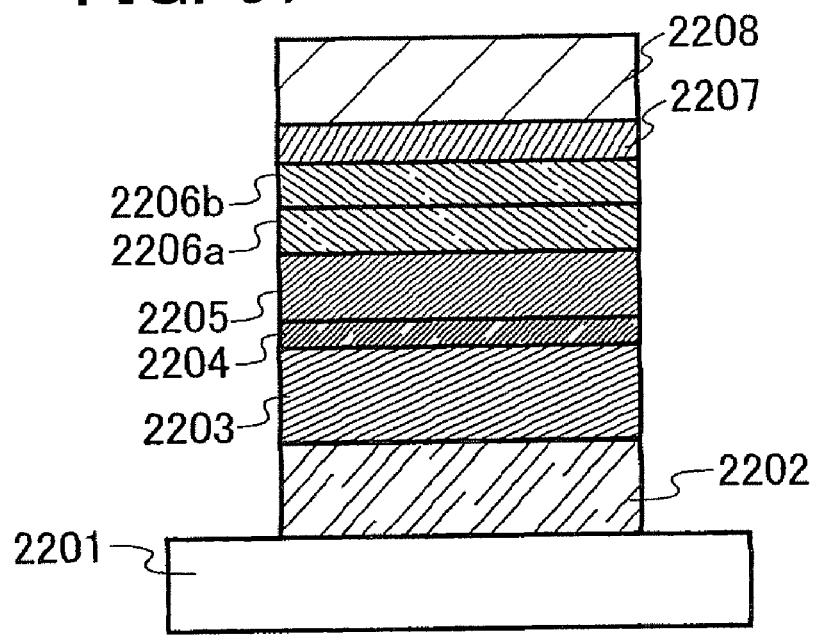
FIG. 67 explains a light-emitting element of Embodiment 12.

Embodiment 12 will explain a light-emitting element of the present invention with reference to FIG. 67. The following shows a chemical formula of a material used in this embodiment.

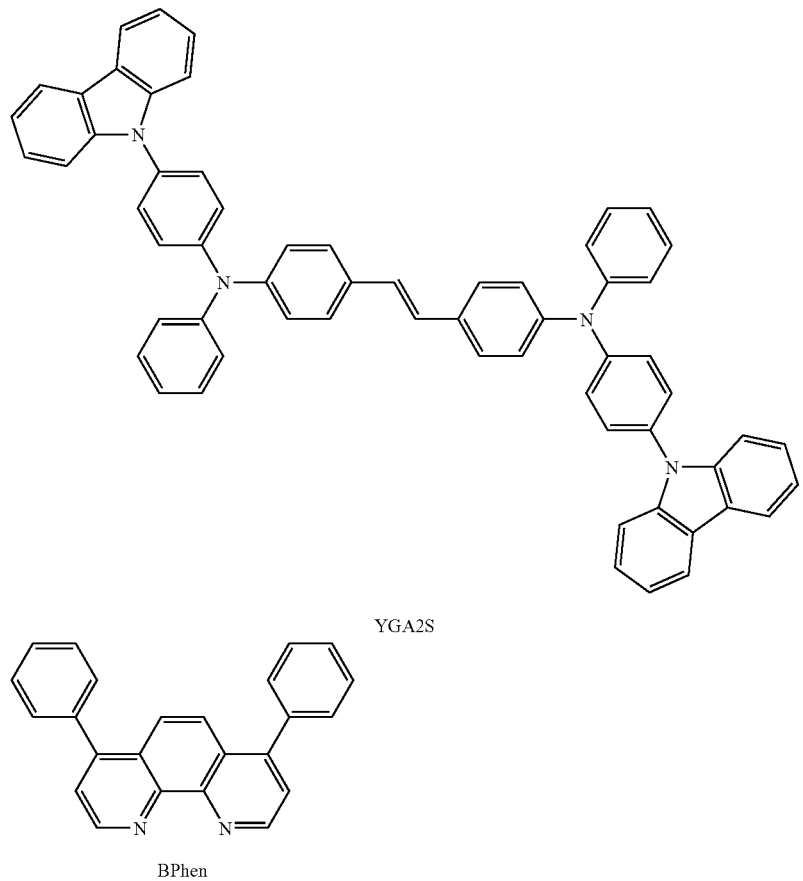

YGA2S

BPhen (Light-Emitting Element 7)

First, indium tin oxide including silicon oxide was formed over a glass substrate 2201 by a sputtering method, thereby forming a first electrode 2202. The first electrode 2202 has a thickness of 110 nm and an electrode area of 2 mm×2 mm.

Next, the substrate over which the first electrode was formed was fixed to a substrate holder provided in a vacuum evaporation apparatus in such a way that a surface of the substrate having the first electrode faced downward. The pressure was reduced to be about $10^{-4}$ Pa and then, NPB and molybdenum oxide (VI) were co-evaporated on the first electrode 2202, thereby forming a layer 2203 containing a composite material of an organic compound and an inorganic compound. The film thickness of the layer 2203 was 50 nm, and the weight ratio between NPB and molybdenum oxide (VI) was set 4:1(=NPB:molybdenum oxide). It is to be noted that the co-evaporation method is an evaporation method in which evaporation is performed from plural evaporation sources in one process chamber.

Subsequently, a hole-transporting layer 2204 was formed in 10 nm thick over the layer 2203 containing a composite material by using 4-(carbazol-9-yl)phenyl-4'-phenyltriphenylamine (abbr.: YGA1BP) expressed by Structure Formula (52) by an evaporation method using resistance heating.

Further, a light-emitting layer 2205 of 30 nm thick was formed over the hole-transporting layer 2204 by co-evaporating 9-[4-(N-carbazolyl)]phenyl-10-phenylanthracene (abbr.: CzPA) and N,N'-bis[4-(9H-carbazol-9-yl)phenyl]-N,N'-diphenylstylbene-4,4'-diamine (abbr.: YGA2S). Here, the weight ratio between CzPA and YGA2S was adjusted so as to be 1:0.04(=CzPA:YGA2S).

After that, a first electron-transporting layer 2206a was formed of Alq in 20 nm thick over the light-emitting layer 2205 by an evaporation method using resistance heating.

Moreover, a second electron-transporting layer 2206b was formed of bathophenanthroline (abbr.: BPhen) in 10 nm thick over the first electron-transporting layer 2206a by an evaporation method using resistance heating.

Moreover, an electron-injecting layer 2207 was formed in 1 nm thick by evaporating lithium fluoride over the second electron-transporting layer 2206b by an evaporation method using resistance heating.

Lastly, a second electrode 2208 was formed of aluminum in 200 nm thick over the electron-injecting layer 2207 by an evaporation method using resistance heating. Thus, the light-emitting element 7 was manufactured.

(Light-Emitting Element 8)

As the hole-transporting layer 2204, 4-(carbazol-9-yl)phenyl-2'-phenyltriphenylamine (abbr.: oYGA1BP) expressed by Structure Formula (70) was formed in 10 nm thick. The structure other than the hole-transporting layer is similar to that of the light-emitting element 7.

(Light-Emitting Element 9)

As the hole-transporting layer 2204, 4-(carbazol-9-yl)phenyl-3'-phenyltriphenylamine (abbr.: mYGA1BP) expressed by Structure Formula (69) was formed in 10 nm thick. The structure other than the hole-transporting layer is similar to that of the light-emitting element 7.

(Comparative Light-Emitting Element 10)

As the hole-transporting layer 2204, NPB was formed in 10 nm thick. The structure other than the hole-transporting layer is similar to that of the light-emitting element 7.

Figure 68:
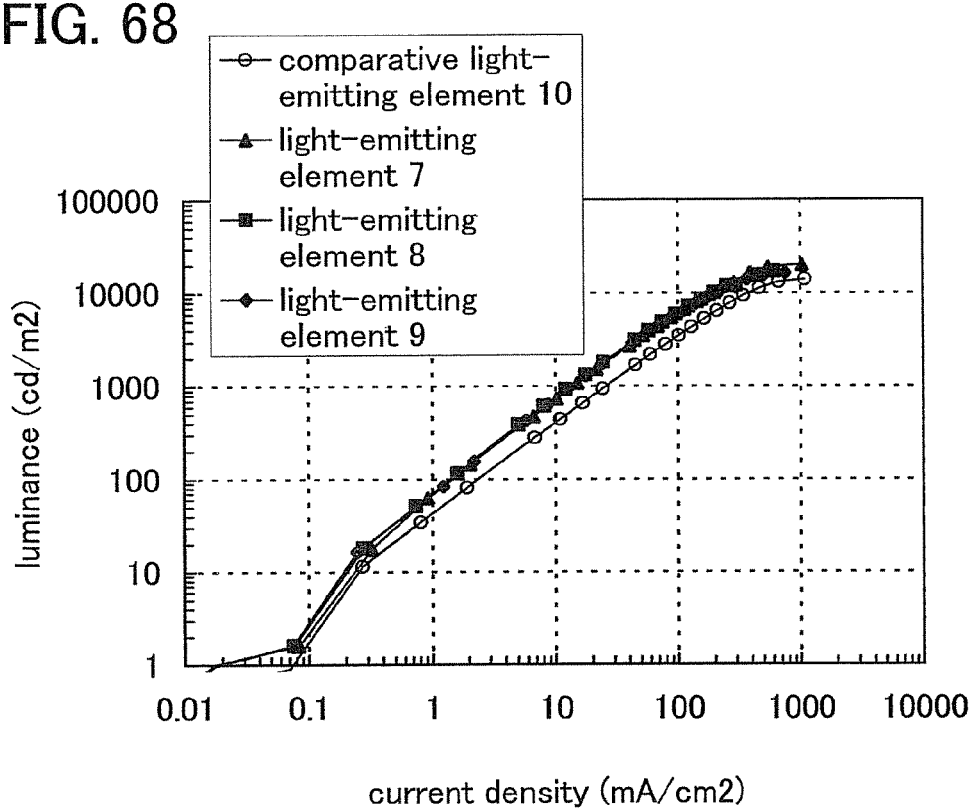
FIG. 68 shows current density-luminance characteristics of a light-emitting element manufactured in accordance with Embodiment 12.
Figure 69:
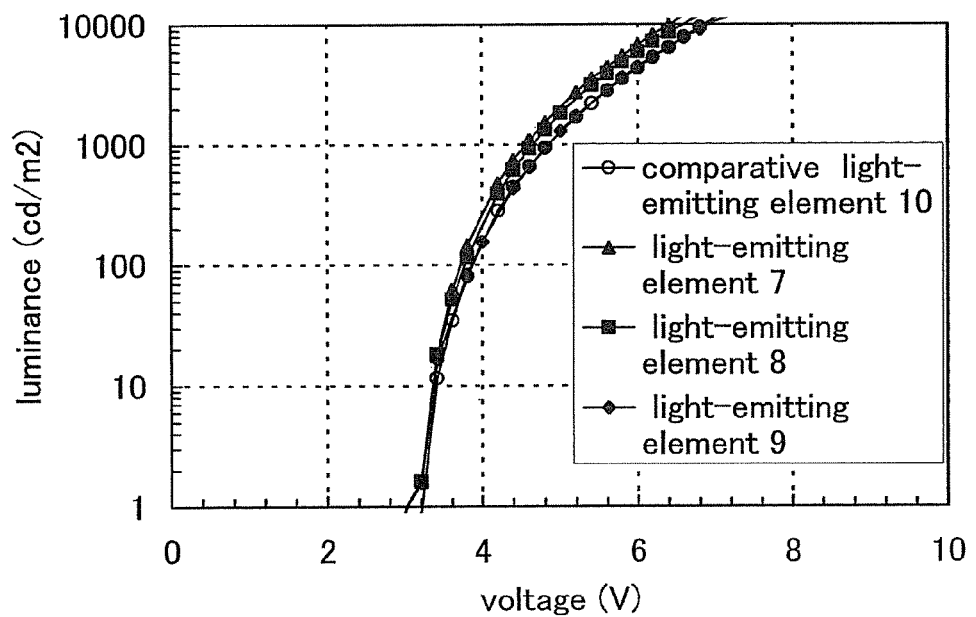
FIG. 69 shows voltage-luminance characteristics of a light-emitting element manufactured in accordance with Embodiment 12.
Figure 70:
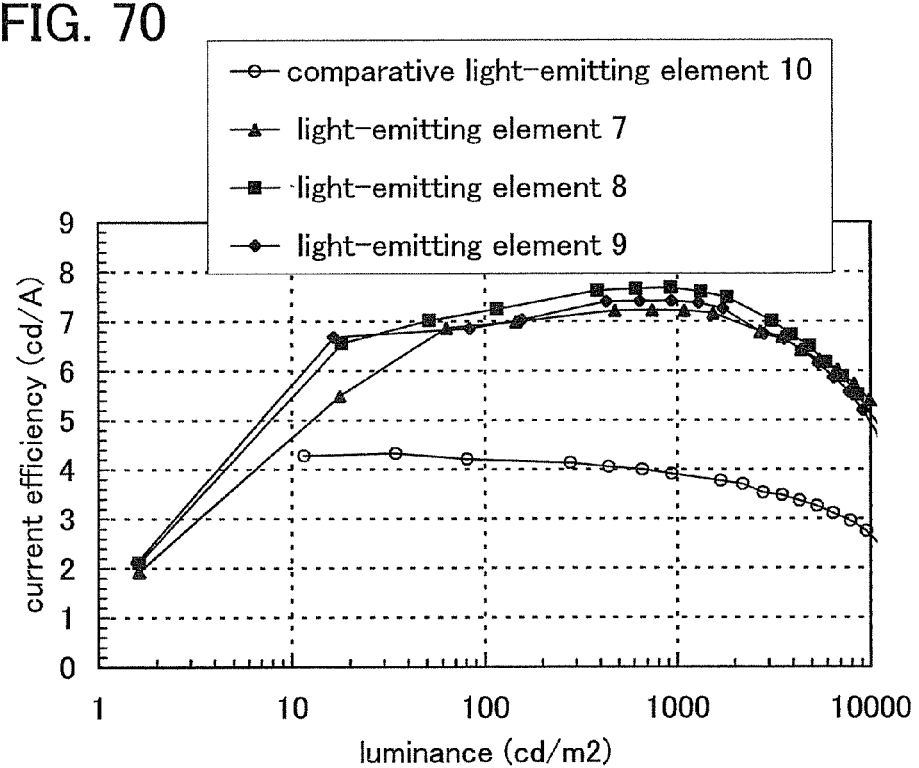
FIG. 70 shows luminance-current efficiency characteristics of a light-emitting element manufactured in accordance with Embodiment 12.
Figure 71:
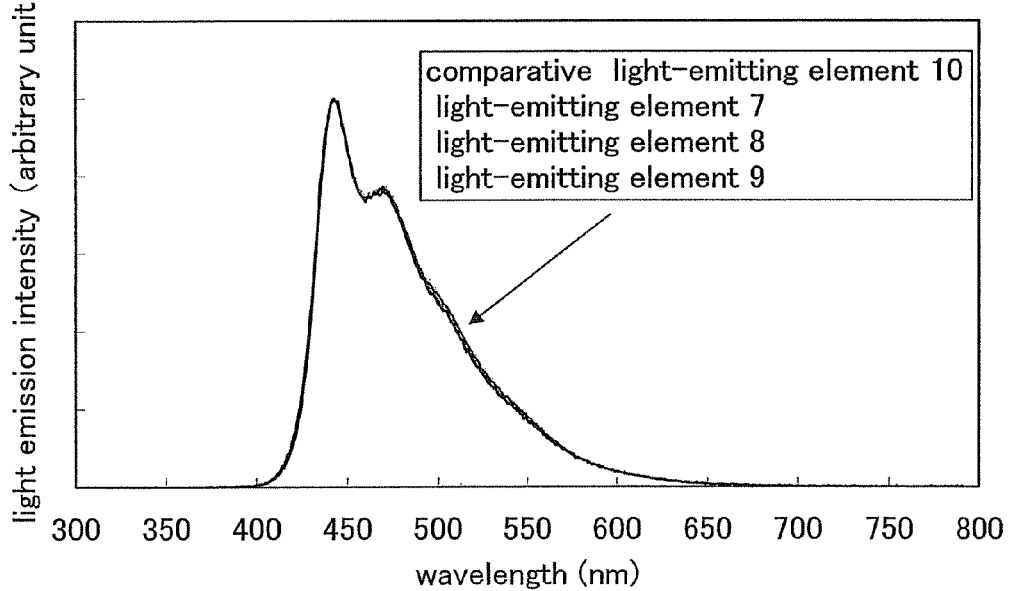
FIG. 71 shows a light emission spectrum of a light-emitting element manufactured in accordance with Embodiment 12.

FIG. 68 shows current density-luminance characteristics of the light-emitting elements 7 to 9 and the comparative light-emitting element 10. FIG. 69 shows voltage-luminance characteristics thereof, and FIG. 70 shows luminance-current efficiency characteristics thereof. In addition, FIG. 71 shows light emission spectra thereof when a current of 1 mA flows.

As can be seen from FIG. 69, the light-emitting element using the aromatic amine compound of the present invention has high current efficiency although the chromaticity coordinate thereof is similar to that of the comparative light-emitting element 10. As shown in FIG. 68, the light-emitting element of the present invention has almost the same drive voltage as the comparative light-emitting element 10. Therefore, by the use of the aromatic amine compound of the present invention, the light-emitting element with high power efficiency and low power consumption can be obtained.

Specifically, the comparative light-emitting element 10 showed blue light emission with its CIE chromaticity coordinate (x=0.16, y=0.17) at a luminance of 930 cd/m². At a luminance of 930 cd/m², the current efficiency thereof was 3.9 cd/A, the voltage thereof was 4.8 V, the current density thereof was 24 mA/cm², and the power efficiency thereof was 2.61 m/W.

On the other hand, the light-emitting element 7 showed blue light emission with its CIE chromaticity coordinate (x=0.16, y=0.17) at a luminance of 1090 cd/m². At a luminance of 1090 cd/m², the current efficiency thereof was as high as 7.2 cd/A, the voltage thereof was 4.6 V, the current density thereof was 15 mA/cm², and the power efficiency thereof was as high as 4.91 m/W.

The light-emitting element 8 showed blue light emission with its CIE chromaticity coordinate (x=0.16, y=0.17) at a luminance of 930 cd/m². At a luminance of 930 cd/m², the current efficiency thereof was as high as 7.6 cd/A, the voltage thereof was 4.6 V, the current density thereof was 12 mA/cm², and the power efficiency thereof was as high as 5.21 m/W.

The light-emitting element 9 showed blue light emission. At a luminance of 930 cd/m², the current efficiency thereof was as high as 7.4 cd/A, the voltage thereof was 4.8 V, the current density thereof was 13 mA/cm², and the power efficiency thereof was as high as 4.81 m/W.

As thus described, YGA1BP, which is the aromatic amine compound of the present invention, has higher triplet-excitation energy than NPB used for the comparative light-emitting element 10. In particular, YGA1BP has high triplet-excitation energy with an asymmetrical structure. In addition, the wavelength corresponding to the triplet-excitation energy of the aromatic amine compound of the present invention is about 450 nm, which corresponds to blue color. On the other hand, the wavelength corresponding to the triplet-excitation energy of NPB used for the comparative light-emitting element 10 is about 500 nm, which corresponds to green color. Moreover, the singlet-excitation energy is higher than the triplet-excitation energy. In other words, since the wavelength corresponding to the triplet-excitation energy of the aromatic amine compound of the present invention corresponds to blue color, the wavelength corresponding to the singlet-excitation energy is shorter than the wavelength of blue color. Therefore, when the aromatic amine compound is used for a layer which is in contact with a blue fluorescent material, the energy does not transfer from the excited blue fluorescent material to the aromatic amine compound of the present invention. Moreover, when the aromatic amine compound of the present invention is excited, the energy can transfer to the fluorescent material. Thus, high luminous efficiency can be realized.

In this manner, by the use of the aromatic amine compound of the present invention for the hole-transporting layer, the light-emitting element with favorable characteristics can be obtained.

Embodiment 13

This embodiment will explain the material used in another embodiment.

Synthesis Example of YGAO11

Described hereinafter is a method of synthesizing 2-(4-{N-[4-(carbazol-9-yl)phenyl]-N-phenylamino}phenyl)-5-phenyl-1,3,4-oxadiazole (abbr.: YGAO11) expressed by Structure Formula (201).

(201)

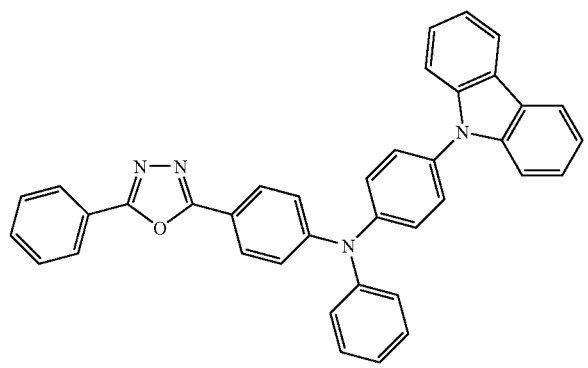

[Step 1]
Synthesis of 2-(4-bromophenyl)-5-phenyl-1,3,4-oxadiazole (abbr.: O11Br) is explained. In Step 1, O11Br was synthesized in accordance with the following procedure (i) to (iii).

(i) Synthesis of 4-bromobenzohydrazide

First, 3.0 g (13.9 mmol) of methyl-4-bromobenzoate was put in a 100-mL three-necked flask, 10 mL of ethanol was added therein, and the mixture was stirred. Thereafter, 4.0 mL of hydrazine monohydrate was added therein, and the mixture was heated and stirred at 78° C. for five hours. The obtained solid was washed with water and collected by suction filtration; thus, 2.0 g of a white solid of 4-bromobenzohydrazide as a target matter was obtained (yield: 67%).

(ii) Synthesis of
1-benzoyl-2-(4-bromobenzoyl)hydrazine

Subsequently, 2.0 g (13.9 mmol) of the 4-bromobenzohydrazide obtained in (i) above was put in a 300-mL three-necked flask, 7 mL of N-methyl-2-pyrrolidone (abbr.: NMP) was added therein, and then the mixture was stirred. Thereafter, a mixture of 2.5 mL of N-methyl-2-pyrrolidone and 2.5 mL (21.5 mmol) of benzoyl chloride was dropped through a 50-mL dropping funnel, and the mixture was stirred at 80° C. for three hours. The obtained solid was washed with water and a sodium carbonate aqueous solution in this order and collected by suction filtration. Then, the solid was recrystallized with acetone; thus, 3.6 g of a white solid of 1-benzoyl-2-(4-bromobenzoyl)hydrazine as a target matter was obtained (yield: 80%).

(iii) Synthesis of O11Br

Further, 15 g (47 mmol) of the 1-benzoyl-2-(4-bromobenzoyl)hydrazine obtained by the method shown in (ii) above was put in a 200-mL three-necked flask, 100 mL of phosphoryl chloride was added therein, and the mixture was heated and stirred at 100° C. for five hours. After the reaction, the solid obtained by completely distilling off phosphoryl chloride was washed with water and a sodium carbonate aqueous solution in this order and collected by suction filtration. Then, the solid was recrystallized with methanol; thus, 13 g of a white solid of O11Br as a target matter of Step 1 was obtained (yield: 89%). A synthesis scheme of Step 1 described above is shown in the following scheme (E-1).

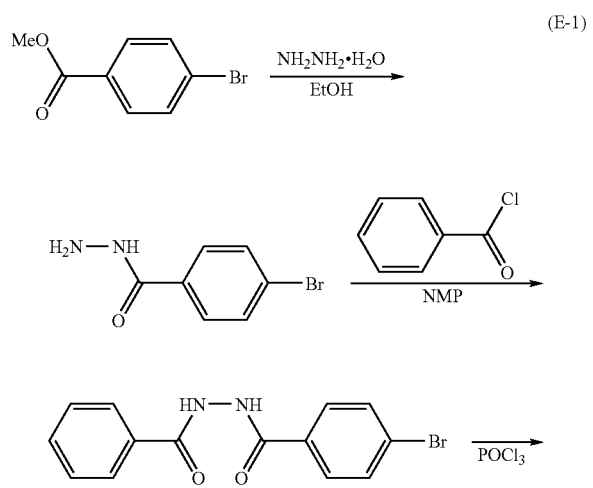

[Step 2]

Synthesis of 2-(4-{N-[4-(carbazol-9-yl)phenyl]-N-phenylamino}phenyl)-5-phenyl-1,3,4-oxadiazole (abbr.: YGAO11)

In a 100-mL three-necked flask, 3.0 g (10.0 mmol) of O11Br obtained in Step 1, 3.4 g (10.0 mmol) of YGA obtained in Step 1 of Embodiment 1, and 1.9 g (19.9 mmol) of sodium tert-butoxide were put, and nitrogen substitution was carried out. Then, 45 mL of toluene, 0.3 mL of a 10% hexane solution of tri(tert-butyl)phosphine, and 0.3 g (0.6 mmol) of bis(dibenzylideneacetone)palladium(0) were added therein, and the mixture was heated and stirred at 120° C. for five hours. After the reaction, the mixture was filtered through Celite, and the filtrate was washed with water and then dried with magnesium sulfate. After being dried, the solution was filtrated, and the filtrate was concentrated. The obtained solid was dissolved in toluene and purified by silica gel column chromatography. Purification by column chromatography was performed by using toluene as a developing solvent and then using a mixed solvent of toluene:ethyl acetate=1:1 as a developing solvent. The purified solid was recrystallized with chloroform and hexane; thus, 4.7 g of a light-yellow solid YGAO11 as a target matter of this synthesis example was obtained with a yield of 85%. The following scheme (E-2) shows the synthesis scheme of Step 3 in the above description.

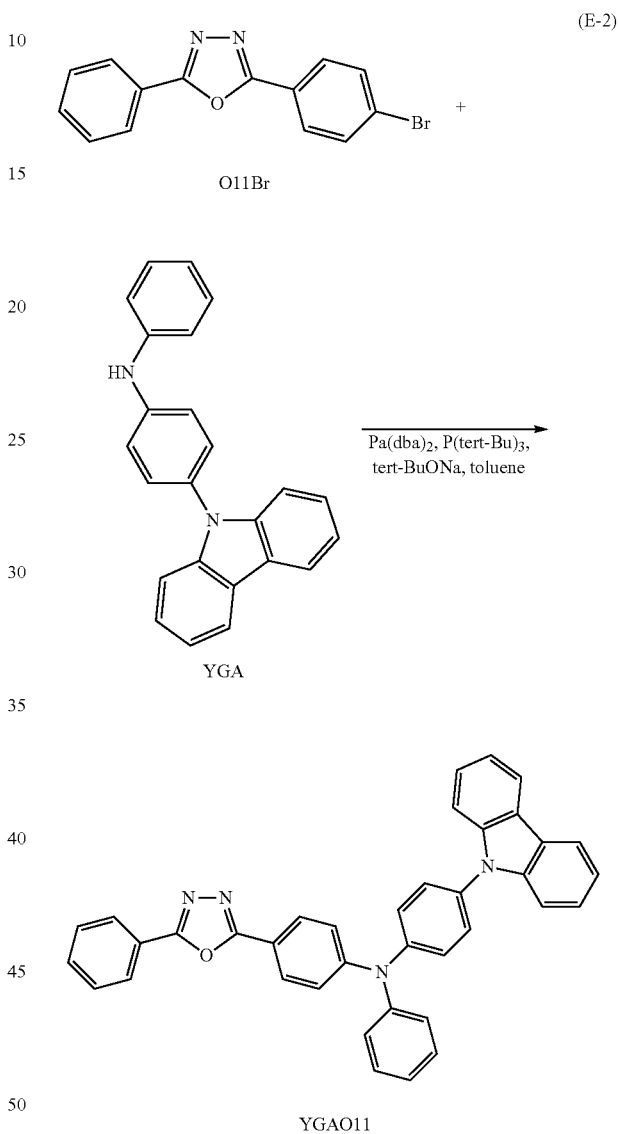

Figure 43A:
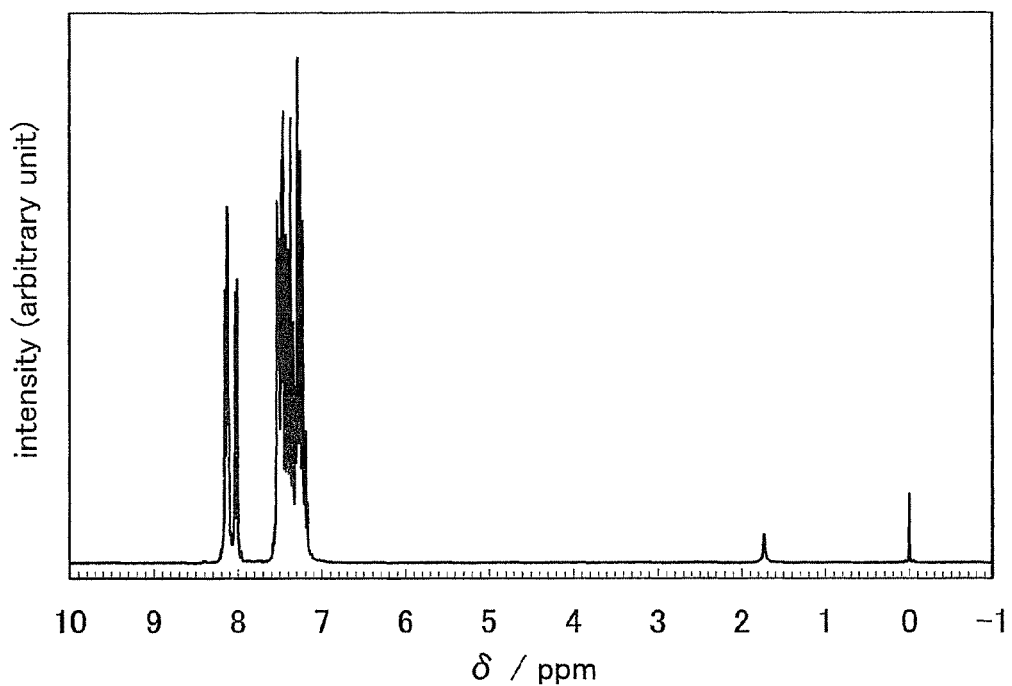
FIGS. 43A and 43B each show a $^1$H-NMR chart of 2-(4-{N-[4-(carbazol-9-yl)phenyl]-N-phenylamino}phenyl)-5-phenyl-1,3,4-oxadiazole.
Figure 43B:
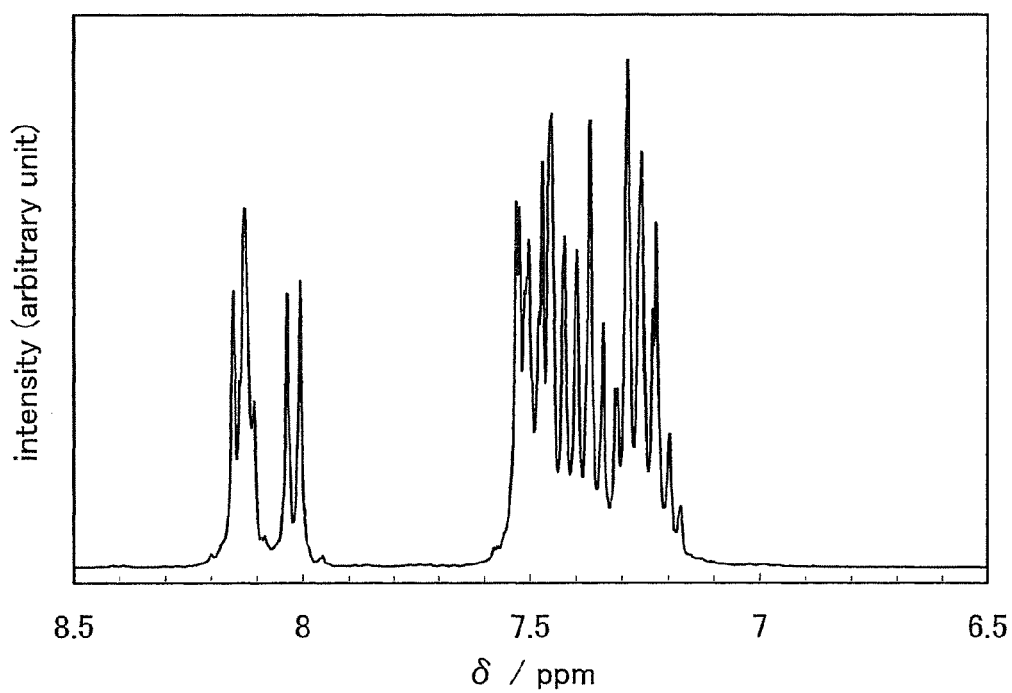

The following shows a result of analyzing YGAO11 that was obtained by nuclear magnetic resonance spectroscopy ($^1$H-NMR). FIG. 43A shows a $^1$H-NMR chart and FIG. 43B shows an enlarged chart thereof.

$^1$H-NMR (300 MHz, CDCl$_3$): δ=7.14-7.53 (m, 19H), δ=8.03 (d, J=8.7, 2H), δ=8.11-8.15 (m, 4H).

Synthesis Example of YGAPA

Described hereinafter is a method of synthesizing 9-(4-{N-[4-(carbazol-9-yl)phenyl]-N-phenylamino}phenyl)-10-phenylanthracene (abbr.: YGAPA) expressed by Structure Formula (202).

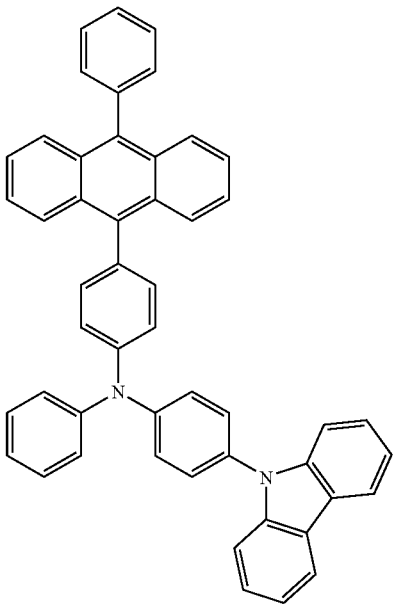

(202)

[Step 1]

A method of synthesizing 9-phenyl-10-(4-bromophenyl)anthracene (abbr.: PA) will be explained.

(i) Synthesis of 9-phenylanthracene

The following shows Synthesis Scheme (F-1) of 9-phenylanthracene.

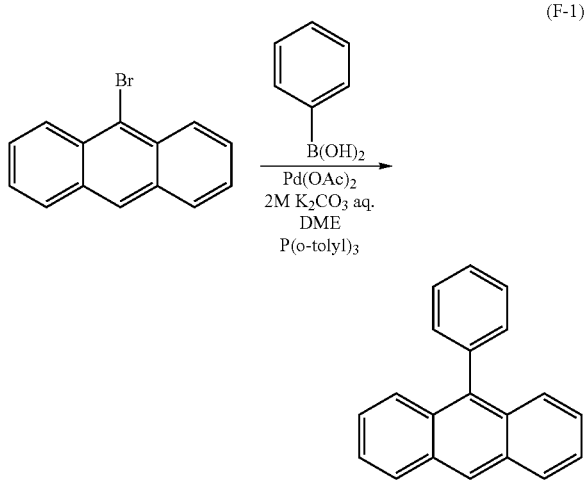

(F-1)

First, 5.4 g (21.1 mmol) of 9-bromoanthracene, 2.6 g (21.1 mmol) of phenylboronic acid, 60 mg (0.21 mmol) of palladium acetate (Pd(OAc)$_2$), 10 mL (20 mmol) of a potassium carbonate (K$_2$CO$_3$) aqueous solution (2 mol/L), 263 mg (0.84 mmol) of tri(o-tolyl)phosphine (P(o-tolyl)$_3$), and 20 mL of 1,2-dimethoxyethane (abbr.: DME) were mixed and stirred at 80° C. for nine hours. After the reaction, the precipitated solid was collected by suction filtration, dissolved in toluene, and filtered through Florisil, Celite, and alumina. The filtrate was washed with water and saturated saline and then dried with magnesium sulfate. After the solution was filtered naturally and the filtrate was concentrated, 21.5 g of a light-brown solid of 9-phenylanthracene as a target matter was obtained with a yield of 85%.

(ii) Synthesis of 10-bromo-9-phenylanthracene

The following shows Synthesis Scheme (F-2) of 10-bromo-9-phenylanthracene.

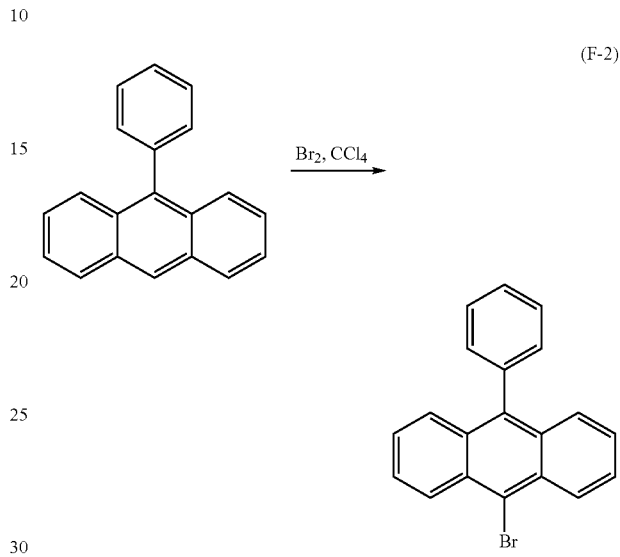

(F-2)

After 6.0 g (23.7 mmol) of 9-phenylanthracene was dissolved in 80 mL of carbon tetrachloride, a solution of 3.80 g (21.1 mmol) of bromine dissolved in 10 mL of carbon tetrachloride was dropped through a dropping funnel into the reaction solution. After the dropping, the solution was stirred at room temperature for one hour After the reaction, a sodium thiosulfate aqueous solution was added to stop the reaction. An organic layer was washed with a sodium hydroxide (NaOH) aqueous solution and saturated saline and dried with magnesium sulfate. After the solution was filtered naturally, the filtrate was concentrated, dissolved in toluene, and filtered through Florisil, Celite, and alumina. When the filtrate was concentrated and recrystallized with dichloromethane and hexane, 7.0 g of a light-yellow solid of 10-bromo-9-phenylanthracene, which is a target matter, was obtained with a yield of 89%.

(iii) Synthesis of 9-iodo-10-phenylanthracene

The following shows Synthesis Scheme (F-3) of 9-iodo-10-phenylanthracene.

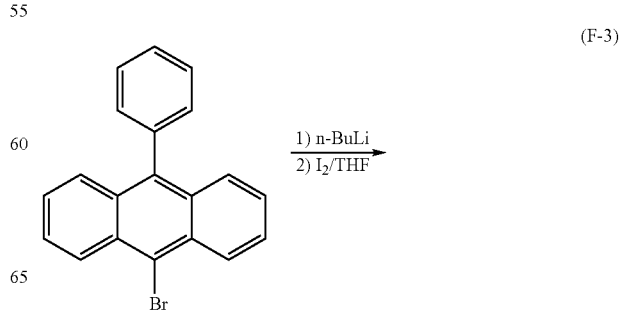

(F-3)

-continued

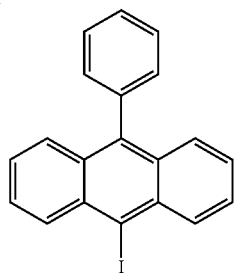

After 3.33 g (10 mmol) of 9-bromo-10-phenylanthracene was dissolved in 80 mL of tetrahydrofuran (abbreviation: THF) and cooled to −78° C., 7.5 mL (12.0 mmol) of n-BuLi (1.6 mol/L) was dropped through a dropping funnel into the reaction solution, and the mixture was stirred for one hour. Subsequently, a solution of 5 g (20.0 mmol) of iodine dissolved in 20 mL of THF was dropped, and the solution was further stirred at −78° C. for two hours. After the reaction, a sodium thiosulfate aqueous solution was added to stop the reaction. An organic layer was washed with a sodium thiosulfate aqueous solution and saturated saline and dried with magnesium sulfate. After the solution was filtered naturally, the filtrate was concentrated and recrystallized with ethanol; thus, 3.1 g of a light-yellow solid of 9-iodo-10-phenylanthracene as a target matter was obtained with a yield of 83%.

(iv) Synthesis of 9-phenyl-10-(4-bromophenyl)anthracene (abbreviation: PA)

The following shows Synthesis Scheme (F-4) of 9-phenyl-10-(4-bromophenyl)anthracene (abbreviation: PA).

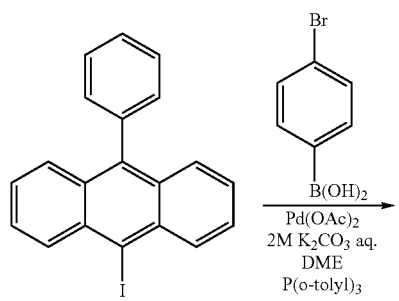

(F-4)

First, 1.0 g (2.63 mmol) of 9-iodo-10-phenylanthracene, 542 mg (2.70 mmol) of p-bromophenylboronic acid, 46 mg (0.03 mmol) of tetrakis(triphenylphosphine)palladium(0) (Pd(PPh$_3$)$_4$), 3 mL (6 mmol) of a potassium carbonate (K$_2$CO$_3$) aqueous solution (2 mol/L), and 10 mL of toluene were mixed and stirred at 80° C. for nine hours. After the reaction, toluene was added therein, and the mixture was filtered through Florisil, Celite, and alumina. The filtrate was washed with water and saturated saline and then dried with magnesium sulfate. After the solution was filtered naturally, the filtrate was concentrated and recrystallized with chloroform and hexane; thus, 562 mg of a light-brown solid of 9-phenyl-10-(4-bromophenyl)anthracene as a target matter was obtained with a yield of 45%.

[Step 2]

A method of synthesizing 9-(4-{N-[4-(carbazol-9-yl)phenyl]-N-phenylamino}phenyl)-10-phenylanthracene (abbreviation: YGAPA) will be explained. The following shows Synthesis Scheme (F-5) of YGAPA.

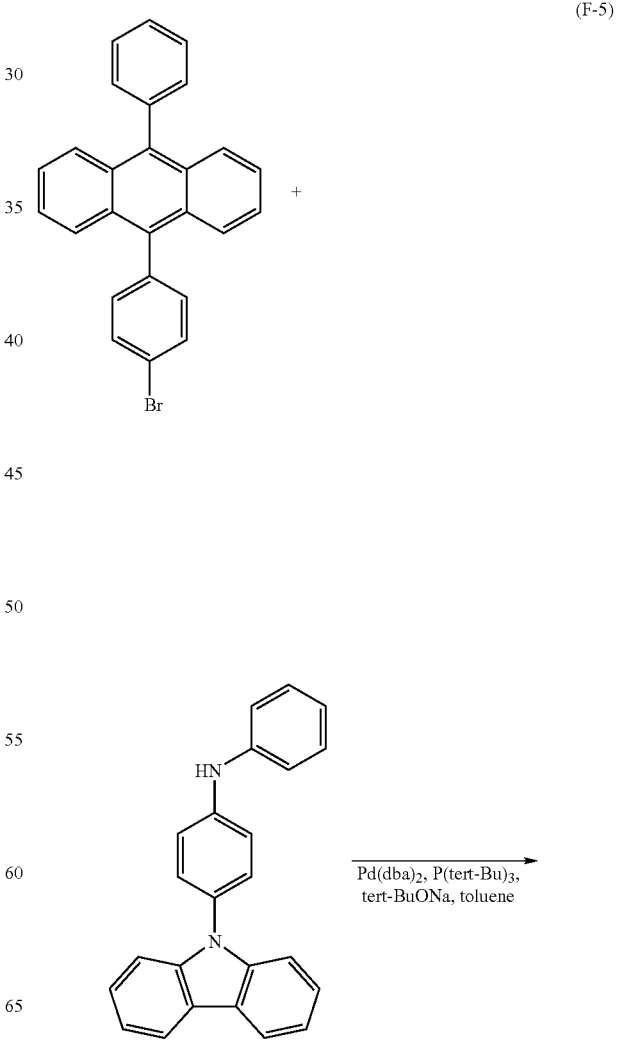

(F-5)

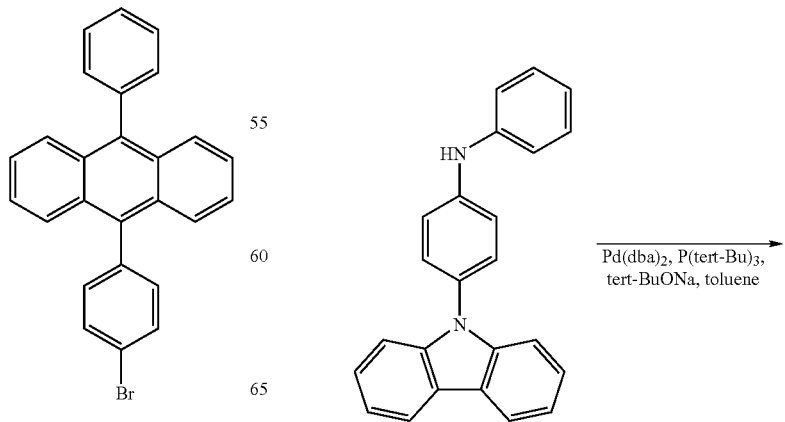

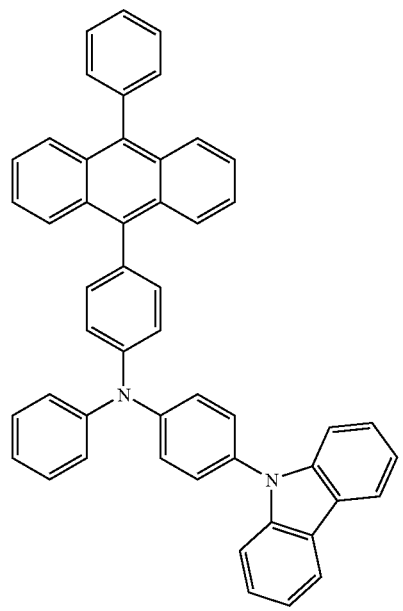

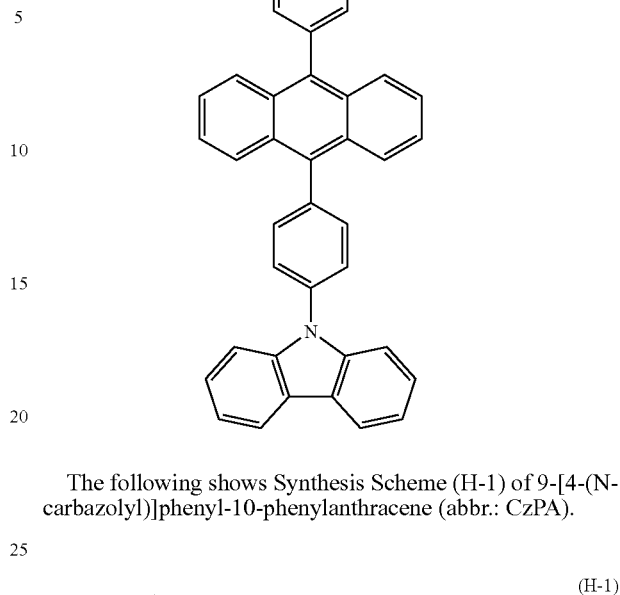

The following shows Synthesis Scheme (H-1) of 9-[4-(N-carbazolyl)]phenyl-10-phenylanthracene (abbr.: CzPA).

Figure 44A:
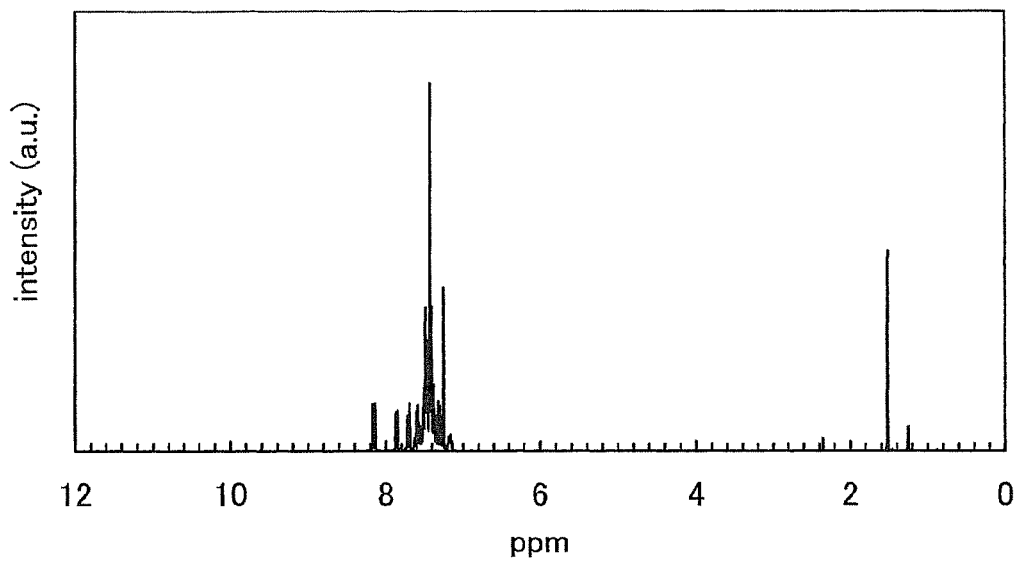
FIGS. 44A and 44B each show a $^1$H-NMR chart of 9-(4-{N-[4-(carbazol-9-yl)phenyl]-N-phenylamino}phenyl)-10-phenylanthracene.
Figure 44B:
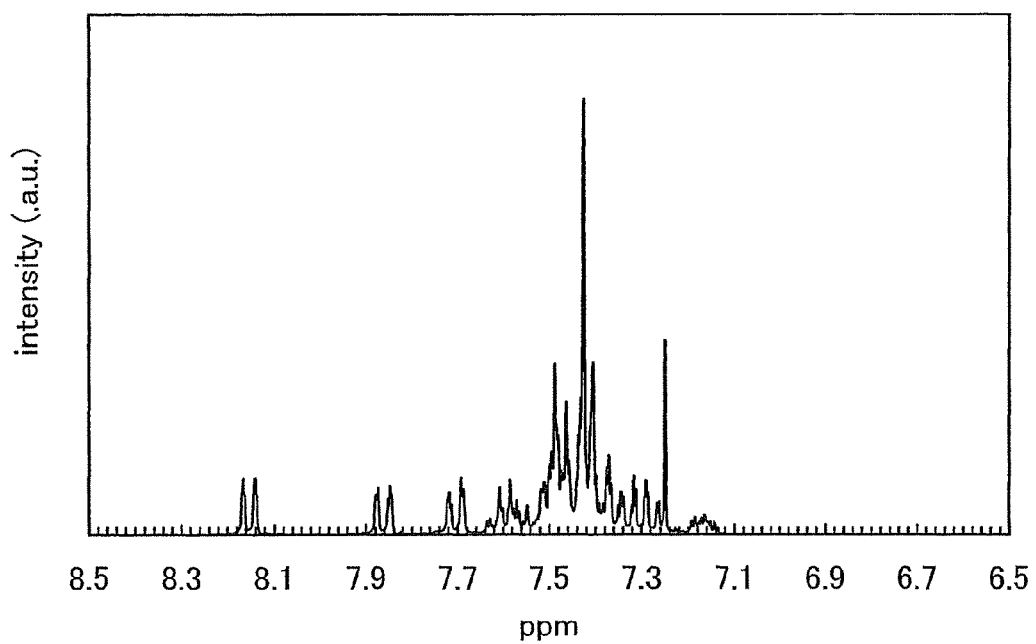

First, 409 mg (1.0 mmol) of 9-phenyl-10-(4-bromophenyl)anthracene, 339 mg (1.0 mmol) of YGA obtained in Step 1 of Embodiment 1, 6 mg (0.01 mmol) of bis(dibenzylideneacetone)palladium(0), 500 mg (5.2 mmol) of sodium tert-butoxide, 0.1 mL of tri(tert-butyl)phosphine (10 wt % hexane solution), and 10 mL of toluene were mixed and stirred at 80° C. for four hours. After the reaction, the reaction solution was washed with water, a water layer was extracted with toluene, and the water layer together with an organic layer was washed with saturated saline and then dried with magnesium sulfate. After the solution was filtered naturally and concentrated, the obtained oil-like substance was purified by silica gel column chromatography (hexane:toluene=7:3) and recrystallized with dichloromethane and hexane. Then, 534 mg of a yellow powder-like solid of YGAPA as a target matter was obtained with a yield of 81%. When this compound was measured by nuclear magnetic resonance spectrometry (NMR), it was confirmed that the compound was 9-(4-{N-[4-(carbazol-9-yl)phenyl]-N-phenylamino}phenyl)-10-phenylanthracene (abbreviation: YGAPA). FIGS. 44A and 44B show $^1$H-NMR charts of YGAPA.

Synthesis Example of CzPA

A method of synthesizing 9-[4-(N-carbazolyl)]phenyl-10-phenylanthracene (abbr.: CzPA) expressed by Structure Formula (203) is explained.

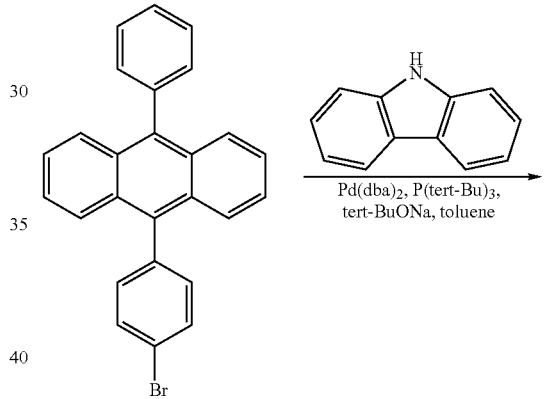

A mixture of 1.3 g (3.2 mmol) of 9-phenyl-10-(4-bromophenyl)anthracene, 578 mg (3.5 mmol) of carbazole, 50 mg (0.10 mmol) of bis(dibenzylideneacetone)palladium(0), 1.0 g (10 mmol) of tert-butoxysodium, 0.1 mL of tri(tert-butyl)phosphine (10 wt % hexane solution), and 30 mL of toluene was heated to reflux at 110° C. for 10 hours. After the reaction, the reaction solution was washed with water, a water layer was extracted with toluene, and the water layer together with an organic layer was washed with saturated saline and then dried with magnesium sulfate. After the solution was filtered naturally and concentrated, the obtained oil-like substance was purified by silica gel column chromatography (hexane:toluene=7:3) and recrystallized with dichloromethane and hexane. Then, 1.5 g of 9-[4-(N-carbazolyl)]phenyl-10-phenylanthracene (abbreviation: CzPA) as a target matter was obtained with a yield of 93%.

Figure 45:
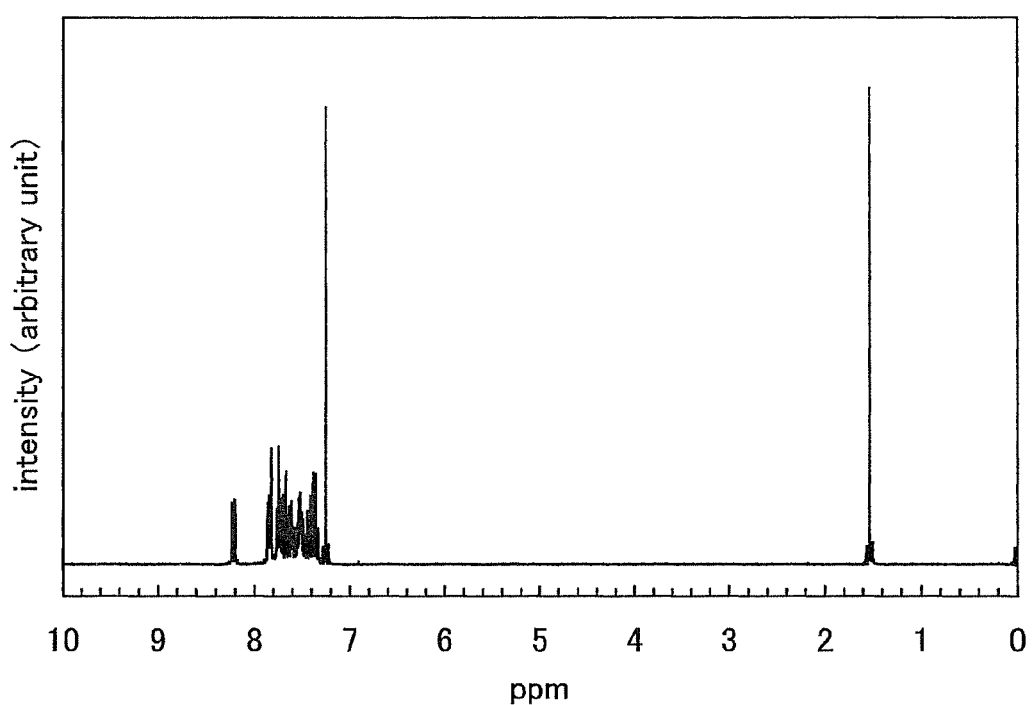
FIG. 45 shows a $^1$H-NMR chart of 9-[4-(N-carbazolyl)]phenyl-10-phenylanthracene.

The NMR data on the obtained CzPA is shown. $^1$H-NMR (300 MHz, CDCl$_3$): δ=8.22 (d, J=7.8 Hz, 2H), 7.86-7.82 (m, 3H), and 7.61-7.36 (m, 20H). In addition, FIG. 45 shows a $^1$H-NMR chart.

When 5.50 g of the obtained CzPA was sublimed and purified for 20 hours under the conditions of a temperature at 270° C., in argon flow (flow rate: 3.0 mL/min), and a pressure of 6.7 Pa, 3.98 g of CzPa was collected with a yield of 72%.

This application is based on Japanese Patent Application serial no. 2006-077631 filed in Japan Patent Office on Mar. 20, 2006, the entire contents of which are hereby incorporated by reference.

What is claimed is:

1. An aromatic amine compound expressed by General Formula (2)

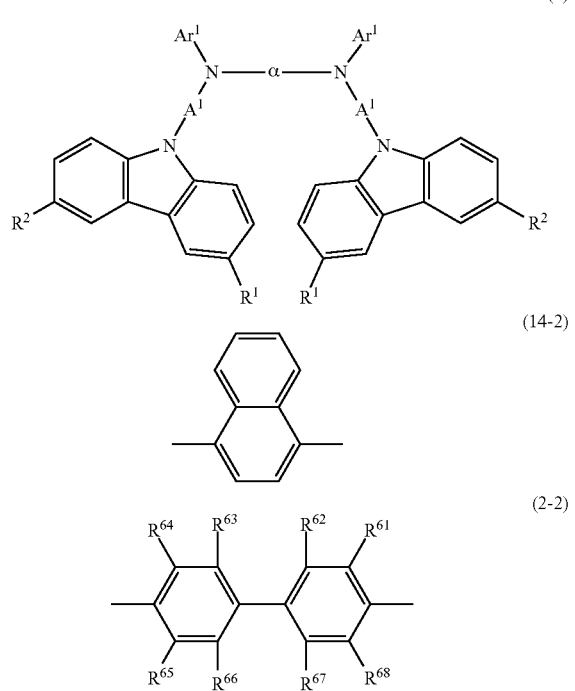

wherein in the formula, R$^1$ and R$^2$ each represent any of a hydrogen atom, an alkyl group having 1 to 4 carbon atoms, and an aryl group having 6 to 25 carbon atoms; A$^1$ represents a substituent expressed by General Formula (14-2); Ar$^1$ represents an aryl group having 6 to 25 carbon atoms; and α represents a substituent expressed by General Formula (2-2), and R$^{61}$ to R$^{68}$ each represent a hydrogen atom or an alkyl group having 1 to 4 carbon atoms.

2. A light-emitting element comprising:
a light-emitting layer and the aromatic amine compound according to claim 1 between a pair of electrodes.

3. A light-emitting element comprising:
a light-emitting layer and a layer containing the aromatic amine compound according to claim 1, between a pair of electrodes,
wherein the layer containing the aromatic amine compound is in contact with the light-emitting layer.

4. A light-emitting element comprising:
a light-emitting layer and the aromatic amine compound according to claim 1, between a pair of electrodes,
wherein the aromatic amine compound is included in the light-emitting layer.

5. The light-emitting element according to claim 2, wherein the light-emitting layer contains a phosphorescent material which emits phosphorescent light.

6. The light-emitting element according to claim 5, wherein the phosphorescent material emits green light.

7. The light-emitting element according to claim 2, wherein the light-emitting layer contains a fluorescent material which emits fluorescent light.

8. The light-emitting element according to claim 7, wherein the fluorescent material emits blue light.

9. A light-emitting device comprising:
the light-emitting element according to claim 2; and
a controller for controlling light emission of the light-emitting element.

10. An electronic appliance comprising a display portion,
wherein the display portion is provided with the light-emitting element according to claim 2 and a controller for controlling light emission of the light-emitting element.

11. An aromatic amine compound expressed by General Formula (115)

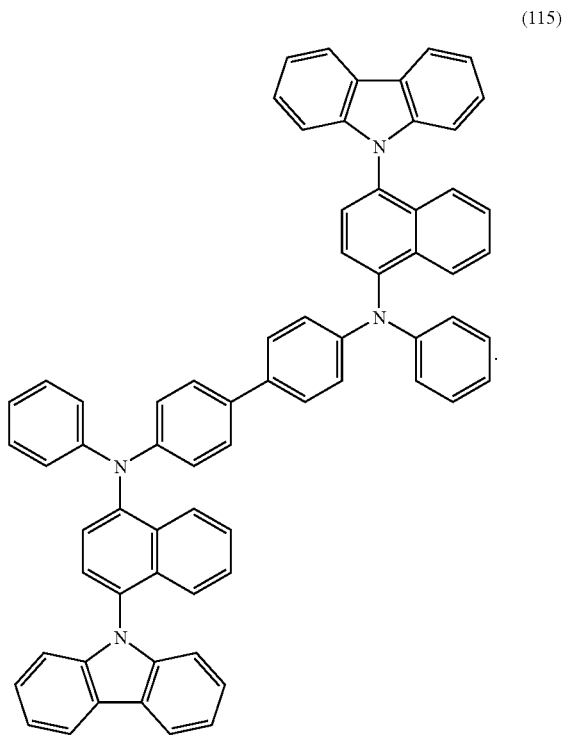

12. An aromatic amine compound expressed by General Formula (120)

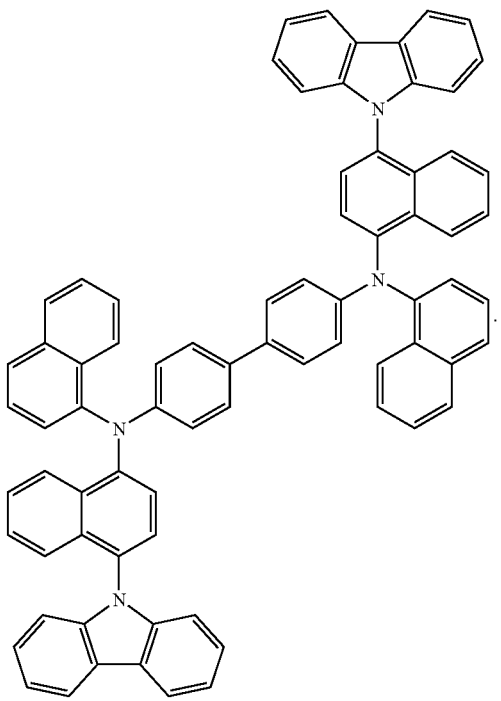

(120)

13. A light-emitting element comprising:

an anode;

a first layer over the anode, the first layer comprising an aromatic amine compound and an inorganic compound which exhibits an electron-accepting property with respect to the aromatic amine compound;

a second layer over the first layer;

a light-emitting layer over the second layer; and a cathode over the light-emitting layer, wherein the second layer comprises an organic compound which is the same as the aromatic amine compound included in the first layer, and wherein the aromatic amine compound is expressed by General Formula (2):

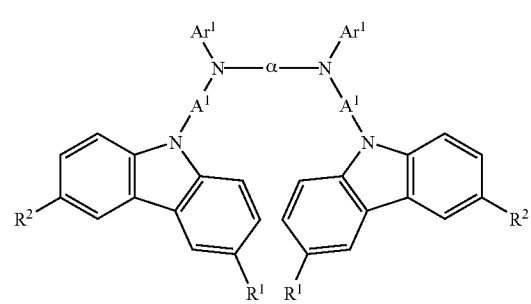

(2)

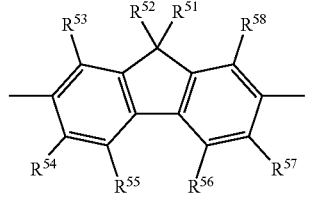

(2-1)

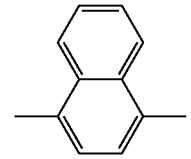

(14-2)

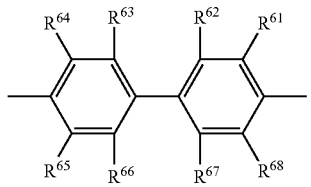

(2-2)

wherein in the formula, $R^1$ and $R^2$ each represent any of a hydrogen atom, an alkyl group having 1 to 4 carbon atoms, and an aryl group having 6 to 25 carbon atoms; $A^1$ represents a substituent expressed by General Formula (14-2); $Ar^1$ represents an aryl group having 6 to 25 carbon atoms; and α represents a substituent expressed by General Formula (2-1) or (2-2), in which $R^{51}$ and $R^{52}$ each represent any of a hydrogen atom, an alkyl group having 1 to 4 carbon atoms, and an aryl group having 6 to 12 carbon atoms; $R^{53}$ to $R^{58}$ each represent a hydrogen atom or an alkyl group having 1 to 4 carbon atoms; and $R^{61}$ to $R^{68}$ each represent a hydrogen atom or an alkyl group having 1 to 4 carbon atoms.

14. The light-emitting element according to claim 13, wherein the inorganic compound is an oxide of a metal belonging to any of Groups 4 to 8 in the periodic table.

15. The light-emitting element according to claim 13, wherein the inorganic compound is selected from a group consisting of vanadium oxide, niobium oxide, tantalum oxide, chromium oxide, molybdenum oxide, tungsten oxide, manganese oxide, and rhenium oxide.

16. The light-emitting element according to claim 13, wherein the first layer is in contact with the second layer.

17. The light-emitting element according to claim 13, wherein the second layer is in contact with the light-emitting layer.

18. The light-emitting element according to claim 13, wherein the light-emitting layer comprises a fluorescent material.

19. The light-emitting element according to claim 13, wherein the light-emitting layer comprises a fluorescent material which emits blue light.

20. The light-emitting element according to claim 13, wherein the light-emitting layer comprises a phosphorescent material.

21. An electronic appliance including a display portion, wherein the display portion comprises the light-emitting element according to claim 13.

22. An illumination apparatus including the light-emitting element according to claim 13.

23. A light-emitting element comprising:
an anode;
a first layer over the anode, the first layer comprising an aromatic amine compound and an inorganic compound which exhibits an electron-accepting property with respect to the aromatic amine compound;
a second layer over the first layer;
a light-emitting layer over the second layer; and
a cathode over the light-emitting layer,
wherein the second layer comprises an organic compound which is the same as the aromatic amine compound included in the first layer, and
wherein the aromatic amine compound is expressed by General Formula (115):

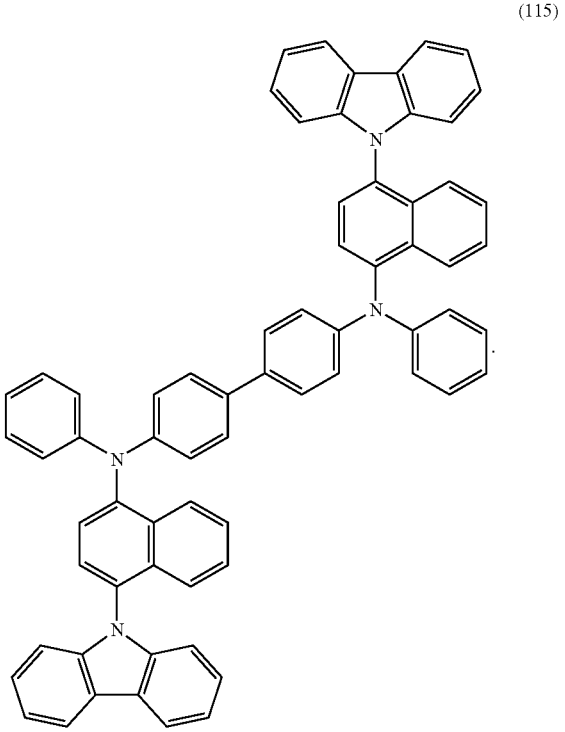

(115)

24. The light-emitting element according to claim 23, wherein the inorganic compound is an oxide of a metal belonging to any of Groups 4 to 8 in the periodic table.
25. The light-emitting element according to claim 23, wherein the inorganic compound is selected from a group consisting of vanadium oxide, niobium oxide, tantalum oxide, chromium oxide, molybdenum oxide, tungsten oxide, manganese oxide, and rhenium oxide.
26. The light-emitting element according to claim 23, wherein the first layer is in contact with the second layer.
27. The light-emitting element according to claim 23, wherein the second layer is in contact with the light-emitting layer.
28. The light-emitting element according to claim 23, wherein the light-emitting layer comprises a fluorescent material.
29. The light-emitting element according to claim 23, wherein the light-emitting layer comprises a fluorescent material which emits blue light.
30. The light-emitting element according to claim 23, wherein the light-emitting layer comprises a phosphorescent material.

31. An electronic appliance including a display portion, wherein the display portion comprises the light-emitting element according to claim 23.
32. An illumination apparatus including the light-emitting element according to claim 23.
33. A light-emitting element comprising:
an anode;
a first layer over the anode, the first layer comprising an aromatic amine compound and an inorganic compound which exhibits an electron-accepting property with respect to the aromatic amine compound;
a second layer over the first layer;
a light-emitting layer over the second layer; and
a cathode over the light-emitting layer,
wherein the second layer comprises an organic compound which is the same as the aromatic amine compound included in the first layer,
wherein the aromatic amine compound is expressed by General Formula (120):

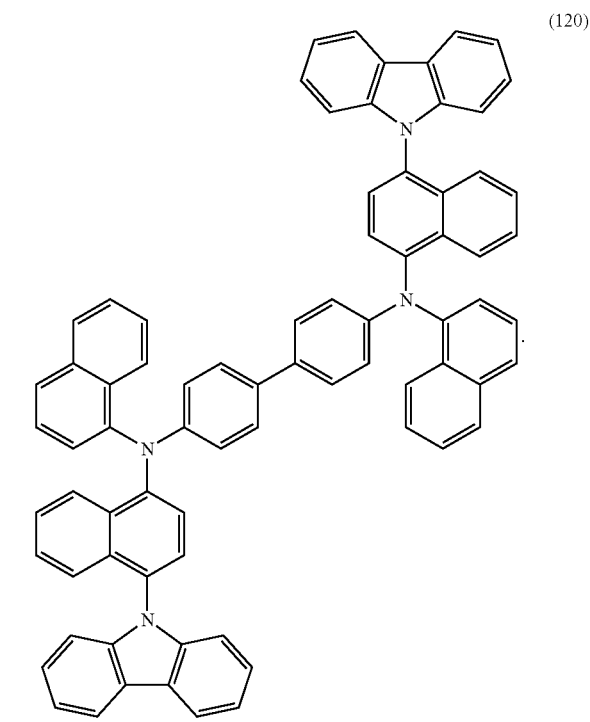

(120)

34. The light-emitting element according to claim 33, wherein the inorganic compound is an oxide of a metal belonging to any of Groups 4 to 8 in the periodic table.
35. The light-emitting element according to claim 33, wherein the inorganic compound is selected from a group consisting of vanadium oxide, niobium oxide, tantalum oxide, chromium oxide, molybdenum oxide, tungsten oxide, manganese oxide, and rhenium oxide.
36. The light-emitting element according to claim 33, wherein the first layer is in contact with the second layer.
37. The light-emitting element according to claim 33, wherein the second layer is in contact with the light-emitting layer.
38. The light-emitting element according to claim 33, wherein the light-emitting layer comprises a fluorescent material.

39. The light-emitting element according to claim 33, wherein the light-emitting layer comprises a fluorescent material which emits blue light.

40. The light-emitting element according to claim 33, wherein the light-emitting layer comprises a phosphorescent material.

41. An electronic appliance including a display portion, wherein the display portion comprises the light-emitting element according to claim 33.

42. An illumination apparatus including the light-emitting element according to claim 33.

* * * * *